United States Patent
Pham et al.

(10) Patent No.: US 11,306,071 B2
(45) Date of Patent: Apr. 19, 2022

(54) HETEROCYCLIC COMPOUNDS AS ADENOSINE ANTAGONISTS

(71) Applicant: Nuvation Bio Inc., New York, NY (US)

(72) Inventors: Son Minh Pham, San Francisco, CA (US); Jayakanth Kankanala, St. Paul, MN (US); Pradeep S. Jadhavar, Uttar Pradesh (IN); Baban Mohan Mulik, Uttar Pradesh (IN); Farha Khan, Uttar Pradesh (IN); Sreekanth A. Ramachandran, Uttar Pradesh (IN)

(73) Assignee: Nuvation Bio Inc., New York, NY (US)

( * ) Notice: Subject to any disclaimer, the term of this patent is extended or adjusted under 35 U.S.C. 154(b) by 24 days.

(21) Appl. No.: 16/746,763

(22) Filed: Jan. 17, 2020

(65) Prior Publication Data
US 2020/0231570 A1    Jul. 23, 2020

Related U.S. Application Data

(60) Provisional application No. 62/796,046, filed on Jan. 23, 2019, provisional application No. 62/794,537, filed on Jan. 18, 2019.

(51) Int. Cl.
| | |
|---|---|
| C07D 401/04 | (2006.01) |
| C07D 403/04 | (2006.01) |
| C07D 417/04 | (2006.01) |
| C07D 401/14 | (2006.01) |
| C07D 405/14 | (2006.01) |
| A61P 35/00 | (2006.01) |
| C07D 413/14 | (2006.01) |
| C07D 403/14 | (2006.01) |

(52) U.S. Cl.
CPC ............ *C07D 403/04* (2013.01); *A61P 35/00* (2018.01); *C07D 401/04* (2013.01); *C07D 401/14* (2013.01); *C07D 403/14* (2013.01); *C07D 405/14* (2013.01); *C07D 413/14* (2013.01); *C07D 417/04* (2013.01)

(58) Field of Classification Search
CPC ... C07D 401/04; C07D 403/04; C07D 417/04
See application file for complete search history.

(56) References Cited

U.S. PATENT DOCUMENTS

| | | | |
|---|---|---|---|
| 6,992,087 B2 | 1/2006 | Verhoest | |
| 7,407,961 B2 | 8/2008 | Yonishi | |
| 7,728,141 B2 | 6/2010 | Debenham | |
| 7,790,728 B2 | 9/2010 | Vidal | |
| 8,754,085 B2 | 6/2014 | Charlton | |
| 9,132,127 B2 | 9/2015 | Charlton | |
| 10,028,058 B2 | 7/2018 | Anderson | |
| 10,112,923 B2 | 10/2018 | Congreve | |
| RE47,351 E | 4/2019 | Zablocki | |
| 10,253,044 B2 | 4/2019 | Wang | |
| 10,292,968 B2 | 5/2019 | Brown | |
| 10,307,407 B2 | 6/2019 | Wang | |
| 10,328,074 B2 | 6/2019 | Engelhardt | |
| 10,336,697 B2 | 7/2019 | Ujjinamatada | |
| 10,336,722 B2 | 7/2019 | Bair | |
| 10,363,257 B2 | 7/2019 | Quinn | |
| 10,370,356 B2 | 8/2019 | Atkinson | |
| 10,370,374 B2 | 8/2019 | Ibrahim | |
| 10,377,769 B2 | 8/2019 | Bair | |
| 10,391,175 B2 | 8/2019 | Wang | |
| 10,399,962 B2 | 9/2019 | Beatty | |
| 10,472,347 B2 | 11/2019 | Kuang | |
| 10,793,561 B2 | 10/2020 | Pham et al. | |
| 11,028,058 B2 | 6/2021 | Pham et al. | |
| 2005/0113387 A1 | 5/2005 | Yonishi et al. | |
| 2005/0222159 A1 | 10/2005 | Tsutsumi et al. | |
| 2006/0293339 A1 | 12/2006 | Chakravarty | |
| 2007/0072874 A1 | 3/2007 | Cui | |
| 2009/0042891 A1 | 2/2009 | Vidal Juan et al. | |
| 2009/0247567 A1 | 10/2009 | Do | |
| 2011/0288090 A1 | 11/2011 | Armstrong | |
| 2013/0203774 A1 | 8/2013 | Jensen | |
| 2014/0174537 A1 | 6/2014 | Fadhel | |
| 2014/0243346 A1 | 8/2014 | Charlton | |
| 2015/0094312 A1 | 4/2015 | Adcock | |
| 2016/0083349 A1 | 3/2016 | Lin et al. | |
| 2016/0130253 A1 | 5/2016 | Arancio | |
| 2016/0311784 A1 | 10/2016 | Leach | |
| 2019/0023666 A1 | 1/2019 | Pham | |
| 2019/0023702 A1 | 1/2019 | Pham | |

(Continued)

FOREIGN PATENT DOCUMENTS

| | | |
|---|---|---|
| AU | 2019205984 A1 | 8/2019 |
| CN | 104341386 A | 2/2015 |

(Continued)

OTHER PUBLICATIONS

Cheong et al. International Journal of Medicinal Chemistry, vol. 2011, p. 1-15. (Year: 2011).*
Effendi et al. Cells 2020, 9, 785 p. 1-36 . (Year: 2020).*
Allard, B. et al. (2013; e-pub. Aug. 27, 2013). "Targeting CD73 Enhances the Antitumor Activity of Anti-PD-1 and Anti-CTLA-4 mAbs," Clinical Cancer Research 19(20):1-10.
Allard, B. et al. (2016) "Immunosuppressive Activities of Adenosine in Cancer," Current Opinion in Pharmacology 29:7-16.
Allard, D. et al. (Apr. 2017; e-published Feb. 8, 2017). "Targeting A2 Adenosine Receptors in Cancer," Immunology and Cell Biology 95(4):333-339; 34 pages.
Allard, D. et al. (Feb. 2016; e-pub. Jan. 25, 2016). "CD73—Adenosine: A Next-Generation Target in Immuno-Oncology," Immunotherapy 8(2):143-163, 19 pages.

(Continued)

*Primary Examiner* — Emily A Bernhardt
(74) *Attorney, Agent, or Firm* — Morrison & Foerster LLP

(57) ABSTRACT

5,6-disubstituted 2-aminopyrazine compounds as modulators of an adenosine receptor are provided. The compounds may find use as therapeutic agents for the treatment of diseases mediated through a G-protein-coupled receptor signaling pathway and may find particular use in oncology.

20 Claims, No Drawings

(56) References Cited

U.S. PATENT DOCUMENTS

| | | |
|---|---|---|
| 2019/0135784 A1 | 5/2019 | Strum |
| 2019/0135811 A1 | 5/2019 | Strum |
| 2019/0135820 A1 | 5/2019 | Smith |
| 2019/0248795 A1 | 8/2019 | Burkamp |
| 2019/0276473 A1 | 9/2019 | Crosignani |
| 2019/0292188 A1 | 9/2019 | Wang |
| 2019/0337957 A1 | 11/2019 | Wang |
| 2020/0231589 A1 | 7/2020 | Pham |
| 2020/0330458 A1 | 10/2020 | Qi |
| 2020/0331918 A1 | 10/2020 | Zeng |
| 2021/0292285 A1 | 9/2021 | Pham et al. |

FOREIGN PATENT DOCUMENTS

| | | |
|---|---|---|
| CN | 107221611 A | 9/2017 |
| CN | 112055709 A | 12/2020 |
| EP | 3230277 B1 | 9/2019 |
| WO | WO2003030909 A1 | 4/2003 |
| WO | 2005047285 A1 | 5/2005 |
| WO | WO2005040151 A1 | 5/2005 |
| WO | WO2007017096 A1 | 2/2007 |
| WO | 2010136817 A1 | 12/2010 |
| WO | WO2011095625 A1 | 8/2011 |
| WO | WO2012168358 A1 | 12/2012 |
| WO | WO2014145485 A2 | 9/2014 |
| WO | WO2014145485 A3 | 11/2014 |
| WO | WO2015017335 A1 | 2/2015 |
| WO | WO2016081290 A1 | 5/2016 |
| WO | WO2017025918 A1 | 2/2017 |
| WO | WO2017112917 A1 | 6/2017 |
| WO | WO2018081863 A1 | 5/2018 |
| WO | WO2018178338 A1 | 10/2018 |
| WO | WO2019002606 A1 | 1/2019 |
| WO | WO2019018583 A1 | 1/2019 |
| WO | WO2019018584 A1 | 1/2019 |
| WO | WO2019090347 A1 | 5/2019 |
| WO | WO2019096322 A1 | 5/2019 |
| WO | WO2019118313 A1 | 6/2019 |
| WO | WO2019120234 A2 | 6/2019 |
| WO | WO2019134539 A1 | 7/2019 |
| WO | WO2019141131 A1 | 7/2019 |
| WO | WO2019148161 A1 | 8/2019 |
| WO | WO2019154294 A1 | 8/2019 |
| WO | WO2019158070 A1 | 8/2019 |
| WO | WO2019160829 A1 | 8/2019 |
| WO | WO2019165204 A1 | 8/2019 |
| WO | WO2019169065 A2 | 9/2019 |
| WO | WO2019173082 A1 | 9/2019 |
| WO | 2020035052 A1 | 2/2020 |
| WO | 2020150675 A1 | 7/2020 |
| WO | 2020150677 A1 | 7/2020 |
| WO | 2021146629 A1 | 7/2021 |
| WO | 2021146631 A1 | 7/2021 |

OTHER PUBLICATIONS

Allard, D. et al. (Jan. 2019; e-pub. May 24, 2018). "Targeting the CD73-Adenosine Axis in Immuno-Oncology," Immunology Letters 205:31-39.

Arab, S. et al. (Mar. 2017). "Increased Efficacy of a Dendritic Cell-based Therapeutic Cancer Vaccine with Adenosine Receptor Antagonist and CD73 Inhibitor," Tumor Biology, pp. 1-8.

Azambuja, J.H. et al. (May 2019; e-pub Aug. 16, 2018). "CD73 Downregulation Decreases In Vitro and In Vivo Glioblastoma Growth," Molecular Neurobiology 56(5):3260-3279, 20 pages.

Badawneh, M. et al. (Sep. 2003) "Synthesis of 3- or 4-Phenyl-1,8-Naphthyridine Derivatives and Evaluation of Antimycobacterial and Antimicrobial Activity," II Farmaco 58(9):859-862.

Banuelos, J. et al. (Feb. 18-22, 2019). "Targeting Innate Immune Cells for the Treatment of Cancer," #1008, Poster presented at Keystone Conference, Uncovering Mechanisms of Immune-Based Therapy in Cancer and Autoimmunity, Breckenridge, CO, 1 page.

Barbosa, R.S.S. et al. (2019). "Sequential Combination of Bortezomib and WEE1 Inhibitor, MK-1775, Induced Apoptosis in Multiple Myeloma Cell Lines," Biochemical and Biophysical Research Communications pp. 1-8.

Bastid, J. et al. (Mar. 3, 2015, e-pub. Nov. 17, 2014). "Inhibition of CD39 Enzymatic Function at the Surface of Tumor Cells Alleviates Their Immunosuppressive Activity," Cancer Immunology Research 3(3):254-265.

Beavis, P.A. et al. (Mar. 2017). "Targeting the Adenosine 2A Receptor Enhances Chimeric Antigen Receptor T Cell Efficacy," The Journal of Clinical Investigation 127(3):929-941.

Beavis, P.A. et al. (May 2015; e-pub. Feb. 11, 2015). "Adenosine Receptor 2A Blockade Increases the Efficacy of Anti-PD-1 through Enhanced Antitumor T-cell Responses," Cancer Immunology Research 3(5):506-517.

Beavis, P.A. et al. (Nov. 2015). "CD73: A Potential Biomarker for Anti-PD-1 Therapy," OncoImmunology 4(11): e1046675, 3 pages.

Beavis, P.V. et al. (Sep. 3, 2013). "Blockade of A2A Receptors Potently Suppresses the Mestasis of CD73+ Tumors," Proc. Natl. Acad. Sci 110(36):14711-14716.

Becker, A. et al. (2018). "CD73 Inhibitors (CD73i) Reverse the AMP/Adenosine-Mediated Impairment of Immune Effector Cell Activation by Immune Checkpoint Inhibitors (ICI)," Abstract No. 3501, Poster present at Annual Meeting of the American Association of Cancer Research, Chicago, IL, 1 page.

Bendell, J. et al. (Mar. 29-Apr. 4, 2019). "Evidence of Immune Activation in the First-in-Human Phase Ia Dose Escalation Study of the Adenosine 2a Receptor Antagonist, AZD4635, in Patients with Advanced Solid Tumors," Poster presented at the American Association for Cancer Research Annual Meeting, Atlanta, GA, 1 page.

Blay, J. et al. (Jul. 1, 1997). "The Extracellular Fluid of Solid Carcinomas Contains Immunosuppressive Concentrations of Adenosine," Cancer Research 57(13):2602-2605.

Borodovsky, A. et al. (Apr. 17, 2018). "Inhibition of A2AR by AZD4635 Induces Anti-tumor Immunity Alone and in Combination with Anti-PD-L1 in Preclinical Models," Poster Presented at the AACR Annual Meeting, Chicago, IL, 1 page.

Borodovsky, A. et al. (Apr. 5, 2017). "Preclinical Pharmacodynamics and Antitumor Activity of AZD4635, A Novel Adenosine 2A Receptor Inhibitor That Reverses Adenosine Mediated T Cell Suppression," AACR 2017 Annual Meeting, Washington, D.C, Poster 5580, 1 page.

Burkholder, B. et al. (2014; e-pub. Jan. 17, 2014). "Tumor-induced Perturbations of Cytokines and Immune Cell Networks," Biochimica Biophysica Acta 1845:182-201.

Cekic, C. et al. (2011). "Adenosine A2B Receptor Blockade Slows Growth of Bladder and Breast Tumors," J. Immunol. 188(1):198-205.

Cekic, C. et al. (Mar. 2016). "Purinergic Regulation of the Immune System," Nature Reviews 16:177-192.

Chen, J.-F. et al. (Apr. 2013). "Adenosine Receptors as Drug Targets—What are the Challenges?," Nature Reviews 12:265-286.

Chen, X.-W. (Nov. 6, 2017; e-pub. Sep. 19, 2017). "Hydrogen-Transfer-Mediated α-Functionalization of 1,8-Naphthyridines by a Strategy Overcoming the Over-Hydrogenation Barrier," Angew Chem Int Ed. 56 (45):14232-14236.

Congreve, M. et al. (2012). "Discovery of 1,2,4-Triazine Derivatives as Adenosine A2A Antagonists using Structure Based Drug Design," Journal of Medicinal Chemistry 55:1898-1903, (with Supplementary material, 18 pages).

Congreve, M. et al. (Nov. 2018; e-pub. Oct. 18, 2018). "Targeting Adenosine A2A Receptor Antagonism for Treatment of Cancer," Expert Opinion on Drug Discovery 13(11):997-1003, 8 pages.

Corvus Pharmaceuticals. (Oct. 2, 2018). Corporate Presentation at Cantor Global Healthcare Conference, 25 pages.

Cretella, D. et al. (2019, e-pub. Sep. 10, 2019). "Pre-Treatment With the CDK4/6 Inhibitor Palbociclib Improves the Efficacy of Paclitaxel in TNBC Cells," Scientific Reports 9(13014):1-11.

Dastjerdi, N. et al. (2016). "Adenosine A1 Receptor Modifies PTE Expression and Apoptosis in Breast Cancer Cell Line Mcf-7," Bratisl. Med. J. 117(4):242-246.

(56) References Cited

OTHER PUBLICATIONS

De Lera Ruiz, M. et al. (May 8, 2014; e-pub. Nov. 15, 2013). "Adenosine A2A Receptor as a Drug Discovery Target," J. Med. Chem. 57(9):3623-3650, 28 pages.

De Mendonca, A. et al. (2000). "Adenosine: Does it have a Neuroprotective Role After All?," Brain Research Reviews 33:258-274.

Debenham, J.S. et al. (Feb. 1, 2006, e-pub. Nov. 2, 2005). "Synthesis of Functionalized 1,8-Naphthyridinones and their Evaluation as Novel, Orally Active CB1 Receptor Inverse Agonists," Bioorg & Med Chem Lett 16(3):681-685.

Di Sante, G. et al. (2019). "Recent Advances With Cyclin-Dependent Kinase Inhibitors: Therapeutic Agents for Breast Cancer and Their Role in Immuno-Oncology," Expert Review of Anticancer Therapy 19(7):569-587.

Dosa, P.I. et al. (Feb. 11, 2016; e-pub. Sep. 21, 2015). "Tactical Approaches to Interconverting GPCR Agonists and Antagonists," Journal of Medicinal Chemistry 59(3):810-840, 31 pages.

Draper-Joyce, C.J. et al. (2018). "Structure of the Adenosine-bound Human Adenosine A1 Receptor—Gi Complex," Nature 558:559-563, 21 pages.

Dörwald, F.Z. (2005). "Side Reactions in Organic Synthesis: A Guide to Successful Synthesis Design," Weinheim Wiley-Vch, 4 pages.

Eastwood, P. et al. (2010; e-pub. Jan. 20, 2010). "Discovery of N-(5,6-diarylpyridin-2-yl)amide Derivatives as Potent and Selective A2B Adenosine Receptor Antagonists," Bioorganic & Medicinal Chemistry Letters 20:1697-1700.

Eastwood, P. et al. (2011; e-pub. Dec. 20, 2010). "Discovery of LAS101057: A Potent, Selective, and Orally Efficacious A2B Adenosine Receptor Antagonist," Bioorganic & Medicinal Chemistry Letters 2:213-218.

Fang, Y. et al. (Jun. 10, 2019). "Sequential Therapy with PARP and WEE1 Inhibitors Minimizes Toxicity while Maintaining Efficacy," Cancer Cell 35:851-867, 25 pages.

Ferrarini, P.L. et al. (Nov. 23, 2000). "Synthesis and Antiplatelet Activity of Some 3-Phenyl-1,8-Naphthyridine Derivatives," Il Farmaco 55(9-10):603-610.

Garapaty, S. et al. (Jun. 2018). "Novel, Heterocyclic Small Molecule Inhibitors of PD-1/PD-L1 Pathway," Jubliant Biosys Ltd., Poster presented at AACR, 1 page.

Gessi, S. et al. (Dec. 1, 2017). "Inhibition of A2A Adenosine Receptor Signaling in Cancer Cells Proliferation by the Novel Antagonist TP455," Frontiers in Pharmacology 8(Article 888), 13 pages.

Gessi, S. et al. (May 2011; e-pub. Oct. 1, 2010). "Adenosine Receptorsand Cancer," Biochim Biophys Acta 1808 (5):1400-1412.

Glukhova, A. et al. (Feb. 23, 2017). "Structure of the Adenosine A1 Receptor Reveals the Basis for Subtype Selectivity," Cell 168:867-877, 25 pages.

Goulding, J. et al. (2018; e-pub. Oct. 26, 2017). "Characterisation of Endogenous A2A and A2B Receptor-mediated Cyclic AMP Responses in HEK 293 Cells Using the GloSensorTM Biosensor: Evidence for an Allosteric Mechanism of Action for the A2B-Selective Antagonist PSB 603," Biochemical Pharmacology 147:55-66.

Gutierrez-De-Teran, H. et al. (2017). "Structure-Based Rational Design of Adenosine Receptor Ligands," Current Topics in Medicinal Chemistry 17(1):40-58.

Hafner, M. et al. (Aug. 15, 2019). "Multiomics Profiling Establishes the Polypharmacology of FDA-Approved CDK4/6 Inhibitors and the Potential for Differential Clinical Activity," Cell Chemical Biology 26:1-14. 23 pages.

Harter, M. et al. (2019). "Novel Non-Xanthine Antagonist of the A2B Adenosine Receptor: From HTS Hit to Lead Structure," European Journal of Medicinal Chemistry 7163:763-778.

Hausler, S. et al. (2014). "Anti-CD39 and Anti-CD73 Antibodies A1 and 7G2 Improve Targeted Therapy in Ovarian Cancer by Blocking Adenosine-Dependent Immune Evasion," Am J Transl Res 6(2):129-139.

Hinz, S. et al. (2018). "Adenosine A2A Receptor Ligand Recognition and Signaling is Blockedby A2B Receptors," Oncotarget 9(17):13593-13611.

Hocher, B. (2010; e-pub. Jun. 30, 2010). "Adenosine A1 Receptor Antagonists in Clinical Research and Development," Kidney International 78:438-445.

Houthuys, E. et al. (Sep. 2017). "A Novel Non-Competitive and Non-Brain Penetrant Adenosine A2A Receptor Antagonist Designed to Reverse Adenosinemediated Suppression of Anti-tumor Immunity," Poster prepsented at ICIC, 1 page.

Hu, Y. et al. (2018, e-pub. Dec. 24, 2018). "Pharmacophore Modeling, Multiple Docking, and Molecular Dynamics Studies on Wee1 Kinase Inhibitors," Journal of Biomolecular Structure and Dynamics 1-14.

Huang, S. et al. (Aug. 15, 1997). "Role of A2a Extracellular Adenosine Receptor-Mediated Signaling in Adenosine-Mediated Inhibition of T-Cell Activation and Expansion," Blood 90(4):1600-1610.

Iannone, R. et al. (Dec. 2013). "Blockade of A2B Adenosine Receptor Reduces Tumor Growth and Immune Suppression Mediated by Myeloid-Derived Suppressor Cells in a Mouse Model of Melanoma," Neoplasia, 15 (12):1400-1409.

Iannone, R. et al. (Mar. 15, 2014; e-pub. Mar. 1, 2014). "Adenosine Limits the Therapeutic Effectiveness of Anti-CTLA4 mAb in a Mouse Melanoma Model," Am J Cancer Res 4(2):172-181.

Invitation to Pay Additional Fees, dated Feb. 28, 2020, for PCT Application No. PCT/US2020/14206, 4 pages.

Invitrogen. (Dec. 1, 2010). "GeneBLAzer ADORA2A CHO-K1 DA Cell-Based Assay" 12 pages.

Invitrogen. (Sep. 1, 2008). "GeneBLAzer ADORA2A CHO-K1 DA Assay Kit," 5 pages.

Ismayilova, N. et al. (2004). "Effects of Adenosine A1, Dopamine D1 and Metabotropic Glutamate 5 Receptors-modulating Agents on Locomotion of the Reserpinised Rats," European Journal of Pharmacology 497:187-195.

Jaakola, V.-P. et al. (Nov. 21, 2008). "The 2.6 Angstrom Crystal Structure of a Human A2A Adenosine Receptor Bound to an Antagonist," Science 322:1211-1217.

Jajoo, S. et al. (Nov. 2009). "Adenosine A3 Receptor Suppresses Prostate Cancer Metastasis by Inhibiting NADPH Oxidase Activity," Neoplasia 11(11):1132-1145, 17 pages.

Jazayeri, A. et al. (Jan. 11, 2017; e-pub. Jun. 22, 2016). "Structurally Enabled Discovery of Adenosine A2A Receptor Antagonists," Chemical Reviews 117(1):21-37, 17 pages.

Jiang, J. et al. (2019). "A2B Adenosione Receptor Antagonists With Picomolar Potency," J. Med. Chem. 32:4032-4055.

Jin, M.H. et al. (2019). "Therapeutic Co-Targeting of WEE1 and ATM Downregulates PD-L1 Expression in Pancreatic Cancer," Cancer Research and Treatment (CRT) pp. 1-40.

Kang, N.S. et al. (Jun. 1, 2009, e-pub. Apr. 17, 2009). "Predictive Models of Cannabinoid-1 Receptor Antagonists Derived from Diverse Classes," Bioorg & Med Chem Lett 19(11):2990-2996.

Katritch, V. et al. (Feb. 25, 2010). "Structure-Based Discovery of Novel Chemotypes for Adenosine A2A Receptor Antagonists," J Med Chem. 53(4):1799-1809, 30 pages.

Kjaergaard, J. et al. (Jul. 15, 2018; e-pub. May 25, 2018). "A2A Adenosine Receptor Gene Deletion or Synthetic A2A Antagonist Liberate Tumor-Reactive CD8+ T Cells from Tumor-Induced Immunosuppression," The Journal of Immunology 201(2):782-791, 10 pages.

Koszalka, P. et al. (2014). "Inhibition of CD73 Stimulates the Migration and Invasion of B16F10 Melanoma Cells In Vitro, but Results in Impaired Angiogenesis and Reduced Melanoma Growth In Vivo," Oncology Reports 31:819-827.

Kumar, V. (2013; e-pub. Dec. 28, 2012). "Adenosine as an Endogenous Immunoregulator in Cancer Pathogenesis: Where to go?," Purinergic Signalling 9(2):145-165.

Kuzu, O.F. et al. (2017). "Improving Pharmacological Targeting of AKT in Melanoma," Cancer Letters 404:29-36.

Köse, M. et al. (May 24, 2018; e-pub. May 15, 2018). "Fluorescent-Labeled Selective Adenosine A2B Receptor Antagonist Enables Competition Binding Assay by Flow Cytometry," Journal of Medicinal Chemistry 61(10):4301-4316, 16 pages.

(56) References Cited

OTHER PUBLICATIONS

Lappas, C.M. et al. (2005). "A2A Adenosine Receptor Induction Inhibits IFN-γ Production in Murine CD4+ T Cells," The Journal of Immunology 174:1073-1080.

Leclerc, B.G. et al. (Jan. 1, 2016; e-pub. Aug. 7, 2015). "CD73 Expression Is an Independent Prognostic Factor in Prostate Cancer," Clinical Cancer Research 22(1):158-166.

Leone, R.D. et al. (2015; e-pub. Apr. 8, 2015). "A2aR Antagonists: Next Generation Checkpoint Blockade for Cancer Immunotherapy," Computational and Structural Biotechnology Journal 13:265-272.

Leone, R.D. et al. (2018). "Targeting Adenosine for Cancer Immunotherapy," Journal for ImmunoTherapy of Cancer 6:57, 9 pages.

Leone, R.D. et al. (Aug. 2018; e-pub. Jun. 19, 2018). "Inhibition of the Adenosine A2a Receptor Modulates Expression of T Cell Coinhibitory Receptors and Improves Effector Function for Enhanced Checkpoint Blockade and ACT in Murine Cancer Models," Cancer Immunology Immunotherapy 67(8):1271-1284, 14 pages.

Lertsuwan, K. et al. (2017). "Purinergic Receptor Expression and Cellular Responses to Purinergic Agonists in Human Prostate Cancer Cells," Anticancer Research 37:529-537.

Li, Q.-X. et al. (May 2017; e-pub. Feb. 4, 2017). "Experimental Animal Modeling for Immuno-Oncology," Pharmacology & Therapeutics 173:34-46, 13 pages.

Liang, J. et al. (Sep. 24, 2019). "Genome-Wide CRIPSR-cas9 Screen Reveals Selective Vulnerability of ATRX-Mutant Cancers to WEE1 Inhibition," State Key Laboratory of Medical Molecular Biology, Institute of Basic Medical Sciences, Chinese Academy of Medical Sciences, Peking Union Medical School, Manuscript, 42 pages.

Lin, C.A. (2013). "Structural Characteristics of Cannabinoid Type 1 Receptor Antagonists," 160:536900 Abstract 34 (5):1240-1245, 1 page.

Lin, Z. et al. (Feb. 25, 2010). "Adenosine A1 Receptor, a Target and Regulator of ERα Action, Mediates the Proliferative Effects of Estradiol in Breast Cancer," Oncogene 29(8):1114-1122, 18 pages.

Linden, J. et al. (1999). "Characterization of Human A2B Adenosine Receptors: Radioligand Binding, Western Blotting, and Coupling to Gq in Human Embryonic Kidney 293 Cells and HMC-1 Mast Cells," Molecular Pharmacology 56:705-713.

Lingam, V.S. et al. (Oct. 22, 2015; e-pub. Sep. 30, 2015). "Design, Synthesis and Pharmacological Evaluation of 5,6-Disubstituted Pyridin-2(1H)-one Derivatives as Phosphodiesterase 10A (PDE10A) Antagonists," J. Med. Chem 58(20):8292-8308.

Liu, D. et al. (2019). "Enhancement of Chemosensitivity by WEE1 Inhibition in EGFR-TKIs Resistant Non-Small Cell Lung Cancer," Biomedicine & Pharmacotherapy 117(109185):1-8.

Liu, W. et al. (2019, e-pub. Jun. 13, 2019). "Targeting the WEE1 Kinase Strengthens the Antitumor Activity of Imatinib Via Promoting KIT Autophagic Degradation in Gastrointestinal Stromal Tumors," Gastric Cancer pp. 1-13.

Lübbehüsen, c. et al. (2019, e-pub. Apr. 23, 2019). "Characterization of Three Novel H3F3A-mutated Giant Cell Tumor Cell Lines and Targeting of Their Wee1 Pathway," Scientific Reports 9(6458):1-10.

Ma, S.-R. et al. (2017). "Blockade of Adenosine A2A Receptor Enhances CD8+ T Cells Response and Decreases Regulatory T Cells in Head and Neck Squamous Cell Carcinoma," Molecular Cancer 16:99, 15 pages.

Madsen-Duggen, C.B. et al. (Jun. 15, 2010, e-pub. Apr. 21, 2010). "Dihydro-Pyrano[2,3-B]Pyridines and Tetrahydro-1,8-Naphthyridines as CB1 Receptor Inverse Agonists: Synthesis, SAR and Biological Evaluation," Bioorg & Med Chem Lett 20(12):3750-3754.

Maemoto, T. et al. (2004). "Pharmacological Characterization of FR194921, a New Potent, Selective, and Orally Active Antagonist for Central Adenosine A1 Receptors," J Pharmacol 96:42-52.

Mantri, M. et al. (2008; e-pub. Jul. 19, 2008). "2-Amino-6-furan-2-yl-4-substituted Nicotinonitriles as A2A Adenosine Receptor Antagonists," J. Med. Chem. 51(15):4449-4455.

Massie, B.M. et al. (Oct. 7, 2010). "Rolofylline, an Adenosine A1-Receptor Antagonist, in Acute Heart Failure," The New England Journal of Medicine 363(15):1419-1428.

Mastracchio, A. et al. (2019). "Investigation of Biaryl Heterocycles as Inhibitors of Wee1 Kinase," Bioorganic & Medicinal Chemistry Letters 29:1481-1486.

McCoull, W. et al. (2018). "Development of a Novel B-Cell Lymphoma 6 (BCL6) PROTAC To Provide Insight into Small Molecule Targeting of BCL6," ACS Chemical Biology 11 pages.

McCoull, W. et al. (Nov. 16, 2018; e-pub. Oct. 17, 2018). "Development of a Novel B-Cell Lymphoma 6 (BCL6) Protac To Provide Insight into Small Molecule Targeting of BCL6," ACS Chem. Biol. 13(11):3131-3141, 11 pages.

Medialvilla-Varela, M. et al. (Jul. 2017). "A Novel Antagonist of the Immune Checkpoint Protein Adenosine A2a Receptor Restores Tumor—Infiltrating Lymphocyte Activity in the Context of the Tumor Microenvironment," Neoplasia 19(7):530-536.

Medialvilla-Varela, M. et al. (Sep. 2013; e-pub. Jul. 17, 2013). "Antagonism of Adenosine A2A Receptor Expressed by Lung Adenocarcinoma Tumor Cells and Cancer Associated Fibroblasts Inhibits Their Growth," Cancer Biology & Therapy 14(9):860-868.

Mendonca, A.D. et al. (2000). "Adenosine: Does it Have a Neuroprotective Role After All?," Brain Research Reviews 33:258-274.

Mihara, T. et al. (2007). "Pharmacological Characterization of a Novel, Potent Adenosine A1 and A2A Receptor Dual Antagonist, 5-[5-Amino-3-(4-fluorophenyl)pyrazin-2-yl]-1-isopropylpyridine-2(1H)-one (ASP5854), in Models of Parkinson's Disease and Cognition," The Journal of Pharmacology and Experimental Therapeutics 323(2):708-719.

Mittal, D. et al. (Aug. 1, 2016; e-pub. May 24, 2016). "Adenosine 2B Receptor Expression on Cancer Cells Promotes Metastasis," Cancer Research 76(15):1-11.

Mittal, D. et al. (Jul. 15, 2014; e-pub. Jul. 1, 2014). "Antimetastatic Effects of Blocking PD-1 and the Adenosine A2A Receptor," Cancer Research 74(14):3652-3658.

Mokyr, M.B. et al. (Dec. 1, 1998). "Realization of the Therapeutic Potential of CTLA-4 Blockade in Low-Dose Chemotherapy-treated Tumor-bearing Mice," Cancer Research 58:5301-5304.

Moriyama, K. et al. (Dec. 10, 2010). "Adenosine A2A Receptor Is Involved in Cell Surface Expression of A2B Receptor," The Journal of Biology Chemistry 285(50):39271-39288.

Mousavi, S. et al. (2015; e-pub. Feb. 20, 2015). "Expression of Adenosine Receptor Subclasses in Malignant and Adjacent Normal Human Prostate Tissues," The Prostate 75:735-747.

Nikbakht, D.M. et al. (2016). "Adenosine A1 Receptor Modifies P53 Expression and Apoptosis in Breast Cancer Cell Line Mcf-7," Bratisl Med J 117(4):242-246.

Novío, S. et al. (2017; e-pub. Mar. 30, 2017). "Adenosine Signaling Pathways as Potential Therapeutic Targets in Prostate Cancer Disease," Molecular Oncology: Underlying Mechanisms and Translational Advancements pp. 93-107.

Ohana, G. et al. (2001; e-pub. Nov. 30, 2000). "Differential Effect of Adenosine on Tumor and Normal Cell Growth: Focus on the A3 Adenosine Receptor," Journal of Cellular Physiology 186:19-23.

Ohta, A. (Mar. 29, 2016). "A Metabolic Immune Checkpoint: Adenosine in Tumor Microenvironment," Frontiers in Immunology 7(Article 109), 11 pages.

Palmer, B.D. et al. (2006, e-pub. Jul. 15, 2006). "4-Phenylpyrrolo[3,4-c]carbazole-1,3(2H,6H)-dione Inhibitors of the Checkpoint Kinase Wee1. Structure-Activity Relationships for Chromophore Modification and Phenyl Ring Substitution," J. Med. Chem. 49:4896-4911.

Pandey, K. et al. (2019). "Molecular Mechanisms of Resistance to CDK4/6 Inhibitors in Breast Cancer: A review," International Journal of Cancer 145:1179-1188.

Panjehpour, M. et al. (Summer 2010). "Adenosine Receptor Expression in Two Different Human Cancer Cell Lines at Molecular Level," Iran J Cancer Prev 3(3):111-116.

Pinna, A. et al. (2014; e-pub. Apr. 1, 2014). "Adenosine A2A Receptor Antagonists in Parkinson's Disease: Progress in Clinical Trials from the Newly Approved Istradefylline to Drugs in Early Development and Those Already Discontinued," CNS Drugs 28:455-474.

(56) References Cited

OTHER PUBLICATIONS

Popoli, P. et al. (Mar. 1, 2002). "Blockade of Striatal Adenosine A2A Receptor Reduces, Through a Presynaptic Mechanism, Quinolinic Acid-Induced Excitotoxicity: Possible Relevance to Neuroprotective Interventions in Neurodegenerative Diseases of the Striatum," J. Neurosci 22(5):1967-1975.
Powderly, J. et al. (May 2019). "AB928, a Novel Dual Adenosine Receptor Antagonist, Combined With Chemotherapy or AB122 (anti-PD-1) in Patients With Advanced Tumors: Preliminary Results From Ongoing Phase I Studies," ASCO 2019, Abstract No. 2604, 1 page.
Preti, D. et al. (Jul. 2015; e-pub. Mar. 27, 2015). "History and Perspectives of A2A Adenosine Receptor Antagonists as Potential Therapeutic Agents," Med. Res. Rev. 35(4):790-848, 59 pages.
Pubchem. CID 66665902 (Nov. 30, 2012)."6,7-Diphenyl-1,2,3,4-Tetrahydro-[1,8] Naphthyridine," Located at https://pubchem.ncbi.nlm.nih.gov/compound/66665902, last visited on Sep. 1, 2018, 13 pages.
Rahimova, R. et al. (Jan. 29, 2018). "Identification of Allosteric Inhibitors of the Ecto-5'-Nucleotidase (CD73) Targeting the Dimer Interface," PLoS Comput Biol 14(1):e1005943, 23 pages.
Remington'S Pharmaceutical Sciences, Mack Publishing Company, Philadelphia, PA, 21th ed. (2000) TOC, 4 Pages.
Restelli, V. et al. (2019, e-pub. May 7, 2019). "DNA Damage Response Inhibitor Combinations Exert Synergistic Antitumor Activity In Aggressive B Cell Lymphomas," American Association for Cancer Research Manuscript pp. 1-25.
Rosse, G. (Dec. 8, 2016; e-pub. Nov. 2, 2016); "Quinazoline Carboxamides as Selective Antagonists of Adenosine 2A Receptor," ACS Med. Chem. Lett. 7(12):1014-1015.
Rusinov, V.L. et al., (Dec. 2005). "Synthesis and Antiviral Activity of 2-Amino-3-Ethoxycarbonylpyrazine Derivatives," Pharmaceutical Chemistry Journal 39(12):630-635.
Schuler, P.J. et al. (2014). "Human CD4+CD39+ Regulatory T Cells Produce Adenosine Upon Co-Expression of Surface CD73 or Contact with CD73+ Exosomes or CD73+ Cells," Clinical and Experimental Immunology 177:531-543.
Segala, E. et al. (Jul. 14, 2016; e-published Jul. 1, 2016). "Controlling the Dissociation of Ligands from the Adenosine A2A Receptor Through Modulation of Salt Bridge Strength," J. Med. Chem. 59(13):6470-6479, 41 pages.
Sek, K. et al. (Dec. 2, 2018). "Targeting Adenosine Receptor Signaling in Cancer Immunotherapy," Int. J. Mol. Sci. 19:3837, 23 pages.
Serpico, A.F. et al. (2019, e-pub. Jun. 13, 2019). "Wee1 Rather Than Plk1 Is Inhibited by AZD1775 at Therapeutically Relevant Concentrations," Cancers 11:1-10.
Shook, B.C. et al. (2010; e-pub. Oct. 25, 2010). "In Vivo Characterization of a Dual Adenosine A2A/A1 Receptor Antagonist in Animal Models of Parkinson's Disease," J. Med. Chem. 53(22):8104-8115.
Sitkovsky, M. et al. (Jul. 2014). "Hostile, Hypoxia-A2-Adenosinergic Tumor Biology as the Next Barrier to Overcome for Tumor Immunologists," Cancer Immunol. Res. 2(7):598-605, 15 pages.
Sivakumar, P.M. et al. (Jun. 2012). "QSAR Studies on Substituted 3- or 4-Phenyl-1,8-Naphthyridine Derivatives as Antimicrobial Agents," Med Chem Res 21(6):788-795.
Sorrentino, C. et al. (Jul. 17, 2017). "Role of Adenosine in Tumor Progression: Focus on A2B Receptor as Potential Therapeutic Target," Journal of Cancer Metastasis and Treatment 3:127-138.
Sorrentino, C. et al. (Sep. 29, 2015; e-pub. Jul. 25, 2015). "Myeloid-Derived Suppressor Cells Contribute to A2B Adenosine Receptor-Induced VEGF Production and Angiogenesis in a Mouse Melanoma Model," Oncotarget 6 (29):27478-27489.
Takashima, Y. et al. (2019). "Bromodomain and Extraterminal Domain Inhibition Synergizes with WEE1-Inhibitor AZD1775 Effect by Impairing Non-Homologous End Joining and Enhancing DNA Damage in Non-Small Cell Lung Dancer," Department of Respiratory Medicine, Faculty of Medicine and Graduate School of Medicine, Hokkaido University pp. 1-33.
Tarkhov, I. et al. (2005). "Photoluminescence of Some Indolylpyrazines." Materialovedenie 4:16-22. with English Translation.
Tarkhov, I. et al., (2005). "Analysis of Electronic Transitions During Photoluminescence for some Indolylpyrazines," Materialovedenie 10:18-21. with English Translation.
Thomas, A. et al. (Oct. 4, 2015, e-pub. Sep. 30, 2015). "Design, Synthesis and Pharmacological Evaluation of 5,6-Disubstituted Pyridin-2(1H)-one Derivatives as Phosphodiesterase 10A (PDE10A) Antagonists," Journal of Medicinal Chemistry 62 pages.
Tuite, P. et al. (Aug. 2003). "Recent Developments in the Pharmacological Treatment of Parkinson's Disease," Expert Opin. Investig. Drugs 12(8):1335-1352.
U.S. Appl. No. 16/746,769, for Son et al., filed Jan. 17, 2020.
Van Waarde, A. et al. (Jan. 2018; e-pub. Jan. 27, 2017). "Potential Therapeutic Applications of Adenosine A2A Receptor Ligands and Opportunities for A2A Receptor Imaging," Med. Res. Rev. 38(1):1-56, 52 pages.
Varani, K. et al. (1997). "Characterization of A2A Adenosine Receptors in Human Lymphocyte Membranes by [3H]-SCH 58261 Binding," British Journal of Pharmacology 122:386-392.
Vaupel, P. et al. (Dec. 21, 2017). "Accomplices of the Hypoxic Tumor Microenvironment Compromising Antitumor immunity: Adenosine, Lactate, Acidosis, Vascular Endothelial Growth Factor, Potassium Ions, and Phosphatidylserine," Frontiers in Immunology 8(Article 1887), 6 pages.
Vecchio, E. A. et al. (Apr. 2016). "Ligand-Independent Adenosine A2B Receptor Constitutive Activity as a Promoter of Prostate Cancer Cell Proliferation," J Pharmacol Exp Ther 357:36-44.
Vecchio, E.A. et al. (Jun. 2019). "The Adenosine A2B G Protein-Coupled Receptor: Recent Advances and Therapeutic Implications," Pharmacology and Therapeutics 198:20-33, 50 pages.
Vijayan, D. et al. (Dec. 2017; e-pub. Oct. 23, 2017). "Targeting Immunosuppressive Adenosine in Cancer," Nature Rev Cancer 17(12):709-724.
Vilgelm, A.E. (Aug. 14, 2019). "MDM2 Antagonists Overcome Intrinsic resistance to CDK4/6 Inhibition by Inducing p21," Sci. Transl. Med. 11(eaav7171):1-15.
Virgilio, F.D. et al. (2017; e-pub. Jun. 20, 2016). "Extracellular Purines, Purinergic Receptors and Tumor Growth," Oncogene 36:293-303.
Voors, A.A. et al. (May 10, 2011). "Effects of the Adenosine A1 Receptor Antagonist Rolofylline on Renal Function in Patients With Acute Heart Failure and Renal Dysfunction," J Am Coll Cardiol 57(19):1899-1907.
Waickman, A.T. et al. (Jun. 2012). "Enhancement of Tumor Immunotherapy by Deletion of the A2A Adenosine Receptor," Cancer Immunol Immunother. 61(6):917-926, 17 pages.
Walters, M.J. et al. (2017). "Characterization of AB928, an A2R Antagonist for the Treatment of Cancer," Poster presented at AACR, 1 page.
Walters, M.J. et al. (2018). "Combining Adenosine Receptor Inhibition, with AB928, and Chemotherapy Results in Greater Immune Activation and Tumor Control," Abstract 5556, Poster presented at AACR, 1 page.
Wang, J. et al. (Sep. 2018; e-pub. Aug. 1, 2018). "Adenosinergic Signaling as a Target for Natural Killer Cell Immunotherapy," Journal of Molecular Medicine 96(9):903-913, 11 pages.
Wei, Q. et al. (2013; e-pub. Jan. 15, 2013). "A2B Adenosine Receptor Blockade Inhibits Growth of Prostate Dancer Cells," Purinergic Signalling 9:271-280.
Whiteside, T.L. et al. (Jun. 2017; e-pub. Apr. 27, 2017). "Targeting Adenosine in Cancer Immunotherapy: A Review of Recent Progress," Expert Review of Anticancer Therapy 17(6):527-535, 36 pages.
Wichapong, K. et al. (2009, e-pub. Sep. 20, 2008). "Receptor-based 3D-QSAR studies of checkpoint Wee1 kinase inhibitors," European Journal of Medicinal Chemistry 44:1383-1395.
Willingham, S.B. et al. (Oct. 2018; e-pub. Aug. 21, 2018). "A2AR Antagonism with CPI-444 Induces Antitumor Responses and Augments Efficacy to Anti-PD-(L)1 and Anti-CTLA-4 in Preclinical Models," Cancer Immunol Res. 6(10):1-14.

(56) References Cited

OTHER PUBLICATIONS

Willingham, S.B. et al. (Oct. 2018; e-pub. Aug. 21, 2018). "A2AR Antagonism with CPI-444 Induces Antitumor Responses and Augments Efficacy to Anti-PD-(L)1 and Anti-CTLA-4 in Preclinical Models," Cancer Immunol Res. 6(10):1136-1149, (with Supplementary material, 30 pages).

Yang, Q. et al. (2013, e-pub. May 8, 2013). "Overexpression of CD73 in Prostate Cancer is Associated with Lymph Node Metastasis," Pathol. Oncol. Res. 4 pages.

Yang, X. et al. (2017). "Tiamulin Inhibits Breast Cancer Growth and Pulmonary Metastasis by Decreasing the Activity of CD73," BMC Cancer 17:255, 12 pages.

Yang_X. et al. (2018; e-pub. Aug. 6, 2018). "An Affinity-Based Probe for the Human Adenosine A2A Receptor," J. Med. Chem. 61:7892-7901.

Young, A. et al. (Sep. 12, 2016). "Co-inhibition of CD73 and A2AR Adenosine Signaling Improves Anti-tumor Immune Responses," Cancer Cell 30:391-403.

Yuan, G. et al. (2014). "Towards Next Generation Adenosine A2A Receptor Antagonists," Current Medicinal Chemistry 21(34):3918-3935.

Zhang, P. et al. (2019, e-pub. Jul. 21, 2019). "BRD4 Inhibitor AZD5153 Suppresses the Proliferation of Colorectal Cancer Cells and Sensitizes the Anticancer Effect of PARP Inhibitor," Int. J. Biol. Sci. 15(9):1942-1954.

Zhou, J.Z. et al. (Apr. 2, 2015). "Differential Impact of Adenosine Nucleotides Released by Osteocytes on Breast Cancer Growth and Bone Metastasis," Oncogene 34(14):1831-1842, 31 pages.

Ex Parte CAO (Sep. 21, 2011). Decision Rendered by the Board of Patent Appeals and Interferences in U.S. Appl. No. 10/696,862, 11 pages.

International Search Report and Written Opinion dated Apr. 22, 2020, for PCT Application No. PCT/US2020/14206, filed on Jan. 17, 2020, 20 pages.

Pubchem. CID 66665561 (Nov. 30, 2012). "2,3-Diphenyl-5,6,7,8-Tetrahydropyrido[3,2-b]pyrazine," Located at https://pubchem.ncbi.nlm.nih.gov/compound/66665561, last visited on Sep. 1, 2018, 9 pages.

Chen, X. et al. (2018). "Transfer Hydrogenative para-Selective Aminoalkylation of Aniline Derviates With N-Heteroarenes via Ruthenium/Acid Dual Catalysis," Chemical Communications 54(65):9087-9090.

Ferrarini, P.L. et al. (Sep.-Oct. 1997). "Unusual Nitration of Substituted 7-Amino-1,8-Naphthyridine in the Synthesis of Compounds With Antiplatelet Activity," J. Heterocyclic Chem. 34(5):1501-1510.

International Preliminary Report on Patentability, dated Jun. 16, 2021, for PCT Application No. PCT/US2020/14206, filed on Jan. 17, 2020, 9 pages.

\* cited by examiner

HETEROCYCLIC COMPOUNDS AS ADENOSINE ANTAGONISTS

CROSS REFERENCE TO RELATED APPLICATIONS

This application claims priority to U.S. Application Ser. No. 62/794,537, filed Jan. 18, 2019, and U.S. Application Ser. No. 62/796,046, filed Jan. 23, 2019, each of which is hereby incorporated herein by reference in its entirety.

FIELD OF THE INVENTION

This disclosure relates generally to therapeutics for treatment mediated through a G-protein-coupled receptor (GPCR) signaling pathway and, more particularly, to compounds that inhibit an adenosine receptor (such as an $A_{2A}$ antagonist). The disclosure also provides pharmaceutically acceptable compositions comprising such compounds and methods of using the compounds or compositions in the treatment of a disease associated with a GPCR signaling pathway

BACKGROUND OF THE INVENTION

Adenosine receptors (ARs) are distributed throughout the body and are responsible for numerous biological functions. The seven trans-membrane G-protein-coupled receptors (GPCRs) have been divided into four different subtypes: $A_1$, $A_{2A}$, $A_{2B}$, and $A_3$. The $A_{2A}$ and $A_{2B}$ ARs stimulate activity of the adenylyl cyclase, inducing an increase of cAMP levels. $A_{2A}$ ARs have a distinct tissue localization, different biochemical pathways, and specific pharmacological profiles.

Adenosine is one of the human body's most important neuromodulators in both the central and the peripheral nervous systems. Adenosine is released from tumor cells and its concentration in the extracellular fluid of tumors can reach immunosuppressive levels (Blay et al. (1997), *Cancer Res.*, 57(13), pp. 2602-5). The extracellular fluid of solid carcinomas contains immunosuppressive concentrations of adenosine. Id. This increase in adenosine concentration is a result of increases in CD73 (ecto-5'-nucleotidase) and CD39 (nucleoside triphosphate dephosphorylase) enzymes, which are responsible for directly catabolizing ATP into adenosine. These upregulations are triggered by hypoxia and the generation of HIF-1α. High levels of adenosine around tumor cells act to regulate multiple immune cells (e.g., CD4+ T-cells and cytotoxic CD8+ T-cells) via activation of multiple adenosine receptor subtypes, but particularly $A_{2A}$ receptors, resulting in the suppressing of pro-inflammatory activities and upregulation of anti-inflammatory molecules and immunoregulatory cells (Kumar et al. (2013), Adenosine as an endogenous immunoregulator in cancer pathogenesis: where to go? *Purinergic Signal.*, 9(2), pp 145-65 and Sitkowsky et al., Hostile, hypoxia-A2-adenosinergic tumor biology as the next barrier to overcome for tumor immunologists. *Cancer Immunol. Res.* 2(7), pp 598-605; Ohta (2016), A Metabolic Immune Checkpoint: Adenosine in Tumor Microenvironment. *Frontiers in Immunology.*, 7 article #109, pp 1-11). It was demonstrated that chimeric antigen receptor (CAR) T cells upregulate A2ARs upon antigen-specific stimulation in vitro and in vivo (Beavls (2017), Targeting the Adenosine 2A Receptor Enhances Chimeric Antigen Receptor T Cell Efficacy. *J of Clin Invest.* 127 (3): pp 929-941).

Survival of cancer cells is dependent on their ability to avoid attack by the immune system. In addition, tumor cells can overtake the immune system to facilitate tumor survival and metastasis. Adenosine, whose concentration increases within hypoxic regions of solid tumors, has been recognized as being able to interfere with the recognition of tumor cells by cytolytic effector cells of the immune system. (Tuite and Riss (2013). Recent developments in the pharmacological treatment of Parkinson's disease. *Expert Opin. Investig. Drugs*, 12(8) pp 1335-52, Popoli et al. (2002). Blockade of striatal adenosine $A_{2A}$ receptor reduces, through a presynaptic mechanism, quinolinic acid-induced excitotoxicity: possible relevance to neuroprotective interventions in neurodegenerative diseases of the striatum, *J. Neurosci*, 22(5) pp. 1967-75, Gessi et al. (2011). Adenosine receptors and cancer. *Biochim Biophys Acta*, 1808(5), pp. 1400-12).

Although all adenosine receptors now have an increasing number of recognized biological roles in tumors, the $A_{2A}$ and $A_3$ subtypes appear promising targets for therapeutic development. In particular, activation of $A_{2A}$ receptors leads to immunosuppressive effects, which decreases anti-tumoral immunity and thereby encourages tumor growth.

The $A_{2B}$ receptor is another potential target for therapeutic development. Autocrine/paracrine stimulation of $A_{2B}$ expressed on tumor cells is believed to enhance their metastatic potential and $A_{2B}$ blockade may reduce tumor metastasis in an immune-independent manner (Beavis et al. (2013). Blockade of $A_{2A}$ receptors potently suppresses the metabolism of CD73+ Tumors. *Proc. Natl. Acad. Sci.*, 110 (36) pp. 14711-6). $A_{2B}$ expression also correlates with relapse-free survival (RFS) in triple negative breast cancer suggesting that this pathway may be clinically relevant. $A_{2B}$ blockade also has the potential to modulate the immunosuppressive properties of tumor-associated immune cells including dendritic cells and myeloid-derived suppressor cells (MDSCs) (Cekic et al. (2011). Adenosine $A_{2B}$ receptor blockade slows growth of bladder and breast tumors. *J. Immunol.* 188(1), pp. 198-205; Sorrentino et al. (2015). Myeloid-derived suppressor cells contribute to $A_{2B}$ adenosine receptor-induced VEGF production and angiogenesis in a mouse melanoma model. *Oncotarget* 6(29), pp. 27478-89; Iannone et al. (2013). Blockade of $A_{2B}$ adenosine receptor reduces tumor growth and immune suppression mediated by myeloid-derived suppressor cells in a mouse model of melanoma. *Neoplasia*, 15(12), pp. 1400-9.

There remains a continuing need for new therapies for the treatment of diseases and disorders related to the adenosine signaling pathway.

BRIEF SUMMARY OF THE INVENTION

In one aspect, provided is a compound of the formula (I):

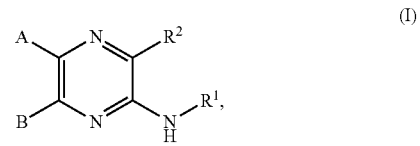

or a tautomer or isomer thereof, or a pharmaceutically acceptable salt of any of the foregoing, wherein A, B, $R^1$ and $R^2$ are as detailed herein. In some embodiments, provided is a compound of formula (I), or a salt thereof.

In one aspect, provided is a compound of the formula (II):

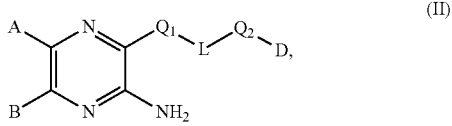

(II)

or a tautomer or isomer thereof, or a pharmaceutically acceptable salt of any of the foregoing, wherein L, $Q_1$, $Q_2$, A, B and D are as detailed herein. In some embodiments, provided is a compound of formula (II), or a salt thereof.

In some embodiments, the compound of the formula (I), or a tautomer or isomer thereof, or a pharmaceutically acceptable salt of any of the foregoing, is of the formula (II) or a tautomer or isomer thereof, or a pharmaceutically acceptable salt of any of the foregoing, as detailed herein.

In another aspect, provided is a compound of the formula (III):

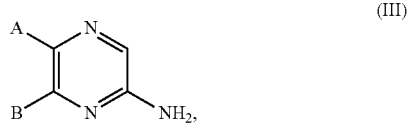

(III)

or a tautomer or isomer thereof, or a pharmaceutically acceptable salt of any of the foregoing, wherein A and B are as detailed herein.

In another aspect, provided is a method for any one or more of: (a) treating a disease, such as a proliferative disease, in an individual in need thereof; (b) enhancing an immune response in an individual in need thereof; (c) inhibiting tumor metastasis in an individual in need thereof; (d) modulating the activity of a G protein coupled receptor signaling pathway in an individual in need thereof; (e) modulating the activity of an adenosine receptor, such as an $A_{2A}$ receptor, in an individual in need thereof; and (f) increasing the activity of a natural killer cell in an individual in need thereof, wherein the method comprises administering to the individual an effective amount of a compound of formulae (I), (II) or (III), or a tautomer or isomer thereof, or a pharmaceutically acceptable salt of any of the foregoing. In some embodiments, provided is a method for any one or more of: (a) treating a disease, such as a proliferative disease, in an individual in need thereof; (b) enhancing an immune response in an individual in need thereof; (c) inhibiting tumor metastasis in an individual in need thereof; (d) modulating the activity of a G protein coupled receptor signaling pathway in an individual in need thereof; (e) modulating the activity of an adenosine receptor, such as an $A_{2A}$ receptor, in an individual in need thereof; and (f) increasing the activity of a natural killer cell in an individual in need thereof, wherein the method comprises administering to the individual an effective amount of a compound of formulae (I), (II) or (III), or a salt thereof. In one aspect, the compound of formulae (I), (II) or (III), or a salt thereof is administered to the individual in combination with another therapeutic agent. In some embodiments, the compound of formulae (I), (II) or (III), or a tautomer or isomer thereof, or a pharmaceutically acceptable salt of any of the foregoing is administered to the individual in combination with another therapeutic agent. In some embodiments, the compound of formulae (I), (II) or (III), or a tautomer or isomer thereof, or a pharmaceutically acceptable salt of any of the foregoing is a compound of formulae (I), (II) or (III), or a tautomer or isomer thereof, or a pharmaceutically acceptable salt of any of the foregoing.

Also provided are pharmaceutical compositions comprising (A) a compound detailed herein, such as a compound of formulae (I), (II) or (III), or a tautomer or isomer thereof, or a pharmaceutically acceptable salt of any of the foregoing, or a compound of formulae (I), (II) or (III), or a tautomer or isomer thereof, or a pharmaceutically acceptable salt of any of the foregoing, and (B) a pharmaceutically acceptable carrier or excipient. In some embodiments, provided are pharmaceutical compositions comprising (A) a compound detailed herein, such as a compound of formulae (I), (II) or (III), or a salt thereof, and (B) a pharmaceutically acceptable carrier or excipient. Kits comprising a compound detailed herein or a tautomer or isomer thereof, or a pharmaceutically acceptable salt of any of the foregoing and instructions for use are also provided. Kits comprising a compound detailed herein or a salt thereof and instructions for use are also provided. A compound detailed herein or a tautomer or isomer thereof, or a pharmaceutically acceptable salt of any of the foregoing is also provided for the manufacture of a medicament for the treatment of cancer. Compounds as detailed herein or a pharmaceutically acceptable salt thereof are also provided for the manufacture of a medicament for the treatment of cancer.

DETAILED DESCRIPTION OF THE INVENTION

Definitions

For use herein, unless clearly indicated otherwise, use of the terms "a", "an" and the like refers to one or more.

"Alkenyl" as used herein refers to an unsaturated linear or branched univalent hydrocarbon chain or combination thereof, having at least one site of olefinic unsaturation (i.e., having at least one moiety of the formula C=C) and having the number of carbon atoms designated (i.e., $C_2$-$C_{10}$ means two to ten carbon atoms). The alkenyl group may be in "cis" or "trans" configurations, or alternatively in "E" or "Z" configurations. Particular alkenyl groups are those having 2 to 20 carbon atoms (a "$C_2$-$C_{20}$ alkenyl"), having 2 to 8 carbon atoms (a "$C_2$-$C_8$ alkenyl"), having 2 to 6 carbon atoms (a "$C_2$-$C_6$ alkenyl"), or having 2 to 4 carbon atoms (a "$C_2$-$C_4$ alkenyl"). Examples of alkenyl include, but are not limited to, groups such as ethenyl (or vinyl), prop-1-enyl, prop-2-enyl (or allyl), 2-methylprop-1-enyl, but-1-enyl, but-2-enyl, but-3-enyl, buta-1,3-dienyl, 2-methylbuta-1,3-dienyl, homologs and isomers thereof, and the like.

The term "alkyl" refers to and includes saturated linear and branched univalent hydrocarbon structures and combination thereof, having the number of carbon atoms designated (i.e., $C_1$-$C_{10}$ means one to ten carbons). Particular alkyl groups are those having 1 to 20 carbon atoms (a "$C_1$-$C_{20}$ alkyl"). More particular alkyl groups are those having 1 to 8 carbon atoms (a "$C_1$-$C_8$ alkyl"), 3 to 8 carbon atoms (a "$C_3$-$C_8$ alkyl"), 1 to 6 carbon atoms (a "$C_1$-$C_6$ alkyl"), 1 to 5 carbon atoms (a "$C_1$-$C_5$ alkyl"), or 1 to 4 carbon atoms (a "$C_1$-$C_4$ alkyl"). Examples of alkyl include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

"Alkylene" as used herein refers to the same residues as alkyl, but having bivalency. Particular alkylene groups are those having 1 to 6 carbon atoms (a "$C_1$-$C_6$ alkylene"), 1 to 5 carbon atoms (a "$C_1$-$C_5$ alkylene"), 1 to 4 carbon atoms (a "$C_1$-$C_4$ alkylene") or 1 to 3 carbon atoms (a "$C_1$-$C_3$ alkylene"). Examples of alkylene include, but are not limited to, groups such as methylene (—$CH_2$—), ethylene (—$CH_2CH_2$—), propylene (—$CH_2CH_2CH_2$—), butylene (—$CH_2CH_2CH_2CH_2$—), isopropylene (—$CH_2C(H)(CH_3)CH_2$—), and the like.

"Alkynyl" as used herein refers to an unsaturated linear or branched univalent hydrocarbon chain or combination thereof, having at least one site of acetylenic unsaturation (i.e., having at least one moiety of the formula C≡C) and having the number of carbon atoms designated (i.e., $C_2$-$C_{10}$ means two to ten carbon atoms). Particular alkynyl groups are those having 2 to 20 carbon atoms (a "$C_2$-$C_{20}$ alkynyl"), having 2 to 8 carbon atoms (a "$C_2$-$C_8$ alkynyl"), having 2 to 6 carbon atoms (a "$C_2$-$C_6$ alkynyl"), or having 2 to 4 carbon atoms (a "$C_2$-$C_4$ alkynyl"). Examples of alkynyl include, but are not limited to, groups such as ethynyl (or acetylenyl), prop-1-ynyl, prop-2-ynyl (or propargyl), but-1-ynyl, but-2-ynyl, but-3-ynyl, homologs and isomers thereof, and the like.

The term "aryl" refers to and includes polyunsaturated aromatic hydrocarbon groups. Aryl may contain additional fused rings (e.g., from 1 to 3 rings), including additionally fused aryl, heteroaryl, cycloalkyl, and/or heterocyclyl rings. In one variation, the aryl group contains from 6 to 14 annular carbon atoms. Examples of aryl groups include, but are not limited to, phenyl, naphthyl, biphenyl, and the like.

The term "cycloalkyl" refers to and includes cyclic univalent hydrocarbon structures, which may be fully saturated, mono- or polyunsaturated, but which are non-aromatic, having the number of carbon atoms designated (e.g., $C_1$-$C_{10}$ means one to ten carbons). Cycloalkyl can consist of one ring, such as cyclohexyl, or multiple rings, such as adamantyl, but excludes aryl groups. A cycloalkyl comprising more than one ring may be fused, spiro or bridged, or combinations thereof. A preferred cycloalkyl is a cyclic hydrocarbon having from 3 to 13 annular carbon atoms. A more preferred cycloalkyl is a cyclic hydrocarbon having from 3 to 8 annular carbon atoms (a "$C_3$-$C_8$ cycloalkyl"). Examples of cycloalkyl include, but are not limited to, cyclopropyl, cyclobutyl, cyclopentyl, cyclohexyl, 1-cyclohexenyl, 3-cyclohexenyl, cycloheptyl, norbornyl, and the like.

"Halo" or "halogen" refers to elements of the Group 17 series having atomic number 9 to 85. Preferred halo groups include fluoro, chloro, bromo and iodo. Where a residue is substituted with more than one halogen, it may be referred to by using a prefix corresponding to the number of halogen moieties attached, e.g., dihaloaryl, dihaloalkyl, trihaloaryl etc. refer to aryl and alkyl substituted with two ("di") or three ("tri") halo groups, which may be but are not necessarily the same halo; thus 4-chloro-3-fluorophenyl is within the scope of dihaloaryl. An alkyl group in which each hydrogen is replaced with a halo group is referred to as a "perhaloalkyl." A preferred perhaloalkyl group is trifluoroalkyl (—$CF_3$). Similarly, "perhaloalkoxy" refers to an alkoxy group in which a halogen takes the place of each H in the hydrocarbon making up the alkyl moiety of the alkoxy group. An example of a perhaloalkoxy group is trifluoromethoxy (—$OCF_3$).

The term "heteroaryl" refers to and includes unsaturated aromatic cyclic groups having from 1 to 10 annular carbon atoms and at least one annular heteroatom, including but not limited to heteroatoms such as nitrogen, oxygen and sulfur, wherein the nitrogen and sulfur atoms are optionally oxidized, and the nitrogen atom(s) are optionally quaternized. A heteroaryl group can be attached to the remainder of the molecule at an annular carbon or at an annular heteroatom. Heteroaryl may contain additional fused rings (e.g., from 1 to 3 rings), including additionally fused aryl, heteroaryl, cycloalkyl, and/or heterocyclyl rings. Examples of heteroaryl groups include, but are not limited to, pyridyl, pyrimidyl, thiophenyl, furanyl, thiazolyl, and the like. Examples of heteroaryl groups also include, but are not limited to, pyridyl, pyrimidyl, thiophenyl, furanyl, thiazolyl, oxazolyl, isoxazolyl, thiophenyl, pyrrolyl, pyrazolyl, 1,3,4-oxadiazolyl, imidazolyl, isothiazolyl, triazolyl, 1,3,4-thiadiazolyl, tetrazolyl, benzofuranyl, benzothiophenyl, pyrazolopyridinyl, indazolyl, benzothiazolyl, benzooxazolyl or benzoimidazolyl and the like.

In one variation, a heteroaryl containing at least one additional fused ring that is nonaromatic (e.g., cycloakyl or heterocyclyl) is attached to the parent structure at an annular atom of the additional ring. In another variation, a heteroaryl containing at least one additional ring that is nonaromatic (e.g., cycloakyl or heterocyclyl) is attached to the parent structure at an annular atom of the aromatic ring.

The term "heterocycle" or "heterocyclyl" refers to a saturated or an unsaturated non-aromatic group having from 1 to 10 annular carbon atoms and from 1 to 4 annular heteroatoms, such as nitrogen, sulfur or oxygen, and the like, wherein the nitrogen and sulfur atoms are optionally oxidized, and the nitrogen atom(s) are optionally quaternized. A heterocyclyl group may have a single ring or multiple condensed rings, but excludes heteroaryl groups. A heterocycle comprising more than one ring may be fused, spiro or bridged, or any combination thereof. In fused ring systems, one or more of the fused rings can be aryl, cycloalyl or heterocyclyl. Examples of heterocyclyl groups include, but are not limited to, tetrahydropyranyl, dihydropyranyl, piperidinyl, piperazinyl, pyrrolidinyl, thiazolinyl, thiazolidinyl, tetrahydrofuranyl, tetrahydrothiophenyl, 2,3-dihydrobenzo[b]thiophen-2-yl, 4-amino-2-oxopyrimidin-1(2H)-yl, and the like.

In one variation, a heterocyclyl containing at least one additional ring (such as a fused additional ring) that does not contain a heteroatom is attached to the parent structure at an annular atom of the additional ring. In another variation, a heterocyclyl containing at least one additional ring (such as a fused additional ring) that does not contain a heteroatom is attached to the parent structure at an annular atom of the ring containing a heteroatom.

"Oxo" refers to the moiety =O.

"Optionally substituted" unless otherwise specified means that a group may be unsubstituted or substituted by one or more (e.g., 1, 2, 3, 4 or 5) of the substituents listed for that group in which the substituents may be the same of different. In one embodiment, an optionally substituted group has one substituent. In another embodiment, an optionally substituted group has two substituents. In another embodiment, an optionally substituted group has three substituents. In another embodiment, an optionally substituted group has four substituents. In some embodiments, an optionally substituted group has 1 to 2, 2 to 5, 3 to 5, 2 to 3, 2 to 4, 3 to 4, 1 to 3, 1 to 4 or 1 to 5 substituents.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

As used herein, "treatment" or "treating" is an approach for obtaining beneficial or desired results including clinical results. For example, beneficial or desired results include, but are not limited to, one or more of the following:

decreasing symptoms resulting from the disease, increasing the quality of life of those suffering from the disease, decreasing the dose of other medications required to treat the disease, delaying the progression of the disease, and/or prolonging survival of individuals. In reference to cancers or other unwanted cell proliferation, beneficial or desired results include shrinking a tumor (reducing tumor size); decreasing the growth rate of the tumor (such as to suppress tumor growth); reducing the number of cancer cells; inhibiting, retarding or slowing to some extent and preferably stopping cancer cell infiltration into peripheral organs; inhibiting (slowing to some extent and preferably stopping) tumor metastasis; inhibiting tumor growth; preventing or delaying occurrence and/or recurrence of tumor; and/or relieving to some extent one or more of the symptoms associated with the cancer. In some embodiments, beneficial or desired results include preventing or delaying occurrence and/or recurrence, such as of unwanted cell proliferation.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

As used herein, an "effective dosage" or "effective amount" of compound or salt thereof or pharmaceutical composition is an amount sufficient to effect beneficial or desired results. For prophylactic use, beneficial or desired results include results such as eliminating or reducing the risk, lessening the severity of, or delaying the onset of the disease, including biochemical, histological and/or behavioral symptoms of the disease, its complications and intermediate pathological phenotypes presenting during development of the disease. For therapeutic use, beneficial or desired results include ameliorating, palliating, lessening, delaying or decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In reference to cancers or other unwanted cell proliferation, an effective amount comprises an amount sufficient to cause a tumor to shrink and/or to decrease the growth rate of the tumor (such as to suppress tumor growth) or to prevent or delay other unwanted cell proliferation. In some embodiments, an effective amount is an amount sufficient to delay development. In some embodiments, an effective amount is an amount sufficient to prevent or delay occurrence and/or recurrence. An effective amount can be administered in one or more administrations, in the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer. An effective dosage can be administered in one or more administrations. For purposes of this disclosure, an effective dosage of compound or a salt thereof, or pharmaceutical composition is an amount sufficient to accomplish prophylactic or therapeutic treatment either directly or indirectly. It is intended and understood that an effective dosage of a compound or salt thereof, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, the term "individual" is a mammal, including humans. An individual includes, but is not limited to, human, bovine, horse, feline, canine, rodent, or primate. In some embodiments, the individual is human. The individual (such as a human) may have advanced disease or lesser extent of disease, such as low tumor burden. In some embodiments, the individual is at an early stage of a proliferative disease (such as cancer). In some embodiments, the individual is at an advanced stage of a proliferative disease (such as an advanced cancer).

Reference to "about" a value or parameter herein includes (and describes) embodiments that are directed to that value or parameter per se. For example, description referring to "about X" includes description of "X".

It is understood that aspects and variations described herein also include "consisting" and/or "consisting essentially of" aspects and variations.

Compounds

In one aspect, provided is a compound of the formula (I):

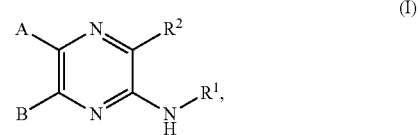

or a tautomer or isomer thereof, or a pharmaceutically acceptable salt of any of the foregoing, wherein:

A is 4-hydroxyphenyl optionally further substituted by $R^3$, 4-hydroxy-2-pyridyl optionally further substituted by $R^4$, a naphthyl substituted by $R^4$, a 9- or 10-membered bicyclic heterocyclyl optionally substituted by $R^4$, or a 9- or 10-membered bicyclic heteroaryl optionally substituted by $R^4$;

B is a phenyl optionally substituted by $R^3$, $C_3$-$C_6$ cycloalkyl optionally substituted by $R^4$, 3- to 6-membered heterocyclyl optionally substituted by $R^4$ or a 5- to 10-membered heteroaryl optionally substituted by $R^4$;

$R^1$ is a hydrogen, $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl), —($C_1$-$C_3$ alkylene)($C_6$ aryl), —C(O)$R^{1a}$, —C(O)O$R^{1a}$, —C(O)NR$^{1b}$R$^{1c}$, —NR$^{1b}$R$^{1c}$, —S(O)$_2$R$^{1a}$, —($C_1$-$C_3$ alkylene)C(O)NR$^{1b}$R$^{1c}$, —($C_1$-$C_3$ alkylene)C(O)R$^{1a}$ or —($C_1$-$C_3$ alkylene)NR$^{1b}$R$^{1c}$, wherein the $C_1$-$C_6$ alkyl, $C_2$-$C_6$ alkenyl, $C_2$-$C_6$ alkynyl, $C_3$-$C_6$ cycloalkyl, 3- to 6-membered heterocyclyl, 5- to 10-membered heteroaryl, —($C_1$-$C_3$ alkylene)($C_3$-$C_6$ cycloalkyl), —($C_1$-$C_3$ alkylene)(3-6-membered heterocyclyl), —($C_1$-$C_3$ alkylene)(5-6-membered heteroaryl), and —($C_1$-$C_3$ alkylene)($C_6$ aryl) of $R^1$ are independently optionally substituted by $R^4$; each $R^a$ is independently hydrogen, $C_1$-$C_6$ alkyl, $C_3$-$C_6$ cycloalkyl, 3-6-membered heterocyclyl, $C_6$ aryl, 5-6-membered heteroaryl, —($C_1$-$C_3$ alkylene)($C_3$-$C_6$ cycloalkyl), —($C_1$-$C_3$ alkylene)(3-6-membered heterocyclyl), —(C$_1$-C$_3$ alkylene)(C$_6$ aryl) or —(C$_1$-C$_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

each R$^{1b}$ and R$^{1c}$ is independently hydrogen, C$_1$-C$_6$ alkyl, C$_3$-C$_6$ cycloalkyl, 3-6-membered heterocyclyl, C$_6$ aryl, 5-6-membered heteroaryl, —(C$_1$-C$_3$ alkylene)(C$_3$-C$_6$ cycloalkyl), —(C$_1$-C$_3$ alkylene)(3-6-membered heterocyclyl), —(C$_1$-C$_3$ alkylene)(C$_6$ aryl) or —(C$_1$-C$_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

or R$^{1b}$ and R$^{1c}$ are taken together with the nitrogen atom to which they are attached to form a 3- to 6-membered heterocyclyl;

R$^2$ is —OR$^{2a}$, —NHR$^{2b}$, —C(O)NHR$^{2b}$, or C$_1$-C$_6$ alkyl, wherein the C$_1$-C$_6$ alkyl of R$^2$ is substituted by —OR$^{2c}$, —NHR$^{2c}$, or —C(O)NHR$^{2c}$;

each R$^{2a}$ and R$^{2b}$ is independently cyclohexane, 6-membered heterocyclyl, —(C$_1$-C$_3$ alkylene)N(C$_2$H$_5$)$_2$, —(C$_1$-C$_3$ alkylene)(C$_3$-C$_6$ cycloalkyl), —(C$_1$-C$_3$ alkylene)(3-6-membered heterocyclyl), or —(C$_1$-C$_3$ alkylene)(5-6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

R$^{2c}$ is 5- or 6-membered heteroaryl, wherein the 5- or 6-membered heteroaryl is further substituted by C$_1$-C$_6$ alkyl optionally substituted by halogen, —OH or oxo;

each R$^3$ is independently C$_1$-C$_6$ alkyl, C$_2$-C$_6$ alkenyl, C$_2$-C$_6$ alkynyl, halogen, —CN, —OR$^5$, —SR$^5$, —NR$^6$R$^7$, —NO$_2$, —C(O)R$^5$, —OC(O)R$^5$, —C(O)OR$^5$, —C(O)NR$^6$R$^7$, —OC(O)NR$^6$R$^7$, —NR$^5$C(O)R$^6$, —NR$^5$C(O)OR$^6$, —NR$^5$C(O)NR$^6$R$^7$, —S(O)R$^5$, —S(O)$_2$R$^5$, —NR$^5$S(O)R$^6$, —C(O)NR$^5$S(O)R$^6$, —NR$^5$S(O)$_2$R$^6$, —C(O)NR$^5$S(O)$_2$R$^6$, —S(O)NR$^6$R$^7$, —S(O)$_2$NR$^6$R$^7$, C$_3$-C$_6$ cycloalkyl, 3- to 6-membered heterocyclyl, —(C$_1$-C$_3$ alkylene)CN, —(C$_1$-C$_3$ alkylene)OR$^5$, —(C$_1$-C$_3$ alkylene)SR$^5$, —(C$_1$-C$_3$ alkylene)NR$^6$R$^7$, —(C$_1$-C$_3$ alkylene)CF$_3$, —(C$_1$-C$_3$ alkylene)NO$_2$, —C=NH(OR$^5$), —(C$_1$-C$_3$ alkylene)C(O)R$^5$, —(C$_1$-C$_3$ alkylene)OC(O)R$^5$, —(C$_1$-C$_3$ alkylene)C(O)OR$^5$, —(C$_1$-C$_3$ alkylene)C(O)NR$^6$R$^7$, —(C$_1$-C$_3$ alkylene)OC(O)NR$^6$R$^7$, —(C$_1$-C$_3$ alkylene)NR$^5$C(O)R$^6$, —(C$_1$-C$_3$ alkylene)NR$^5$C(O)OR$^6$, —(C$_1$-C$_3$ alkylene)NR$^5$C(O)NR$^6$R$^7$, —(C$_1$-C$_3$ alkylene)S(O)R$^5$, —(C$_1$-C$_3$ alkylene)S(O)$_2$R$^5$, —(C$_1$-C$_3$ alkylene)NR$^5$S(O)R$^6$, —C(O)(C$_1$-C$_3$ alkylene)NR$^5$S(O)R$^6$, —(C$_1$-C$_3$ alkylene)NR$^5$S(O)$_2$R$^6$, —(C$_1$-C$_3$ alkylene)C(O)NR$^5$S(O)$_2$R$^6$, —(C$_1$-C$_3$ alkylene)S(O)NR$^6$R$^7$, —(C$_1$-C$_3$ alkylene)S(O)$_2$NR$^6$R$^7$, —(C$_1$-C$_3$ alkylene)(C$_3$-C$_6$ cycloalkyl), —(C$_1$-C$_3$ alkylene)(3-6-membered heterocyclyl), wherein each R$^3$ is independently optionally substituted by halogen, oxo, —CN, —OR$^8$, —NR$^8$R$^9$, —C(O)R$^8$, —C(O)OR$^8$, —C(O)NR$^8$R$^9$, —NR$^8$C(O)R$^9$, —S(O)R$^8$, —S(O)$_2$R$^8$, —S(O)$_2$NR$^8$R$^9$, —NR$^8$S(O)$_2$R$^9$, or C$_1$-C$_6$ alkyl optionally substituted by oxo, —OH or halogen;

each R$^4$ is independently oxo or R$^3$;

R$^5$ is independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of which is optionally substituted by halogen, oxo, —CN, —OR$^8$, —NR$^8$R$^9$, —C(O)R$^8$, —C(O)OR$^8$, —C(O)NR$^8$R$^9$, —NR$^8$C(O)R$^9$, —S(O)R$^8$, —S(O)$_2$R$^8$, —S(O)$_2$NR$^8$R$^9$, —NR$^8$S(O)$_2$R$^9$, or C$_1$-C$_6$ alkyl optionally substituted by oxo, —OH or halogen;

R$^6$ and R$^7$ are each independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of which is optionally substituted by halogen, oxo, —CN, —OR$^8$, —NR$^8$R$^9$, —C(O)R$^8$, —C(O)OR$^8$, —C(O)NR$^8$R$^9$, —NR$^8$C(O)R$^9$, —S(O)R$^8$, —S(O)$_2$R$^8$, —S(O)$_2$NR$^8$R$^9$, —NR$^8$S(O)$_2$R$^9$, or C$_1$-C$_6$ alkyl optionally substituted by oxo, —OH or halogen;

or R$^6$ and R$^7$ are taken together with the atom to which they are attached to form a 3-6 membered heterocyclyl optionally substituted by halogen, oxo, —CN, —OR$^8$, —NR$^8$R$^9$, —C(O)R$^8$, —C(O)OR$^8$, —C(O)NR$^8$R$^9$, —NR$^8$C(O)R$^9$, —S(O)R$^8$, —S(O)$_2$R$^8$, —S(O)$_2$NR$^8$R$^9$, —NR$^8$S(O)$_2$R$^9$ or C$_1$-C$_6$ alkyl optionally substituted by oxo, —OH or halogen;

R$^8$ and R$^9$ are each independently hydrogen, C$_1$-C$_6$ alkyl, C$_2$-C$_6$ alkenyl, C$_2$-C$_6$ alkynyl, C$_3$-C$_6$ cycloalkyl or 3- to 6-membered heterocyclyl, wherein each of which is optionally substituted by halogen, OH, oxo or NH$_2$;

or R$^8$ and R$^9$ are taken together with the atom to which they attached to form a 3-6 membered heterocyclyl optionally substituted by halogen, oxo or C$_1$-C$_6$ alkyl optionally substituted by halogen, OH, oxo or NH$_2$.

In some embodiments, provided is a compound of the formula (I):

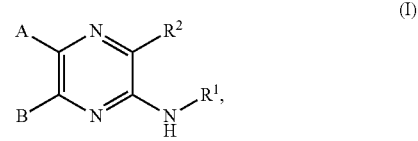

or a salt thereof, wherein:

A is 4-hydroxyphenyl optionally further substituted by R$^3$, 4-hydroxy-2-pyridyl optionally further substituted by R$^4$, or a 9- or 10-membered bicyclic heteroaryl optionally substituted by R$^4$;

B is a phenyl optionally substituted by R$^3$, or a 5- to 6-membered heteroaryl optionally substituted by R$^4$;

R$^1$ is a hydrogen, C$_1$-C$_6$ alkyl, C$_2$-C$_6$ alkenyl, C$_2$-C$_6$ alkynyl, C$_3$-C$_6$ cycloalkyl, 3- to 6-membered heterocyclyl, —C(O)R$^{1a}$, —C(O)OR$^{1a}$, —C(O)NR$^{1b}$R$^{1c}$, or —NR$^{1b}$R$^{1c}$, wherein the C$_1$-C$_6$ alkyl, C$_2$-C$_6$ alkenyl, C$_2$-C$_6$ alkynyl, C$_3$-C$_6$ cycloalkyl and 3- to 6-membered heterocyclyl of R$^1$ are independently optionally substituted by R$^4$;

each R$^{1a}$ is independently hydrogen, C$_1$-C$_6$ alkyl, or C$_3$-C$_6$ cycloalkyl;

each R$^{1b}$ and R$^{1c}$ is independently hydrogen, C$_1$-C$_6$ alkyl, or C$_3$-C$_6$ cycloalkyl;

or R$^{1b}$ and R$^{1c}$ are taken together with the nitrogen atom to which they are attached to form a 3- to 6-membered heterocyclyl;

R$^2$ is —OR$^{2a}$, —NHR$^{2b}$, —C(O)NHR$^{2b}$, or C$_1$-C$_6$ alkyl, wherein the C$_1$-C$_6$ alkyl of R$^2$ is substituted by —OR$^{2c}$, —NHR$^{2c}$, or —C(O)NHR$^{2c}$;

each R$^{2a}$ and R$^{2b}$ is independently cyclohexane, 6-membered heterocyclyl, —(C$_1$-C$_3$ alkylene)N(C$_2$H$_5$)$_2$, —(C$_1$-C$_3$ alkylene)(C$_3$-C$_6$ cycloalkyl), —(C$_1$-C$_3$ alkylene)(3- to 6-membered heterocyclyl), or —(C$_1$-C$_3$ alkylene)(5- or 6-membered heteroaryl), wherein each of which is optionally substituted by methyl, ethyl, halogen, oxo, —CF$_3$, —OH, —OCH$_3$, —CN, —C(O)OCH$_3$, —C(O)OC$_2$H$_5$, —NH$_2$ or —NHCH$_3$;

R$^{2c}$ is 5- or 6-membered heteroaryl, wherein the 5- or 6-membered heteroaryl is further substituted by C$_1$-C$_6$ alkyl optionally substituted by halogen, —OH or oxo;

each R$^3$ is independently C$_1$-C$_6$ alkyl, C$_2$-C$_6$ alkenyl, C$_2$-C$_6$ alkynyl, halogen, —CN, —OR$^5$, —SR$^5$, —NR$^6$R$^7$, —NO$_2$, —C(O)R$^5$, —OC(O)R$^5$, —C(O)OR$^5$, —C(O)NR$^6$R$^7$, —OC(O)NR$^6$R$^7$, —NR$^5$C(O)R$^6$, —NR$^5$C(O)OR$^6$, —NR⁵C(O)NR⁶R⁷, —S(O)R⁵, —S(O)₂R⁵, —NR⁵S(O)R⁶, —C(O)NR⁵S(O)R⁶, —NR⁵S(O)₂R⁶, —C(O)NR⁵S(O)₂R⁶, —S(O)NR⁶R⁷, —S(O)₂NR⁶R⁷, C₃-C₆ cycloalkyl, 3- to 6-membered heterocyclyl, —(C₁-C₃ alkylene)CN, —(C₁-C₃ alkylene)OR⁵, —(C₁-C₃ alkylene)SR⁵, —(C₁-C₃ alkylene)NR⁶R⁷, —(C₁-C₃ alkylene)CF₃, —(C₁-C₃ alkylene)NO₂, —C=NH(OR⁵), —(C₁-C₃ alkylene)C(O)R⁵, —(C₁-C₃ alkylene)OC(O)R⁵, —(C₁-C₃ alkylene)C(O)OR⁵, —(C₁-C₃ alkylene)C(O)NR⁶R⁷, —(C₁-C₃ alkylene)OC(O)NR⁶R⁷, —(C₁-C₃ alkylene)NR⁵C(O)R⁶, —(C₁-C₃ alkylene)NR⁵C(O)OR⁶, —(C₁-C₃ alkylene)NR⁵C(O)NR⁶R⁷, —(C₁-C₃ alkylene)S(O)R⁵, —(C₁-C₃ alkylene)S(O)₂R⁵, —(C₁-C₃ alkylene)NR⁵S(O)R⁶, —C(O)(C₁-C₃ alkylene)NR⁵S(O)R⁶, —(C₁-C₃ alkylene)NR⁵S(O)₂R⁶, —(C₁-C₃ alkylene)C(O)NR⁵S(O)₂R⁶, —(C₁-C₃ alkylene)S(O)NR⁶R⁷, —(C₁-C₃ alkylene)S(O)₂NR⁶R⁷, —(C₁-C₃ alkylene)(C₃-C₆ cycloalkyl), —(C₁-C₃ alkylene)(3-6-membered heterocyclyl), wherein each R³ is independently optionally substituted by halogen, oxo, —CN, —OR⁸, —NR⁸R⁹, —C(O)R⁸, —C(O)OR⁸, —C(O)NR⁸R⁹, —NR⁸C(O)R⁹, —S(O)R⁸, —S(O)₂R⁸, —S(O)₂NR⁸R⁹, —NR⁸S(O)₂R⁹, or C₁-C₆ alkyl optionally substituted by oxo, —OH or halogen;

each R⁴ is independently oxo or R³;

R⁵ is independently hydrogen, C₁-C₆ alkyl, C₂-C₆ alkenyl, C₂-C₆ alkynyl, C₃-C₆ cycloalkyl or 3- to 6-membered heterocyclyl, wherein each of which is optionally substituted by halogen, oxo, —CN, —OR⁸, —NR⁸R⁹, —C(O)R⁸, —C(O)OR⁸, —C(O)NR⁸R⁹, —NR⁸C(O)R⁹, —S(O)R⁸, —S(O)₂R⁸, —S(O)₂NR⁸R⁹, —NR⁸S(O)₂R⁹, or C₁-C₆ alkyl optionally substituted by oxo, —OH or halogen;

R⁶ and R⁷ are each independently hydrogen, C₁-C₆ alkyl, C₂-C₆ alkenyl, C₂-C₆ alkynyl, C₃-C₆ cycloalkyl or 3- to 6-membered heterocyclyl, wherein each of which is optionally substituted by halogen, oxo, —CN, —OR⁸, —NR⁸R⁹, —C(O)R⁸, —C(O)OR⁸, —C(O)NR⁸R⁹, —NR⁸C(O)R⁹, —S(O)R⁸, —S(O)₂R⁸, —S(O)₂NR⁸R⁹, —NR⁸S(O)₂R⁹, or C₁-C₆ alkyl optionally substituted by oxo, —OH or halogen;

or R⁶ and R⁷ are taken together with the atom to which they attached to form a 3-6 membered heterocyclyl optionally substituted by halogen, oxo, —CN, —OR⁸, —NR⁸R⁹, —C(O)R⁸, —C(O)OR⁸, —C(O)NR⁸R⁹, —NR⁸C(O)R⁹, —S(O)R⁸, —S(O)₂R⁸, —S(O)₂NR⁸R⁹, —NR⁸S(O)₂R⁹ or C₁-C₆ alkyl optionally substituted by oxo, —OH or halogen;

R⁸ and R⁹ are each independently hydrogen, C₁-C₆ alkyl, C₂-C₆ alkenyl, C₂-C₆ alkynyl, C₃-C₆ cycloalkyl or 3- to 6-membered heterocyclyl, wherein each of which is optionally substituted by halogen, OH, oxo or NH₂;

or R⁸ and R⁹ are taken together with the atom to which they attached to form a 3-6 membered heterocyclyl optionally substituted by halogen, oxo or C₁-C₆ alkyl optionally substituted by halogen, OH, oxo or NH₂.

In some embodiments, R¹ is a hydrogen, C₁-C₆ alkyl, C₂-C₆ alkenyl, C₂-C₆ alkynyl, C₃-C₆ cycloalkyl, 3- to 6-membered heterocyclyl, 5- to 10-membered heteroaryl, —C(O)R¹ᵃ, —C(O)OR¹ᵃ, —C(O)NR¹ᵇR¹ᶜ, or —S(O)₂R¹ᵃ, wherein the C₁-C₆ alkyl, C₂-C₆ alkenyl, C₂-C₆ alkynyl, C₃-C₆ cycloalkyl, 3- to 6-membered heterocyclyl, and 5- to 10-membered heteroaryl are optionally substituted with R⁴. In some embodiments, R¹ is hydrogen, C₁-C₆ alkyl or —C(O)R¹ᵃ. In certain embodiments, R¹ is hydrogen. In certain embodiments, R¹ is —C(O)R¹ᵃ where R¹ᵃ is C₁-C₆ alkyl (e.g., methyl) or C₃-C₆ cycloalkyl.

It is understood that each R¹ may be combined with each R², A and/or B the same as if each and every combination of R¹ with R², A and/or B were specifically and individually listed. For example, in some embodiments, R¹ is hydrogen in formula (I), wherein R², A and B are as defined herein.

In some embodiments, R² is —OR²ᵃ. In some embodiments, R² is —NHR²ᵇ. In some embodiments, R² is —C(O)NHR²ᵇ. In some embodiments, R² is —OR²ᵃ, —NHR²ᵇ, or —C(O)NHR²ᵇ, wherein each R²ᵃ and R²ᵇ is independently cyclohexane, 6-membered heterocyclyl, —(C₁-C₃alkylene)N(C₂H₅)₂, —(C₁-C₃ alkylene)(C₃-C₆ cycloalkyl), —(C₁-C₃ alkylene)(3-6-membered heterocyclyl), or —(C₁-C₃ alkylene)(5-6-membered heteroaryl), and wherein each of which is optionally substituted by methyl, ethyl, halogen, oxo, —CF₃, —OH, —OCH₃, —CN, —C(O)OCH₃, —C(O)OC₂H₅, —NH₂ or —NHCH₃.

In some embodiments, R²ᵃ and R²ᵇ is independently cyclohexane or 6-membered heterocyclyl, wherein each of which is optionally substituted by methyl, ethyl, halogen, oxo, —CF₃, —OH, —OCH₃, —CN, —C(O)OCH₃, —C(O)OC₂H₅, —NH₂ or —NHCH₃.

In some embodiments, R²ᵃ and R²ᵇ is independently —(C₁-C₃ alkylene)N(C₂H₅)₂, —(C₁-C₃ alkylene)(C₃-C₆ cycloalkyl), —(C₁-C₃ alkylene)(3- to 6-membered heterocyclyl), or —(C₁-C₃alkylene)(5- or 6-membered heteroaryl), wherein each of which is optionally substituted by methyl, ethyl, halogen, oxo, —CF₃, —OH, —OCH₃, —CN, —C(O)OCH₃, —C(O)OC₂H₅, —NH₂ or —NHCH₃.

In some embodiments, R² is substituted C₁-C₆ alkyl. In some embodiments, R² is substituted C₁-C₃ alkyl. In some embodiments, R² is C₁-C₆ alkyl substituted by —OR²ᶜ, —NHR²ᶜ, —SR²ᶜ, —S(O)₂R²ᶜ, —S(O)₂NHR²ᶜ, —NHS(O)₂R²ᶜ—, —C(O) R²ᶜ, —NHC(O)R²ᶜ, —NHC(O)NR²ᶜ, —C(O)OR²ᶜ, —C(O)ONHR²ᶜ—, or —C(O)NHR²ᶜ, wherein R²ᶜ is 5- or 6-membered heteroaryl, and wherein the 5- or 6-membered heteroaryl is further substituted by C₁-C₆ alkyl optionally substituted by halogen, —OH or oxo. In some embodiments, R² is C₁-C₆ alkyl substituted by —NHR²ᶜ, wherein R²ᶜ is 5- or 6-membered heteroaryl, and wherein the 5- or 6-membered heteroaryl is further substituted by C₁-C₆ alkyl optionally substituted by halogen, —OH or oxo. In some embodiments, R²ᶜ is pyridyl further substituted by C₁-C₆ alkyl optionally substituted by halogen, —OH or oxo. For example, in certain embodiments, R²ᶜ is pyridyl further substituted by —C(CH₃)₂OH.

In some embodiments R² is selected from the group consisting of:

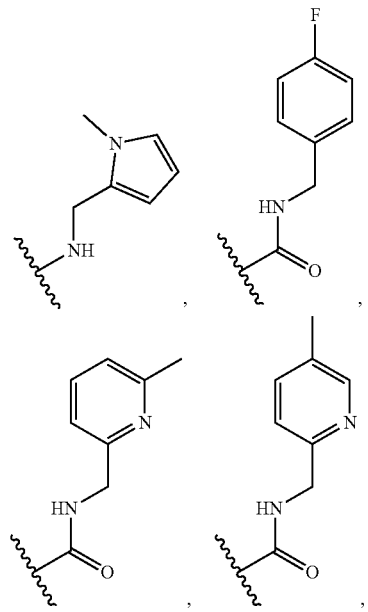

-continued
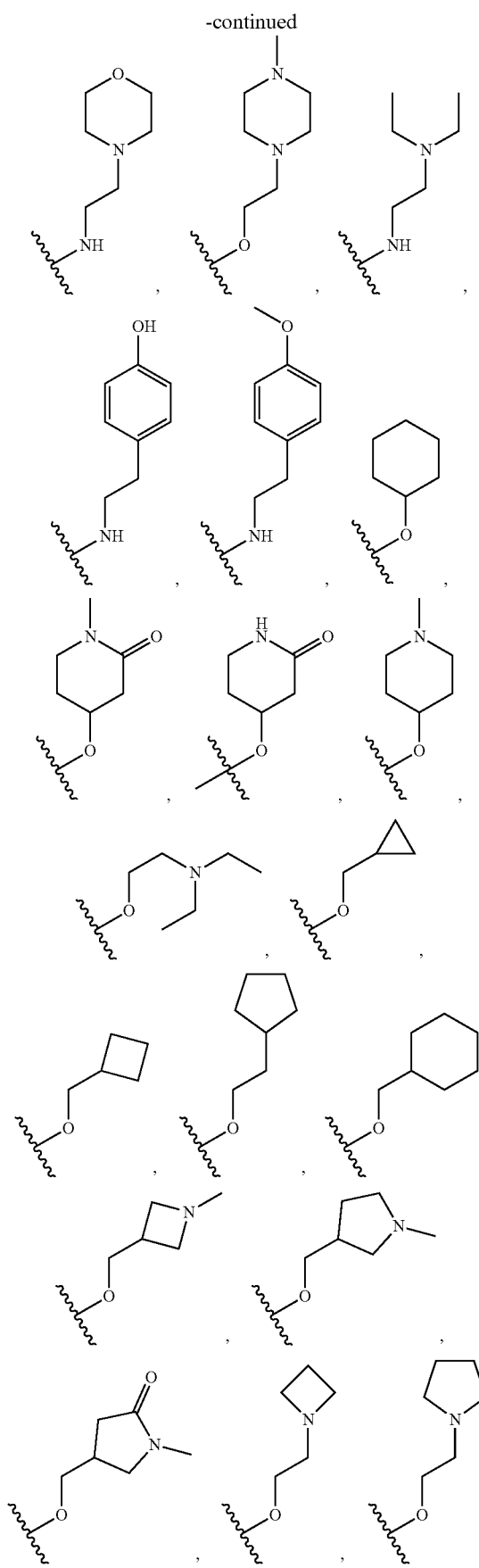
-continued
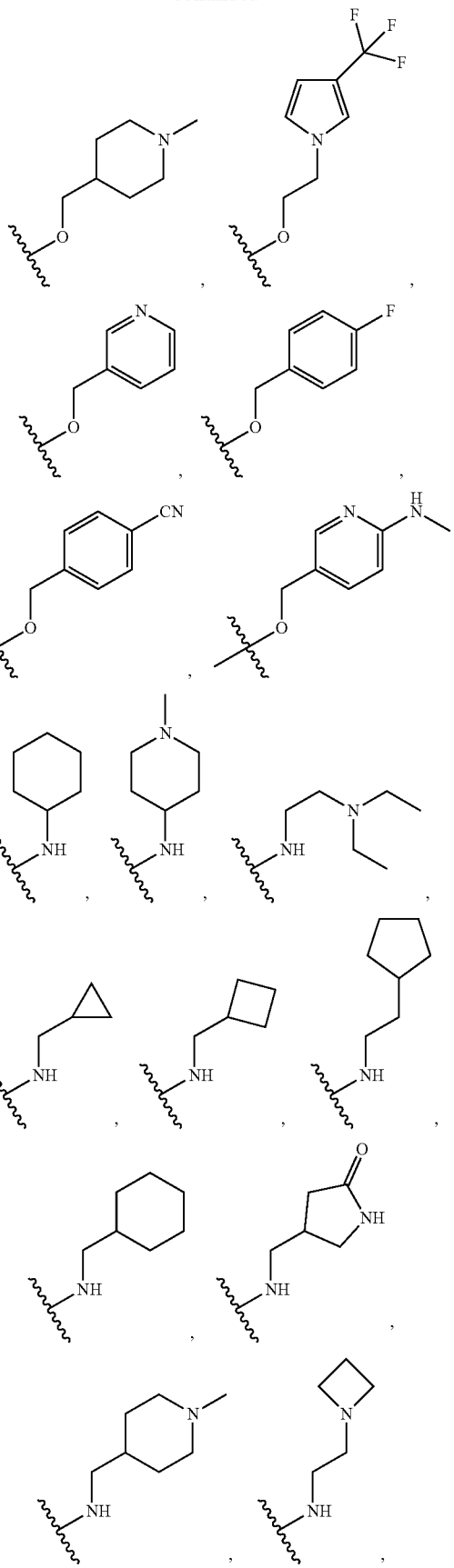

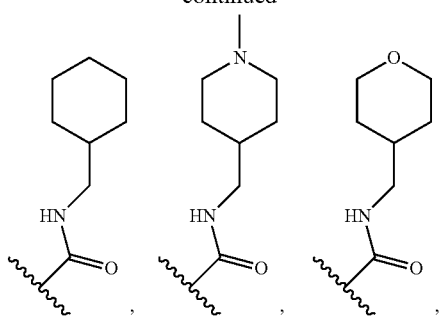
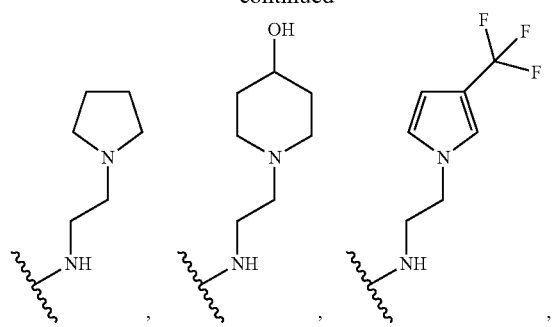
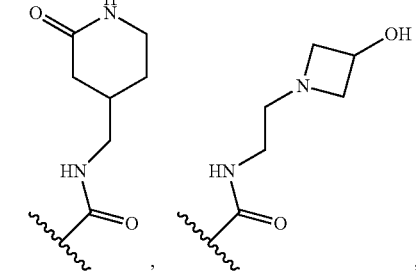
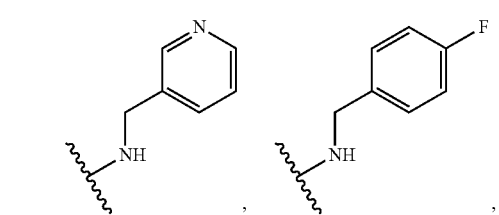
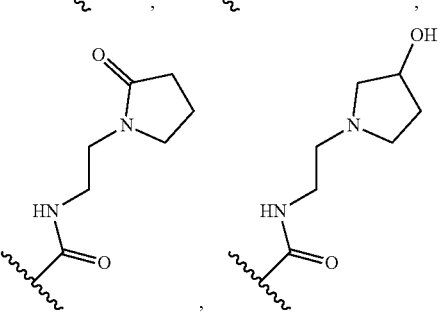
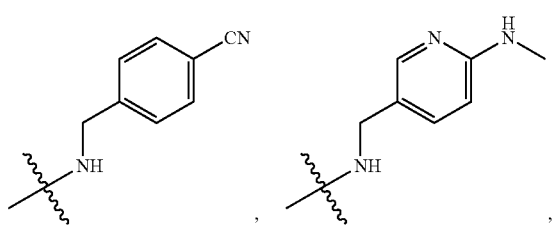
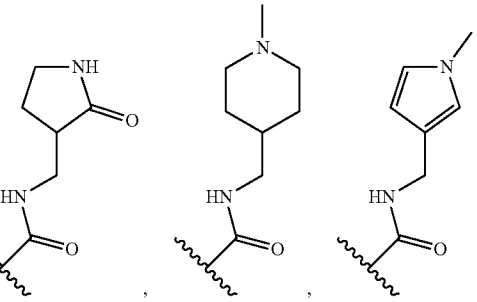
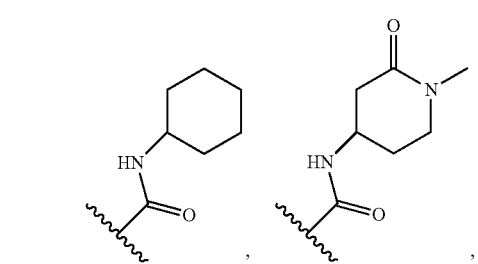
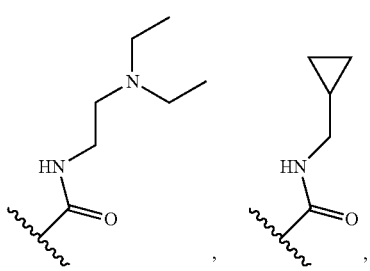
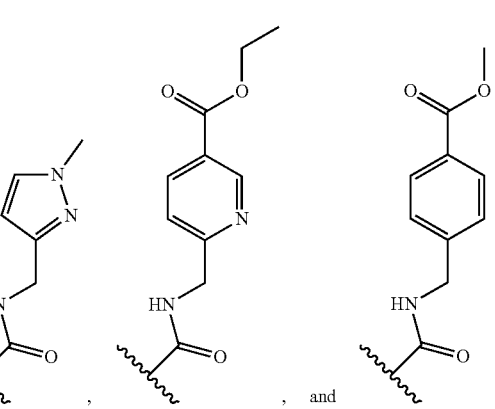
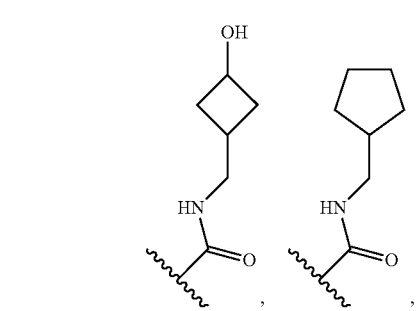
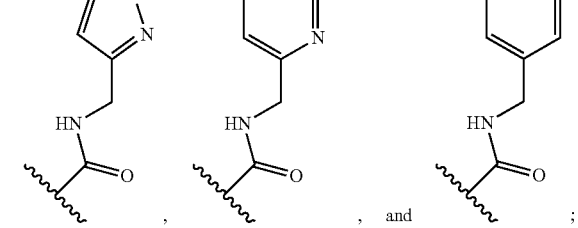
wherein the wavy lines denote attachment points to the parent molecule.

In some embodiments R² is selected from the group consisting of:
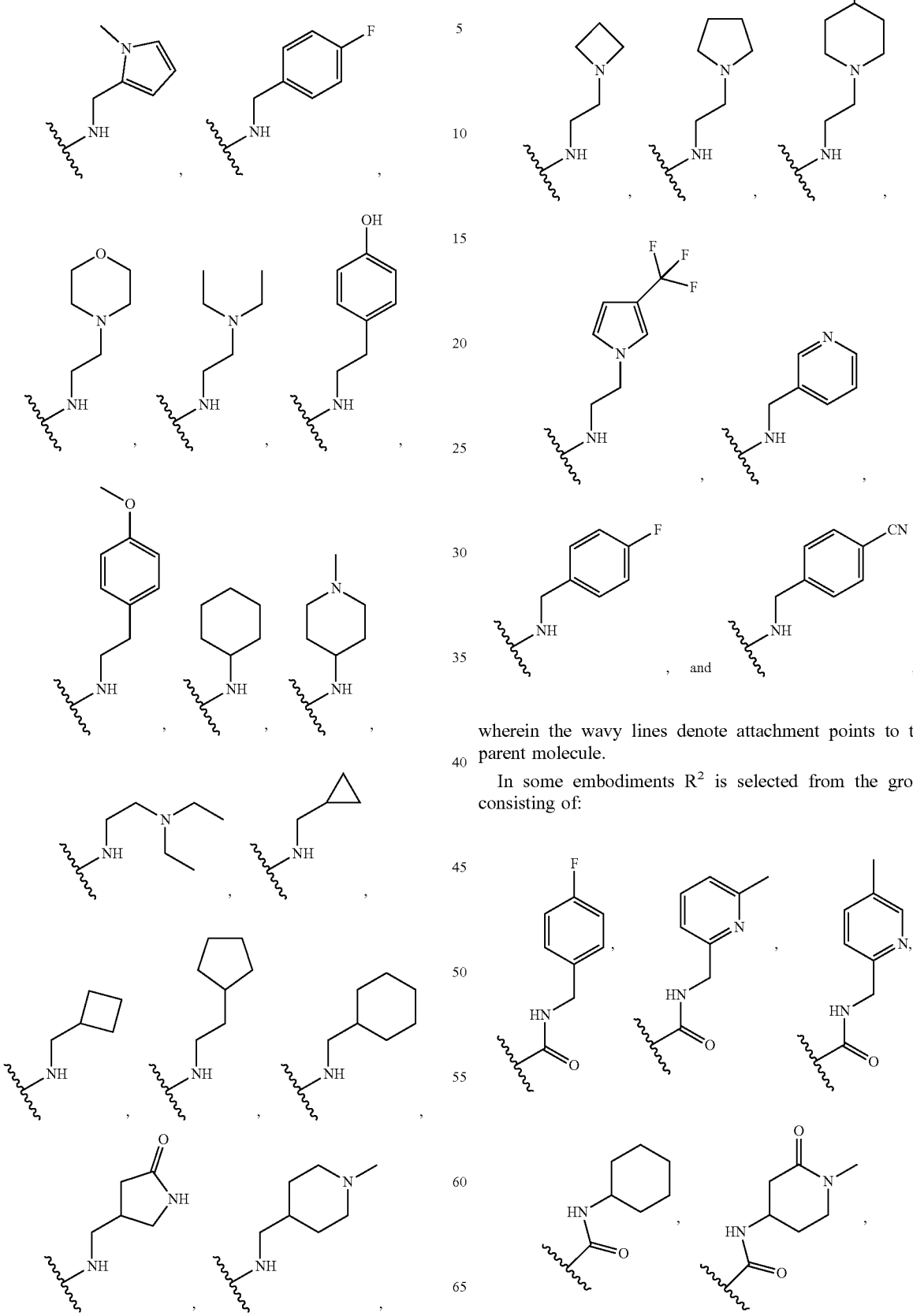
wherein the wavy lines denote attachment points to the parent molecule.
In some embodiments R² is selected from the group consisting of:

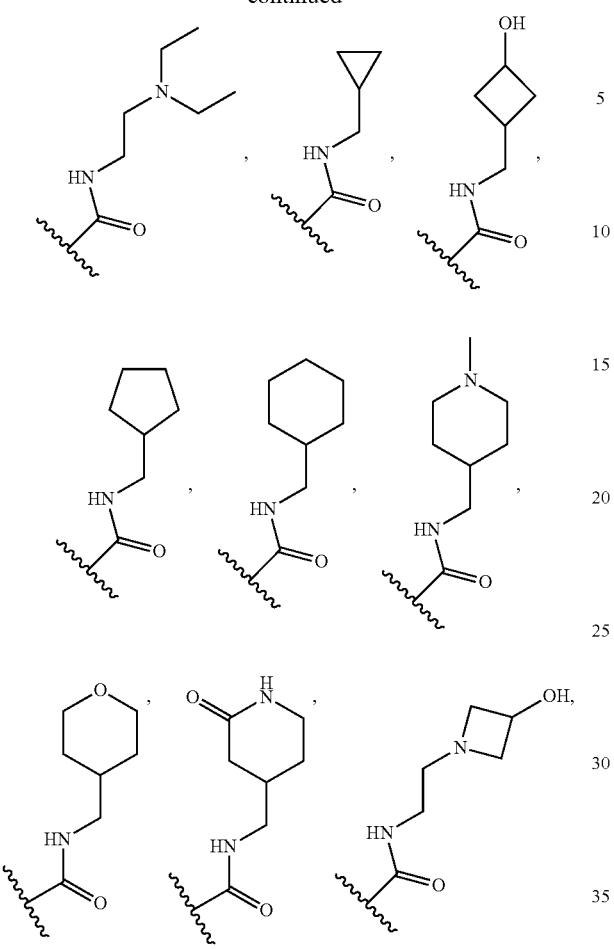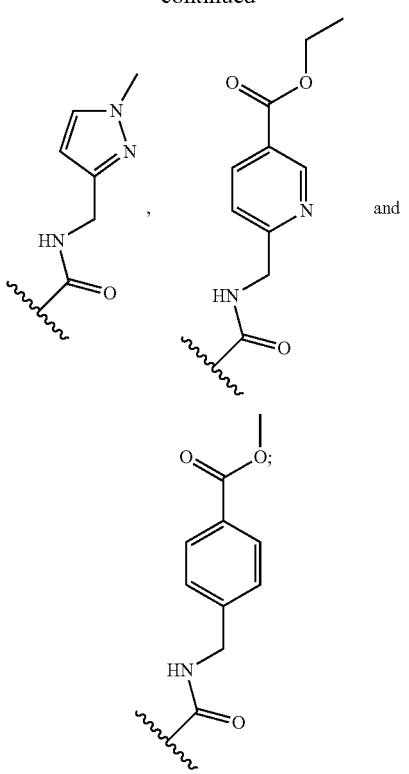
wherein the wavy lines denote attachment points to the parent molecule.
In some embodiments $R^2$ is selected from the group consisting of:
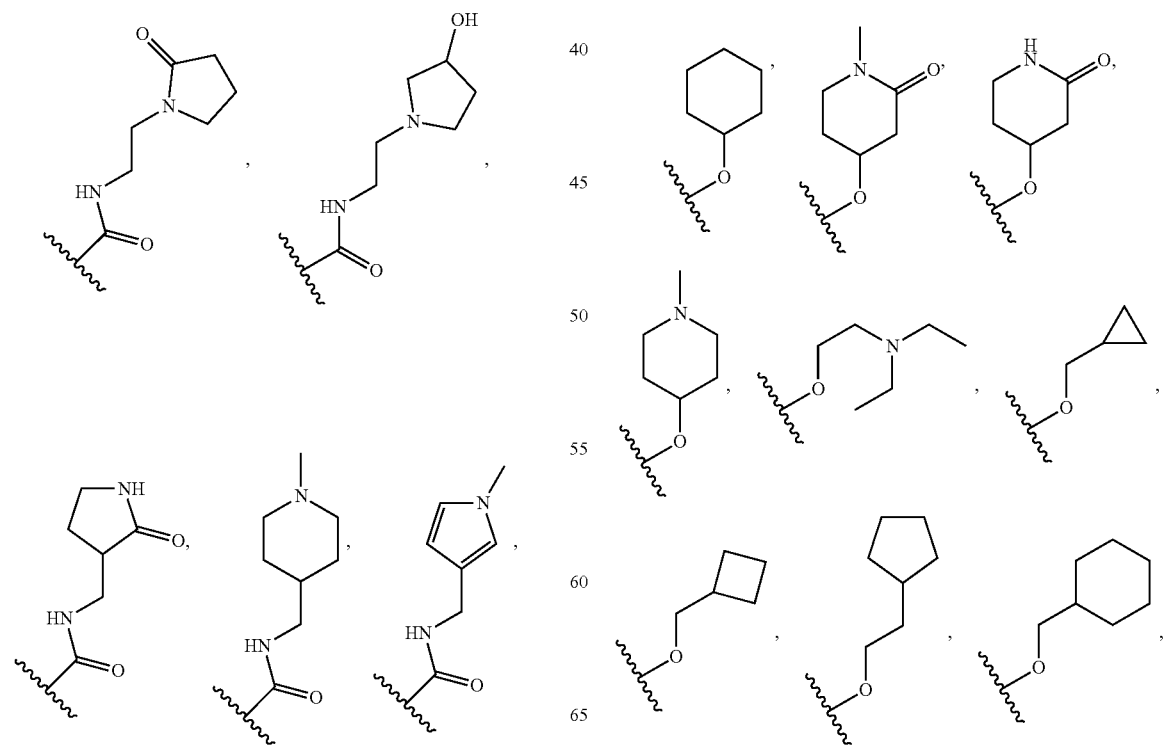

A is 9- or 10-membered bicyclic heteroaryl or a 9- or 10-membered bicylic heterocylyl, each of A is optionally substituted by $R^4$;

B is a phenyl optionally substituted by $R^3$, or a 5- or 6-membered heteroaryl optionally substituted by $R^4$;

one of $Q_1$ and $Q_2$ is —O—, —NH—, or —C(O)NH— and the other is a bond;

L is a bond or $C_1$-$C_4$ alkylene;

D is —$N(C_2H_5)_2$, $C_3$-$C_6$ cycloalkyl, 3- to 6-membered heterocyclyl, or 5- or 6-membered heteroaryl, wherein each of which is optionally substituted by halogen, oxo, —$CF_3$, —OH, —$OCH_3$, —CN, —$C(O)OCH_3$, —$C(O)OC_2H_5$, —$NH_2$, —$NHCH_3$ or $C_1$-$C_6$ alkyl optionally substituted by halogen, —OH or oxo, when L is not a bond, or D is cyclohexane, or 6-membered heterocyclyl, wherein the cyclohexane and 6-membered heterocyclyl is optionally substituted by halogen, oxo, —$CF_3$, —OH, —$OCH_3$, —CN, —$C(O)OCH_3$, —$C(O)OC_2H_5$, —$NH_2$, —$NHCH_3$ or $C_1$-$C_6$ alkyl optionally substituted by halogen, —OH or oxo, when L is a bond;

each $R^3$ is independently $C_1$-$C_6$ alkyl, $C_2$-$C_6$ alkenyl, $C_2$-$C_6$ alkynyl, halogen, —CN, —$OR^5$, —$SR^5$, —$NR^6R^7$, —$NO_2$, —$C(O)R^5$, —$OC(O)R^5$, —$C(O)OR^5$, —$C(O)NR^6R^7$, —$OC(O)NR^6R^7$, —$NR^5C(O)R^6$, —$NR^5C(O)OR^6$, —$NR^5C(O)NR^6R^7$, —$S(O)R^5$, —$S(O)_2R^5$, —$NR^5S(O)R^6$, —$C(O)NR^5S(O)R^6$, —$NR^5S(O)_2R^6$, —$C(O)NR^5S(O)_2R^6$, —$S(O)NR^6R^7$, —$S(O)_2NR^6R^7$, $C_3$-$C_6$ cycloalkyl, 3- to 6-membered heterocyclyl, —($C_1$-$C_3$ alkylene)CN, —($C_1$-$C_3$ alkylene)$OR^5$, —($C_1$-$C_3$ alkylene)$SR^5$, —($C_1$-$C_3$ alkylene)$NR^6R^7$, —($C_1$-$C_3$ alkylene)$CF_3$, —($C_1$-$C_3$ alkylene)$NO_2$, —C=$NH(OR^5)$, —($C_1$-$C_3$ alkylene)$C(O)R^5$, —($C_1$-$C_3$ alkylene)$OC(O)R^5$, —($C_1$-$C_3$ alkylene)$C(O)OR^5$, —($C_1$-$C_3$alkylene)$C(O)NR^6R^7$, —($C_1$-$C_3$ alkylene)$OC(O)NR^6R^7$, —($C_1$-$C_3$ alkylene)$NR^5C(O)R^6$, —($C_1$-$C_3$alkylene)$NR^5C(O)OR^6$, —($C_1$-$C_3$ alkylene)$NR^5C(O)NR^6R^7$, —($C_1$-$C_3$ alkylene)$S(O)R^5$, —($C_1$-$C_3$ alkylene)$S(O)_2R^5$, —($C_1$-$C_3$ alkylene)$NR^5S(O)R^6$, —$C(O)(C_1$-$C_3$ alkylene)$NR^5S(O)R^6$, —($C_1$-$C_3$alkylene)$NR^5S(O)_2R^6$, —($C_1$-$C_3$ alkylene)$C(O)NR^5S(O)_2R^6$, —($C_1$-$C_3$ alkylene)$S(O)NR^6R^7$, —($C_1$-$C_3$ alkylene)$S(O)_2NR^6R^7$, —($C_1$-$C_3$ alkylene)($C_3$-$C_6$ cycloalkyl), —($C_1$-$C_3$ alkylene)(3-6-membered heterocyclyl), wherein each $R^3$ is independently optionally substituted by halogen, oxo, —CN, —$OR^8$, —$NR^8R^9$, —$C(O)R^8$, —$C(O)OR^8$, —$C(O)NR^8R^9$, —$NR^8C(O)R^9$, —$S(O)R^8$, —$S(O)_2R^8$, —$S(O)_2NR^8R^9$, —$NR^8S(O)_2R^9$, or $C_1$-$C_6$ alkyl optionally substituted by oxo, —OH or halogen;

each $R^4$ is independently oxo or $R^3$;

$R^5$ is independently hydrogen, $C_1$-$C_6$ alkyl, $C_2$-$C_6$ alkenyl, $C_2$-$C_6$ alkynyl, $C_3$-$C_6$ cycloalkyl or 3- to 6-membered heterocyclyl, wherein each of which is optionally substituted by halogen, oxo, —CN, —$OR^8$, —$NR^8R^9$, —$C(O)R^8$, —$C(O)OR^8$, —$C(O)NR^8R^9$, —$NR^8C(O)R^9$, —$S(O)R^8$, —$S(O)_2R^8$, —$S(O)_2NR^8R^9$, —$NR^8S(O)_2R^9$, or $C_1$-$C_6$ alkyl optionally substituted by oxo, —OH or halogen;

$R^6$ and $R^7$ are each independently hydrogen, $C_1$-$C_6$ alkyl, $C_2$-$C_6$ alkenyl, $C_2$-$C_6$ alkynyl, $C_3$-$C_6$ cycloalkyl or 3- to 6-membered heterocyclyl, wherein each of which is optionally substituted by halogen, oxo, —CN, —$OR^8$, —$NR^8R^9$, —$C(O)R^8$, —$C(O)OR^8$, —$C(O)NR^8R^9$, —$NR^8C(O)R^9$, —$S(O)R^8$, —$S(O)_2R^8$, —$S(O)_2NR^8R^9$, —$NR^8S(O)_2R^9$, or $C_1$-$C_6$ alkyl optionally substituted by oxo, —OH or halogen;

or $R^6$ and $R^7$ are taken together with the atom to which they attached to form a 3-6 membered heterocyclyl optionally substituted by halogen, oxo, —CN, —$OR^8$, —$NR^8R^9$, —$C(O)R^8$, —$C(O)OR^8$, —$C(O)NR^8R^9$, —$NR^8C(O)R^9$, —$S(O)R^8$, —$S(O)_2R^8$, —$S(O)_2NR^8R^9$, —$NR^8S(O)_2R^9$ or $C_1$-$C_6$ alkyl optionally substituted by oxo, —OH or halogen;

---

[Structures on left column, with wavy lines denoting attachment points]

wherein the wavy lines denote attachment points to the parent molecule.

It is understood that each $R^2$ may be combined with each $R^1$, A and/or B the same as if each and every combination of $R^2$ with $R^1$, A and/or B were specifically and individually listed. In some embodiments, $R^1$ is hydrogen, and each $R^2$ may be combined with each A and/or B the same as if each and every combination of $R^2$ with A and/or B were specifically and individually listed.

In one aspect, provided is a compound of the formula (II):

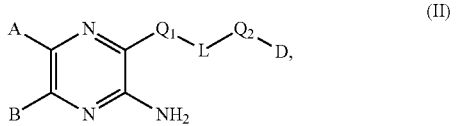

(II)

or a tautomer or isomer thereof, or a pharmaceutically acceptable salt of any of the foregoing, wherein:

$R^8$ and $R^9$ are each independently hydrogen, $C_1$-$C_6$ alkyl, $C_2$-$C_6$ alkenyl, $C_2$-$C_6$ alkynyl, $C_3$-$C_6$ cycloalkyl or 3- to 6-membered heterocyclyl, wherein each of which is optionally substituted by halogen, OH, oxo or $NH_2$;

or $R^8$ and $R^9$ are taken together with the atom to which they attached to form a 3-6 membered heterocyclyl optionally substituted by halogen, oxo or $C_1$-$C_6$ alkyl optionally substituted by halogen, OH, oxo or $NH_2$.

In some embodiments $Q_1$ is —O—. In some embodiments $Q_1$ is —NH—. In some embodiments $Q_1$ is —C(O)NH—. In some embodiments $Q_1$ is a bond.

In some embodiments $Q_2$ is —O—. In some embodiments $Q_2$ is —NH—. In some embodiments $Q_2$ is —C(O)NH—. In some embodiments $Q_2$ is a bond.

In some embodiments, $Q_1$ is —O—, —NH—, or —C(O)NH— and $Q_2$ is a bond. In other embodiments, $Q_2$ is —O—, —NH—, or —C(O)NH— and $Q_1$ is a bond.

In some embodiments, L is a bond. In some embodiments, L is $C_1$-$C_4$ alkylene, for example, —$CH_2$—, —$CH_2CH_2$—, and —$CH_2CH_2CH_2$—.

In one variation, $C_1$-$C_3$ or $C_1$-$C_4$ alkylene as disclosed herein (for example, both in formula (I) and formula (II)) is a linear alkylene. In other variation, $C_1$-$C_3$ or $C_1$-$C_4$ alkylene is a branched alkylene, such as —CH($CH_3$)— and —C($CH_3$)$_2$—. For example, in certain embodiments, —($C_1$-$C_3$ alkylene)(5-6-membered heteroaryl) is —CH($CH_3$)-pyridyl.

In some embodiments, when L is not a bond, D is —N($C_2H_5$)$_2$, $C_3$-$C_6$ cycloalkyl, 3- to 6-membered heterocyclyl, or 5- or 6-membered heteroaryl, wherein each of which is optionally substituted by halogen, oxo, —$CF_3$, —OH, —$OCH_3$, —CN, —C(O)$OCH_3$, —C(O)$OC_2H_5$, —$NH_2$, —$NHCH_3$ or $C_1$-$C_6$ alkyl optionally substituted by halogen, —OH or oxo. In some embodiments, when L is not a bond, D is optionally substituted —N($C_2H_5$)$_2$. In some embodiments, when L is not a bond, D is optionally substituted $C_3$-$C_6$ cycloalkyl. In some embodiments, when L is not a bond, D is optionally substituted 3- to 6-membered heterocyclyl. In some embodiments, when L is not a bond, D is optionally substituted 5- or 6-membered heteroaryl. In some embodiments, D is pyridyl further substituted by $C_1$-$C_6$ alkyl optionally substituted by halogen, —OH or oxo. For example, in certain embodiments, D is pyridyl further substituted by —C($CH_3$)$_2$OH.

In some embodiments, when L is a bond, D is cyclohexane, or 6-membered heterocyclyl, wherein the cyclohexane and 6-membered heterocyclyl is optionally substituted by halogen, oxo, —$CF_3$, —OH, —$OCH_3$, —CN, —C(O)$OCH_3$, —C(O)$OC_2H_5$, —$NH_2$, —$NHCH_3$ or $C_1$-$C_6$ alkyl optionally substituted by halogen, —OH or oxo. In some embodiments, when L is a bond, D is optionally substituted cyclohexane. In some embodiments, when L is a bond, D is optionally substituted 6-membered heterocyclyl. In some embodiments, when L is a bond, $Q_1$ is —C(O)NH—, $Q_2$ is a bond, D is optionally substituted cyclohexane, or optionally substituted 6-membered heterocyclyl.

In some embodiments, $Q_1$, $Q_2$, L and D together are

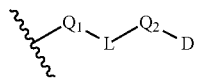

group, which is selected from the group consisting of:

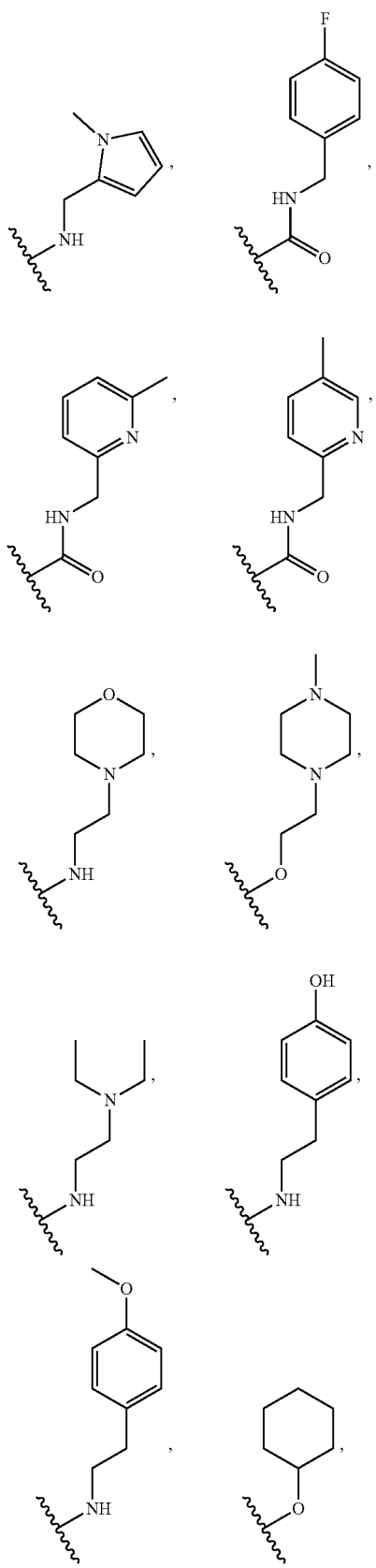

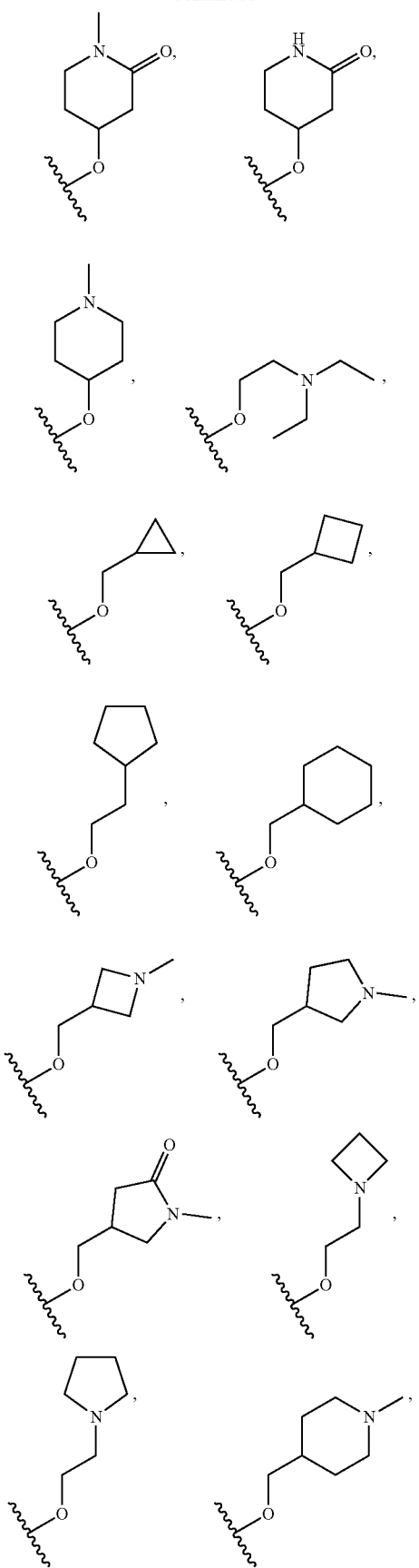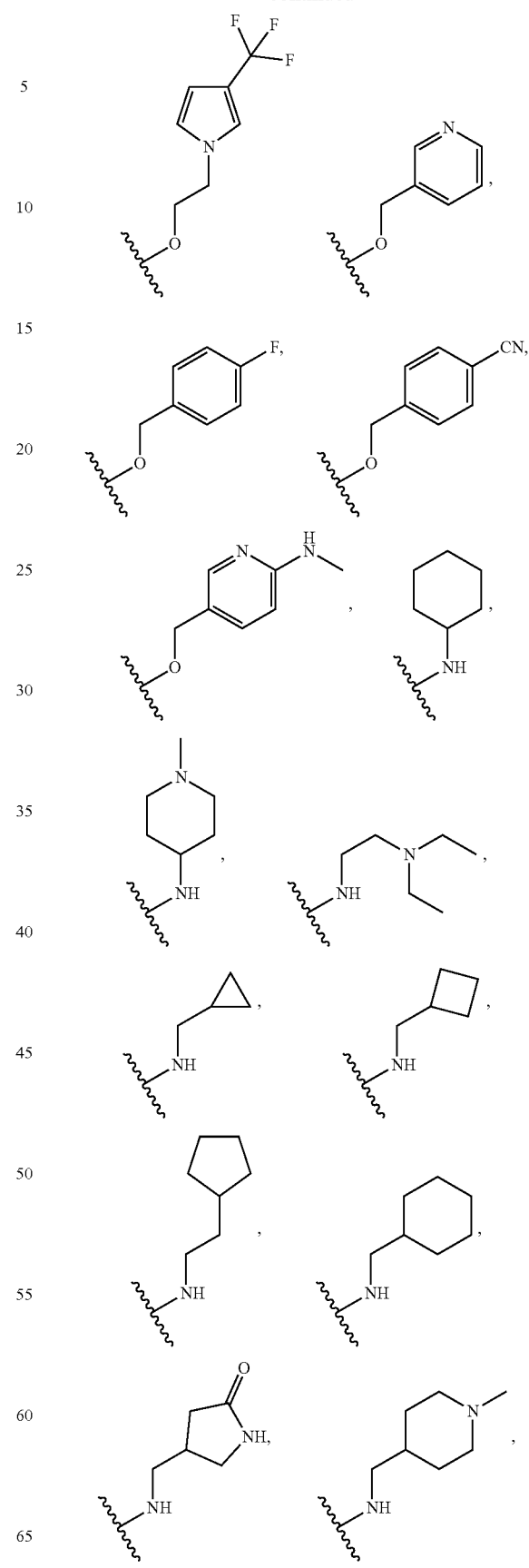

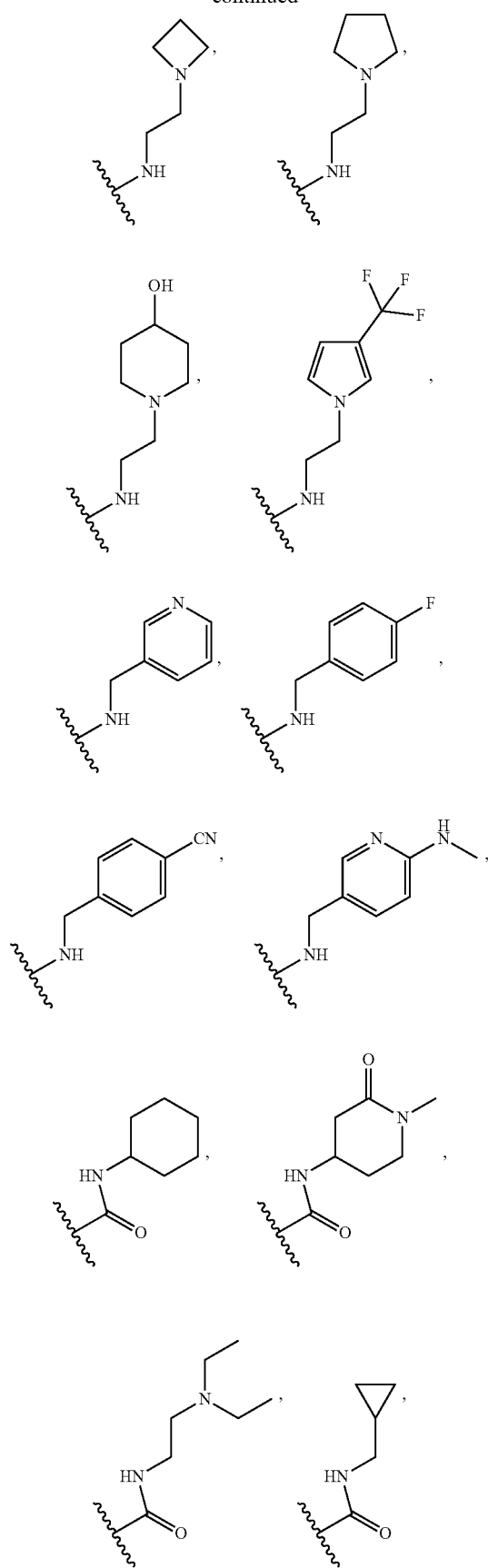
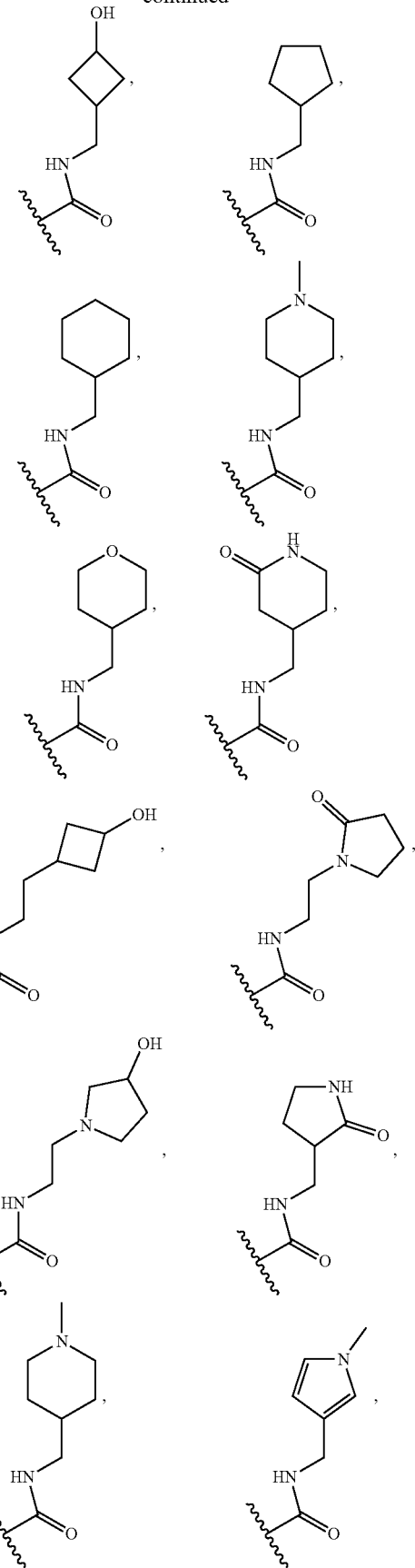

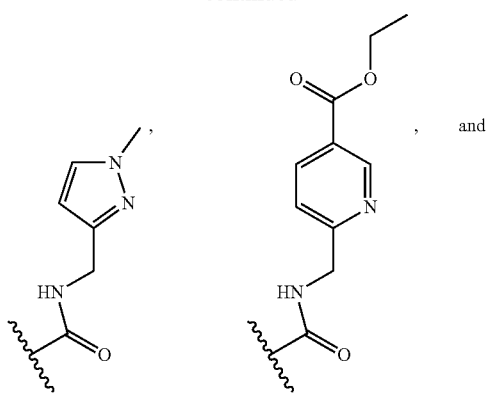
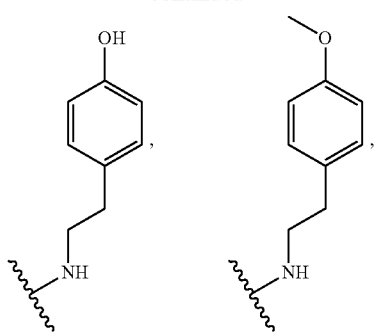
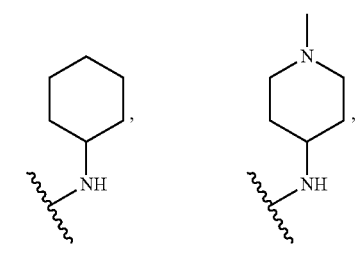
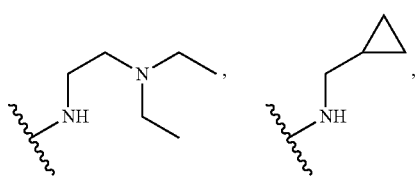
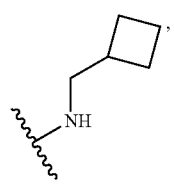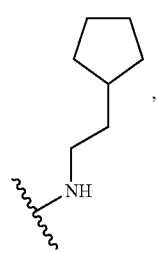
wherein the wavy lines denote attachment points to the parent molecule.
In some embodiments, $Q_1$, $Q_2$, L and D together are
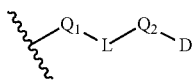
group, which is selected from the group consisting of:
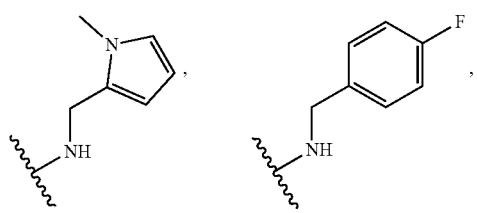
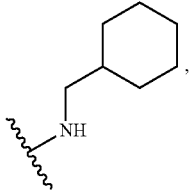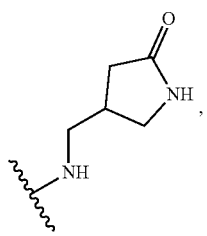
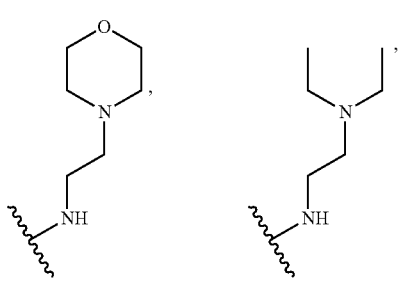
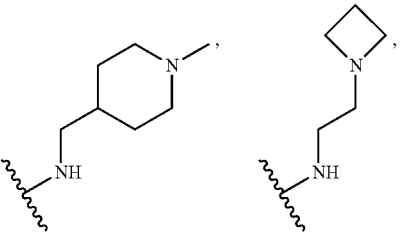

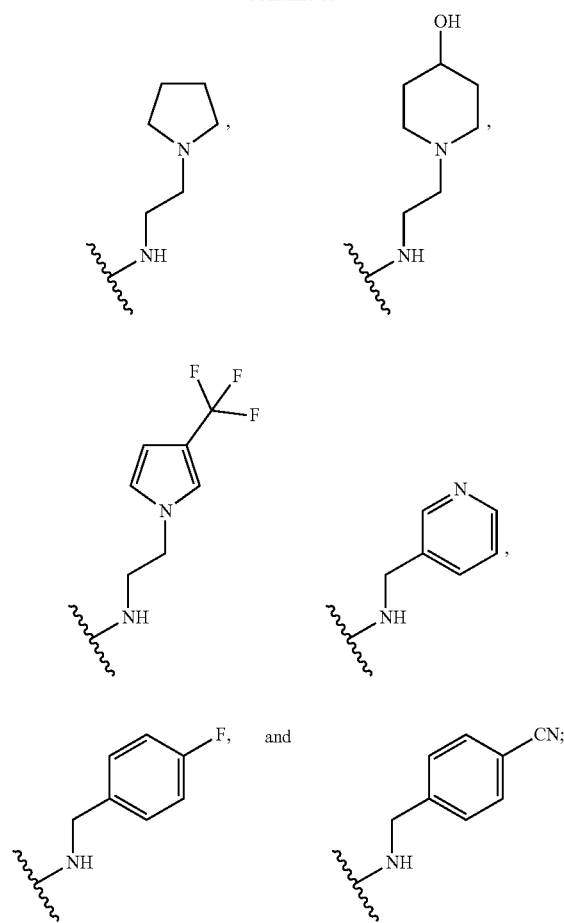
wherein the wavy lines denote attachment points to the parent molecule.
In some embodiments, $Q_1$, $Q_2$, L and D together are
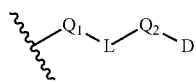
group, which is selected from the group consisting of:
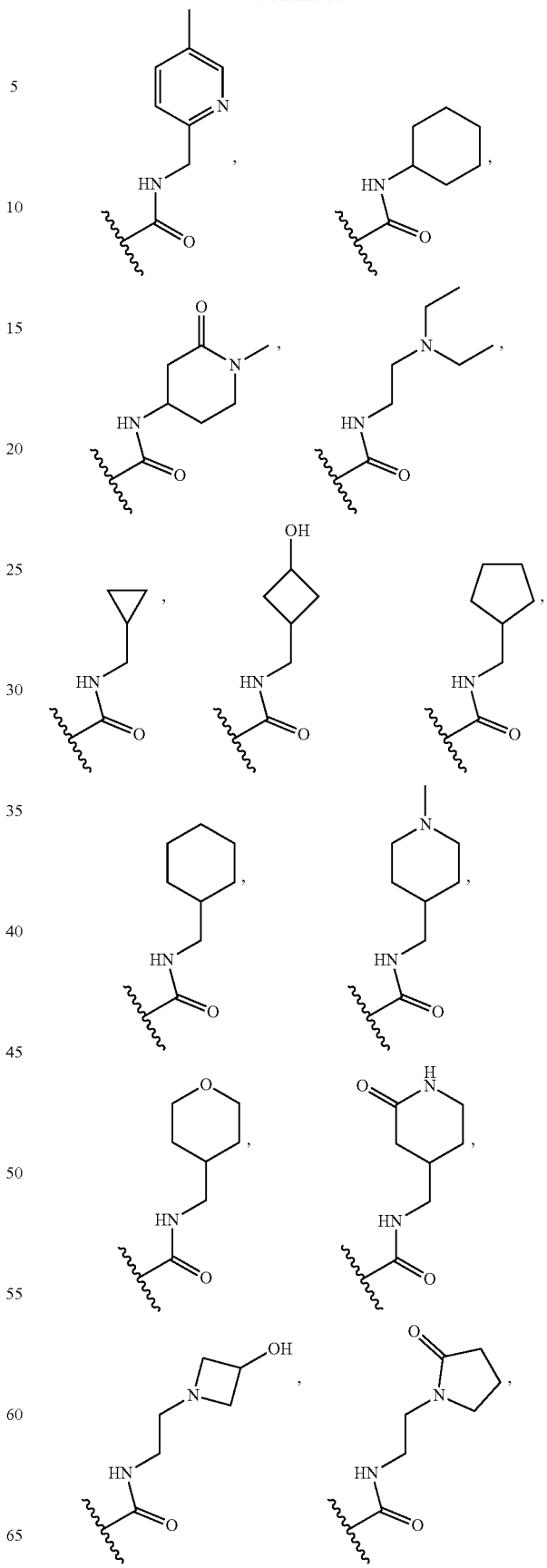

-continued
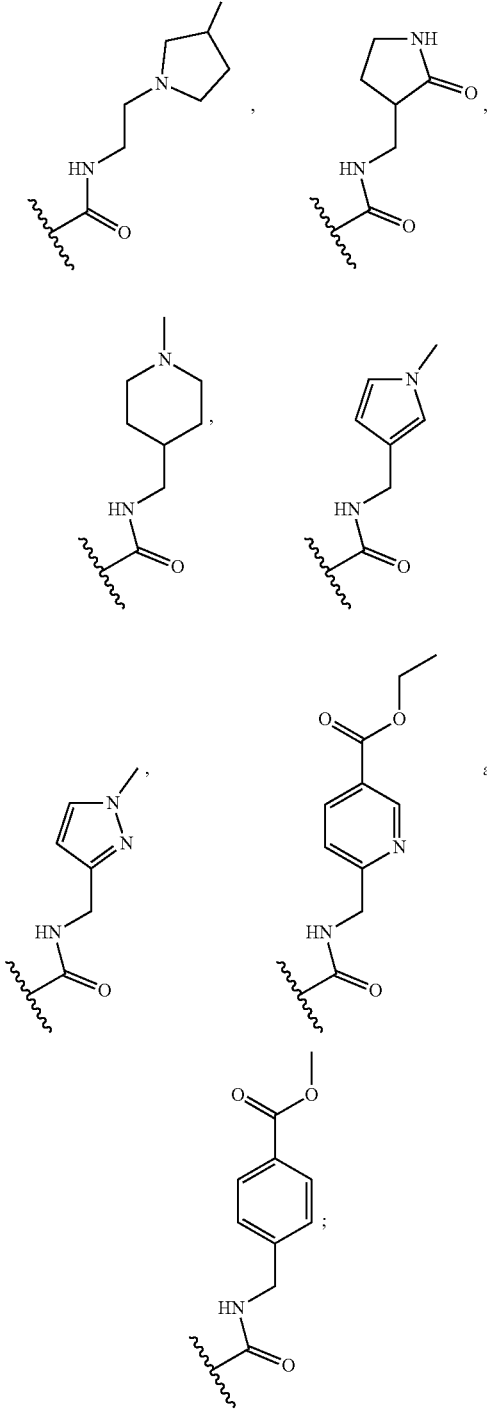
wherein the wavy lines denote attachment points to the parent molecule.
In some embodiments, $Q_1$, $Q_2$, L and D together are
group, which is selected from the group consisting of:
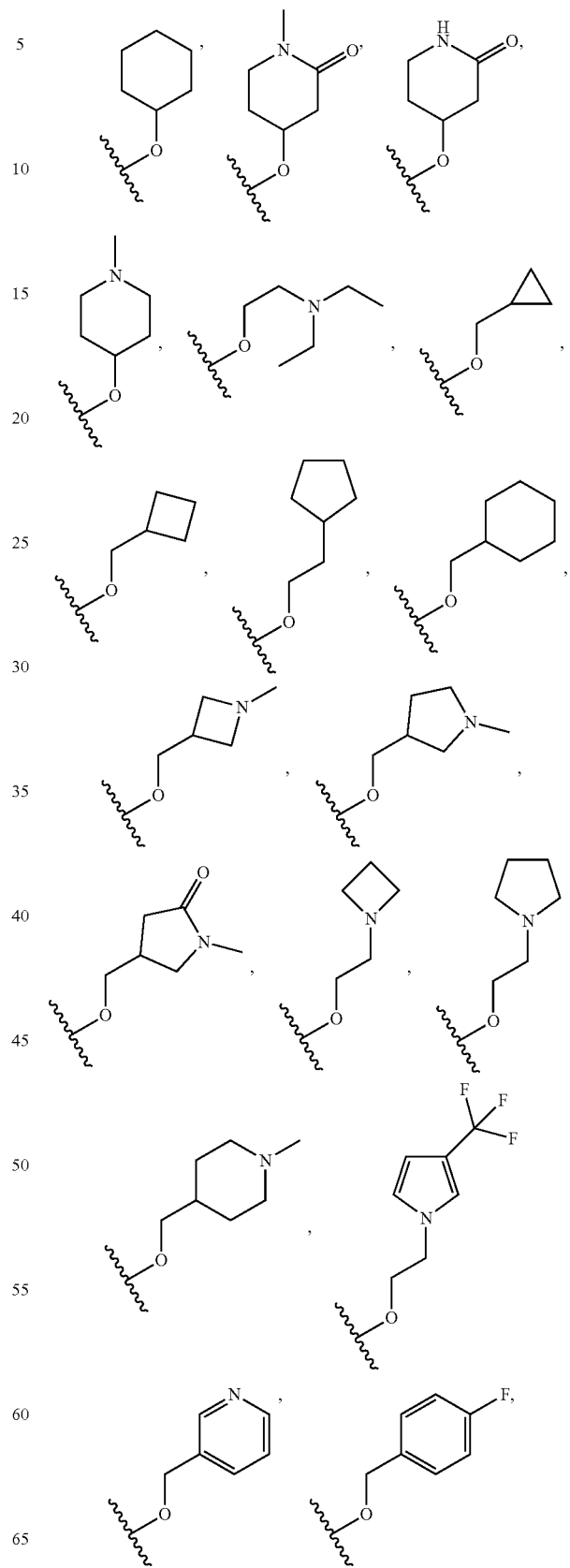

-continued

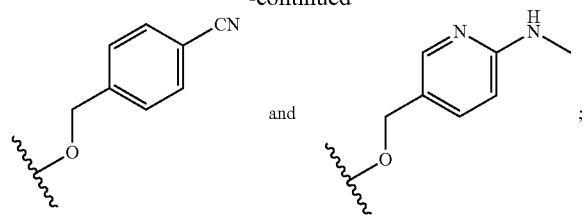

wherein the wavy lines denote attachment points to the parent molecule.

In some embodiments, $Q_1$, $Q_2$, L and D together are

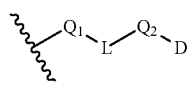

group, which is selected from the group consisting of:

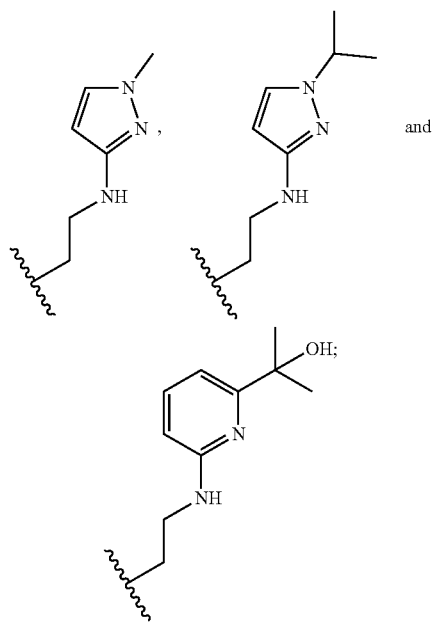

wherein the wavy lines denote attachment points to the parent molecule.

It is understood that each description of every variable of

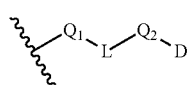

($Q_1$, $Q_2$, L and D) may be combined with each A and/or B the same as if each and every combination of $Q_1$, $Q_2$, L or/and D of

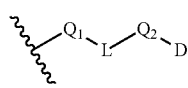

with A and/or B were specifically and individually listed.

In some embodiments, A is 4-hydroxyphenyl optionally further substituted by $R^3$, 4-hydroxy-2-pyridyl optionally further substituted by $R^4$, or a 9- or 10-membered bicyclic heteroaryl optionally substituted by $R^4$.

In some embodiments, A is 9- or 10-membered bicyclic heteroaryl optionally substituted by $R^4$. In some embodiments, A is a 9- or 10-membered bicyclic heterocylyl optionally substituted by $R^4$.

In some embodiments, A is a 9- or 10-membered bicyclic heteroaryl optionally substituted by $R^4$. In some embodiments, A is a 9- or 10-membered bicyclic heteroaryl optionally substituted by $R^4$, wherein one ring is saturated. In some embodiments, A is a 9- or 10-membered bicyclic heteroaryl optionally substituted by $R^4$, wherein both rings are unsaturated. In some embodiments, A is selected from the group consisting of benzimidazolyl, benzoxazolyl, benzothiazolyl, quinolinyl, isoquinolinyl, indazolyl, quinoxalinyl, quinazolinyl, cinnolinyl, naphthyridinyl and naphthyl. In some embodiments, A is selected from the group consisting of benzimidazolyl, benzoxazolyl, benzothiazolyl, quinolinyl, isoquinolinyl, indazolyl, quinoxalinyl, quinazolinyl, cinnolinyl, naphthyridinyl and naphthyl, each of which is optionally substituted by $R^4$. In yet further embodiments, A is a 9- or 10-membered bicyclic heteroaryl optionally substituted by $R^4$, comprising a first and second ring, wherein the first ring has a greater number of ring atoms than the second ring. In certain embodiments, the point of attachment of A to the parent molecule is on the first ring having a greater number of ring atoms. In other embodiments, the point of attachment of A to the parent molecule is on the second ring having a smaller number of ring atoms. In some embodiments, A is a 9- or 10-membered bicyclic heteroaryl optionally substituted by $R^4$, wherein the two rings are selected from the group consisting of: a 5-membered ring and a 6-membered ring or two 6-membered rings.

In one aspect, when A is a 9- or 10-membered bicyclic heteroaryl optionally substituted by $R^4$, A is an unsubstituted 9- or 10-membered bicyclic heteroaryl containing at least one annular nitrogen atom, a 9- or 10-membered bicyclic heteroaryl containing at least two annular nitrogen atoms and optionally substituted by $R^4$ which $R^4$ groups are connected to the parent structure via a carbon atom, or a 10-membered bicyclic heteroaryl optionally substituted by $R^4$.

In some embodiments, A is a 9- or 10-membered bicyclic heteroaryl substituted with 0 to 3 $R^4$ groups which may be the same or different, and which may be present on either one ring or both rings. In one such aspect, A is a 9- or 10-membered bicyclic heteroaryl substituted with 0 to 3 $R^3$ groups which may be the same or different, and which may be present on either one ring or both rings. In one such aspect, A is a 9- or 10-membered bicyclic heteroaryl substituted with 1 $R^3$ group. In another such aspect, A is a 9- or 10-membered bicyclic heteroaryl substituted with 2 $R^3$ groups, which may be the same or different. In another such aspect, A is a 9- or 10-membered bicyclic heteroaryl substituted with 3 $R^3$ groups, which may be the same or different.

In some embodiments, A is selected from the group consisting of:
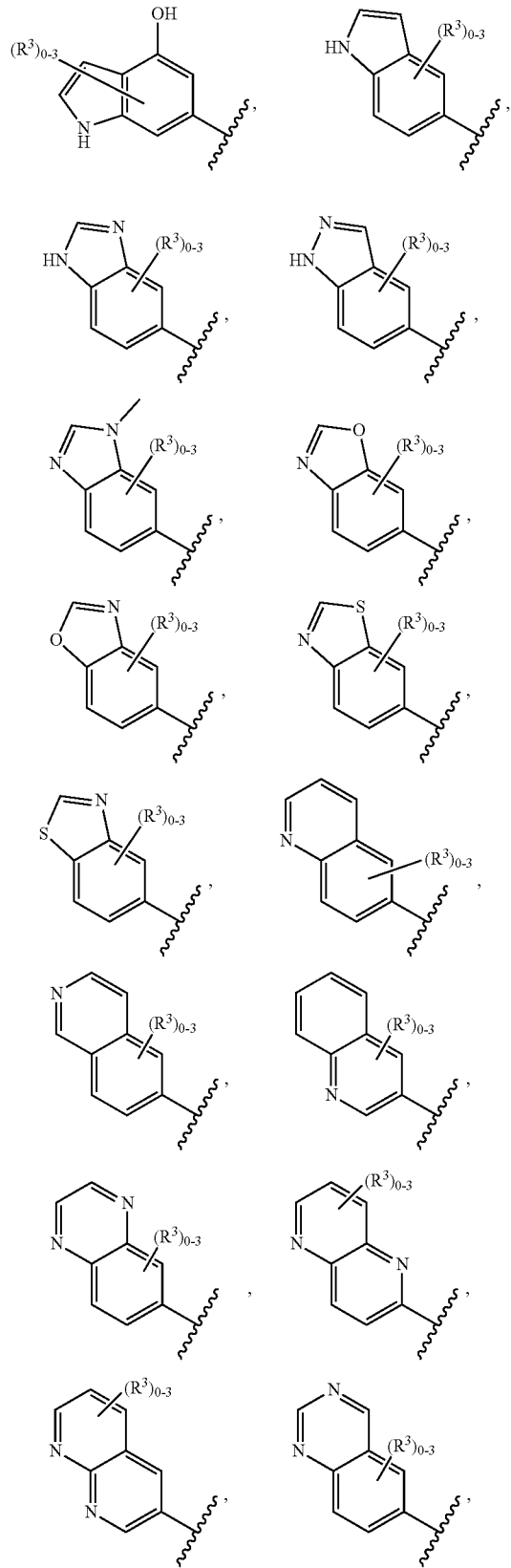
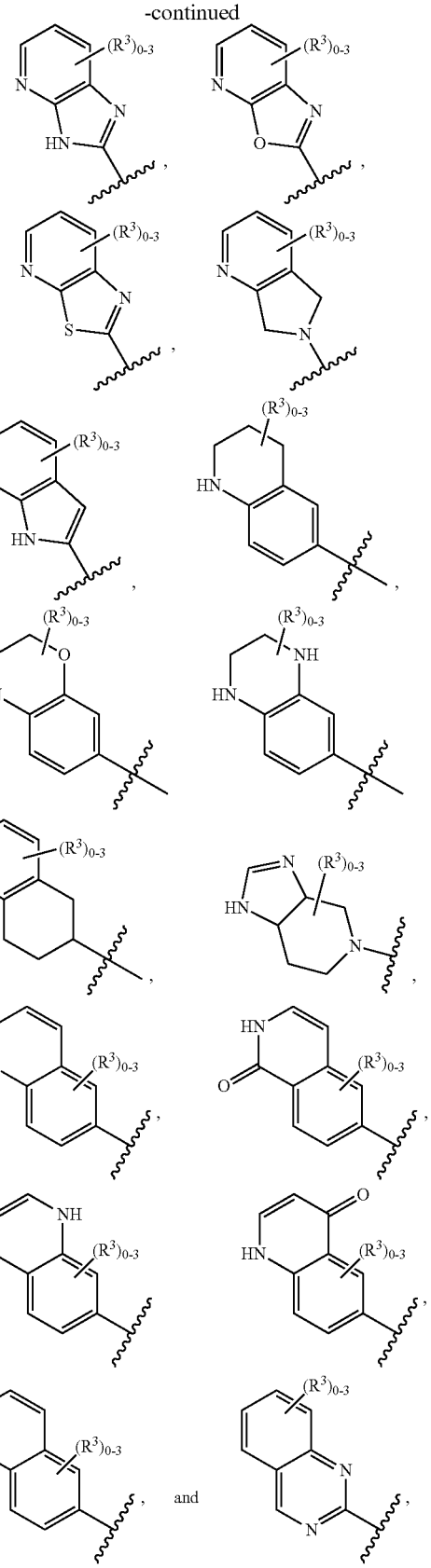
where $R^3$, if present, is attached at any available position on the bicyclic ring system. In one aspect, at least one $R^3$ is present and is attached at a position on the ring bearing the wavy line (on the ring that is the attachment point of the bicyclic ring to the parent molecule). In one aspect, at least one $R^3$ is present and is attached at a position on the ring that does not bear the wavy line (on the ring that is fused to the ring which is the attachment point of the bicyclic ring to the parent molecule).

In some embodiments, A is a 9- or 10-membered bicyclic heteroaryl substituted with 0 to 3 $R^3$ groups which may be the same or different, and which may be present on either one ring or both rings. In some embodiments, A is selected from the group consisting of:

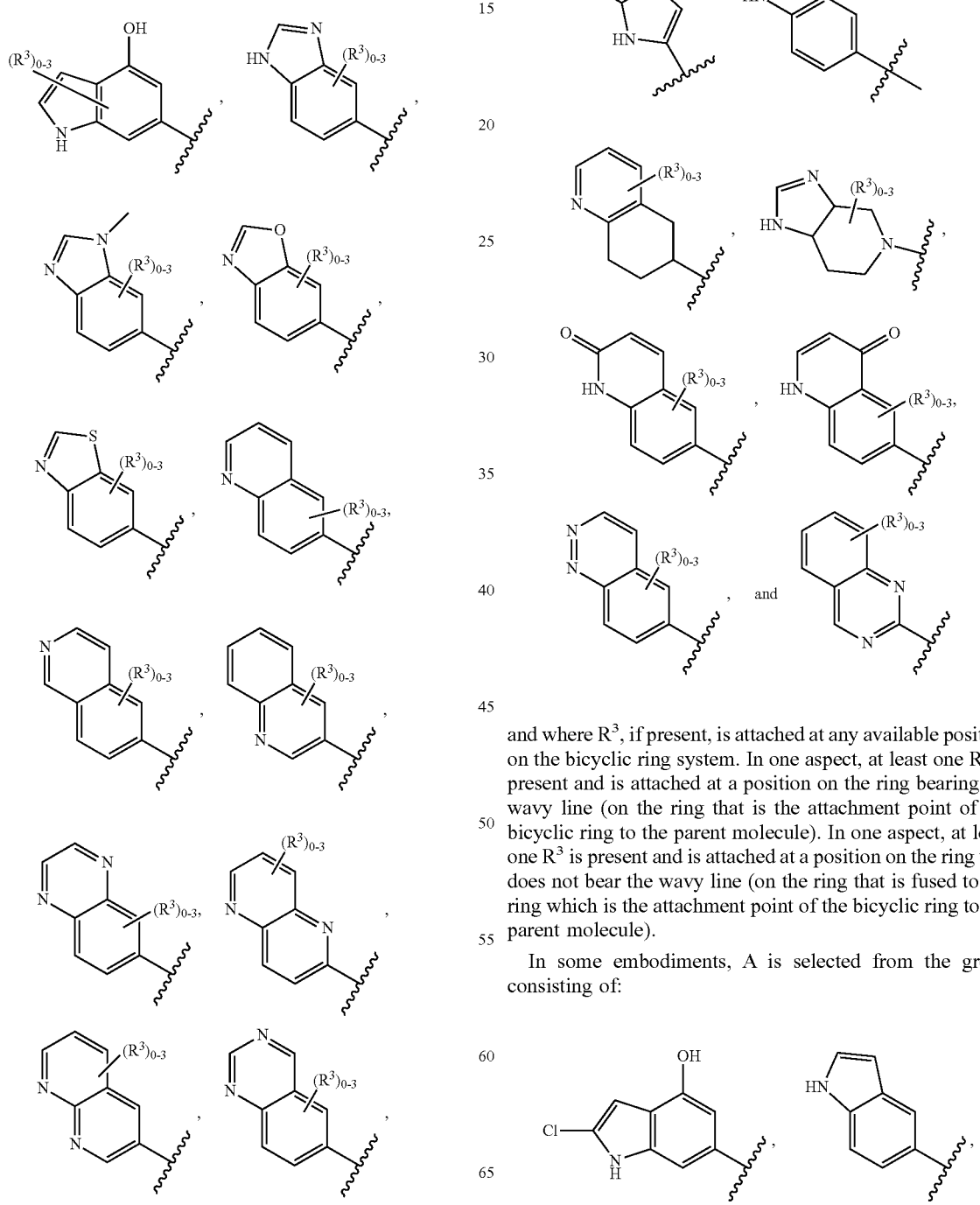

and where $R^3$, if present, is attached at any available position on the bicyclic ring system. In one aspect, at least one $R^3$ is present and is attached at a position on the ring bearing the wavy line (on the ring that is the attachment point of the bicyclic ring to the parent molecule). In one aspect, at least one $R^3$ is present and is attached at a position on the ring that does not bear the wavy line (on the ring that is fused to the ring which is the attachment point of the bicyclic ring to the parent molecule).

In some embodiments, A is selected from the group consisting of:

-continued
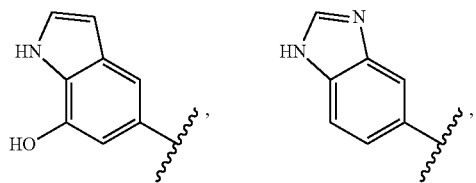
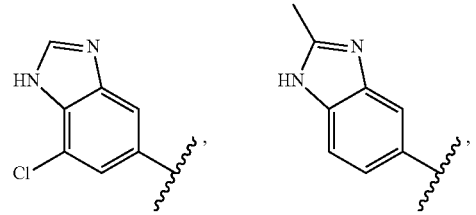
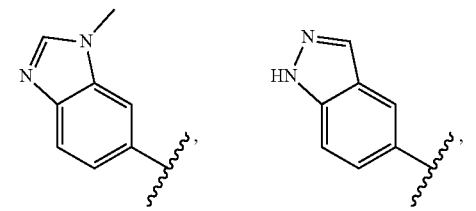
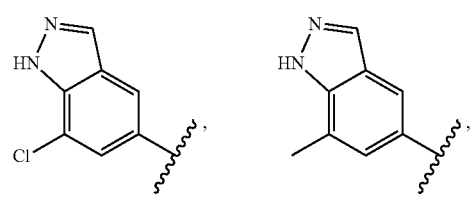
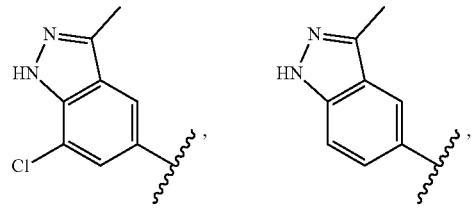
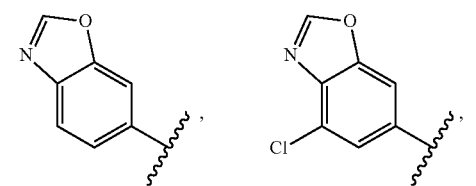
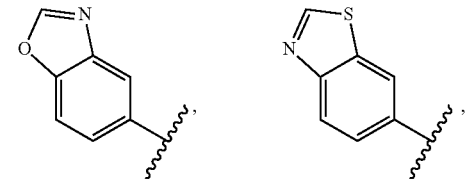
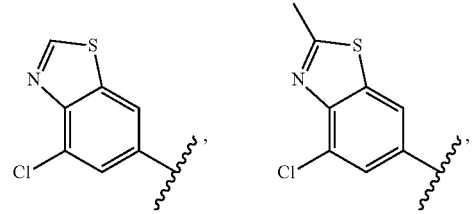
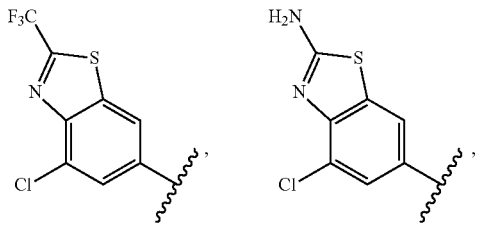
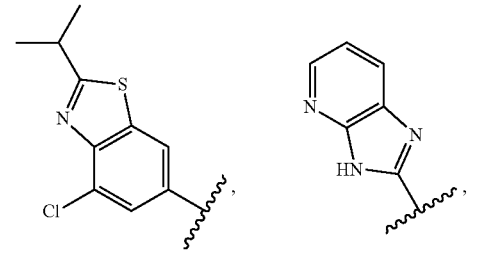
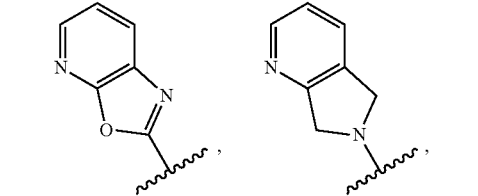
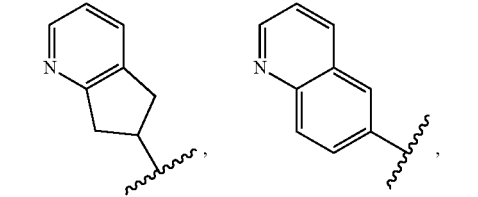
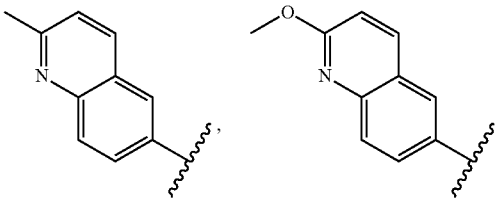
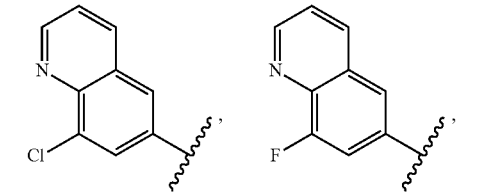
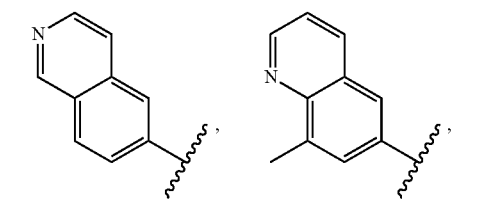
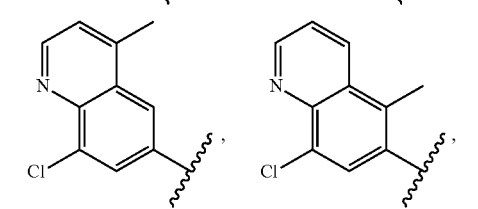

-continued
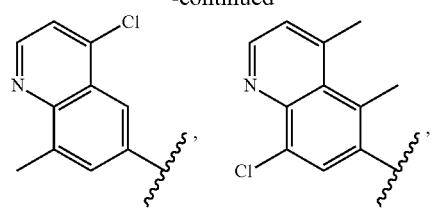
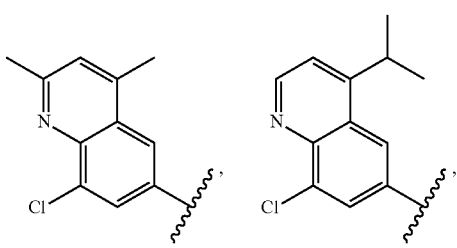
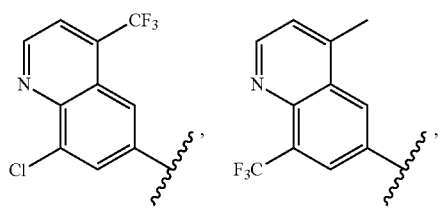
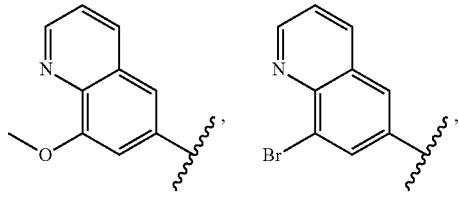
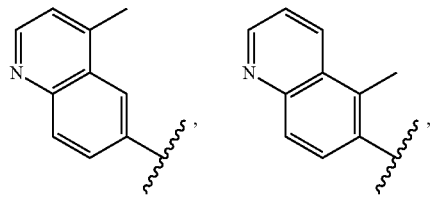
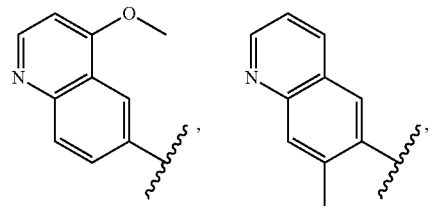
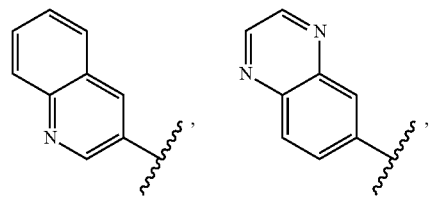
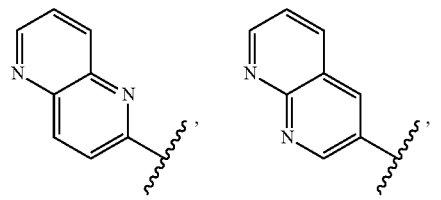
-continued
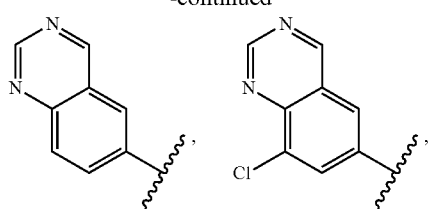
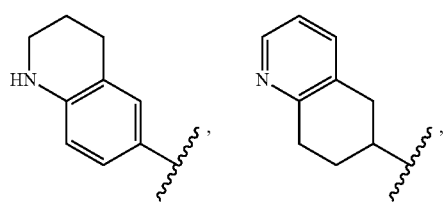
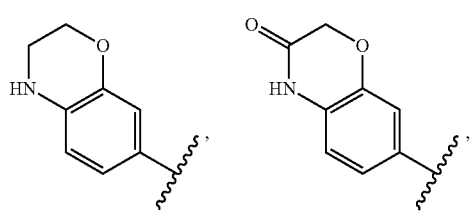
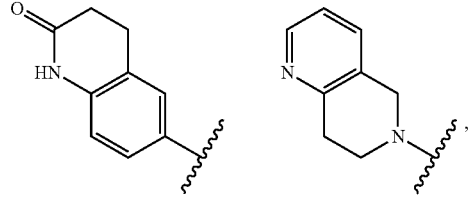
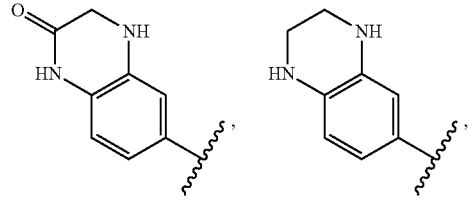
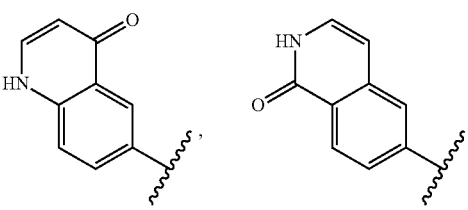
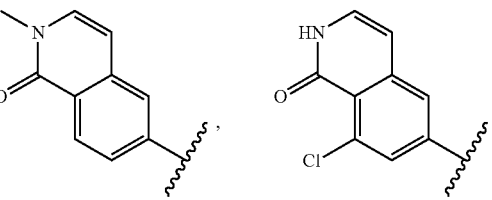
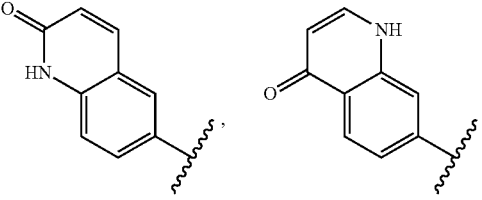

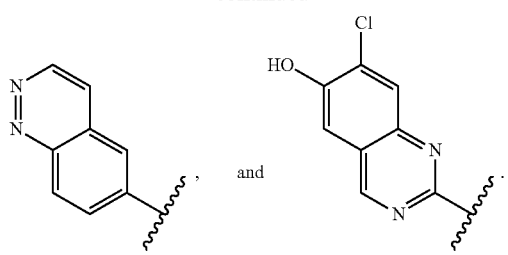, and
In some embodiments, A is selected from the group consisting of:
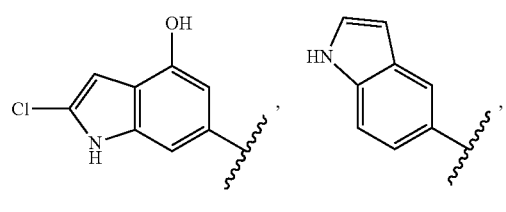
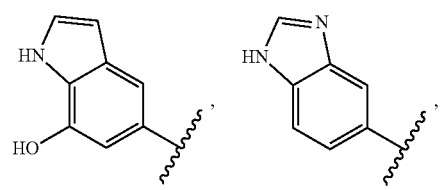
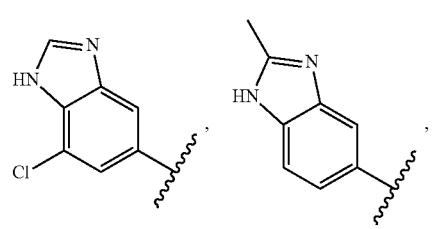
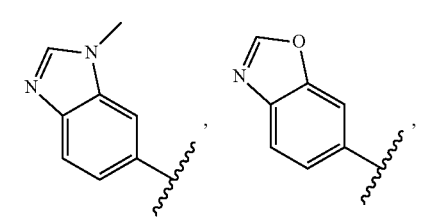
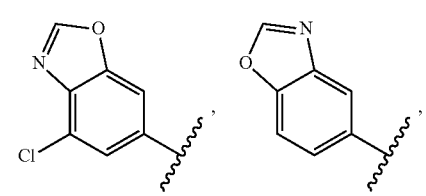
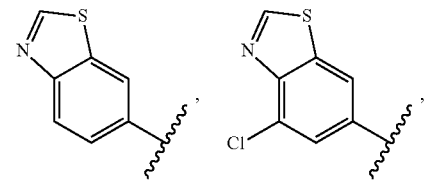
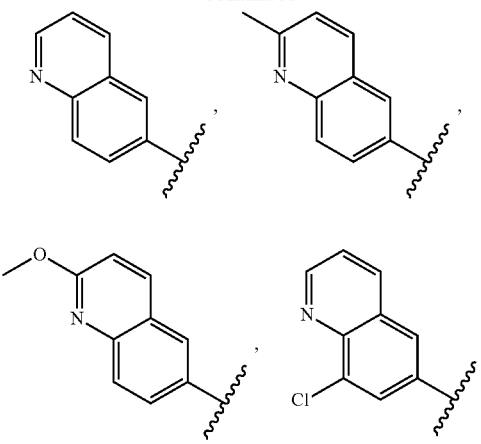
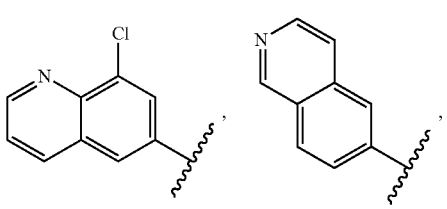
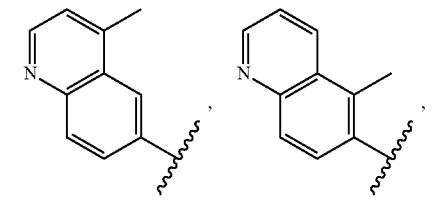
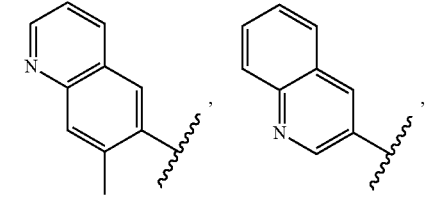
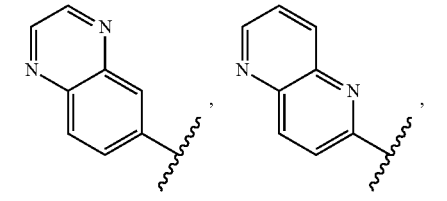
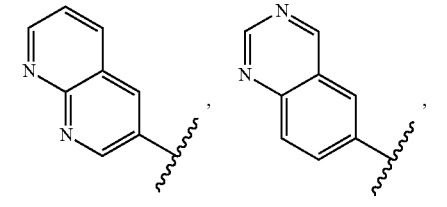
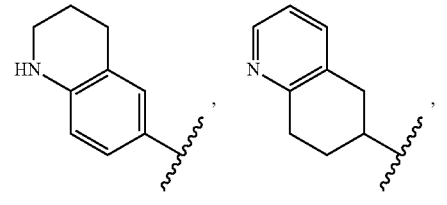

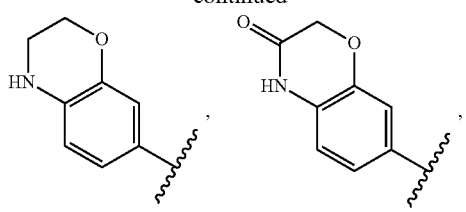
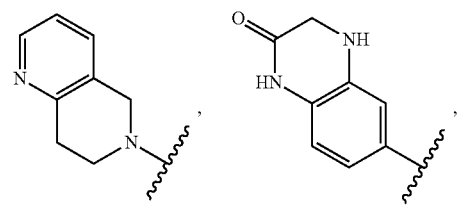
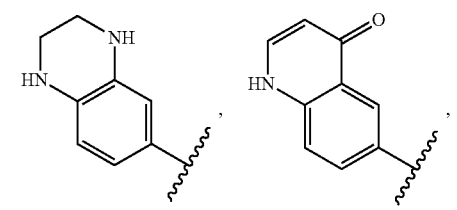
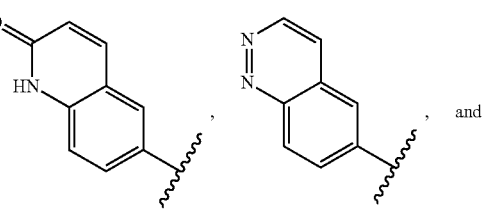
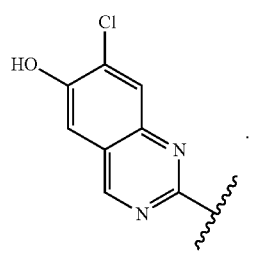, and
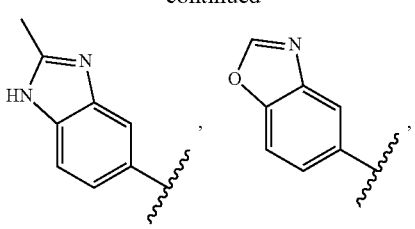
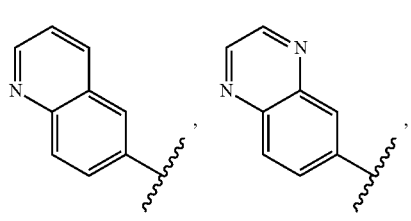
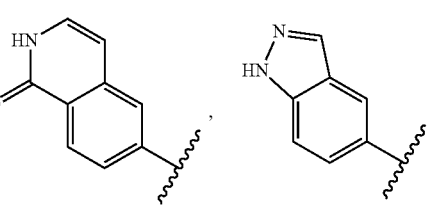
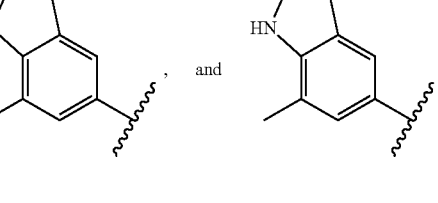
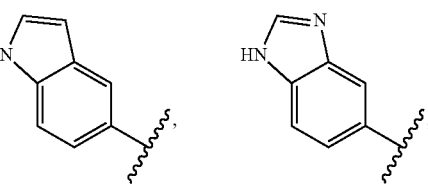, and
wherein the wavy lines denote attachment points to the parent molecule.
In certain embodiments, A is selected from the group consisting of:
In certain embodiments, A is selected from the group consisting of:
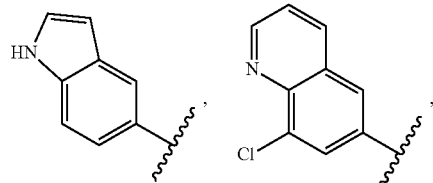
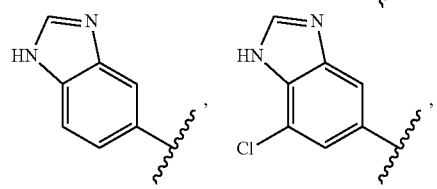
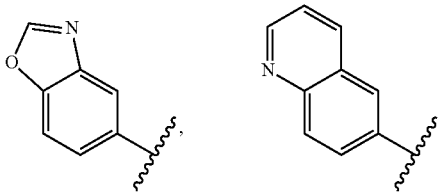

-continued

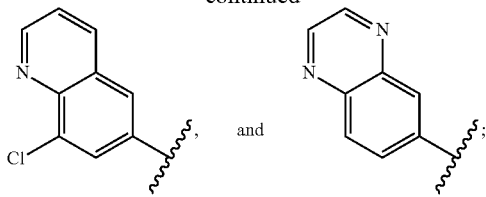
and wherein the wavy lines denote attachment points to the parent molecule.

In certain embodiments, A is selected from the group consisting of:

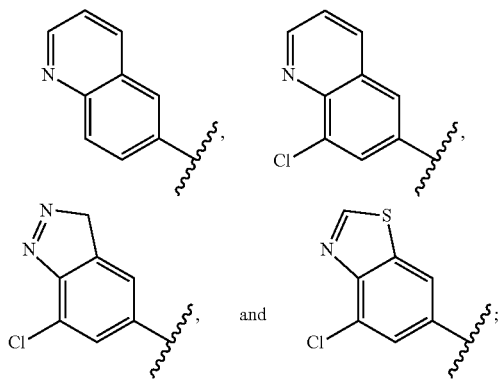
and wherein the wavy lines denote attachment points to the parent molecule. In some embodiments, A is

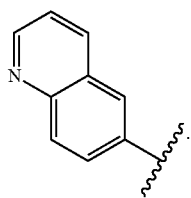 [SMILES: *c1ccc2ncccc2c1]

In some embodiments, A is

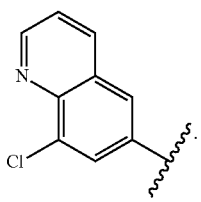 [SMILES: *c1cc(Cl)c2ncccc2c1]

In some embodiments, A is

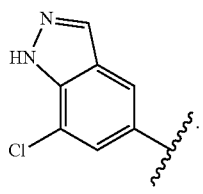 [SMILES: *c1cc(Cl)c2[nH]ncc2c1]

In some embodiments, A is

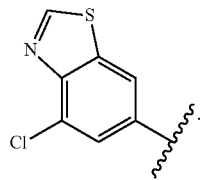 [SMILES: *c1cc(Cl)c2ncsc2c1]

It is understood that each description of A may be combined with each description of B, $R^1$ and/or $R^2$ the same as if each and every combination were specifically and individually listed.

In some embodiments, B is an unsubstituted phenyl. In some embodiments, B is a phenyl optionally substituted by $R^3$. In some embodiments, B is a phenyl substituted by 1 to 3 $R^3$ which $R^3$ groups may be the same or different. In other embodiments, B is a 5- to 6-membered heteroaryl optionally substituted by $R^4$. In other embodiments, B is a 5- to 6-membered heteroaryl substituted by 1 to 3 $R^4$ which $R^4$ may be the same or different. In some embodiments, the 5- to 6-membered heteroaryl of B is a 5-membered heteroaryl selected from the group consisting of furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, which 5-membered heteroaryl is optionally substituted by 1 to 3 $R^4$ which $R^4$ groups may be the same or different.

In other embodiments, the 5- to 6-membered heteroaryl of B is a 6-membered heteroaryl selected from the group consisting of pyridyl, pyridazinyl and pyrimidinyl which 6-membered heteroaryl is optionally substituted to 1 to 3 $R^4$ which $R^4$ groups may be the same or different In some embodiments, B is an unsubstituted phenyl. In some embodiments, B is a phenyl optionally substituted by $R^3$. In some embodiments, B is a phenyl substituted by 1 to 3 $R^3$ which $R^3$ groups may be the same or different. In other embodiments, B is a 5- to 6-membered heteroaryl optionally substituted by $R^4$. In other embodiments, B is a 5- to 6-membered heteroaryl substituted by 1 to 3 $R^4$ which $R^4$ may be the same or different. In some embodiments, the 5- to 6-membered heteroaryl of B is a 5-membered heteroaryl selected from the group consisting of furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, which 5-membered heteroaryl is optionally substituted by 1 to 3 $R^4$ which $R^4$ groups may be the same or different.

In other embodiments, the 5- to 6-membered heteroaryl of B is a 6-membered heteroaryl selected from the group consisting of pyridyl and pyrimidinyl which 6-membered heteroaryl is optionally substituted to 1 to 3 $R^4$ which $R^4$ groups may be the same or different.

In some embodiments of B in which B is a phenyl substituted by $R^3$, such as when B is a phenyl substituted by 1 to 3 $R^3$ which may be the same or different, each $R^3$ of B in one aspect is independently selected from the group consisting of halogen, —CN, —$OR^5$, —$NR^6R^7$, —$C(O)R^5$, $C_3$-$C_6$ cycloalkyl and $C_1$-$C_6$ alkyl optionally substituted by halogen. In other embodiments, each $R^3$ of B is independently selected from the group consisting of halogen and $C_1$-$C_6$ alkyl optionally substituted by halogen (e.g., $CF_3$).

In some embodiments, B is a phenyl substituted with 1 to 3 halo groups which may be the same or different. In some embodiments, B is phenyl, fluoro-phenyl, di-fluoro-phenyl, chloro-phenyl, di-chloro-phenyl or (fluoro)(chloro)-phenyl. In some embodiments, B is selected from the group consisting of:

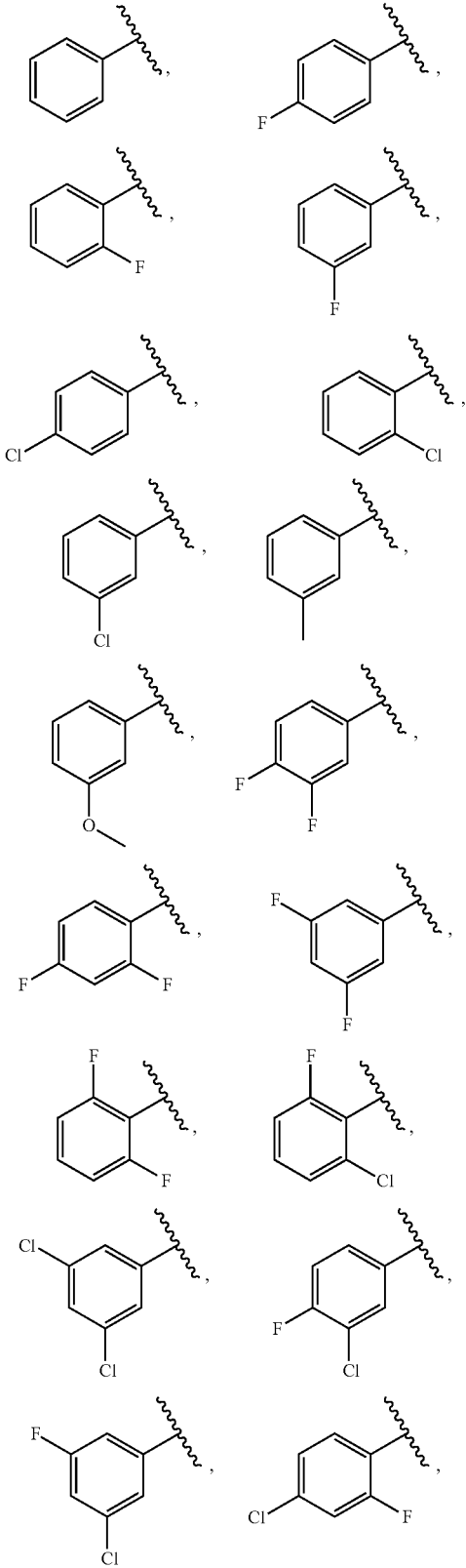

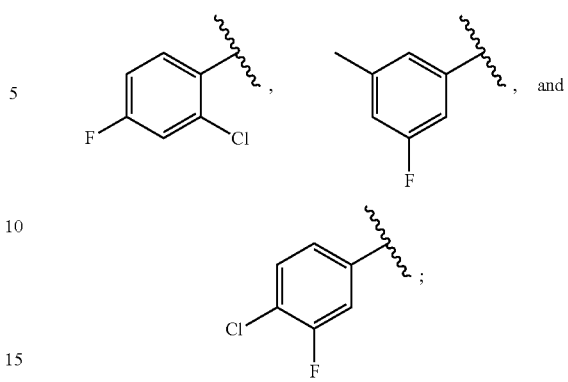

wherein the wavy lines denote attachment points to the parent molecule.

In some embodiments, B is a phenyl substituted with 1 to 3 halo groups which may be the same or different. In some embodiments, B is phenyl, fluoro-phenyl, di-fluoro-phenyl, chloro-phenyl, di-chloro-phenyl or (fluoro)(chloro)-phenyl. In some embodiments, B is selected from the group consisting of:

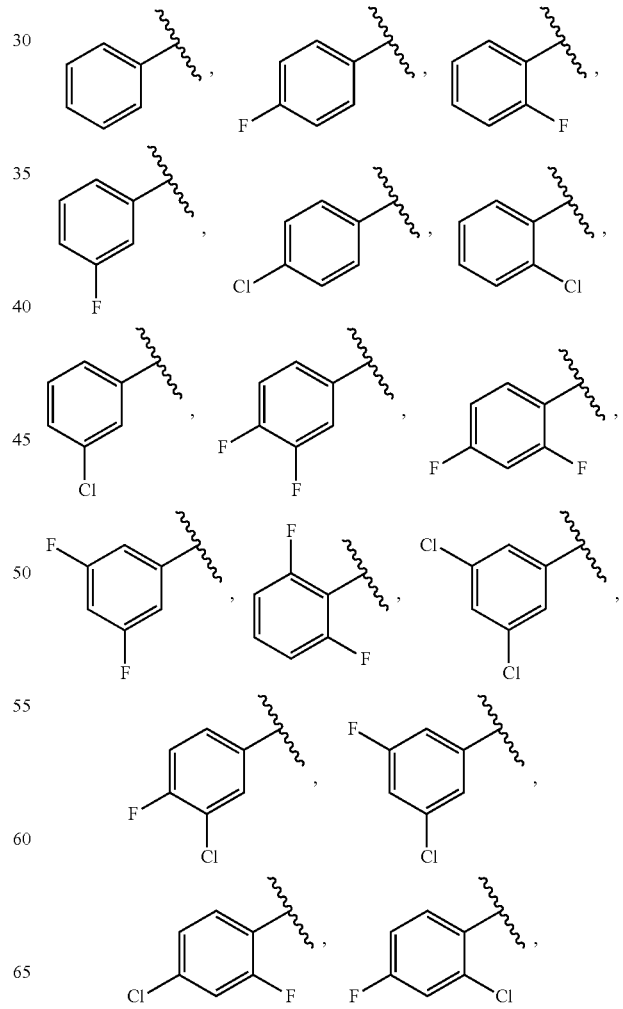

-continued

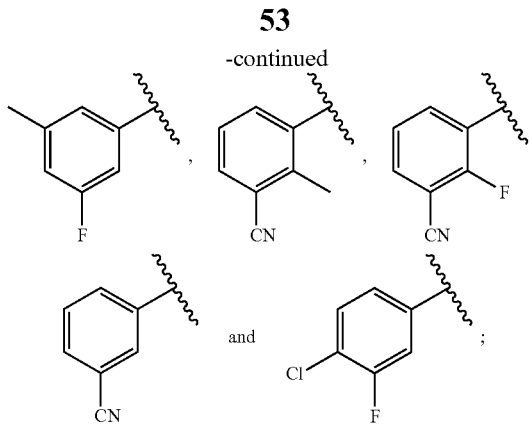

wherein the wavy lines denote attachment points to the parent molecule.

In some embodiments, B is a 5-membered heteroaryl substituted with 0 to 3 $R^4$ groups which may be the same or different. In some embodiments, B is a 5-membered heteroaryl substituted with 0 to 3 $R^3$ groups which may be the same or different. In one such aspect, B is a 5-membered heteroaryl substituted with 1 $R^3$ group. In another such aspect, B is a 5-membered heteroaryl substituted with 2 $R^3$ groups, which may be the same or different. In another such aspect, B is a 5-membered heteroaryl substituted with 3 $R^3$ groups, which may be the same or different. In some embodiments, B is a 5-membered heteroaryl selected from the group consisting of:

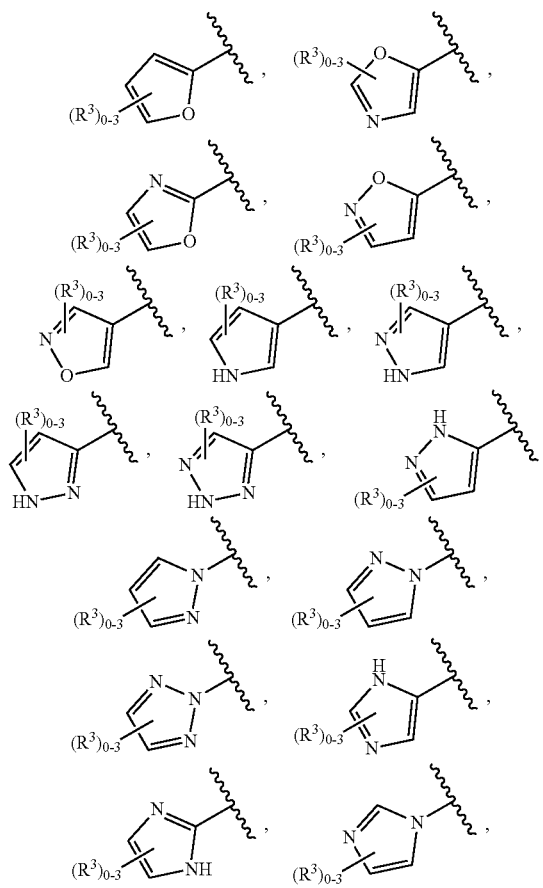

-continued

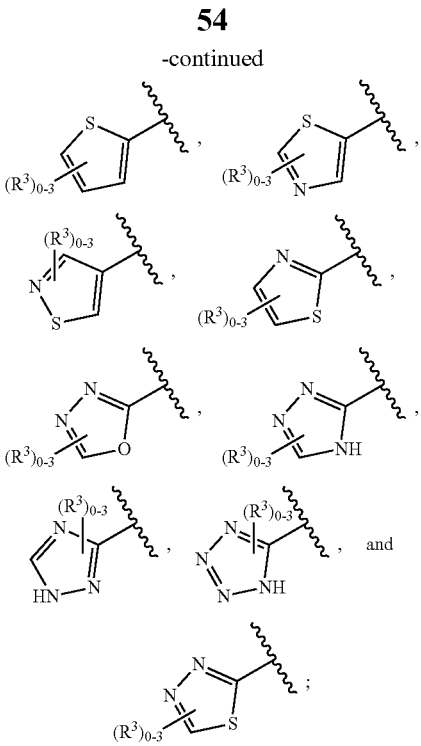

wherein the wavy lines denote attachment points to the parent molecule. It is understood that

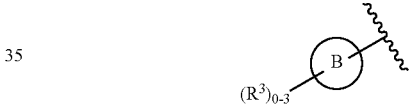

means that the B ring can be substituted with 0, 1, 2, or 3 $R^3$ groups, as valence permits (e.g., when the maximum number of allowed substituents is 2, the B ring can be substituted with 0, 1, or 2 $R^3$ groups).

In some embodiments, B is a 5-membered heteroaryl substituted with 0 to 3 $R^3$ groups which may be the same or different. In some embodiments, B is a 5-membered heteroaryl selected from the group consisting of:

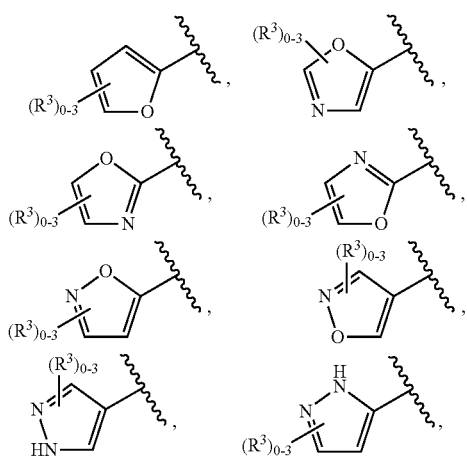

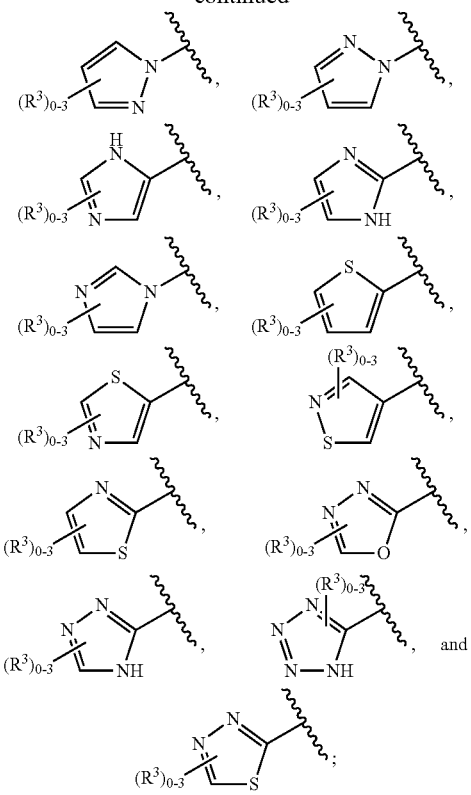
wherein the wavy lines denote attachment points to the parent molecule. It is understood that
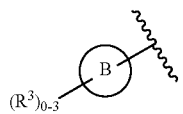
means that the B ring can be substituted with 0, 1, 2, or 3 $R^3$ groups, as valence permits (e.g., when the maximum number of allowed substituents is 2, the B ring can be substituted with 0, 1, or 2 $R^3$ groups).
In some embodiments, B is a 5-membered heteroaryl selected from the group consisting
of:
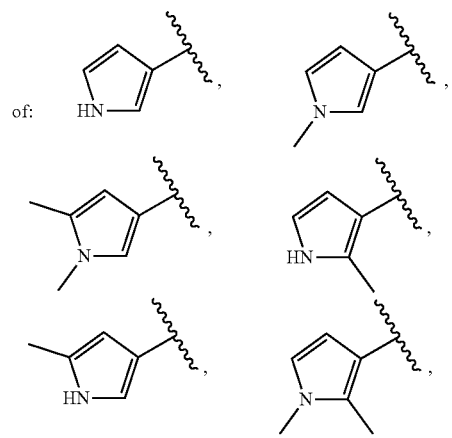
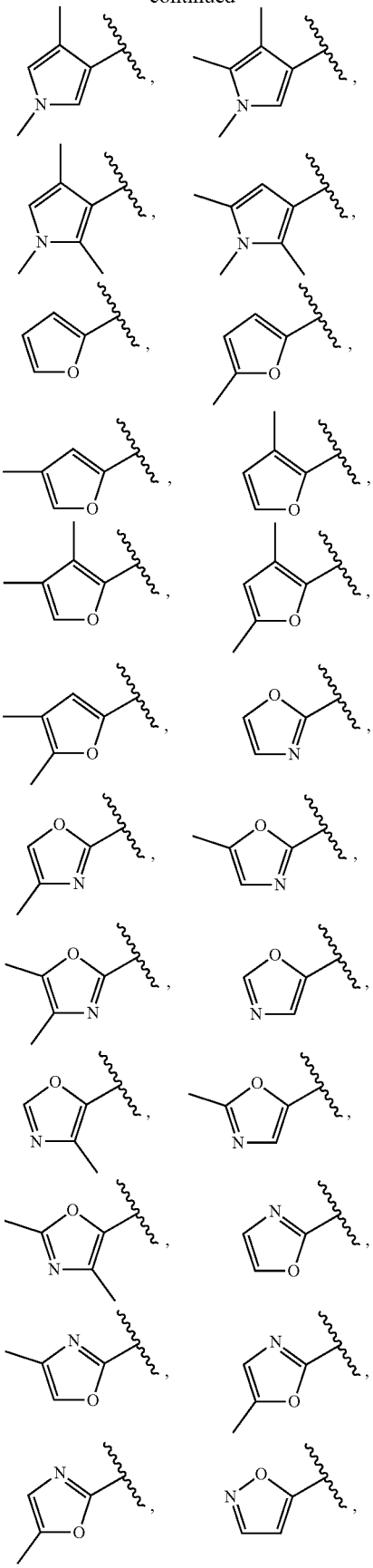

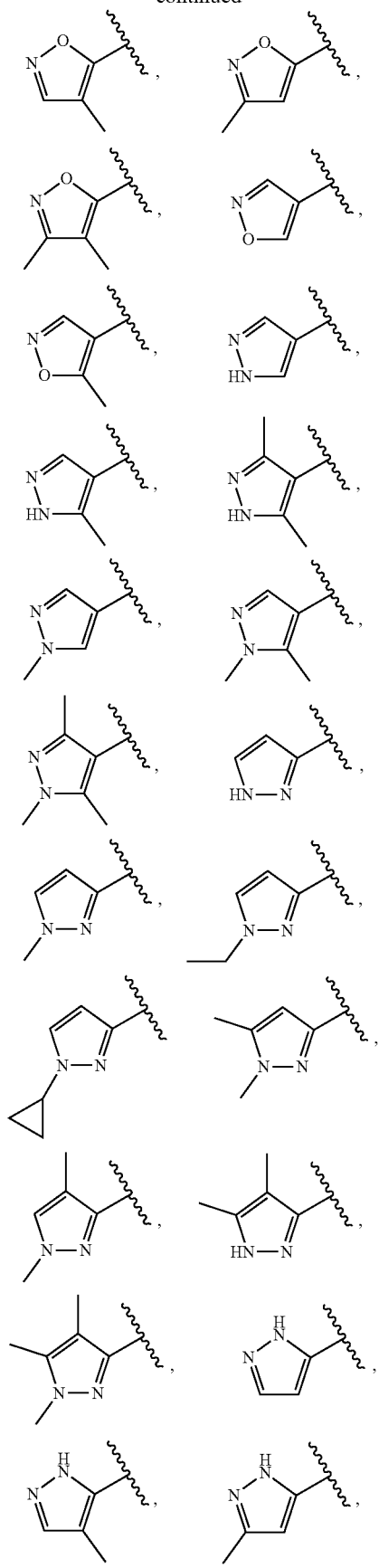
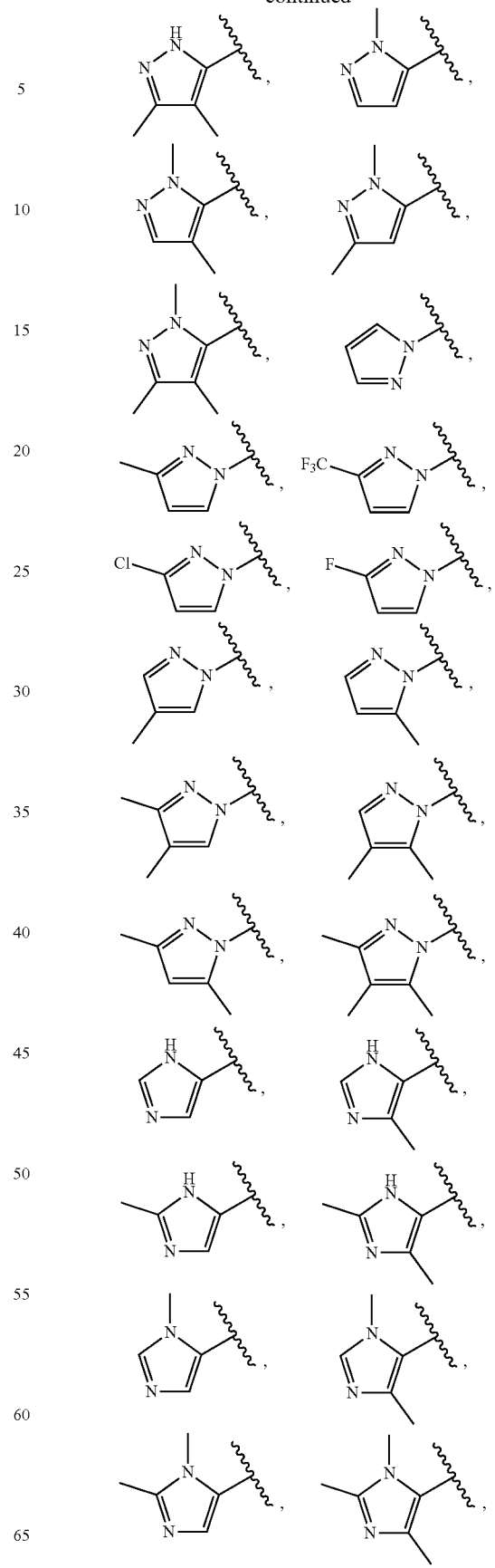

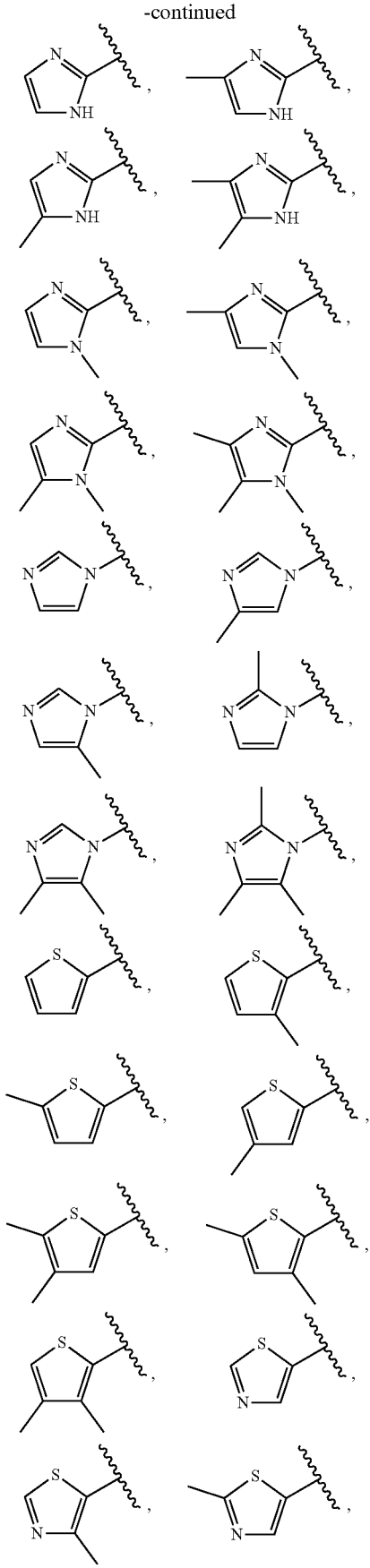
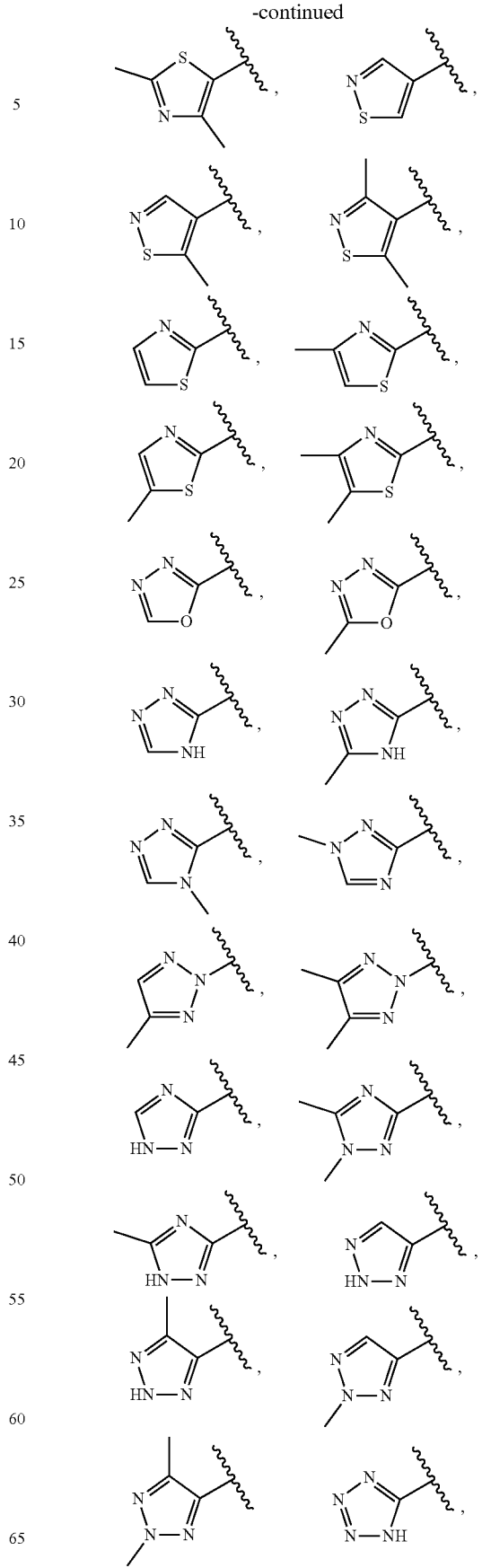

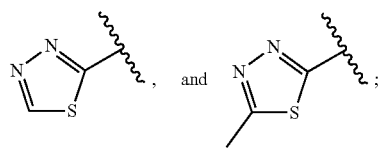
wherein the wavy lines denote attachment points to the parent molecule.
In some embodiments, B is a 5-membered heteroaryl selected from the group consisting
of:
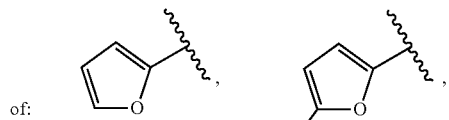
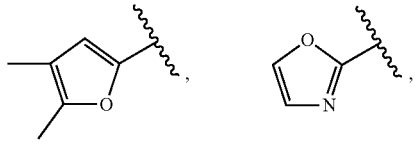
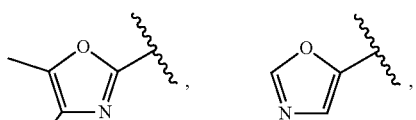
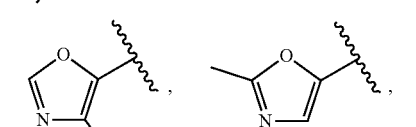
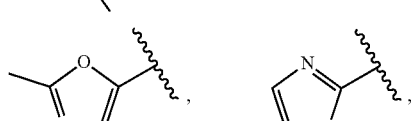
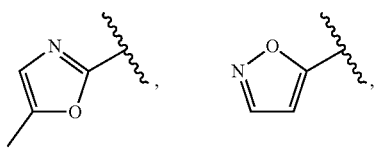
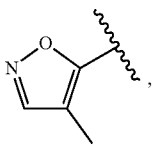 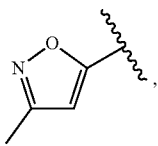
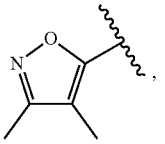 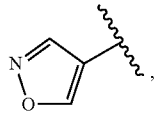
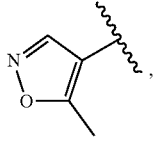 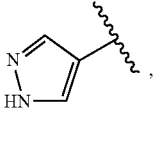
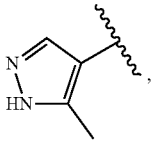 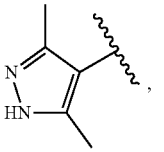
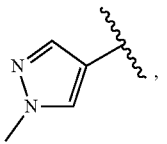 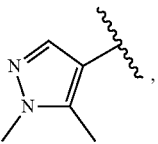
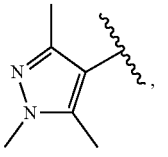 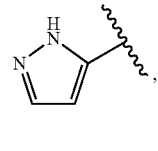
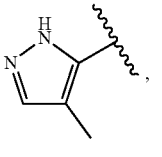 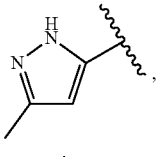
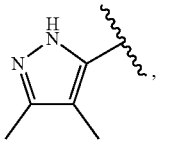 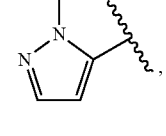
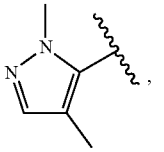 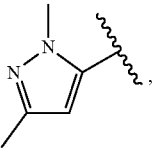
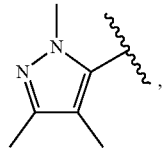 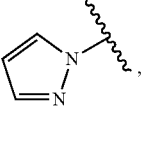

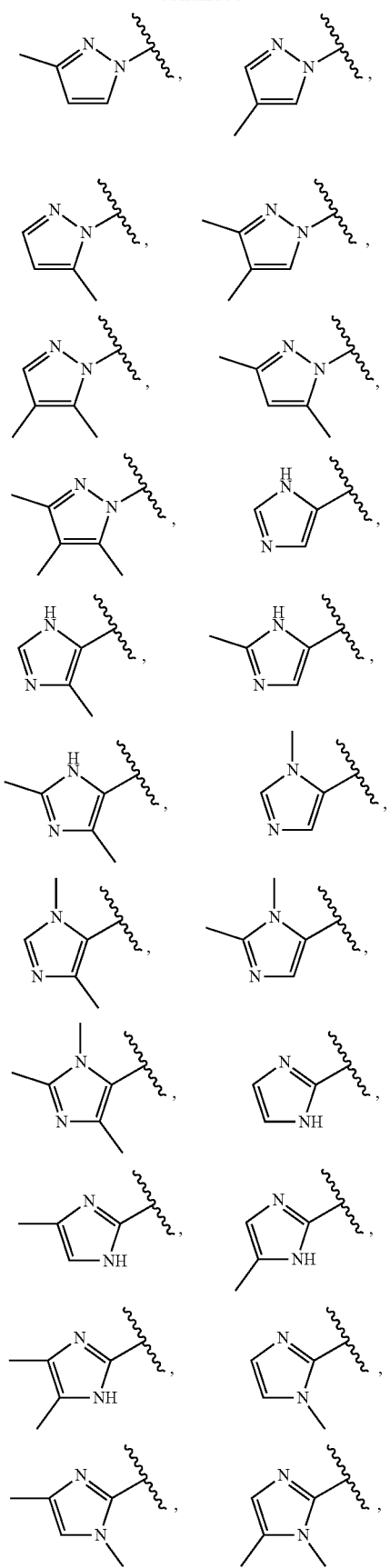
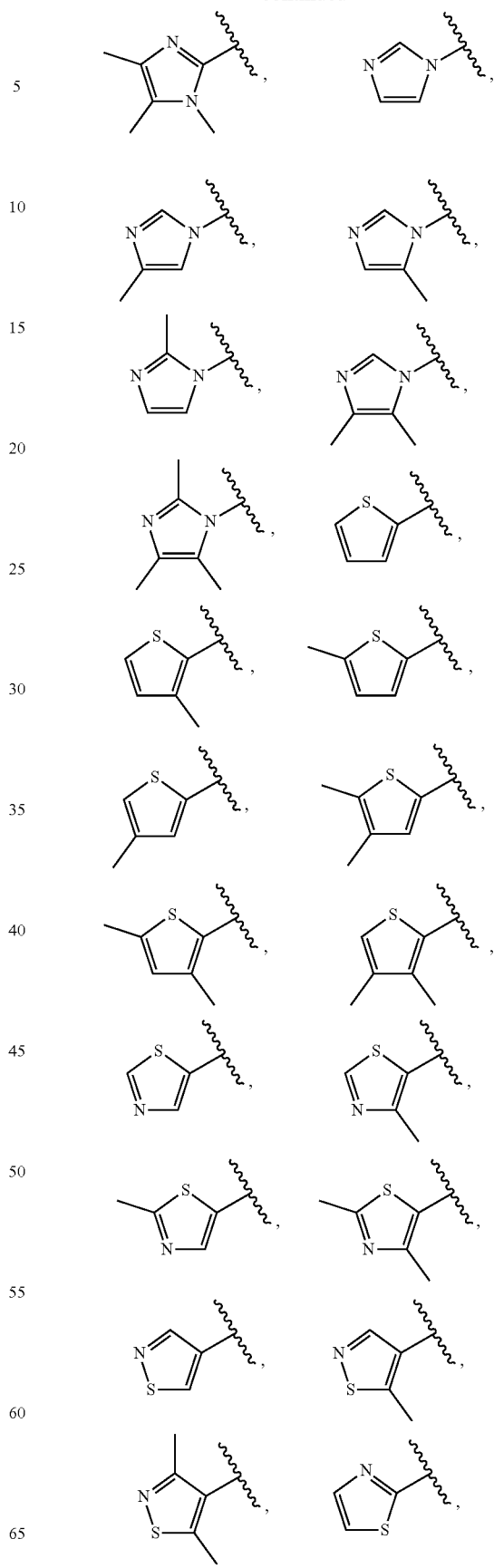

-continued

, ,

, ,

, ,

, ,

, ,

, and ;

wherein the wavy lines denote attachment points to the parent molecule.

In some embodiments, B is a pyridyl or pyrimidyl optionally substituted by 1 to 3 $R^4$, which $R^4$ may be the same or different. In some embodiments, B is a pyridyl or pyrimidyl optionally substituted by 1 to 3 halo groups which may be the same or different. In some embodiments, B is a 6-membered heteroaryl selected from the group consisting of:

, , ,

, , ,

, , ;

wherein the wavy lines denote attachment points to the parent molecule.

In some embodiments, B is a pyridyl or pyrimidyl optionally substituted by 1 to 3 $R^4$, which $R^4$ may be the same or different. In some embodiments, B is a pyridyl or pyrimidyl optionally substituted by 1 to 3 $R^3$, which $R^3$ may be the same or different. In some embodiments, B is a pyridyl or pyrimidyl optionally substituted by 1 to 3 halo groups which may be the same or different. In some embodiments, B is a 6-membered heteroaryl selected from the group consisting of:

wherein the wavy lines denote attachment points to the parent molecule.

In some embodiments, B is selected from the group consisting of:

, , ,

-continued

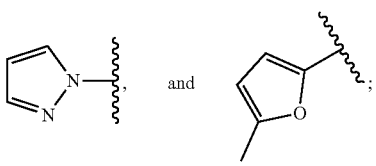

wherein the wavy lines denote attachment points to the parent molecule.

In some embodiments, B is selected from the group consisting of:

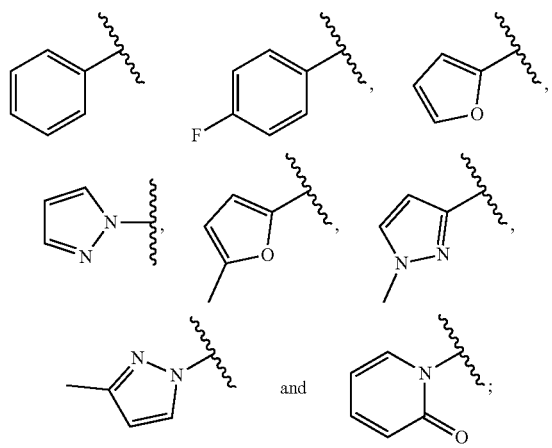

wherein the wavy lines denote attachment points to the parent molecule.

In some embodiments, B is

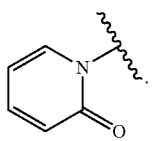 [SMILES: *n1ccccc1=O]

In some embodiments, B is

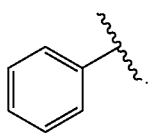 [SMILES: *c1ccccc1]

In some embodiments, B is

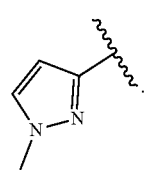

In some embodiments, B is

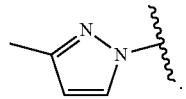 [SMILES: *n1ccc(C)n1]

It is understood that each description of B may be combined with each description of $R^1$ and/or $R^2$ the same as if each and every combination were specifically and individually listed. It is similarly understood that each description of B may be combined with each description of A (and further with each description of $R^1$ and $R^2$) the same as if each and every combination were specifically and individually listed. In one variation, B is as defined in any variation herein, $R^1$ and $R^2$ are as defined in any variation herein and A is 4-hydroxyphenyl optionally further substituted by $R^3$ or 4-hydroxy-2-pyridyl optionally further substituted by $R^4$. In another variation, B is as defined in any variation herein, $R^1$ and $R^2$ are as defined in any variation herein and A is 9- or 10-membered bicyclic heteroaryl (eg., quinolinyl or indazolyl) optionally substituted by $R^4$.

In some embodiments, the compound of formula (I) is a compound of formula (IIIa):

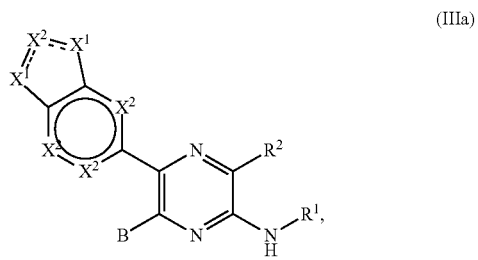

(IIIa)

or a salt thereof, wherein $R^1$, $R^2$ and B are as defined for formula (I);

each $X^1$ is independently O, S, NH, $NR^{4a}$, $CH_2$, $CHR^{4b}$, $CR^{4b}R^{4b}$, N, CH or $CR^{4b}$;

each $X^2$ is independently NH, $NR^{4a}$, $CHR^{4b}$, $CR^{4b}R^{4b}$, CH, $CR^{4b}$ or N;

each = is a single or double bond, provided that when $X^1=X^2$ is a double bond, $X^2=X^1$ is a single bond and when $X^2=X^1$ is a double bond, $X^1=X^2$ is a single bond;

$R^{4a}$ is $C_1$-$C_6$ alkyl;

each $R^{4b}$ is independently halogen, —CN, —$OR^5$, —$SR^5$, —$NR^6R^7$, —$NO_2$, —C(O)$R^5$, —C(O)O$R^5$, —C(O)N$R^6R^7$, —C(O)N$R^5$S(O)$_2R^6$, —OC(O)$R^5$, —OC(O)N$R^6R^7$, —$NR^5$C(O)$R^6$, —$NR^5$C(O)N$R^6R^7$, —S(O)$R^5$, —S(O)$_2R^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl, provided the compound is other than a compound selected from Table IX or a salt thereof.

In some embodiments, provided is a compound of formula (IIIa), or a tautomer or isomer thereof, or a pharmaceutically acceptable salt of any of the foregoing.

In some embodiments, the compound of formula (I) is a compound of formula (IIIb):

(IIIb)

or a salt thereof, wherein $R^1$, $R^2$ and B are as defined for formula (I);

each $X^1$ is independently O, S, NH, $NR^{4a}$, $CH_2$, $CHR^{4b}$, $CR^{4b}R^{4b}$, N, CH or $CR^{4b}$;

each $X^2$ is independently NH, $NR^{4a}$, $CH_2$, $CHR^{4b}$, $CR^{4b}R^{4b}$, CH, $CR^{4b}$ or N;

each = is a single or double bond;

$R^{4a}$ is $C_1$-$C_6$ alkyl;

each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl, provided the compound is other than a compound selected from Table 1X or a salt thereof.

In some embodiments, provided is a compound of formula (IIIb), or a tautomer or isomer thereof, or a pharmaceutically acceptable salt of any of the foregoing.

In some embodiments, the compound of formula (I) is a compound of formula (IIIc):

(IIIc)

or a salt thereof, wherein $R^1$, $R^2$ and B are as defined for formula (I);

each $X^1$ is independently O, S, NH, $NR^{4a}$, $CH_2$, $CHR^{4b}$, $CR^{4b}R^{4b}$, N, CH or $CR^{4b}$;

each $X^2$ is independently CH, $CR^{4b}$ or N;

$R^{4a}$ is $C_1$-$C_6$ alkyl;

each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;

where each $R^5$ is independently hydrogen, $C_1$-$C_6$ alkyl, or $C_3$-$C_6$ cycloalkyl; and $R^6$ and $R^7$ are each independently hydrogen, $C_1$-$C_6$ alkyl, or $C_3$-$C_6$ cycloalkyl;

or $R^6$ and $R^7$ are taken together with the atom to which they attached to form a 3-6 membered heterocyclyl, provided the compound is other than a compound selected from Table 1X or a salt thereof.

In some embodiments, provided is a compound of formula (IIIc), or a tautomer or isomer thereof, or a pharmaceutically acceptable salt of any of the foregoing.

In some embodiments, the compound of formula (I) is a compound of formula (IIIc-1):

(IIIc-1)

or a salt thereof, wherein $R^1$ and $R^2$ are as defined for formula (I);

each $X^1$ and $X^2$ are as defined for formula (IIIc);

$X^4$ is C or N;

provided the compound is other than a compound selected from Table IX or a salt thereof.

In some embodiments, provided is a compound of formula (IIIc-1), or a tautomer or isomer thereof, or a pharmaceutically acceptable salt of any of the foregoing.

In some embodiments, the compound of formula (I) is a compound of formula (IIIc-2):

(IIIc-2)

or a salt thereof, wherein $R^1$, $R^2$ and $R^3$ are as defined for formula (I);

each $X^1$ and $X^2$ are as defined for formula (IIIc);

provided the compound is other than a compound selected from Table 1X or a salt thereof.

In some embodiments, provided is a compound of formula (IIIc-2), or a tautomer or isomer thereof, or a pharmaceutically acceptable salt of any of the foregoing.

In some embodiments, the compound of formula (I) is a compound of formula (IIId):

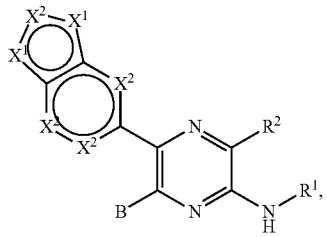
(IIId)

or a salt thereof, wherein $R^1$, $R^2$ and B are as defined for formula (I);

each $X^1$ is independently O, S, NH, CH$_2$, CHR$^{4b}$, CR$^{4b}$R$^{4b}$, N, CH or CR$^{4b}$;

each $X^2$ is independently CH, CR$^{4b}$ or N;

each $R^{4b}$ is independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen;

where each $R^5$ is independently hydrogen, C$_1$-C$_6$ alkyl, or C$_3$-C$_6$ cycloalkyl; and $R^6$ and $R^7$ are each independently hydrogen, C$_1$-C$_6$ alkyl, or C$_3$-C$_6$ cycloalkyl;

or $R^6$ and $R^7$ are taken together with the atom to which they attached to form a 3-6 membered heterocyclyl.

In some embodiments, provided is a compound of formula (IIId), or a tautomer or isomer thereof, or a pharmaceutically acceptable salt of any of the foregoing.

In some embodiments, the compound of formula (I) is a compound of formula (IIIe):

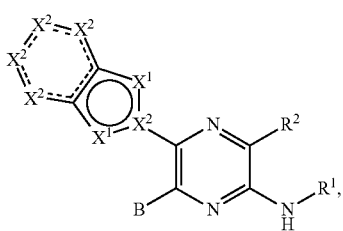
(IIIe)

or a salt thereof, wherein $R^1$, $R^2$ and B are as defined for formula (I);

each $X^1$ is independently O, S, NH, NR$^{4a}$, CH$_2$, CHR$^{4b}$, CR$^{4b}$R$^{4b}$, N, CH or CR$^{4b}$;

each $X^2$ is independently O, CH$_2$, CHR$^{4b}$, CR$^{4b}$R$^{4b}$, CH, CR$^{4b}$ or N;

each $=$ is a single or double bond;

$R^{4a}$ is C$_1$-C$_6$ alkyl;

each $R^{4b}$ is independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen;

where each $R^5$ is independently hydrogen, C$_1$-C$_6$ alkyl, or C$_3$-C$_6$ cycloalkyl; and $R^6$ and $R^7$ are each independently hydrogen, C$_1$-C$_6$ alkyl, or C$_3$-C$_6$ cycloalkyl;

or $R^6$ and $R^7$ are taken together with the atom to which they attached to form a 3-6 membered heterocyclyl, provided the compound is other than a compound selected from Table 1X or a salt thereof.

In some embodiments, provided is a compound of formula (IIIe), or a tautomer or isomer thereof, or a pharmaceutically acceptable salt of any of the foregoing.

In some embodiments, the compound of formula (I) is a compound of formula (IIIf):

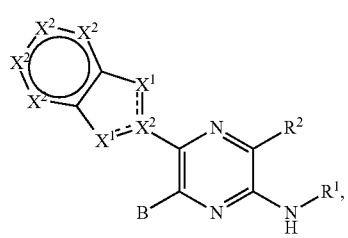
(IIIf)

or a salt thereof, wherein $R^1$, $R^2$ and B are as defined for formula (I);

each $X^1$ is independently O, S, NH, NR$^{4a}$, CH$_2$, CHR$^{4b}$, CR$^{4b}$R$^{4b}$, N, CH or CR$^{4b}$;

each $X^2$ is independently C, CH, CR$^{4b}$ or N;

each $=$ is a single or double bond, provided that when $X^1=X^2$ is a double bond, $X^2=X^1$ is a single bond and when $X^2=X^1$ is a double bond, $X^1=X^2$ is a single bond;

$R^{4a}$ is C$_1$-C$_6$ alkyl;

each $R^{4b}$ is independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen;

where each $R^5$ is independently hydrogen, C$_1$-C$_6$ alkyl, or C$_3$-C$_6$ cycloalkyl; and $R^6$ and $R^7$ are each independently hydrogen, C$_1$-C$_6$ alkyl, or C$_3$-C$_6$ cycloalkyl;

or $R^6$ and $R^7$ are taken together with the atom to which they attached to form a 3-6 membered heterocyclyl, provided the compound is other than a compound selected from Table 1X or a salt thereof.

In some embodiments, provided is a compound of formula (IIIf), or a tautomer or isomer thereof, or a pharmaceutically acceptable salt of any of the foregoing.

In some embodiments, the compound of formula (I) is a compound of formula (IIIg):

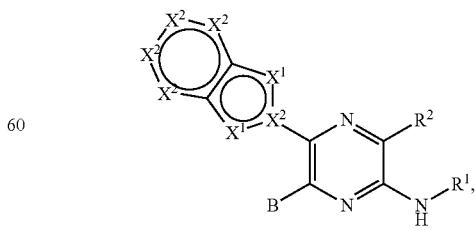
(IIIg)

or a salt thereof, wherein $R^1$, $R^2$ and B are as defined for formula (I);

each $X^1$ is independently O, S, NH, $NR^{4a}$, N, CH or $CR^{4b}$;
each $X^2$ is independently C, CH, $CR^{4b}$ or N;
$R^{4a}$ is $C_1$-$C_6$ alkyl;
each $R^{4b}$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl,
provided the compound is other than a compound selected from Table 1X or a salt thereof.

In some embodiments, provided is a compound of formula (IIIg), or a tautomer or isomer thereof, or a pharmaceutically acceptable salt of any of the foregoing.

In some embodiments of the compound of formula (III), $R^{4b}$ is selected from the group consisting of halogen, —$OR^5$ and $C_1$-$C_6$ alkyl optionally substituted by halogen.

In some embodiments of the compound of formula (III), one of $X^1$ is N, and the other one of $X^1$ is $NR^{4a}$, and each $X^2$ is CH or $CR^{4b}$. In other embodiments of the compound of formula (III), one of $X^1$ is N, and the other one of $X^1$ is O or S, and each $X^2$ is CH or $CR^{4b}$.

In some embodiments, the compound of formula (I) is a compound of formula (IVa):

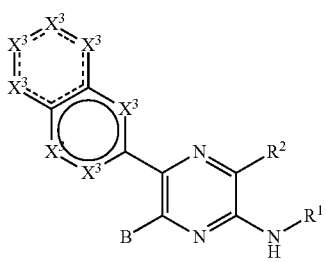

(IVa)

or a salt thereof, wherein $R^1$, $R^2$ and B are as defined for formula (I);
each $X^3$ is independently NH, $NR^4$, $CH_2$, $CHR^4$, $CR^4R^4$, $CR^4$, CH, C=O, O or N;
each = is a single or double bond;
each $R^4$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, —($C_1$-$C_3$ alkylene)(6-membered aryl) optionally substituted by halogen or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl,
provided the compound is other than a compound selected from Table 1X or a salt thereof.

In some embodiments, the compound of formula (I) is a compound of formula (IVa):

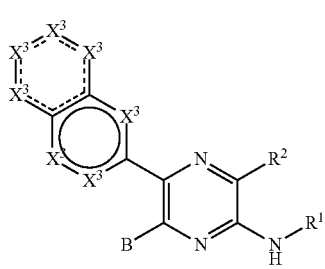

(IVa)

or a salt thereof, wherein $R^1$, $R^2$ and B are as defined for formula (I);
each $X^3$ is independently NH, $NR^4$, $CH_2$, $CHR^4$, $CR^4R^4$, $CR^4$, CH or N;
each = is a single or double bond;
each $R^4$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl,
provided the compound is other than a compound selected from Table 1X or a salt thereof.

In some embodiments, provided is a compound of formula (IVa), or a tautomer or isomer thereof, or a pharmaceutically acceptable salt of any of the foregoing.

In some embodiments, the compound of formula (I) is a compound of formula (IVb):

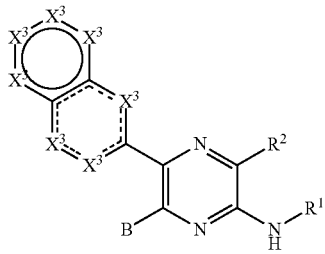

(IVb)

or a salt thereof, wherein $R^1$, $R^2$ and B are as defined for formula (I);
each $X^3$ is independently NH, $NR^4$, $CH_2$, $CHR^4$, $CR^4R^4$, $CR^4$, CH or N;
each = is a single or double bond;
each $R^4$ is independently halogen, —CN, —$OR^5$, —$SR^5$, —$NR^6R^7$, —$NO_2$, —$C(O)R^5$, —$C(O)OR^5$, —$C(O)NR^6R^7$, —$C(O)NR^5S(O)_2R^6$, —$OC(O)R^5$, —$OC(O)NR^6R^7$, —$NR^5C(O)R^6$, —$NR^5C(O)NR^6R^7$, —$S(O)R^5$, —$S(O)_2R^5$, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;

or R⁶ and R⁷ are taken together with the atom to which they attached to form a 3-6 membered heterocyclyl,
provided the compound is other than a compound selected from Table 1X or a salt thereof.

In some embodiments, provided is a compound of formula (IVb), or a tautomer or isomer thereof, or a pharmaceutically acceptable salt of any of the foregoing.

In some embodiments, the compound of formula (I) is a compound of formula (IVc):

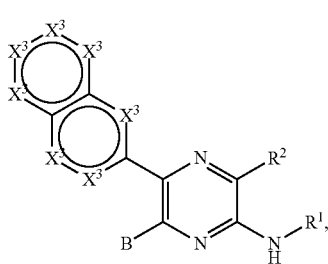

(IVc)

or a salt thereof, wherein $R^1$, $R^2$ and B are as defined for formula (I);
each $X^3$ is independently $CR^4$, CH or N;
each $R^4$ is independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl,
provided the compound is other than a compound selected from Table 1X or a salt thereof.

In some embodiments, provided is a compound of formula (IVc), or a tautomer or isomer thereof, or a pharmaceutically acceptable salt of any of the foregoing.

In some embodiments of formula (IV), $R^4$ is selected from the group consisting of halogen, —OR⁵ and $C_1$-$C_6$ alkyl optionally substituted by halogen.

In some embodiments, one $X^3$ is N, and the remaining $X^3$ are each $CR^4$. In some embodiments, two of the $X^3$ are N, and the remaining $X^3$ are each $CR^4$.

In some embodiments, the compound of formula (I) is a compound of formula (IVc-1):

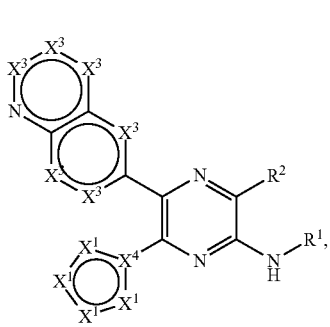

(IVc-1)

or a salt thereof, wherein $R^1$ and $R^2$ are as defined for formula (I);
each $X^1$ is independently O, S, NH, $NR^{4a}$, N, CH or $CR^{4b}$;
$X^4$ is C or N;
each $X^3$ is as defined for formula (IVc)
$R^{4a}$ is $C_1$-$C_6$ alkyl;
each $R^{4b}$ is independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, $C_3$-$C_6$ cycloalkyl, or $C_1$-$C_6$ alkyl optionally substituted by halogen;
where each $R^5$ is independently hydrogen, $C_1$-$C_6$ alkyl, or $C_3$-$C_6$ cycloalkyl; and
$R^6$ and $R^7$ are each independently hydrogen, $C_1$-$C_6$ alkyl, or $C_3$-$C_6$ cycloalkyl;
or $R^6$ and $R^7$ are taken together with the atom to which they attached to form a 3-6 membered heterocyclyl, provided the compound is other than a compound selected from Table 1X or a salt thereof.

In some embodiments, provided is a compound of formula (IVc-1), or a tautomer or isomer thereof, or a pharmaceutically acceptable salt of any of the foregoing.

In some embodiments, the compound of formula (I) is a compound of formula (IVc-2):

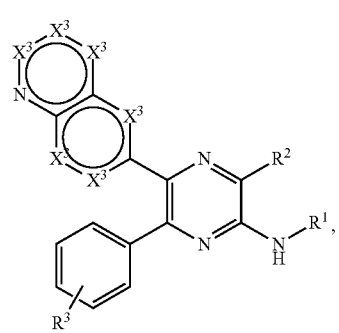

(IVc-2)

or a salt thereof, wherein $R^1$, $R^2$ and $R^3$ are as defined for formula (I);
each $X^3$ is as defined for formula (IVc);
provided the compound is other than a compound selected from Table IX or a salt thereof.

In some embodiments, provided is a compound of formula (IVc-2), or a tautomer or isomer thereof, or a pharmaceutically acceptable salt of any of the foregoing.

In some embodiments of a compound of any of the foregoing formula, A is

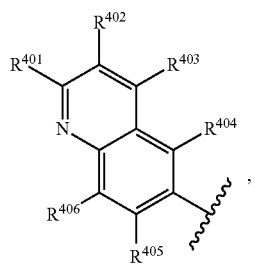

wherein $R^{401}$, $R^{402}$, $R^{403}$, $R^{404}$, $R^{405}$, and $R^{406}$ are each independently $R^4$. In some embodiments, $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen.

In some embodiments, A is

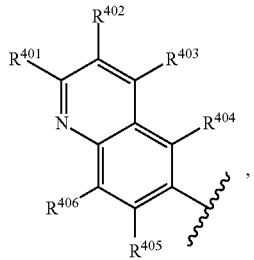

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is phenyl, optionally substituted with R$^3$.

In some embodiments, A is

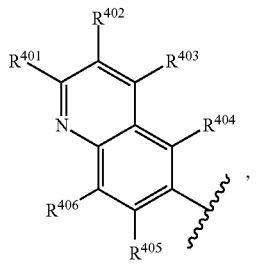

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC(O)NR$^6$R$^7$, —NR$^5$C(O)R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is 5- to 6-membered heteroaryl, optionally substituted with R$^4$.

In some embodiments, A is

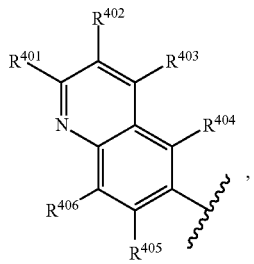

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O) NR$^5$S(O)$_2$R$^6$, —OC(O)R$^5$, —OC(O)NR$^6$R$^7$, —NR$^5$C(O) R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is 5-membered heteroaryl such as furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, each of which optionally substituted with R$^4$.

In some embodiments, A is

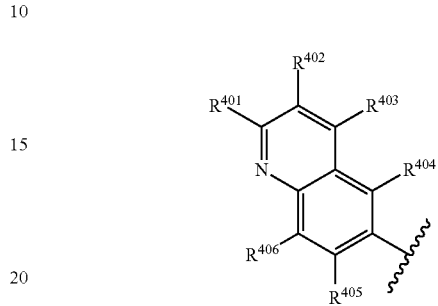

wherein $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O) NR$^5$S(O)$_2$R$^6$, —OC(O)R$^5$, —OC(O)NR$^6$R$^7$, —NR$^5$C(O) R$^6$, —NR$^5$C(O)NR$^6$R$^7$, —S(O)R$^5$, —S(O)$_2$R$^5$, C$_3$-C$_6$ cycloalkyl, or C$_1$-C$_6$ alkyl optionally substituted by halogen; and B is selected from the group consisting of:

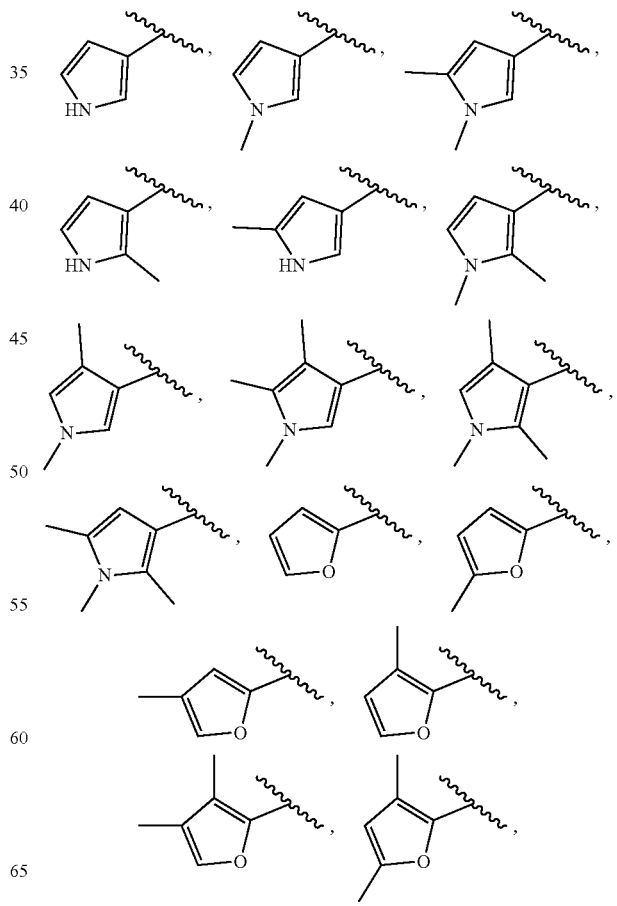

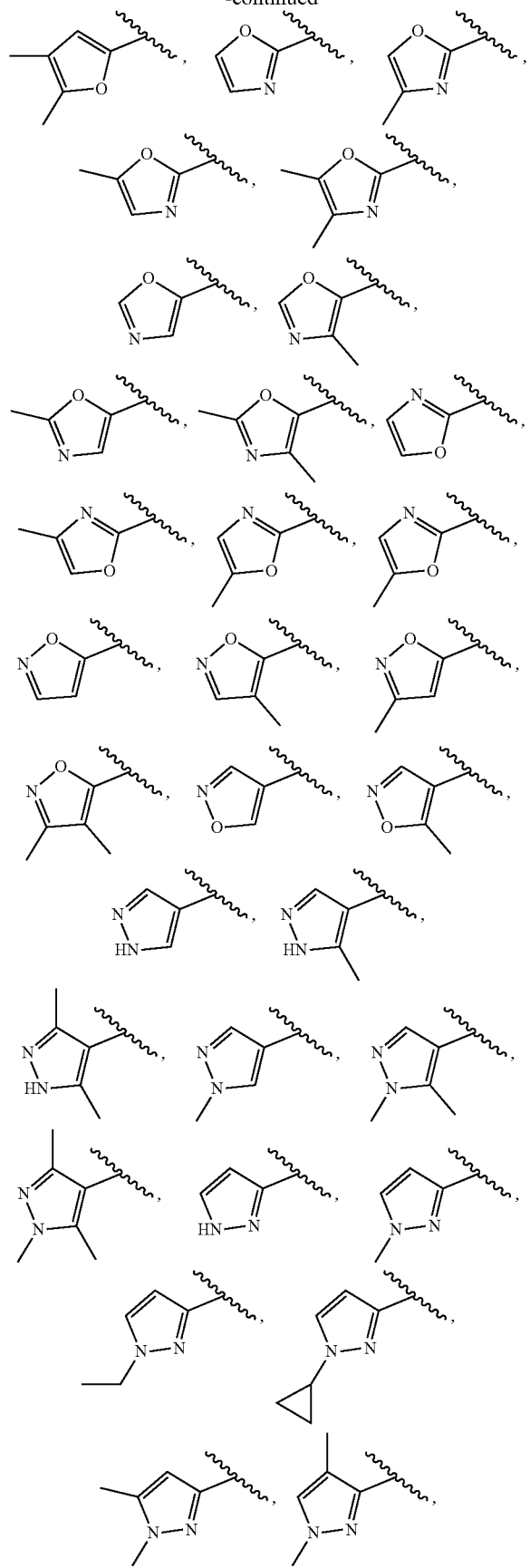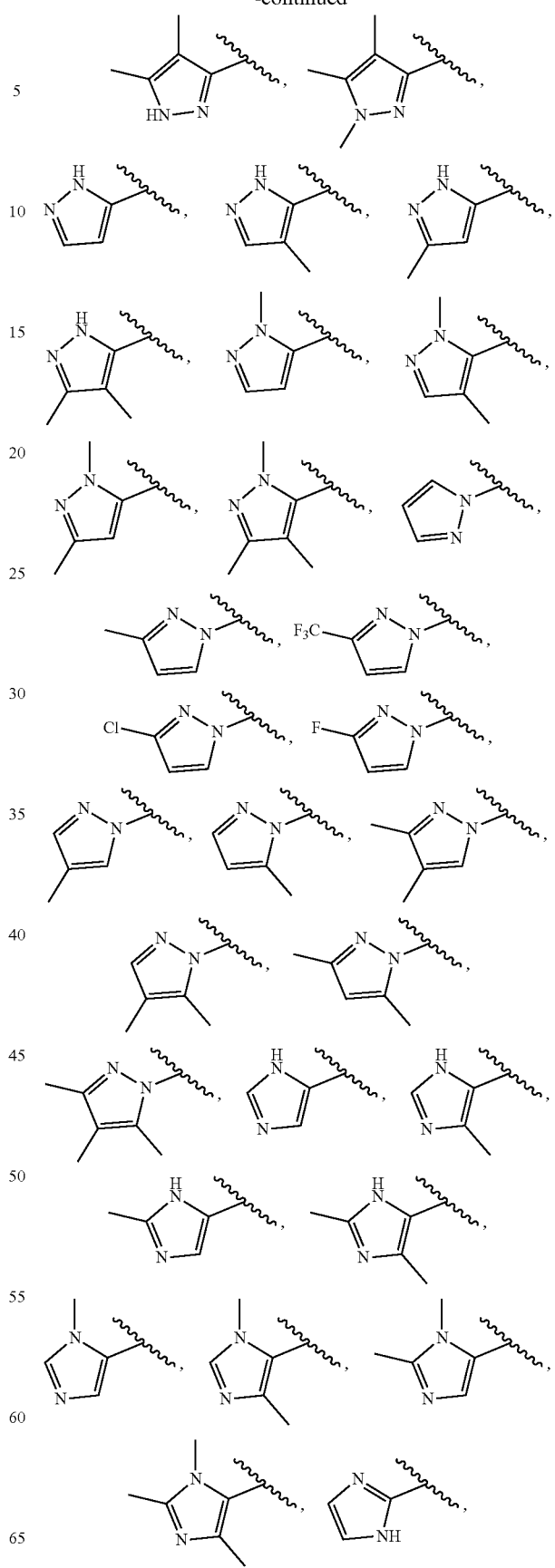

-continued
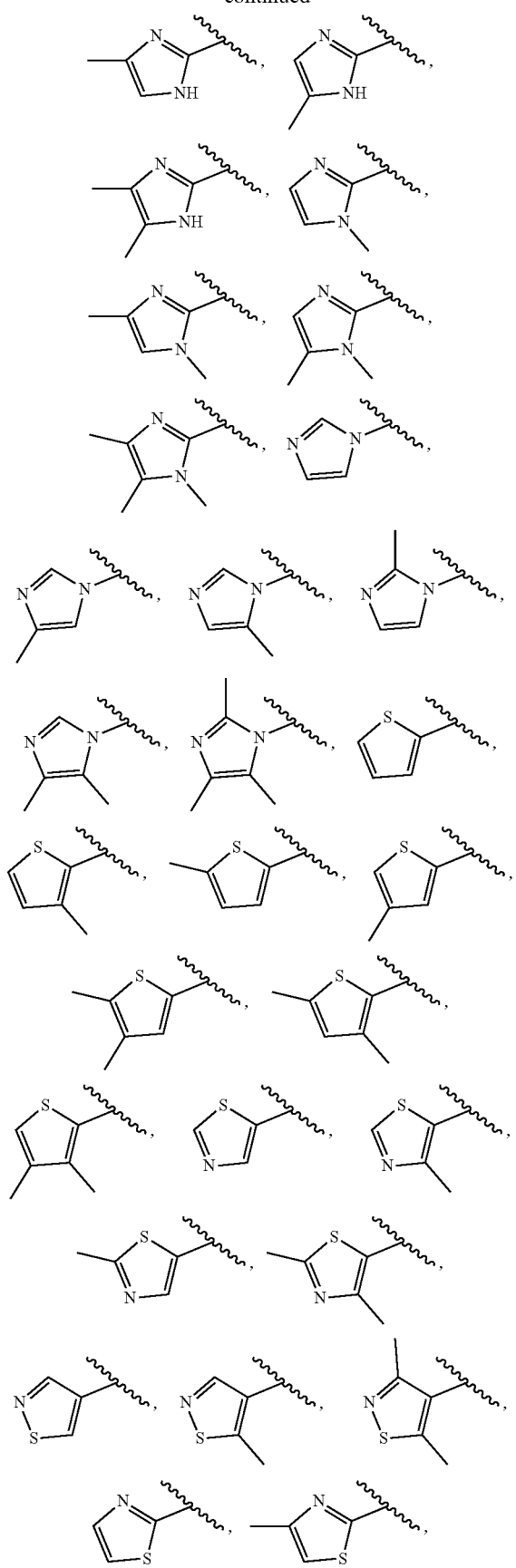
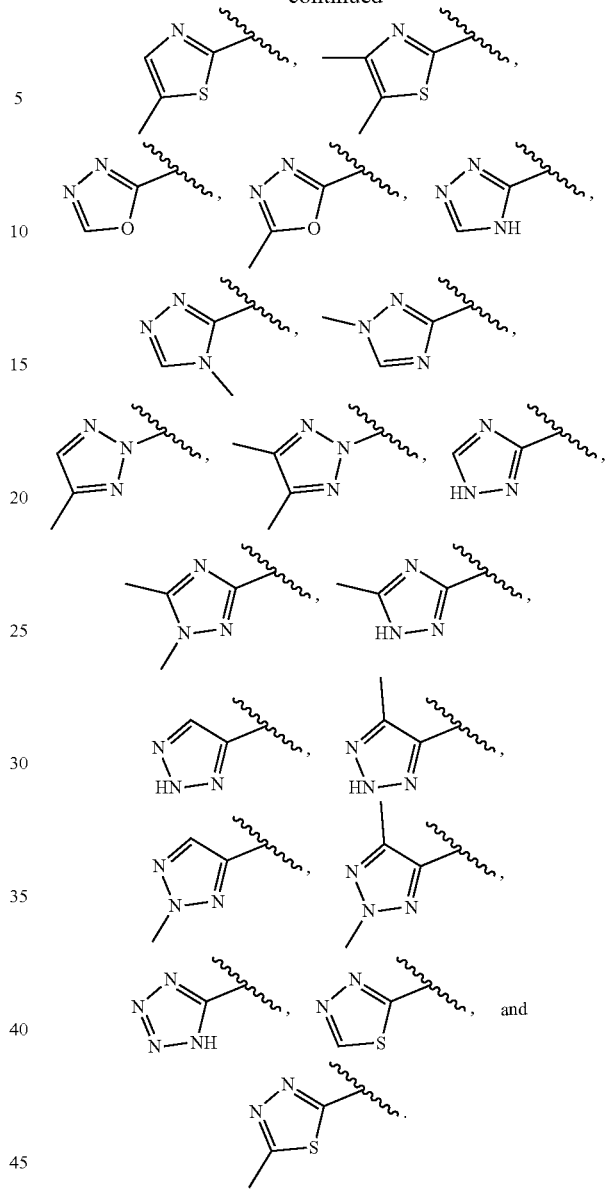
In some embodiments, A is
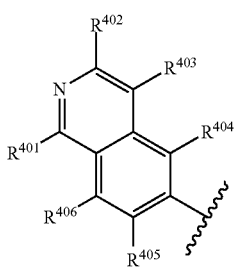
wherein $R^{401}$, $R^{402}$, $R^{403}$, $R^{404}$, $R^{405}$, and $R^{406}$ are each independently $R^4$. In some embodiments, $R^{401}$, $R^{402}$, $R^{403}$, $R^{404}$, $R^{405}$, and $R^{406}$ are each independently halogen, —CN, —OR$^5$, —SR$^5$, —NR$^6$R$^7$, —NO$_2$, —C(O)R$^5$, —C(O)OR$^5$, —C(O)NR$^6$R$^7$, —C(O)NR$^5$S(O)$_2$R$^6$, —OC(O)R$^5$, —OC (O)NR⁶R⁷, —NR⁵C(O)R⁶, —NR⁵C(O)NR⁶R⁷, —S(O)R⁵, —S(O)₂R⁵, C₃-C₆ cycloalkyl, or C₁-C₆ alkyl optionally substituted by halogen.

In some embodiments, A is

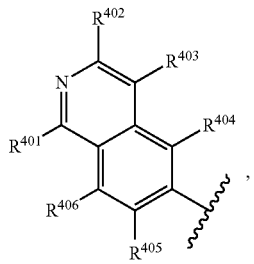

wherein R⁴⁰¹, R⁴⁰², R⁴⁰³, R⁴⁰⁴, R⁴⁰⁵, and R⁴⁰⁶ are each independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, C₃-C₆ cycloalkyl, or C₁-C₆ alkyl optionally substituted by halogen; and B is phenyl, optionally substituted with R³.

In some embodiments, A is

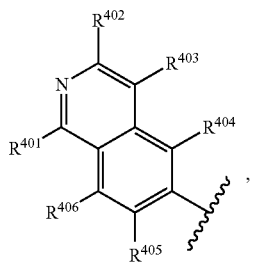

wherein R⁴⁰¹, R⁴⁰², R⁴⁰³, R⁴⁰⁴, R⁴⁰⁵, and R⁴⁰⁶ are each independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, C₃-C₆ cycloalkyl, or C₁-C₆ alkyl optionally substituted by halogen; and B is 5- to 6-membered heteroaryl, optionally substituted with R⁴.

In some embodiments, A is

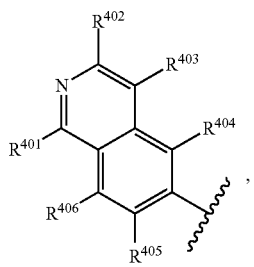

wherein R⁴⁰¹, R⁴⁰², R⁴⁰³, R⁴⁰⁴, R⁴⁰⁵, and R⁴⁰⁶ are each independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, C₃-C₆ cycloalkyl, or C₁-C₆ alkyl optionally substituted by halogen;

and B is 5-membered heteroaryl such as furanyl, oxazolyl, thiophenyl, pyrazolyl, isoxazolyl, 1,3,4-oxadiazolyl, imidazolyl, thiazolyl, isothiazolyl, triazolyl, 1,3,4-thiadiazolyl and tetrazolyl, each of which optionally substituted with R⁴.

In some embodiments, A is

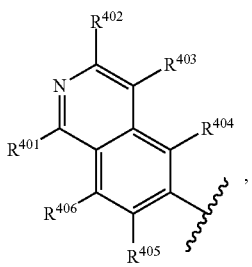

wherein R⁴⁰¹, R⁴⁰², R⁴⁰³, R⁴⁰⁴, R⁴⁰⁵, and R⁴⁰⁶ are each independently halogen, —CN, —OR⁵, —SR⁵, —NR⁶R⁷, —NO₂, —C(O)R⁵, —C(O)OR⁵, —C(O)NR⁶R⁷, —C(O)NR⁵S(O)₂R⁶, —OC(O)R⁵, —OC(O)NR⁶R⁷, —NR⁵C(O)R⁶, —NR⁵C(O)NR⁶R⁷, —S(O)R⁵, —S(O)₂R⁵, C₃-C₆ cycloalkyl, or C₁-C₆ alkyl optionally substituted by halogen; and B is selected from the group consisting of:

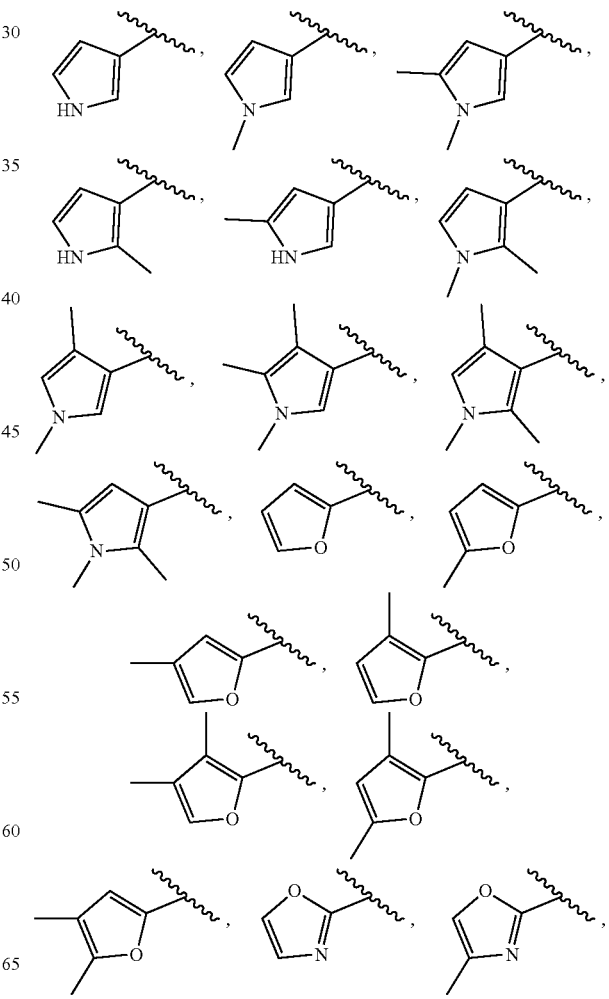

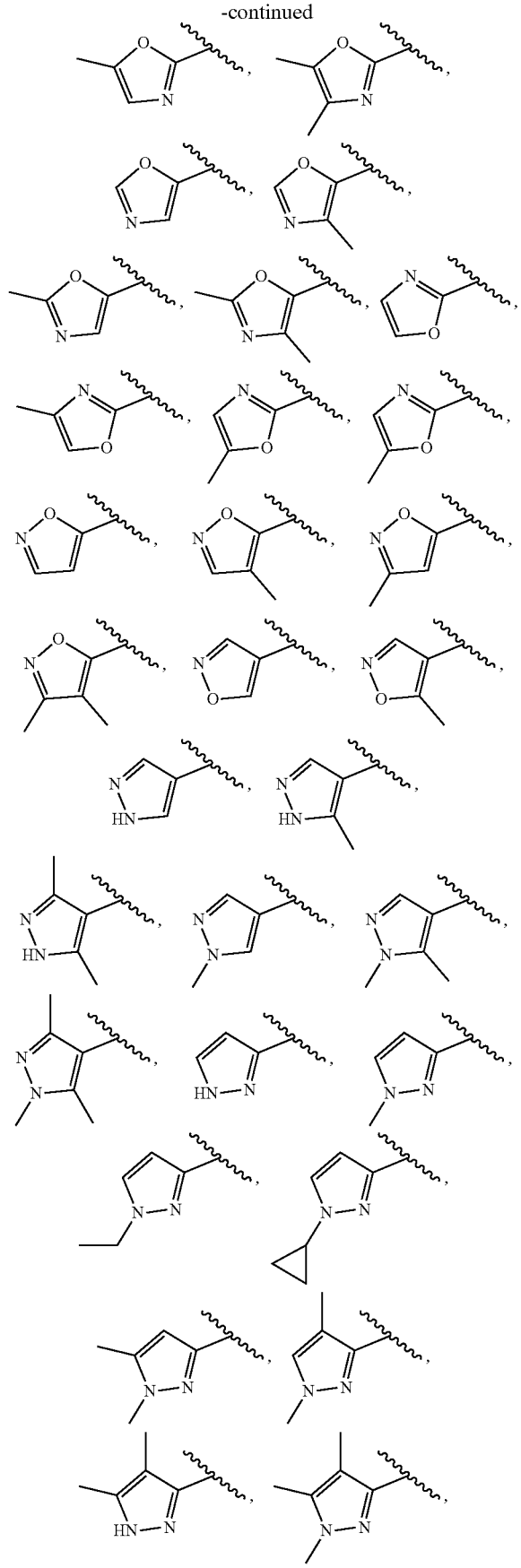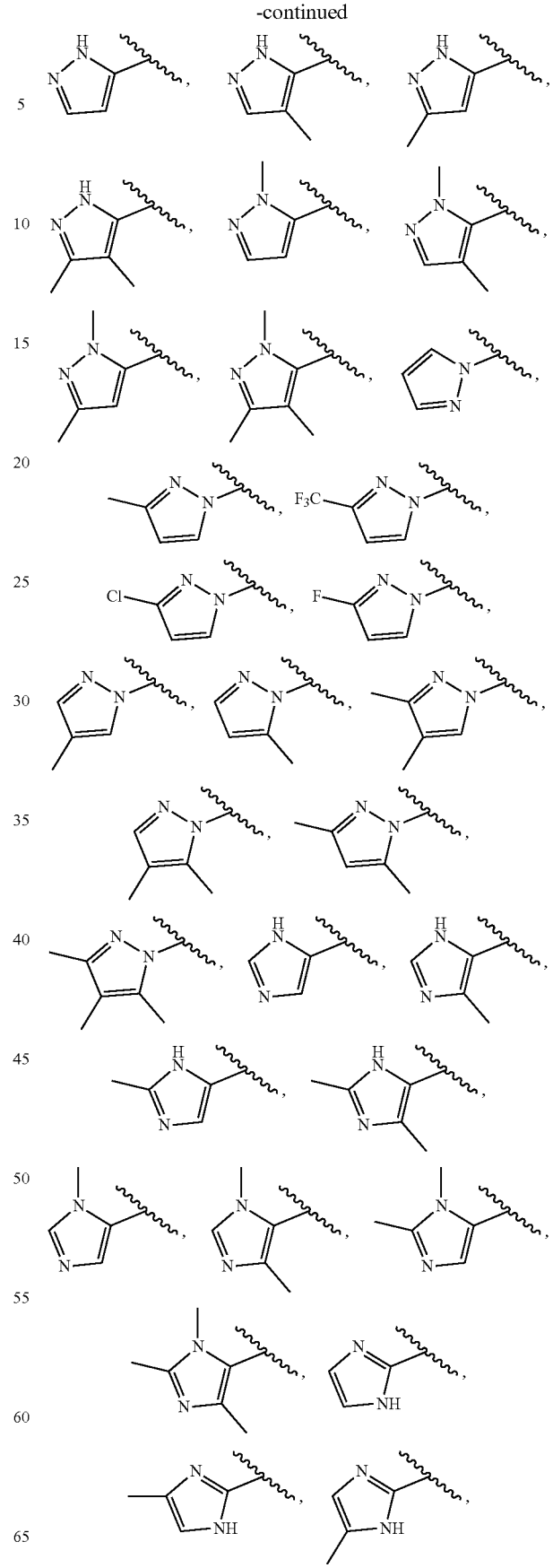

-continued

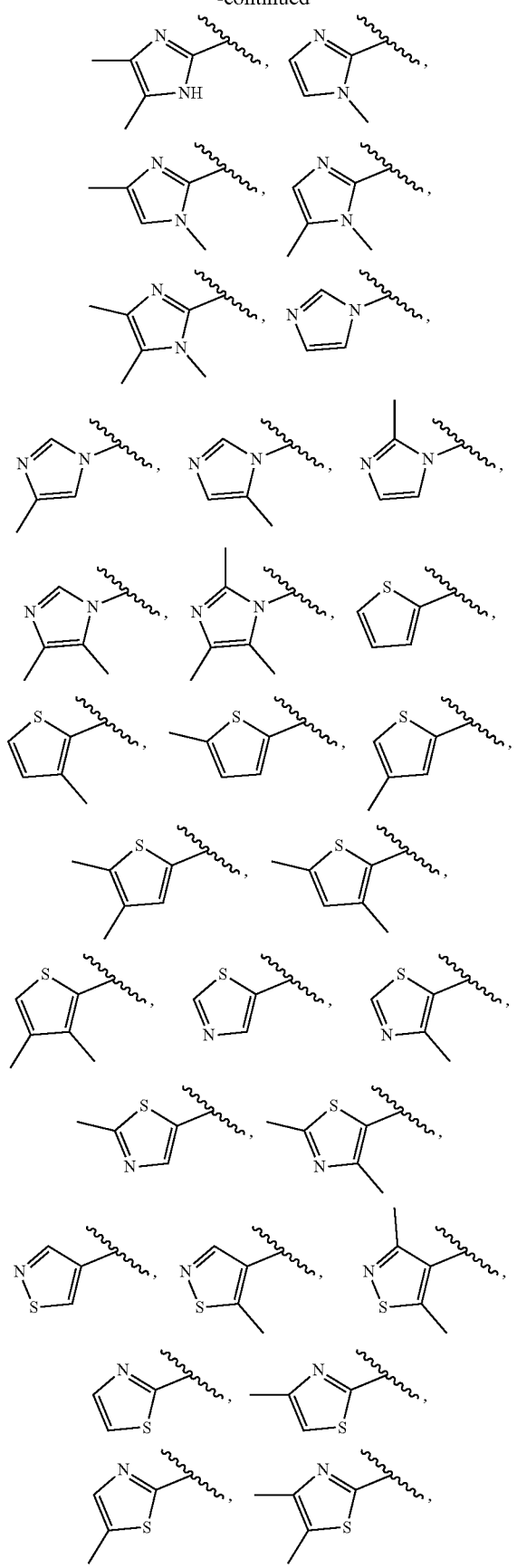

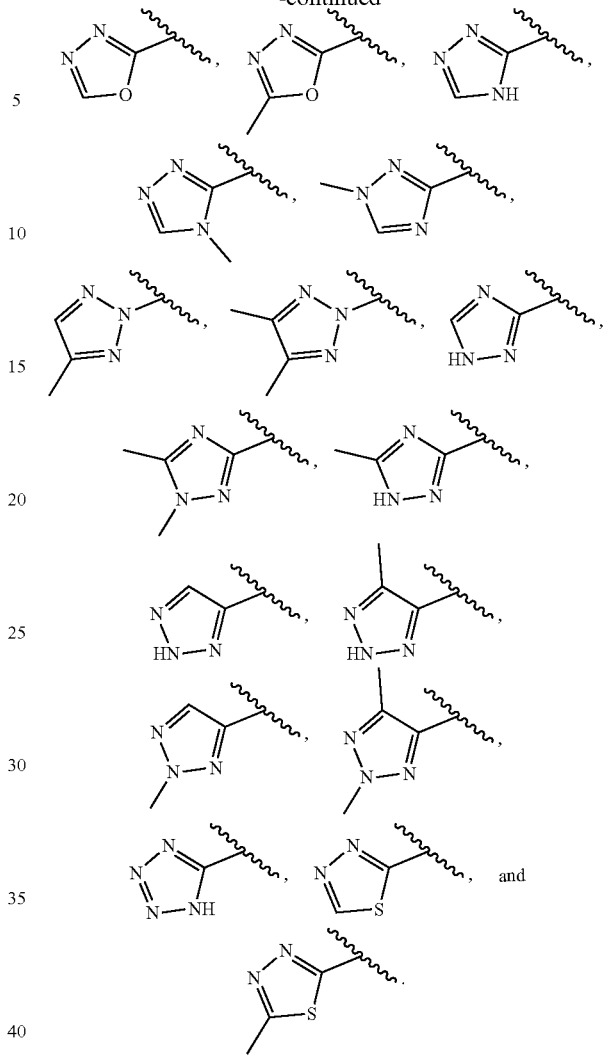

Also provided are salts of compounds referred to herein, such as pharmaceutically acceptable salts. The invention also includes any or all of the stereochemical forms, including any enantiomeric or diastereomeric forms, and any tautomers or other forms of the compounds described.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form. Unless otherwise stated, "substantially pure" intends a composition that contains no more than 35% impurity, wherein the impurity denotes a compound other than the compound comprising the majority of the composition or a salt thereof. In some embodiments, a composition of substantially pure compound or a salt thereof is provided wherein the composition contains no more than 25%, 20%, 15%, 10%, or 5% impurity. In some embodiments, a composition of substantially pure compound or a salt thereof is provided wherein the composition contains or no more than 3%, 2%, 1% or 0.5% impurity.

Representative compounds of formula (I) or (II) are listed in Table 1. In some embodiments, provided herein are compounds described in Table 1, including pharmaceutically acceptable salts thereof, and uses thereof. It is understood that individual enantiomers and diastereomers if not depicted and their corresponding structures can be readily determined therefrom. For example, compounds 75 and 76 are representative stereoisomers of compound 73.

TABLE 1

| Compd No. | Structure |
|---|---|
| 1 | 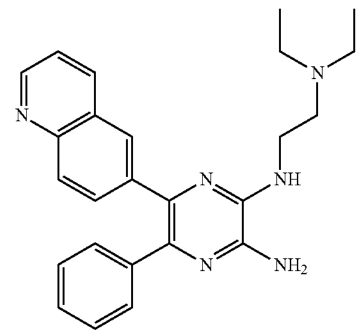 [SMILES: CCN(CC)CCNc1nc(-c2ccc3ncccc3c2)c(-c2ccccc2)nc1N] |
| 2 | 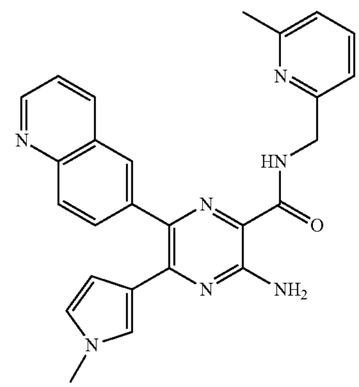 [SMILES: Cc1cccc(CNC(=O)c2nc(-c3ccc4ncccc4c3)c(-c3ccn(C)c3)nc2N)n1] |
| 3 | 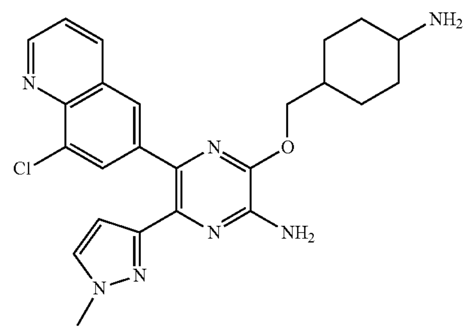 [SMILES: Cn1ccc(-c2nc(N)c(OCC3CCC(N)CC3)nc2-c2cc(Cl)c3ncccc3c2)n1] |
| 4 | 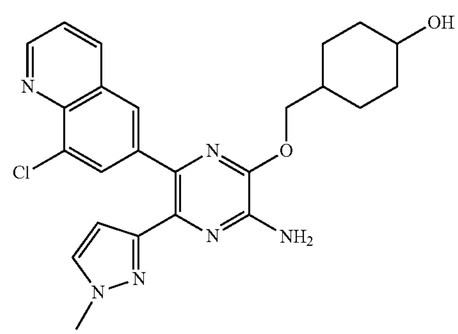 [SMILES: Cn1ccc(-c2nc(N)c(OCC3CCC(O)CC3)nc2-c2cc(Cl)c3ncccc3c2)n1] |

TABLE 1-continued
| Compd No. | Structure |
|---|---|
| 5 | 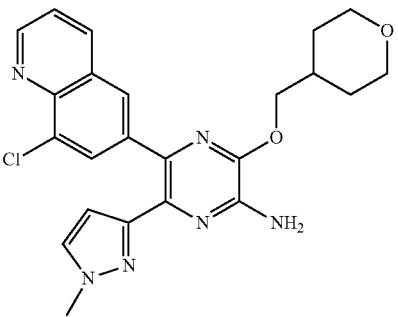 [SMILES: Cn1ccc(-c2nc(N)c(OCC3CCOCC3)nc2-c2cc(Cl)c3ncccc3c2)n1] |
| 6 | 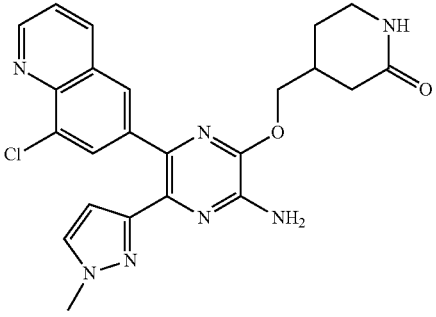 [SMILES: Cn1ccc(-c2nc(N)c(OCC3CCNC(=O)C3)nc2-c2cc(Cl)c3ncccc3c2)n1] |
| 7 | 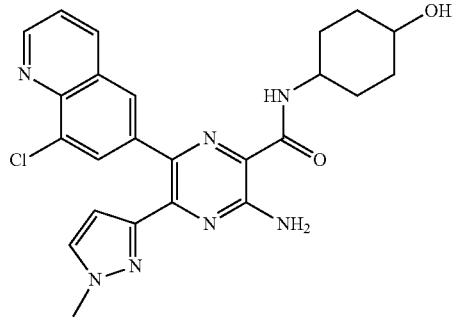 [SMILES: Cn1ccc(-c2nc(N)c(C(=O)NC3CCC(O)CC3)nc2-c2cc(Cl)c3ncccc3c2)n1] |
| 8 | 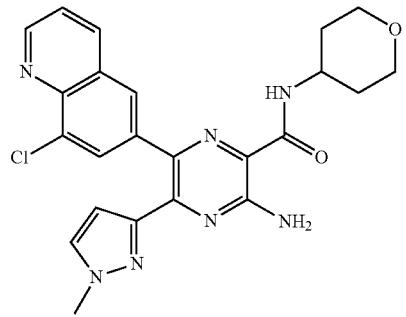 [SMILES: Cn1ccc(-c2nc(N)c(C(=O)NC3CCOCC3)nc2-c2cc(Cl)c3ncccc3c2)n1] |

TABLE 1-continued

| Compd No. | Structure |
|---|---|
| 9 | *8-chloroquinolin-6-yl / 1-methylpyrazol-3-yl / 3-amino-pyrazine-2-carboxamide with N-(2-morpholinoethyl)* |
| 10 | *8-chloroquinolin-6-yl / 1-methylpyrazol-3-yl / 3-amino-pyrazine-2-carboxamide with N-(2-(tetrahydropyran-4-yl)ethyl)* |
| 11 | *8-chloroquinolin-6-yl / 1-methylpyrazol-3-yl / 3-amino-pyrazine with 2-((tetrahydropyran-4-yl)methylamino)* |
| 12 | *7-chloro-1H-indazol-5-yl / phenyl / 3-amino-pyrazine with 2-((4-aminocyclohexyl)methoxy)* |

TABLE 1-continued

| Compd No. | Structure |
|---|---|
| 13 | 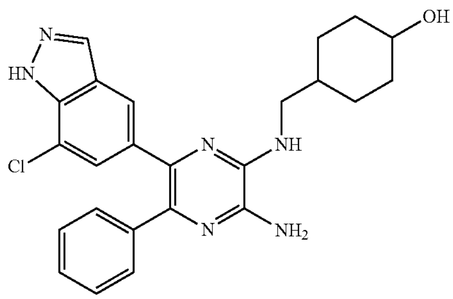 [SMILES: Nc1nc(-c2ccccc2)c(-c2cc(Cl)c3[nH]ncc3c2)nc1NCC1CCC(O)CC1] |
| 14 | 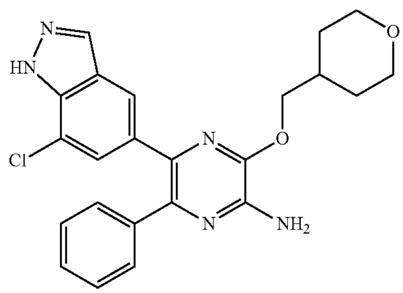 [SMILES: Nc1nc(-c2ccccc2)c(-c2cc(Cl)c3[nH]ncc3c2)nc1OCC1CCOCC1] |
| 15 | 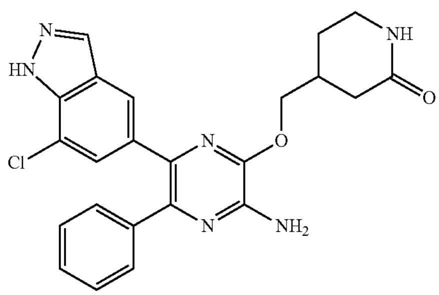 [SMILES: Nc1nc(-c2ccccc2)c(-c2cc(Cl)c3[nH]ncc3c2)nc1OCC1CCNC(=O)C1] |
| 16 | 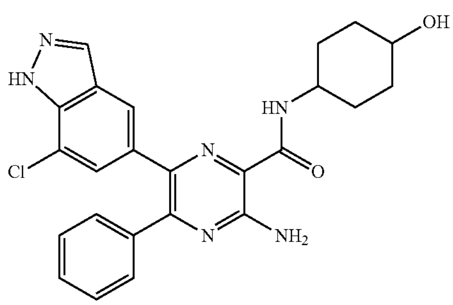 [SMILES: Nc1nc(-c2ccccc2)c(-c2cc(Cl)c3[nH]ncc3c2)nc1C(=O)NC1CCC(O)CC1] |
| 17 | 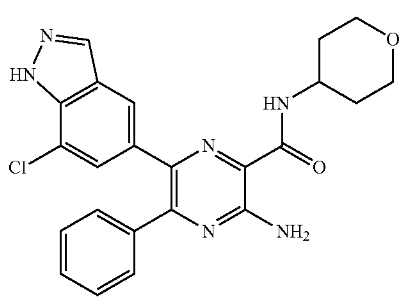 [SMILES: Nc1nc(-c2ccccc2)c(-c2cc(Cl)c3[nH]ncc3c2)nc1C(=O)NC1CCOCC1] |

TABLE 1-continued
| Compd No. | Structure |
|---|---|
| 18 | 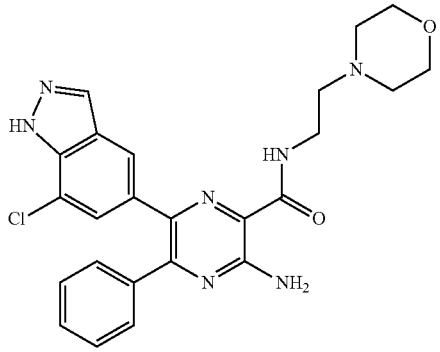 [SMILES: Nc1nc(-c2ccccc2)c(-c2cc(Cl)c3[nH]ncc3c2)nc1C(=O)NCCN1CCOCC1] |
| 19 | 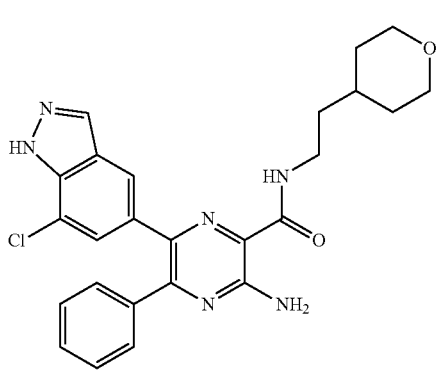 [SMILES: Nc1nc(-c2ccccc2)c(-c2cc(Cl)c3[nH]ncc3c2)nc1C(=O)NCCC1CCOCC1] |
| 20 | 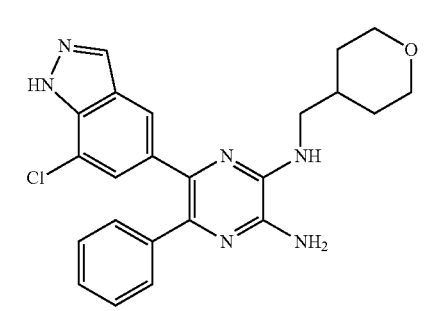 [SMILES: Nc1nc(-c2ccccc2)c(-c2cc(Cl)c3[nH]ncc3c2)nc1NCC1CCOCC1] |
| 21 | 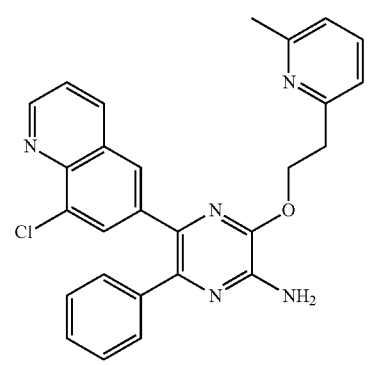 [SMILES: Cc1cccc(CCOc2nc(-c3cc(Cl)c4ncccc4c3)c(-c3ccccc3)nc2N)n1] |

TABLE 1-continued

| Compd No. | Structure |
|---|---|
| 22 | (chemical structure) |
| 23 | (chemical structure) |
| 24 | (chemical structure) |
| 25 | (chemical structure) |

TABLE 1-continued

| Compd No. | Structure |
|---|---|
| 26 | 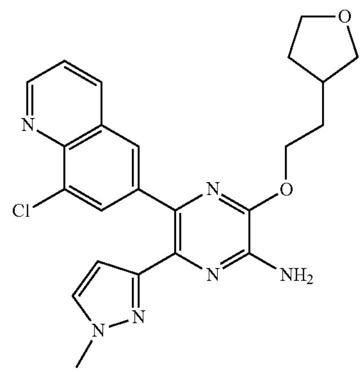 [SMILES: Cn1ccc(-c2nc(N)c(OCCC3CCOC3)nc2-c2cc(Cl)c3ncccc3c2)n1] |
| 27 | 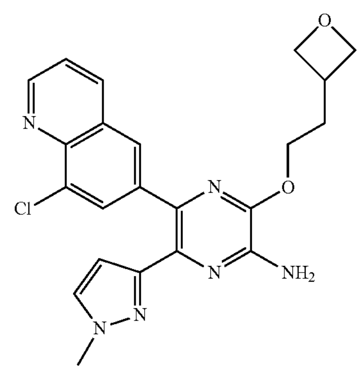 [SMILES: Cn1ccc(-c2nc(N)c(OCCC3COC3)nc2-c2cc(Cl)c3ncccc3c2)n1] |
| 28 | 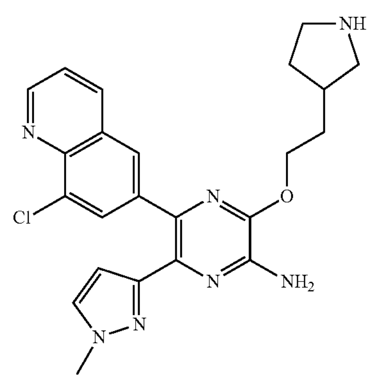 [SMILES: Cn1ccc(-c2nc(N)c(OCCC3CCNC3)nc2-c2cc(Cl)c3ncccc3c2)n1] |
| 29 | 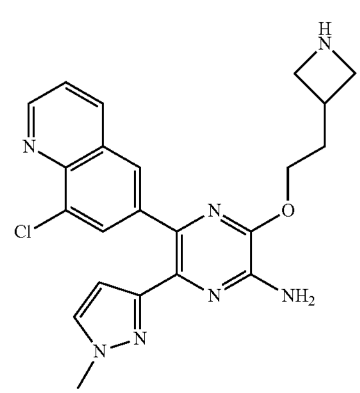 [SMILES: Cn1ccc(-c2nc(N)c(OCCC3CNC3)nc2-c2cc(Cl)c3ncccc3c2)n1] |

TABLE 1-continued

| Compd No. | Structure |
|---|---|
| 30 | (8-chloroquinolin-6-yl / 1-methylpyrazol-3-yl / 2-(1-methyl-1H-imidazol-4-yl)ethoxy substituted aminopyrazine) |
| 31 | (8-chloroquinolin-6-yl / 1-methylpyrazol-3-yl / 2-(1H-imidazol-4-yl)ethoxy substituted aminopyrazine) |
| 32 | (8-chloroquinolin-6-yl / 1-methylpyrazol-3-yl / 2-(2-methylthiazol-4-yl)ethoxy substituted aminopyrazine) |
| 33 | (8-chloroquinolin-6-yl / 1-methylpyrazol-3-yl / 2-(2-methyloxazol-4-yl)ethoxy substituted aminopyrazine) |

TABLE 1-continued
| Compd No. | Structure |
|---|---|
| 34 | 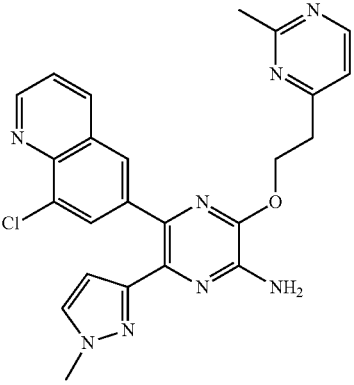 [SMILES: Cc1nccc(CCOc2nc(-c3cc(Cl)c4ncccc4c3)c(-c3ccn(C)n3)nc2N)n1] |
| 35 | 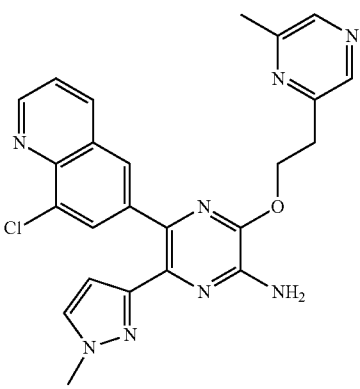 [SMILES: Cc1cncc(CCOc2nc(-c3cc(Cl)c4ncccc4c3)c(-c3ccn(C)n3)nc2N)n1] |
| 36 | 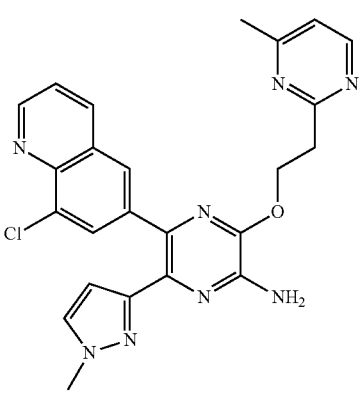 [SMILES: Cc1ccnc(CCOc2nc(-c3cc(Cl)c4ncccc4c3)c(-c3ccn(C)n3)nc2N)n1] |
| 37 | 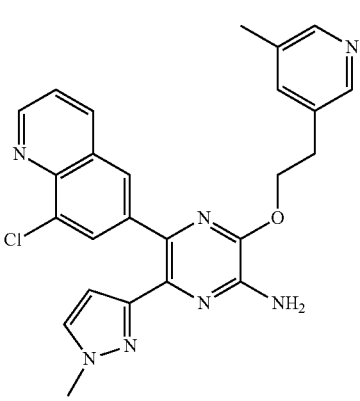 [SMILES: Cc1cncc(CCOc2nc(-c3cc(Cl)c4ncccc4c3)c(-c3ccn(C)n3)nc2N)c1] |

TABLE 1-continued
| Compd No. | Structure |
|---|---|
| 38 | 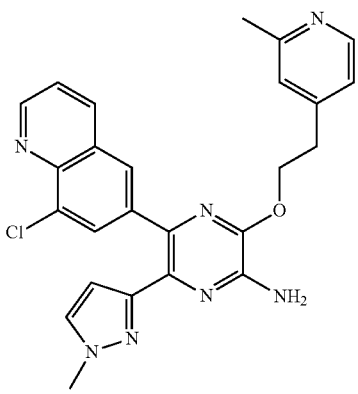 [SMILES: Cc1cc(CCOc2nc(-c3cc(Cl)c4ncccc4c3)c(-c3ccn(C)n3)nc2N)ccn1] |
| 39 | 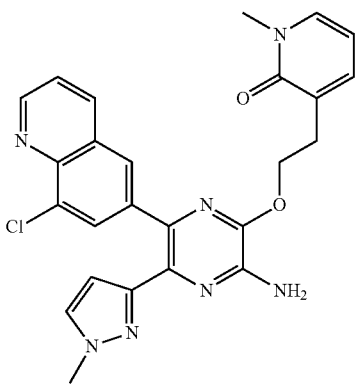 [SMILES: Cn1ccc(-c2nc(N)c(OCCc3cccn(C)c3=O)nc2-c2cc(Cl)c3ncccc3c2)n1] |
| 40 | 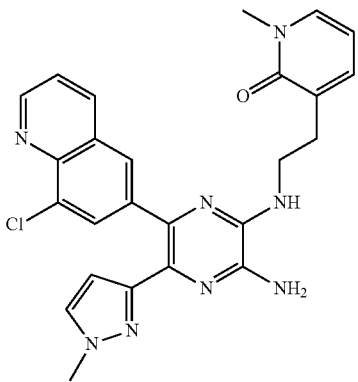 [SMILES: Cn1ccc(-c2nc(N)c(NCCc3cccn(C)c3=O)nc2-c2cc(Cl)c3ncccc3c2)n1] |
| 41 | 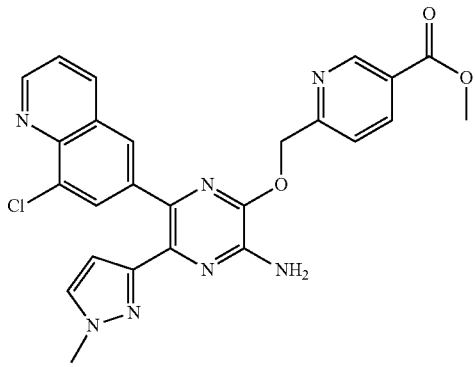 [SMILES: COC(=O)c1ccc(COc2nc(-c3cc(Cl)c4ncccc4c3)c(-c3ccn(C)n3)nc2N)nc1] |

TABLE 1-continued
| Compd No. | Structure |
|---|---|
| 42 | 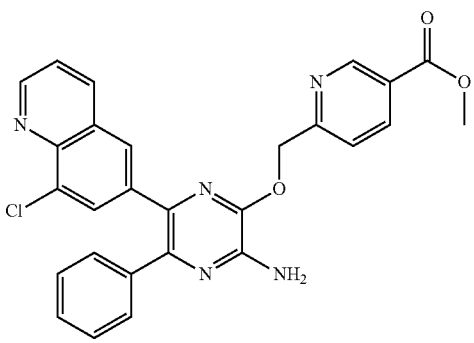 [SMILES: COC(=O)c1ccc(COc2nc(-c3cc(Cl)c4ncccc4c3)c(-c3ccccc3)nc2N)nc1] |
| 43 | 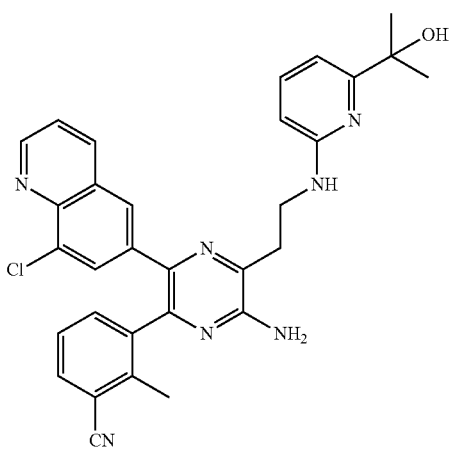 [SMILES: Cc1c(C#N)cccc1-c1nc(N)c(CCNc2cccc(C(C)(C)O)n2)nc1-c1cc(Cl)c2ncccc2c1] |
| 44 | 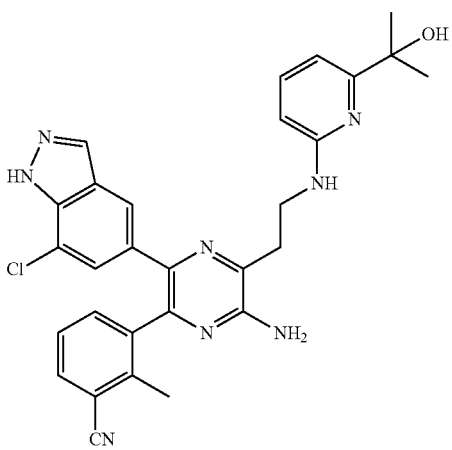 [SMILES: Cc1c(C#N)cccc1-c1nc(N)c(CCNc2cccc(C(C)(C)O)n2)nc1-c1cc(Cl)c2[nH]ncc2c1] |

TABLE 1-continued
| Compd No. | Structure |
|---|---|
| 45 | 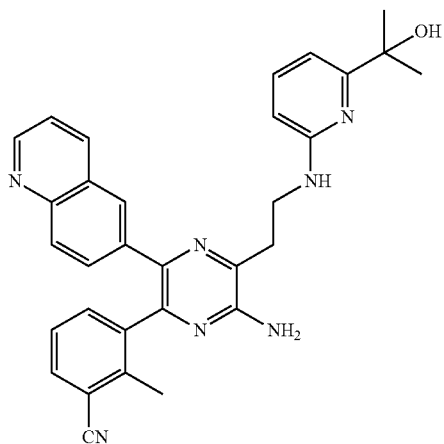 [SMILES: Cc1c(C#N)cccc1-c1nc(N)c(CCNc2cccc(C(C)(C)O)n2)nc1-c1ccc2ncccc2c1] |
| 46 | 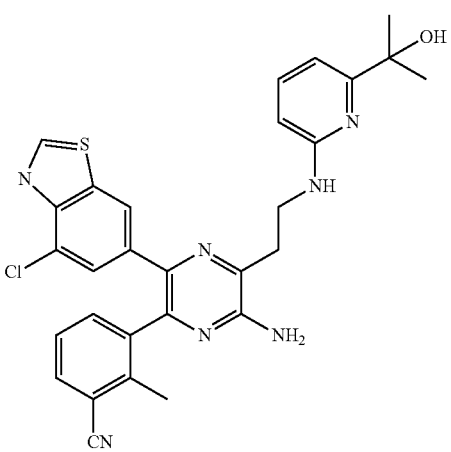 |
| 47 | 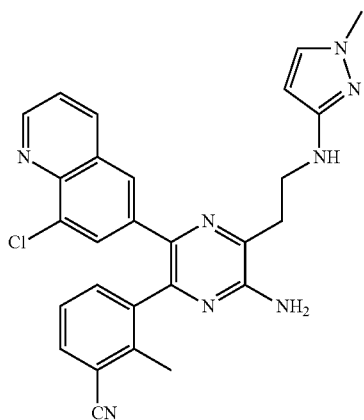 [SMILES: Cc1c(C#N)cccc1-c1nc(N)c(CCNc2ccn(C)n2)nc1-c1cc(Cl)c2ncccc2c1] |

TABLE 1-continued

| Compd No. | Structure |
|---|---|
| 48 | 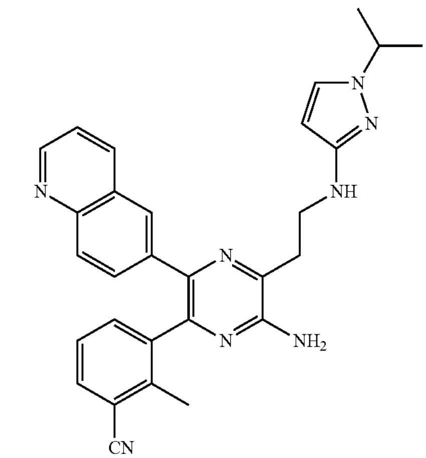 [SMILES: Cc1c(C#N)cccc1-c1nc(N)c(CCNc2ccn(C(C)C)n2)nc1-c1ccc2ncccc2c1] |
| 49 | 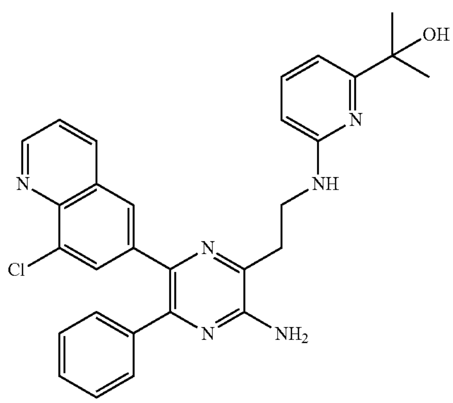 [SMILES: CC(C)(O)c1cccc(NCCc2nc(-c3cc(Cl)c4ncccc4c3)c(-c3ccccc3)nc2N)n1] |
| 50 | 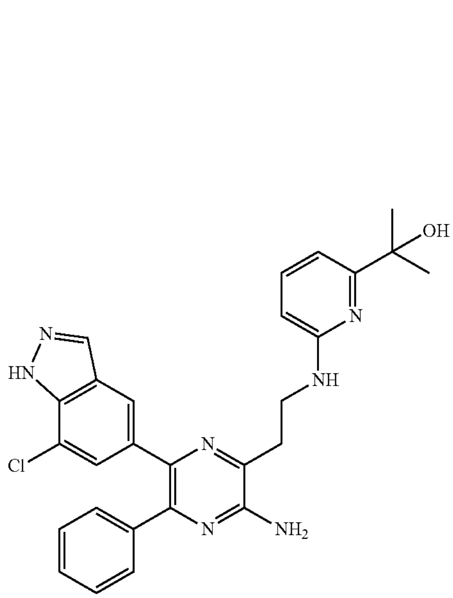 [SMILES: CC(C)(O)c1cccc(NCCc2nc(-c3cc(Cl)c4[nH]ncc4c3)c(-c3ccccc3)nc2N)n1] |

TABLE 1-continued

| Compd No. | Structure |
|---|---|
| 51 | 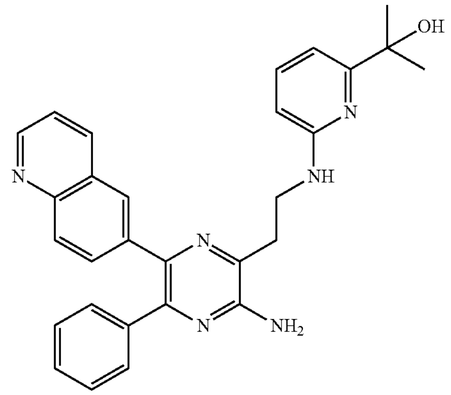 [SMILES: CC(C)(O)c1cccc(NCCc2nc(-c3ccc4ncccc4c3)c(-c3ccccc3)nc2N)n1] |
| 52 | 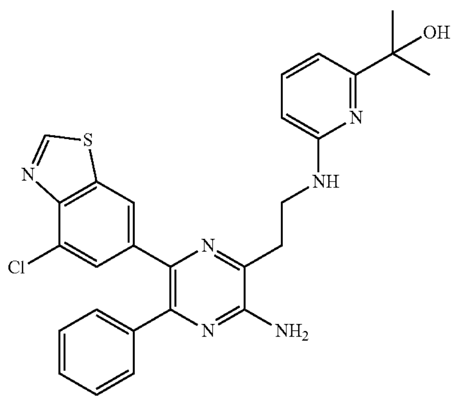 [SMILES: CC(C)(O)c1cccc(NCCc2nc(-c3cc(Cl)c4ncsc4c3)c(-c3ccccc3)nc2N)n1] |
| 53 | 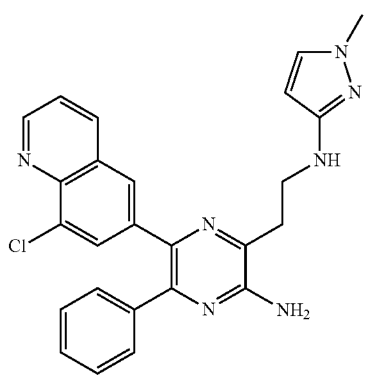 [SMILES: Cn1ccc(NCCc2nc(-c3cc(Cl)c4ncccc4c3)c(-c3ccccc3)nc2N)n1] |
| 54 | 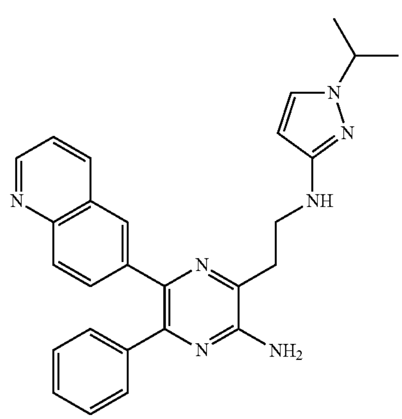 [SMILES: CC(C)n1ccc(NCCc2nc(-c3ccc4ncccc4c3)c(-c3ccccc3)nc2N)n1] |

TABLE 1-continued
| Compd No. | Structure |
|---|---|
| 55 | 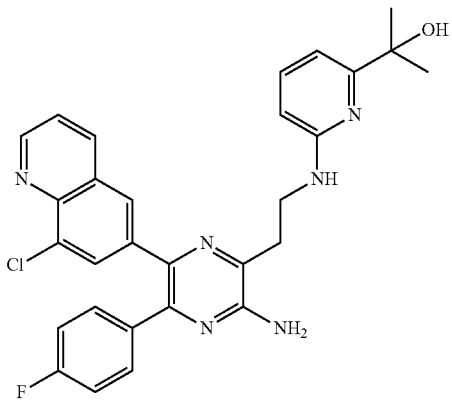 [SMILES: CC(C)(O)c1cccc(NCCc2nc(-c3cc(Cl)c4ncccc4c3)c(-c3ccc(F)cc3)nc2N)n1] |
| 56 | 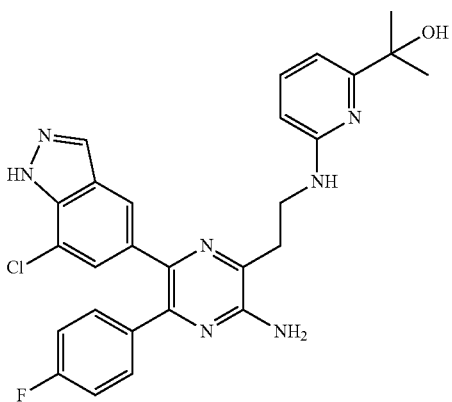 [SMILES: CC(C)(O)c1cccc(NCCc2nc(-c3cc(Cl)c4[nH]ncc4c3)c(-c3ccc(F)cc3)nc2N)n1] |
| 57 | 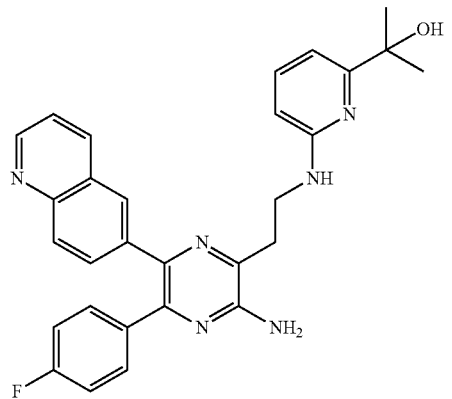 [SMILES: CC(C)(O)c1cccc(NCCc2nc(-c3ccc4ncccc4c3)c(-c3ccc(F)cc3)nc2N)n1] |

TABLE 1-continued
| Compd No. | Structure |
|---|---|
| 58 | 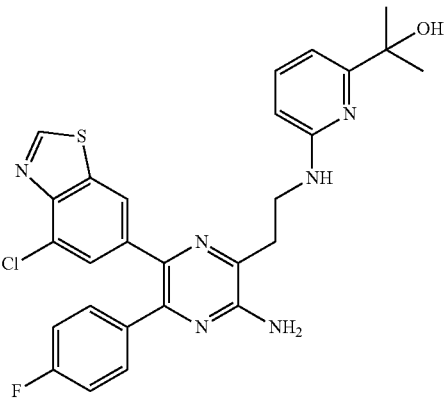 [SMILES: CC(C)(O)c1cccc(NCCc2nc(-c3cc(Cl)c4ncsc4c3)c(-c3ccc(F)cc3)nc2N)n1] |
| 59 | 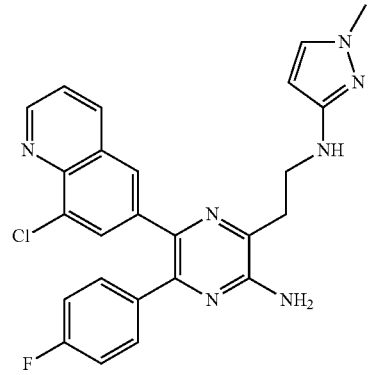 [SMILES: Cn1ccc(NCCc2nc(-c3cc(Cl)c4ncccc4c3)c(-c3ccc(F)cc3)nc2N)n1] |
| 60 | 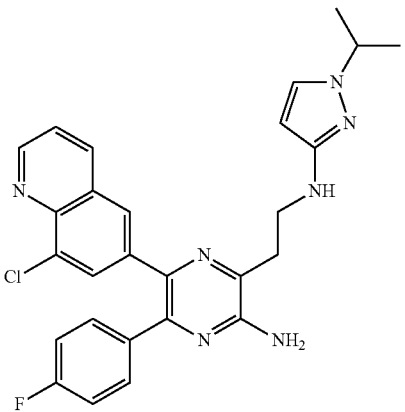 [SMILES: CC(C)n1ccc(NCCc2nc(-c3cc(Cl)c4ncccc4c3)c(-c3ccc(F)cc3)nc2N)n1] |

TABLE 1-continued
| Compd No. | Structure |
|---|---|
| 61 | 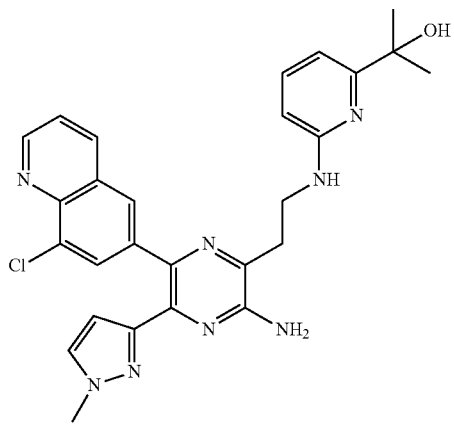 [SMILES: Cn1ccc(-c2nc(N)c(CCNc3cccc(C(C)(C)O)n3)nc2-c2cc(Cl)c3ncccc3c2)n1] |
| 62 | 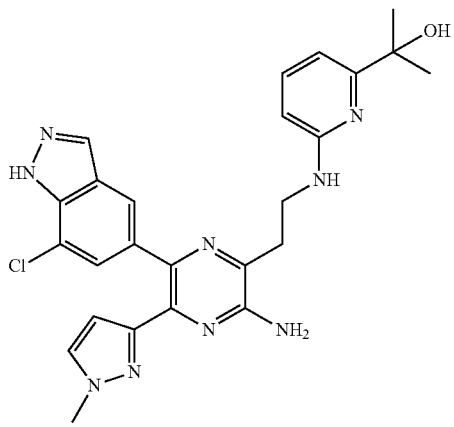 [SMILES: Cn1ccc(-c2nc(N)c(CCNc3cccc(C(C)(C)O)n3)nc2-c2cc(Cl)c3[nH]ncc3c2)n1] |
| 63 | 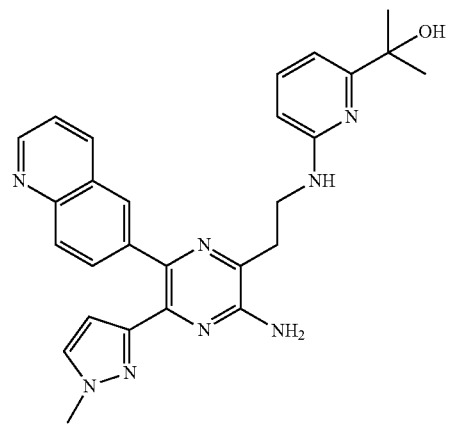 [SMILES: Cn1ccc(-c2nc(N)c(CCNc3cccc(C(C)(C)O)n3)nc2-c2ccc3ncccc3c2)n1] |

TABLE 1-continued
| Compd No. | Structure |
|---|---|
| 64 | 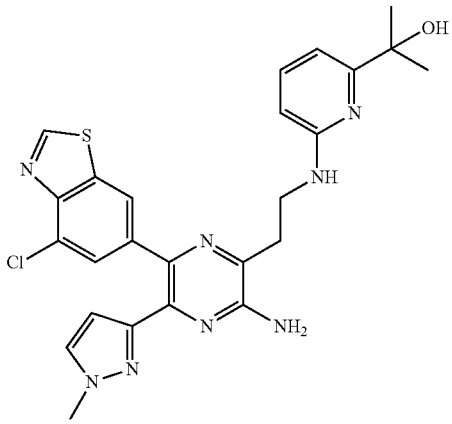 [SMILES: Cn1ccc(-c2nc(N)c(CCNc3cccc(C(C)(C)O)n3)nc2-c2cc(Cl)c3ncsc3c2)n1] |
| 65 | 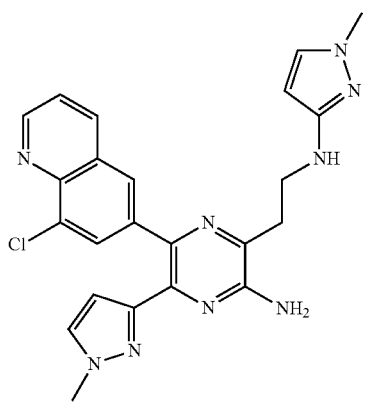 [SMILES: Cn1ccc(NCCc2nc(-c3cc(Cl)c4ncccc4c3)c(-c3ccn(C)n3)nc2N)n1] |
| 66 | 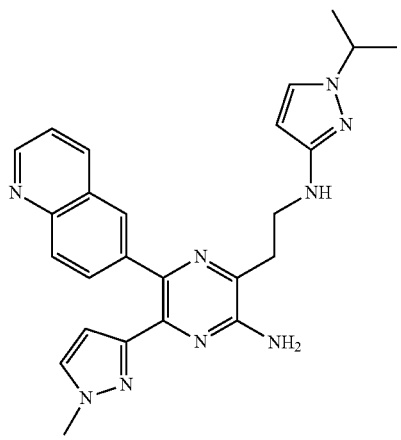 [SMILES: CC(C)n1ccc(NCCc2nc(-c3ccc4ncccc4c3)c(-c3ccn(C)n3)nc2N)n1] |

TABLE 1-continued

| Compd No. | Structure |
|---|---|
| 67 | *(structure)* |
| 68 | *(structure)* |
| 69 | *(structure)* |

TABLE 1-continued
| Compd No. | Structure |
|---|---|
| 70 | 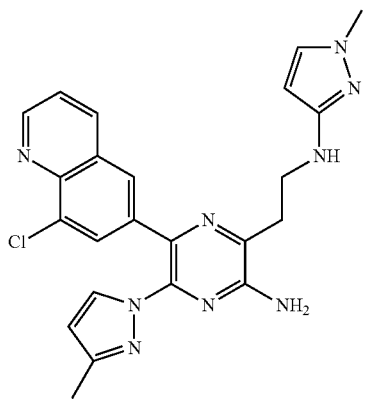 [SMILES: Cc1ccn(-c2nc(N)c(CCNc3ccn(C)n3)nc2-c2cc(Cl)c3ncccc3c2)n1] |
| 71 | 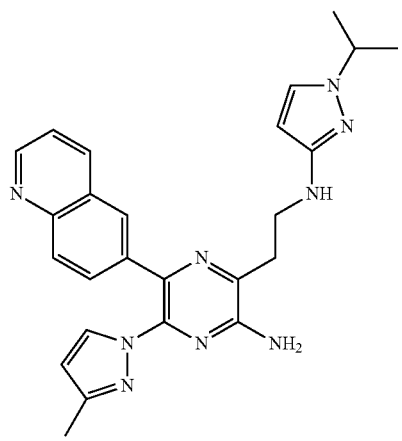 [SMILES: Cc1ccn(-c2nc(N)c(CCNc3ccn(C(C)C)n3)nc2-c2ccc3ncccc3c2)n1] |
| 72 | 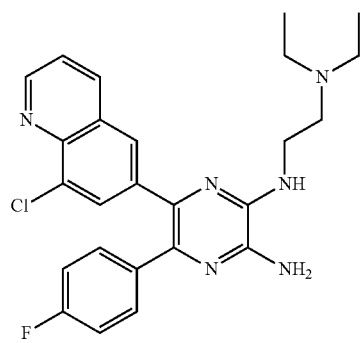 [SMILES: CCN(CC)CCNc1nc(-c2cc(Cl)c3ncccc3c2)c(-c2ccc(F)cc2)nc1N] |
| 73 | 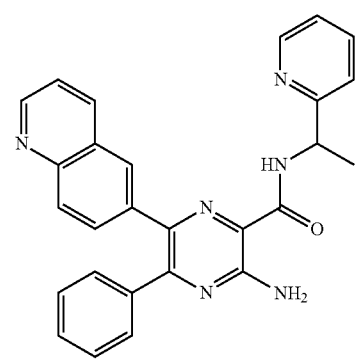 [SMILES: CC(NC(=O)c1nc(-c2ccc3ncccc3c2)c(-c2ccccc2)nc1N)c1ccccn1] |

TABLE 1-continued

| Compd No. | Structure |
|---|---|
| 74 | 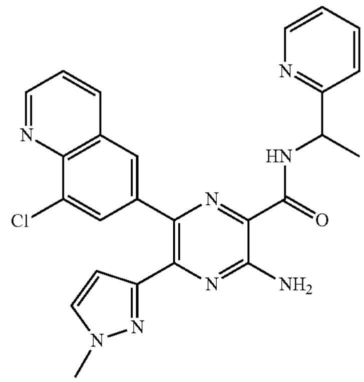 [SMILES: CC(NC(=O)c1nc(-c2cc(Cl)c3ncccc3c2)c(-c2ccn(C)n2)nc1N)c1ccccn1] |
| 75 | 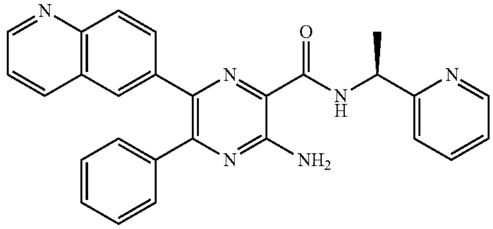 [SMILES: C[C@H](NC(=O)c1nc(-c2ccc3ncccc3c2)c(-c2ccccc2)nc1N)c1ccccn1] |
| 76 | 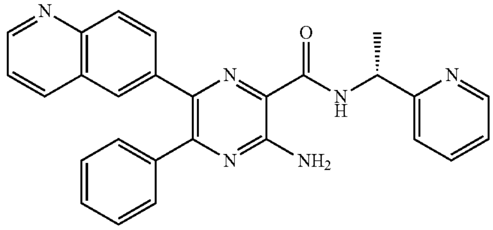 [SMILES: C[C@@H](NC(=O)c1nc(-c2ccc3ncccc3c2)c(-c2ccccc2)nc1N)c1ccccn1] |
| 77 | 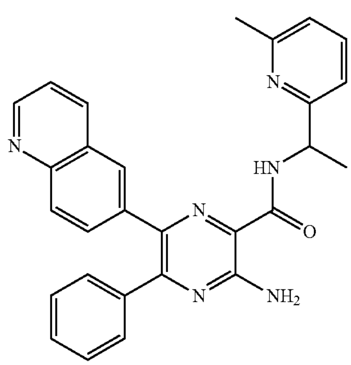 [SMILES: Cc1cccc(C(C)NC(=O)c2nc(-c3ccc4ncccc4c3)c(-c3ccccc3)nc2N)n1] |
| 78 | 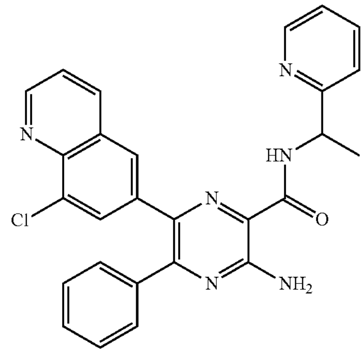 [SMILES: CC(NC(=O)c1nc(-c2cc(Cl)c3ncccc3c2)c(-c2ccccc2)nc1N)c1ccccn1] |

TABLE 1-continued

| Compd No. | Structure |
|---|---|
| 79 | 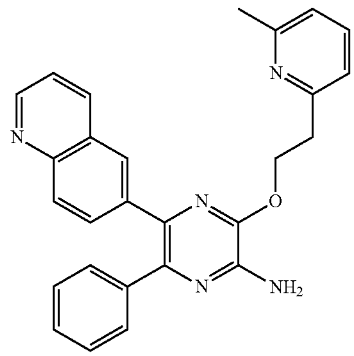 [SMILES: Cc1cccc(CCOc2nc(-c3ccc4ncccc4c3)c(-c3ccccc3)nc2N)n1] |
| 80 | 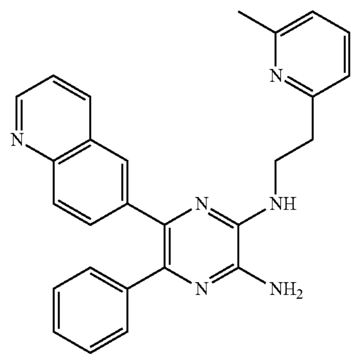 [SMILES: Cc1cccc(CCNc2nc(-c3ccc4ncccc4c3)c(-c3ccccc3)nc2N)n1] |
| 81 | 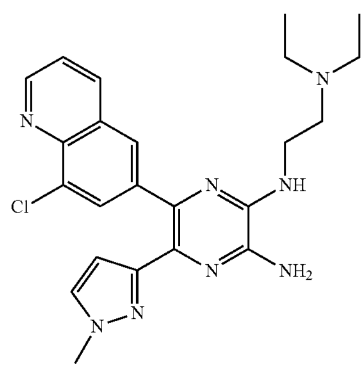 [SMILES: CCN(CC)CCNc1nc(-c2cc(Cl)c3ncccc3c2)c(-c2ccn(C)n2)nc1N] |
| 82 | 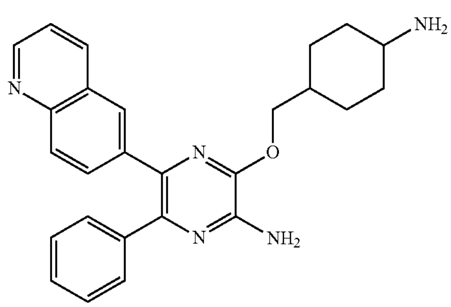 [SMILES: Nc1nc(-c2ccccc2)c(-c2ccc3ncccc3c2)nc1OCC1CCC(N)CC1] |

TABLE 1-continued
| Compd No. | Structure |
|---|---|
| 83 | 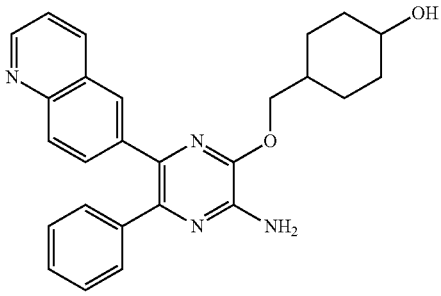 [SMILES: Nc1nc(-c2ccccc2)c(-c2ccc3ncccc3c2)nc1OCC1CCC(O)CC1] |
| 84 | 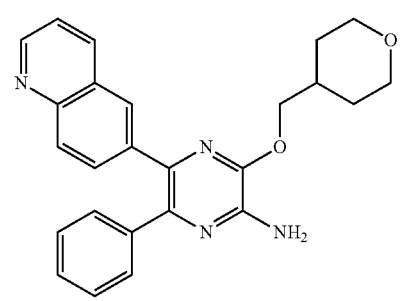 [SMILES: Nc1nc(-c2ccccc2)c(-c2ccc3ncccc3c2)nc1OCC1CCOCC1] |
| 85 | 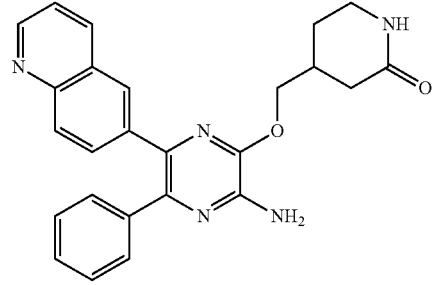 [SMILES: Nc1nc(-c2ccccc2)c(-c2ccc3ncccc3c2)nc1OCC1CCNC(=O)C1] |
| 86 | 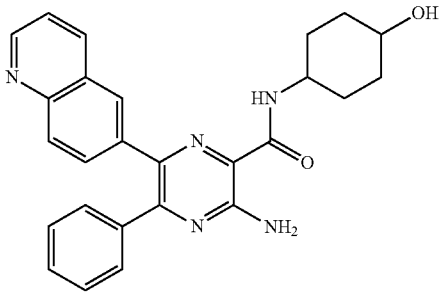 [SMILES: Nc1nc(-c2ccccc2)c(-c2ccc3ncccc3c2)nc1C(=O)NC1CCC(O)CC1] |
| 87 | 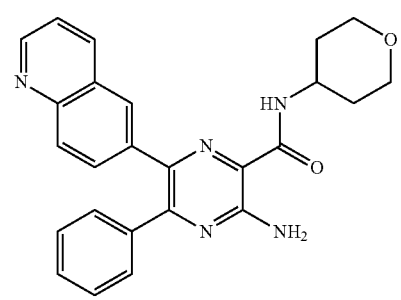 [SMILES: Nc1nc(-c2ccccc2)c(-c2ccc3ncccc3c2)nc1C(=O)NC1CCOCC1] |

TABLE 1-continued
| Compd No. | Structure |
|---|---|
| 88 | 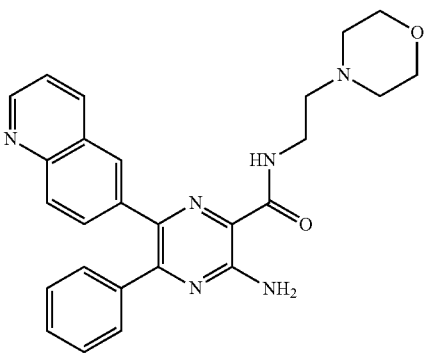 [SMILES: Nc1nc(-c2ccccc2)c(-c2ccc3ncccc3c2)nc1C(=O)NCCN1CCOCC1] |
| 89 | 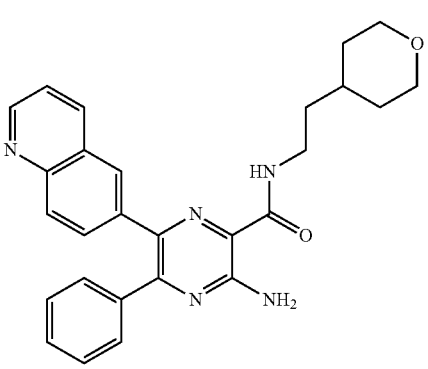 [SMILES: Nc1nc(-c2ccccc2)c(-c2ccc3ncccc3c2)nc1C(=O)NCCC1CCOCC1] |
| 90 | 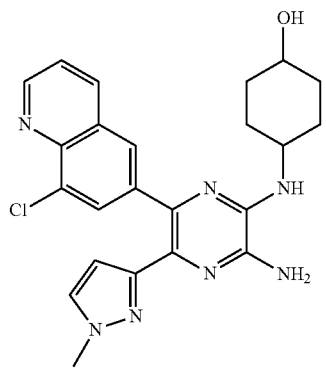 [SMILES: Cn1ccc(-c2nc(N)c(NC3CCC(O)CC3)nc2-c2cc(Cl)c3ncccc3c2)n1] |
| 91 | 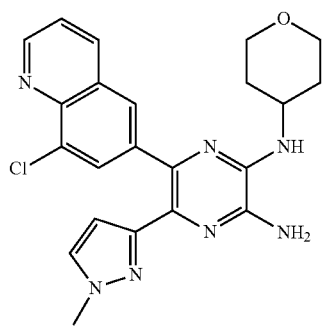 [SMILES: Cn1ccc(-c2nc(N)c(NC3CCOCC3)nc2-c2cc(Cl)c3ncccc3c2)n1] |

TABLE 1-continued
| Compd No. | Structure |
|---|---|
| 92 | 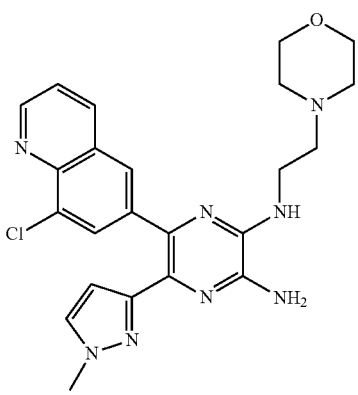 [SMILES: Cn1ccc(-c2nc(N)c(NCCN3CCOCC3)nc2-c2cc(Cl)c3ncccc3c2)n1] |
| 93 | 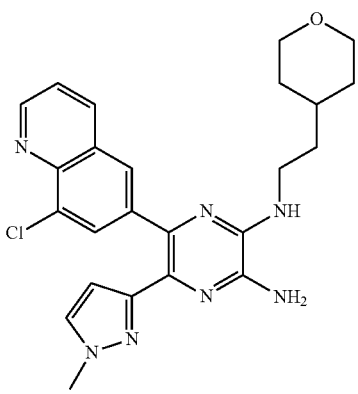 [SMILES: Cn1ccc(-c2nc(N)c(NCCC3CCOCC3)nc2-c2cc(Cl)c3ncccc3c2)n1] |
| 94 | 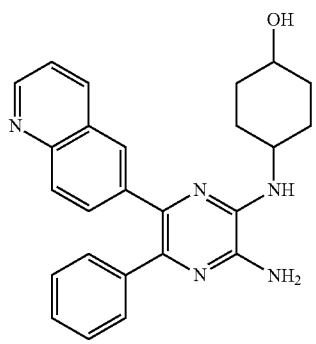 [SMILES: Nc1nc(-c2ccccc2)c(-c2ccc3ncccc3c2)nc1NC1CCC(O)CC1] |
| 95 | 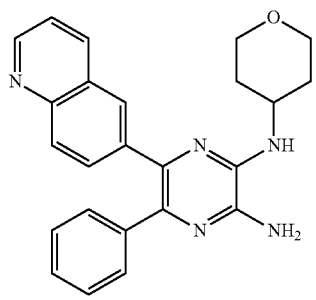 [SMILES: Nc1nc(-c2ccccc2)c(-c2ccc3ncccc3c2)nc1NC1CCOCC1] |

TABLE 1-continued

| Compd No. | Structure |
|---|---|
| 96 | 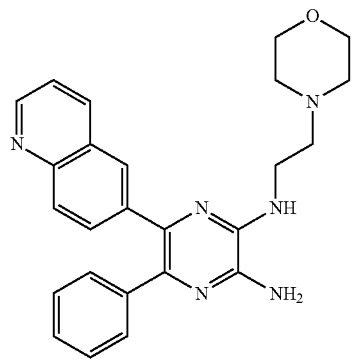 [SMILES: Nc1nc(-c2ccccc2)c(-c2ccc3ncccc3c2)nc1NCCN1CCOCC1] |
| 97 | 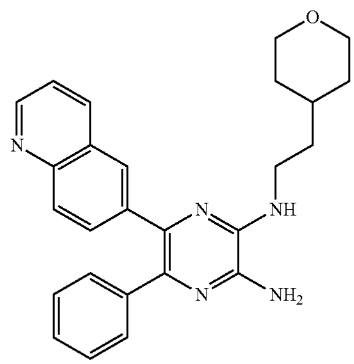 [SMILES: Nc1nc(-c2ccccc2)c(-c2ccc3ncccc3c2)nc1NCCC1CCOCC1] |
| 98 | 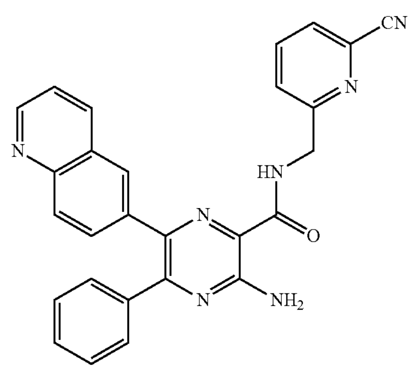 [SMILES: N#Cc1cccc(CNC(=O)c2nc(-c3ccc4ncccc4c3)c(-c3ccccc3)nc2N)n1] |
| 99 | 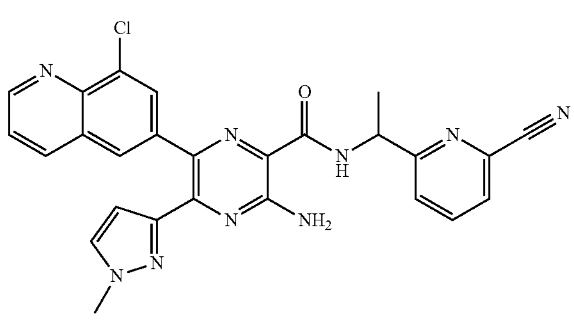 [SMILES: CC(NC(=O)c1nc(-c2cc(Cl)c3ncccc3c2)c(-c2ccn(C)n2)nc1N)c1cccc(C#N)n1] |

TABLE 1-continued

| Compd No. | Structure |
|---|---|
| 100 | 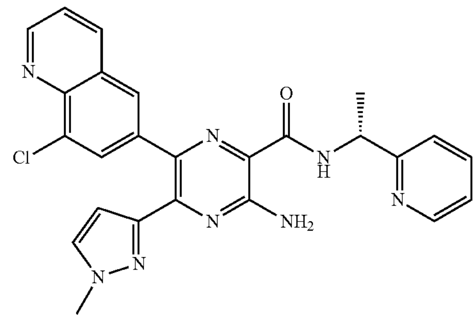 [SMILES: C[C@@H](NC(=O)c1nc(-c2cc(Cl)c3ncccc3c2)c(-c2ccn(C)n2)nc1N)c1ccccn1] |
| 101 | 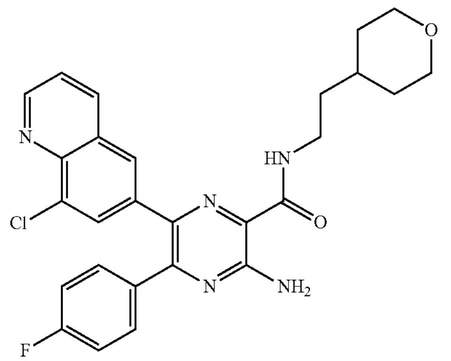 [SMILES: Nc1nc(-c2ccc(F)cc2)c(-c2cc(Cl)c3ncccc3c2)nc1C(=O)NCCC1CCOCC1] |
| 102 | 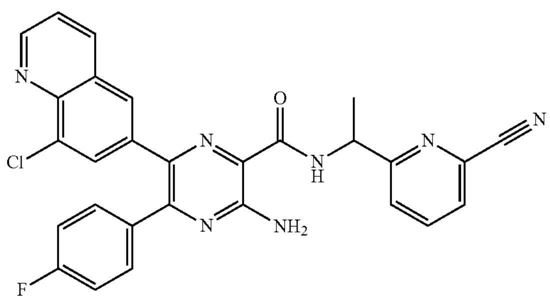 [SMILES: CC(NC(=O)c1nc(-c2cc(Cl)c3ncccc3c2)c(-c2ccc(F)cc2)nc1N)c1cccc(C#N)n1] |
| 103 | 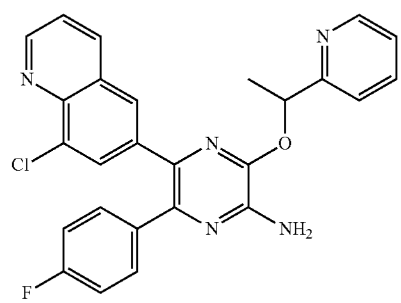 [SMILES: CC(Oc1nc(-c2cc(Cl)c3ncccc3c2)c(-c2ccc(F)cc2)nc1N)c1ccccn1] |
| 104 | 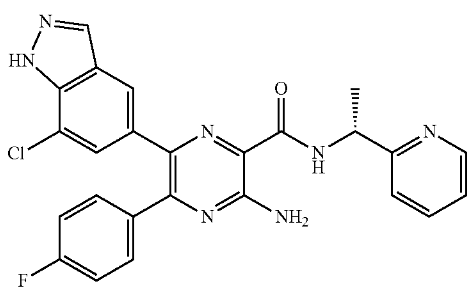 [SMILES: C[C@@H](NC(=O)c1nc(-c2cc(Cl)c3[nH]ncc3c2)c(-c2ccc(F)cc2)nc1N)c1ccccn1] |

TABLE 1-continued

| Compd No. | Structure |
|---|---|
| 105 | 3-amino-6-(8-chloroquinolin-6-yl)-N-((6-cyanopyridin-2-yl)methyl)-5-(4-fluorophenyl)pyrazine-2-carboxamide |
| 106 | 3-amino-6-(8-chloroquinolin-6-yl)-5-(4-fluorophenyl)-N-((S)-1-(pyridin-2-yl)ethyl)pyrazine-2-carboxamide |
| 107 | 3-amino-N-(2-(diethylamino)ethyl)-5-phenyl-6-(quinolin-6-yl)pyrazine-2-carboxamide |
| 108 | 3-amino-5-phenyl-N-(2-(pyridin-2-yl)propan-2-yl)-6-(quinolin-6-yl)pyrazine-2-carboxamide |
| 109 | 3-amino-5-(3-cyanophenyl)-N-((S)-1-(pyridin-2-yl)ethyl)-6-(quinolin-6-yl)pyrazine-2-carboxamide |

TABLE 1-continued
| Compd No. | Structure |
|---|---|
| 110 | 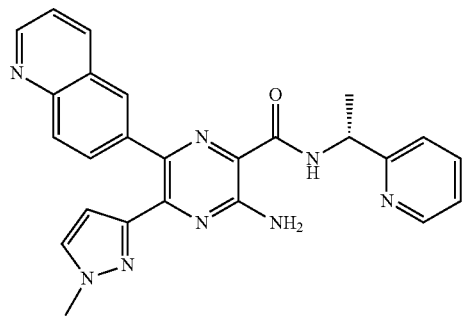 [SMILES: C[C@@H](NC(=O)c1nc(-c2ccc3ncccc3c2)c(-c2ccn(C)n2)nc1N)c1ccccn1] |
| 111 | 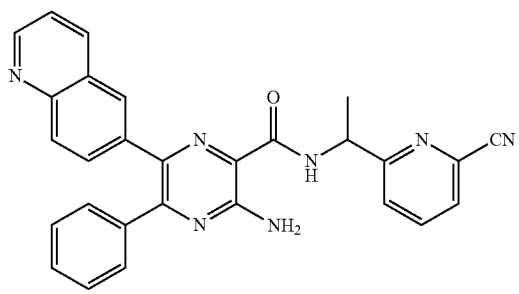 [SMILES: CC(NC(=O)c1nc(-c2ccc3ncccc3c2)c(-c2ccccc2)nc1N)c1cccc(C#N)n1] |
| 112 | 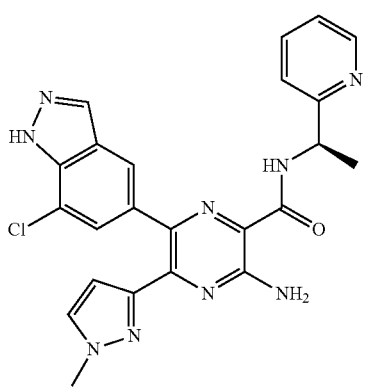 [SMILES: C[C@@H](NC(=O)c1nc(-c2cc(Cl)c3[nH]ncc3c2)c(-c2ccn(C)n2)nc1N)c1ccccn1] |
| 113 | 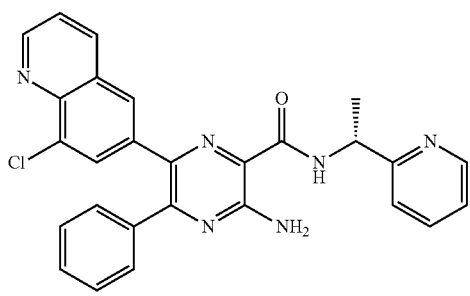 [SMILES: C[C@@H](NC(=O)c1nc(-c2cc(Cl)c3ncccc3c2)c(-c2ccccc2)nc1N)c1ccccn1] |

TABLE 1-continued

| Compd No. | Structure |
|---|---|
| 114 | 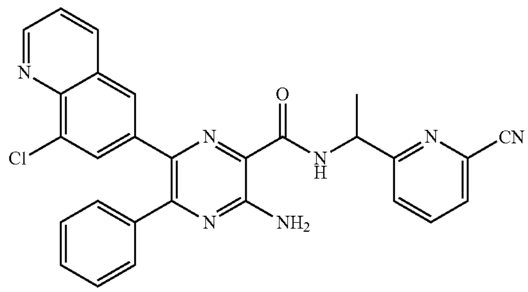 [SMILES: CC(NC(=O)c1nc(-c2cc(Cl)c3ncccc3c2)c(-c2ccccc2)nc1N)c1cccc(C#N)n1] |
| 115 | 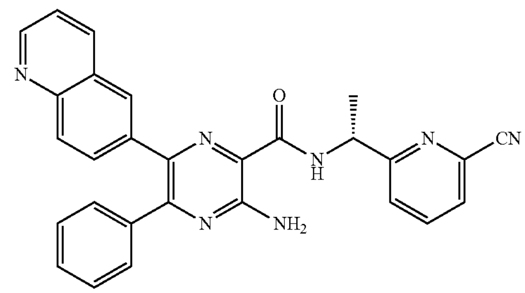 [SMILES: C[C@@H](NC(=O)c1nc(-c2ccc3ncccc3c2)c(-c2ccccc2)nc1N)c1cccc(C#N)n1] |
| 116 | 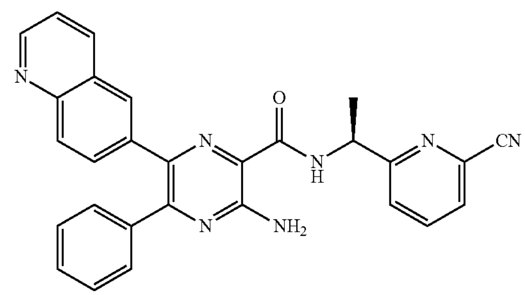 [SMILES: C[C@H](NC(=O)c1nc(-c2ccc3ncccc3c2)c(-c2ccccc2)nc1N)c1cccc(C#N)n1] |
| 117 | 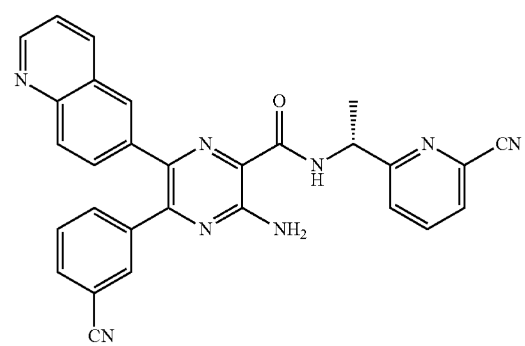 [SMILES: C[C@@H](NC(=O)c1nc(-c2ccc3ncccc3c2)c(-c2cccc(C#N)c2)nc1N)c1cccc(C#N)n1] |
| 118 | 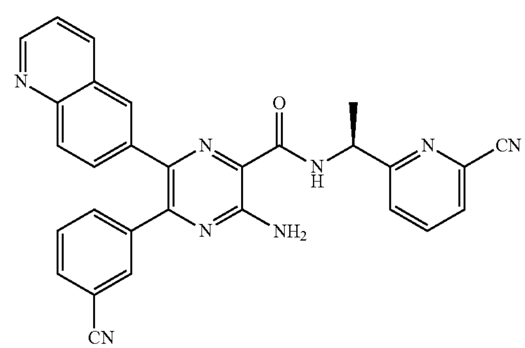 [SMILES: C[C@H](NC(=O)c1nc(-c2ccc3ncccc3c2)c(-c2cccc(C#N)c2)nc1N)c1cccc(C#N)n1] |

TABLE 1-continued

| Compd No. | Structure |
|---|---|
| 119 | 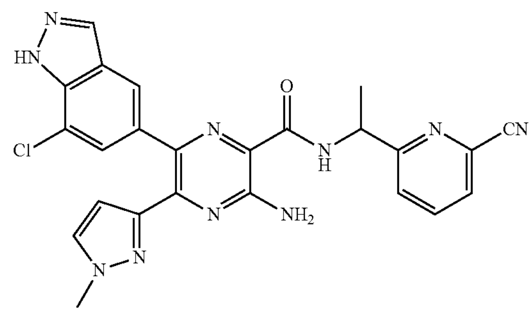 [SMILES: CC(NC(=O)c1nc(-c2cc(Cl)c3[nH]ncc3c2)c(-c2ccn(C)n2)nc1N)c1cccc(C#N)n1] |
| 120 | 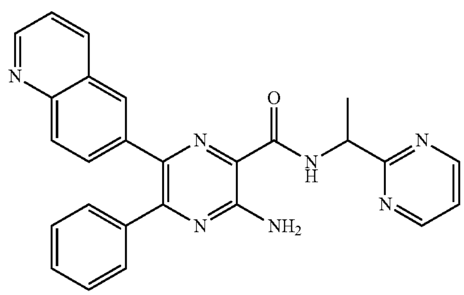 |
| 121 | 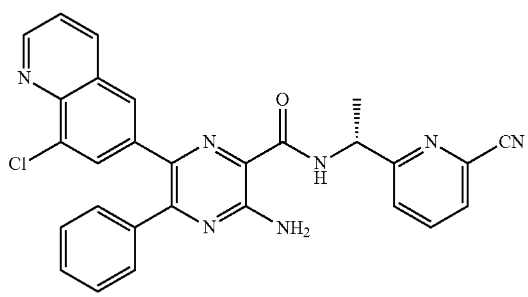 [SMILES: C[C@@H](NC(=O)c1nc(-c2cc(Cl)c3ncccc3c2)c(-c2ccccc2)nc1N)c1cccc(C#N)n1] |
| 122 | 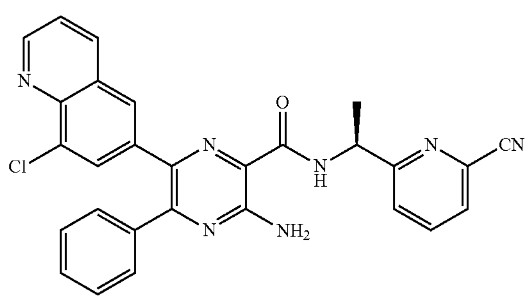 [SMILES: C[C@H](NC(=O)c1nc(-c2cc(Cl)c3ncccc3c2)c(-c2ccccc2)nc1N)c1cccc(C#N)n1] |
| 123 | 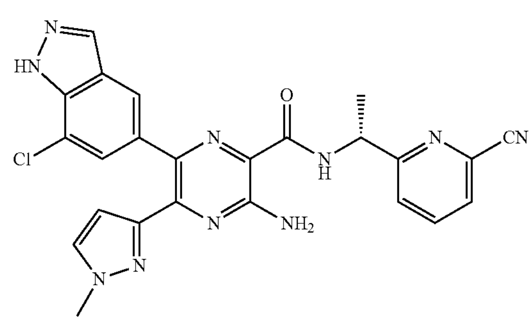 [SMILES: C[C@@H](NC(=O)c1nc(-c2cc(Cl)c3[nH]ncc3c2)c(-c2ccn(C)n2)nc1N)c1cccc(C#N)n1] |

TABLE 1-continued

| Compd No. | Structure |
|---|---|
| 124 | 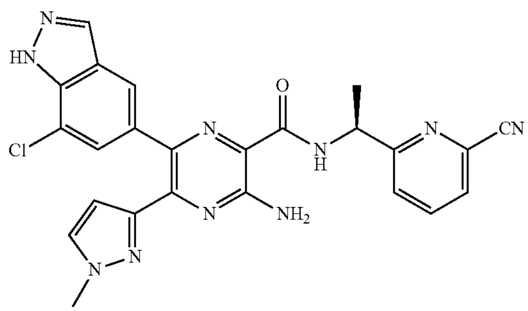 [SMILES: C[C@H](NC(=O)c1nc(-c2cc(Cl)c3[nH]ncc3c2)c(-c2ccn(C)n2)nc1N)c1cccc(C#N)n1] |
| 125 | 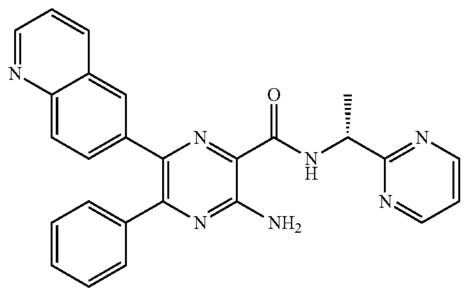 [SMILES: C[C@@H](NC(=O)c1nc(-c2ccc3ncccc3c2)c(-c2ccccc2)nc1N)c1ncccn1] |
| 126 | 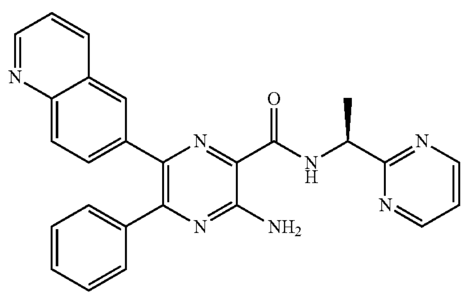 [SMILES: C[C@H](NC(=O)c1nc(-c2ccc3ncccc3c2)c(-c2ccccc2)nc1N)c1ncccn1] |
| 127 | 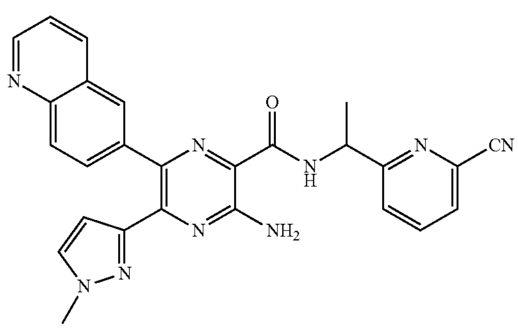 [SMILES: CC(NC(=O)c1nc(-c2ccc3ncccc3c2)c(-c2ccn(C)n2)nc1N)c1cccc(C#N)n1] |
| 128 | 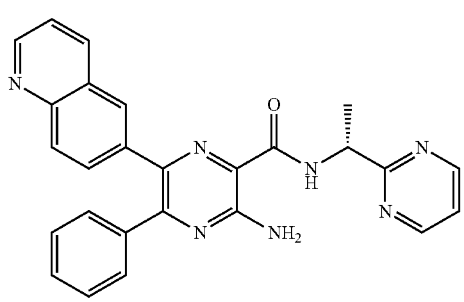 [SMILES: C[C@@H](NC(=O)c1nc(-c2ccc3ncccc3c2)c(-c2ccccc2)nc1N)c1ncccn1] |

TABLE 1-continued

| Compd No. | Structure |
|---|---|
| 129 | 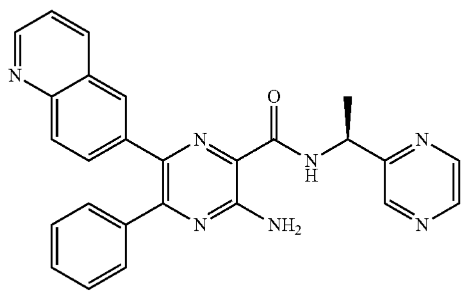 [SMILES: C[C@H](NC(=O)c1nc(-c2ccc3ncccc3c2)c(-c2ccccc2)nc1N)c1cnccn1] |
| 130 | 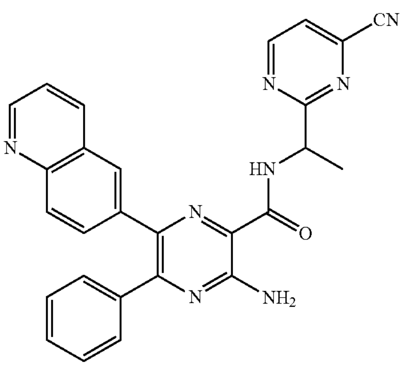 [SMILES: CC(NC(=O)c1nc(-c2ccc3ncccc3c2)c(-c2ccccc2)nc1N)c1nccc(C#N)n1] |
| 131 | 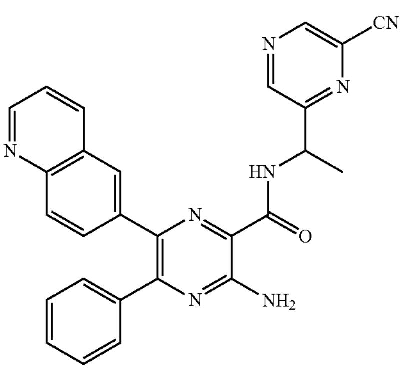 [SMILES: CC(NC(=O)c1nc(-c2ccc3ncccc3c2)c(-c2ccccc2)nc1N)c1cncc(C#N)n1] |
| 132 | 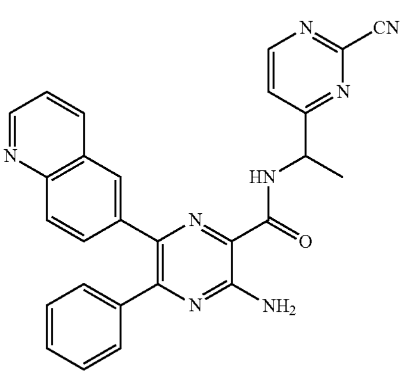 [SMILES: CC(NC(=O)c1nc(-c2ccc3ncccc3c2)c(-c2ccccc2)nc1N)c1ccnc(C#N)n1] |

TABLE 1-continued

| Compd No. | Structure |
|---|---|
| 133 | (structure) |
| 134 | (structure) |
| 135 | (structure) |
| 136 | (structure) |

TABLE 1-continued

| Compd No. | Structure |
|---|---|
| 137 | (structure) |
| 138 | (structure) |
| 139 | (structure) |
| 140 | (structure) |

TABLE 1-continued
| Compd No. | Structure |
|---|---|
| 141 | 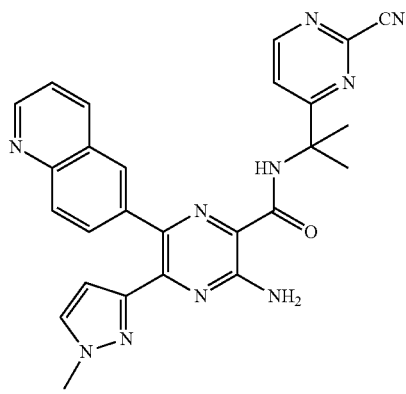 [SMILES: Cn1ccc(-c2nc(N)c(C(=O)NC(C)(C)c3ccnc(C#N)n3)nc2-c2ccc3ncccc3c2)n1] |
| 142 | 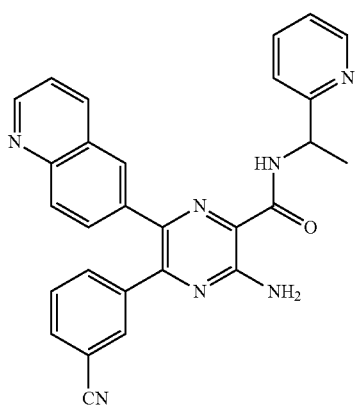 [SMILES: CC(NC(=O)c1nc(-c2ccc3ncccc3c2)c(-c2cccc(C#N)c2)nc1N)c1ccccn1] |
| 143 | 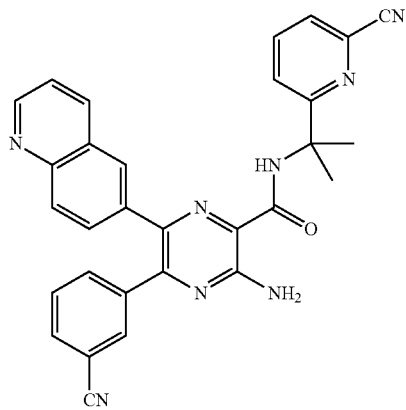 [SMILES: CC(C)(NC(=O)c1nc(-c2ccc3ncccc3c2)c(-c2cccc(C#N)c2)nc1N)c1cccc(C#N)n1] |

TABLE 1-continued

| Compd No. | Structure |
|---|---|
| 144 | 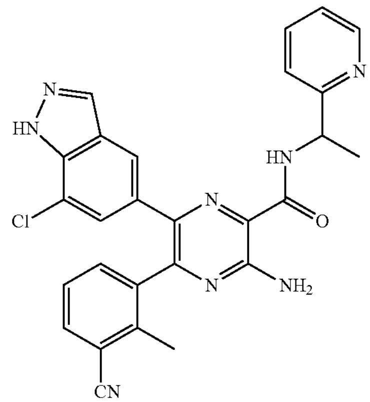 [SMILES: Cc1c(C#N)cccc1-c1nc(N)c(C(=O)NC(C)c2ccccn2)nc1-c1cc(Cl)c2[nH]ncc2c1] |
| 145 | 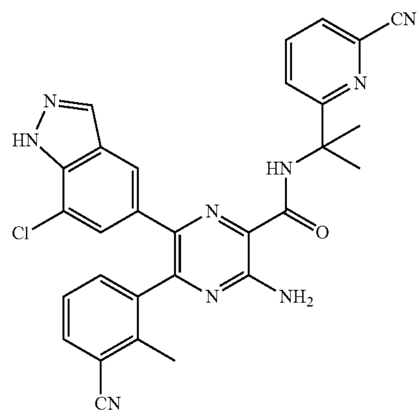 [SMILES: Cc1c(C#N)cccc1-c1nc(N)c(C(=O)NC(C)(C)c2cccc(C#N)n2)nc1-c1cc(Cl)c2[nH]ncc2c1] |
| 146 | 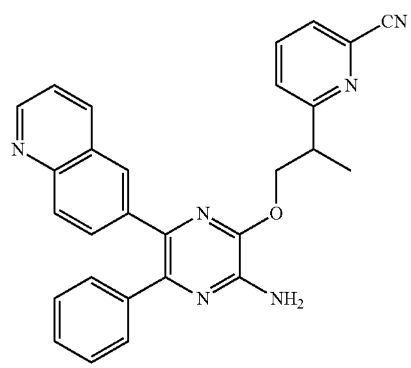 [SMILES: CC(COc1nc(-c2ccc3ncccc3c2)c(-c2ccccc2)nc1N)c1cccc(C#N)n1] |
| 147 | 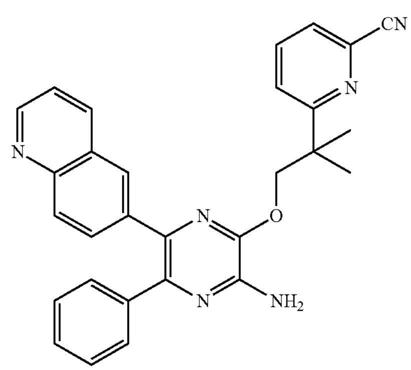 [SMILES: CC(C)(COc1nc(-c2ccc3ncccc3c2)c(-c2ccccc2)nc1N)c1cccc(C#N)n1] |

TABLE 1-continued
| Compd No. | Structure |
|---|---|
| 148 | 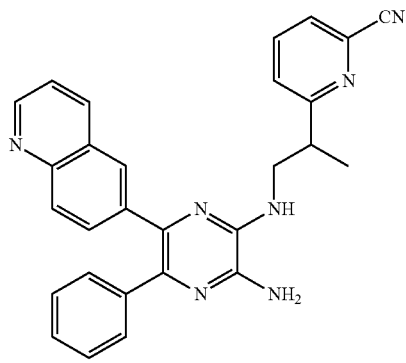 [SMILES: CC(CNc1nc(-c2ccc3ncccc3c2)c(-c2ccccc2)nc1N)c1cccc(C#N)n1] |
| 149 | 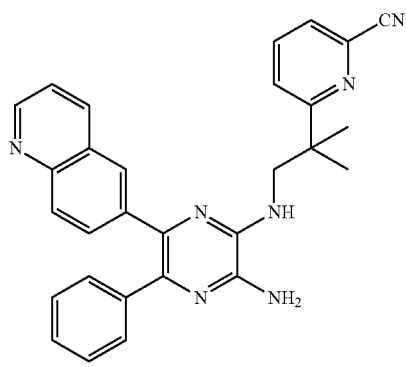 [SMILES: CC(C)(CNc1nc(-c2ccc3ncccc3c2)c(-c2ccccc2)nc1N)c1cccc(C#N)n1] |
| 150 | 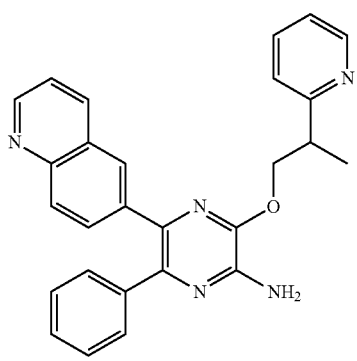 [SMILES: CC(COc1nc(-c2ccc3ncccc3c2)c(-c2ccccc2)nc1N)c1ccccn1] |
| 151 | 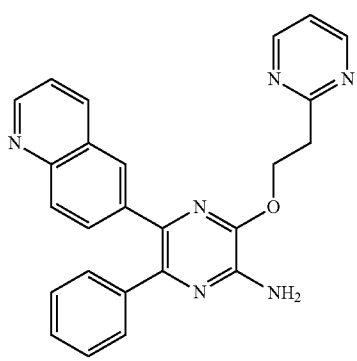 [SMILES: Nc1nc(-c2ccccc2)c(-c2ccc3ncccc3c2)nc1OCCc1ncccn1] |

TABLE 1-continued
| Compd No. | Structure |
|---|---|
| 152 | 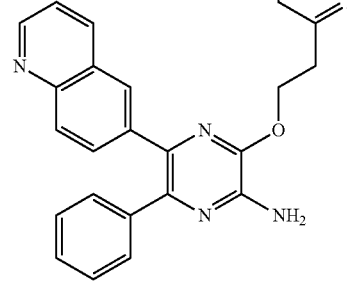 |
| 153 | 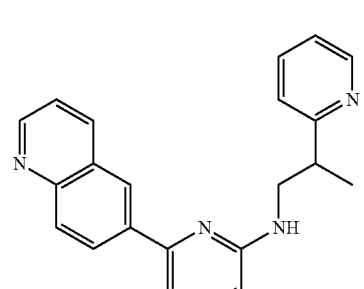 |
| 154 | 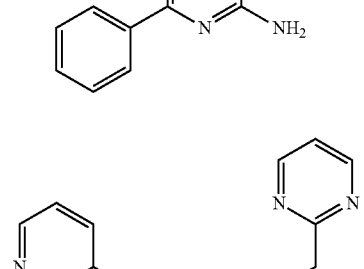 |
| 155 | 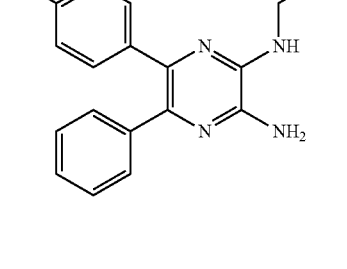 |

TABLE 1-continued
| Compd No. | Structure |
|---|---|
| 156 | 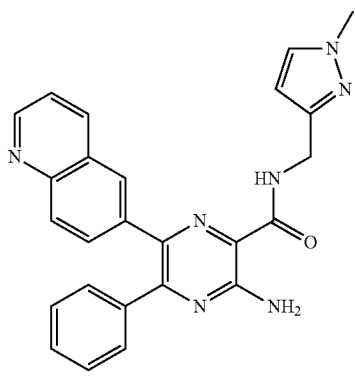 [SMILES: Cn1ccc(CNC(=O)c2nc(-c3ccc4ncccc4c3)c(-c3ccccc3)nc2N)n1] |
| 157 | 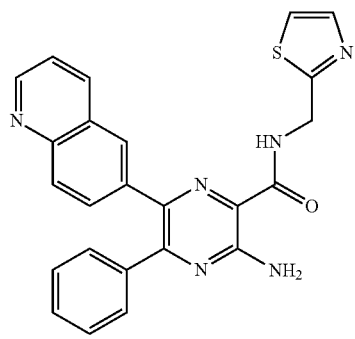 [SMILES: Nc1nc(-c2ccccc2)c(-c2ccc3ncccc3c2)nc1C(=O)NCc1nccs1] |
| 158 | 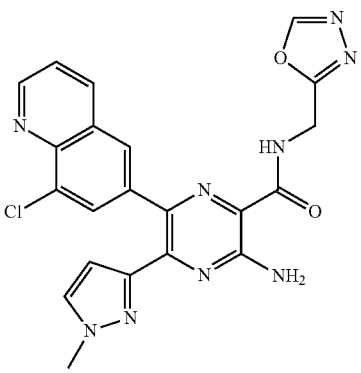 [SMILES: Cn1ccc(-c2nc(N)c(C(=O)NCc3nnco3)nc2-c2cc(Cl)c3ncccc3c2)n1] |
| 159 | 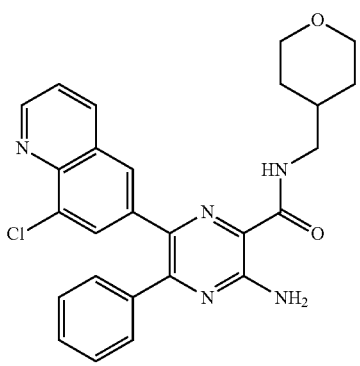 [SMILES: Nc1nc(-c2ccccc2)c(-c2cc(Cl)c3ncccc3c2)nc1C(=O)NCC1CCOCC1] |

TABLE 1-continued
| Compd No. | Structure |
|---|---|
| 160 | 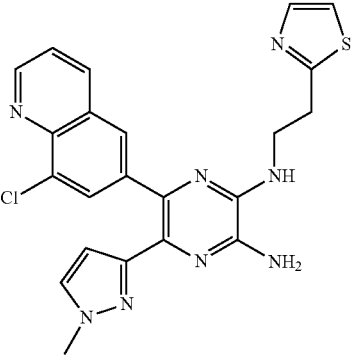 [SMILES: Cn1ccc(-c2nc(N)c(NCCc3nccs3)nc2-c2cc(Cl)c3ncccc3c2)n1] |
| 161 | 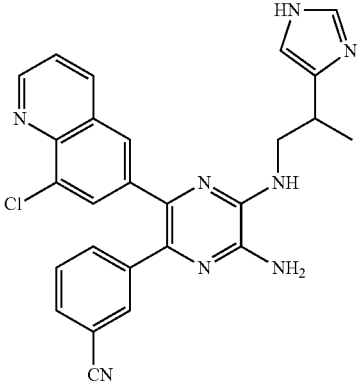 [SMILES: CC(CNc1nc(-c2cc(Cl)c3ncccc3c2)c(-c2cccc(C#N)c2)nc1N)c1c[nH]cn1] |
| 162 | 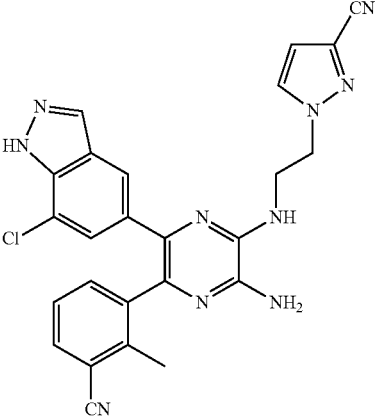 [SMILES: Cc1c(C#N)cccc1-c1nc(N)c(NCCn2ccc(C#N)n2)nc1-c1cc(Cl)c2[nH]ncc2c1] |
| 163 | 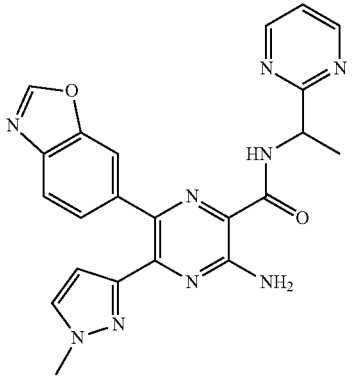 [SMILES: CC(NC(=O)c1nc(-c2ccc3ncoc3c2)c(-c2ccn(C)n2)nc1N)c1ncccn1] |

TABLE 1-continued

| Compd No. | Structure |
|---|---|
| 164 | 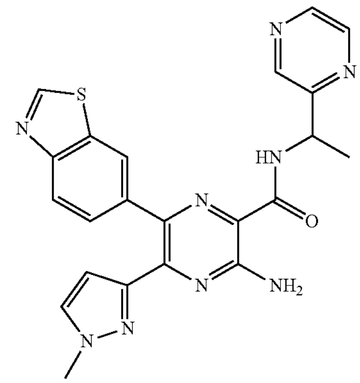 [SMILES: CC(NC(=O)c1nc(-c2ccc3ncsc3c2)c(-c2ccn(C)n2)nc1N)c1cnccn1] |
| 165 | 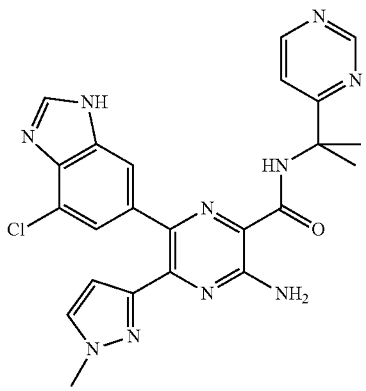 [SMILES: Cn1ccc(-c2nc(N)c(C(=O)NC(C)(C)c3ccncn3)nc2-c2cc(Cl)c3nc[nH]c3c2)n1] |
| 166 | 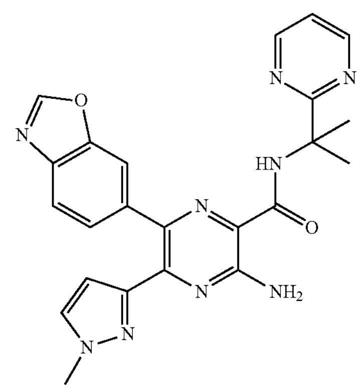 [SMILES: Cn1ccc(-c2nc(N)c(C(=O)NC(C)(C)c3ncccn3)nc2-c2ccc3ncoc3c2)n1] |
| 167 | 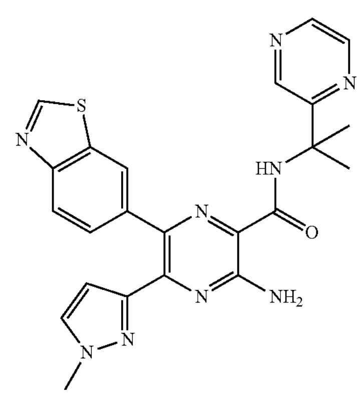 [SMILES: Cn1ccc(-c2nc(N)c(C(=O)NC(C)(C)c3cnccn3)nc2-c2ccc3ncsc3c2)n1] |

TABLE 1-continued

| Compd No. | Structure |
|---|---|
| 168 | 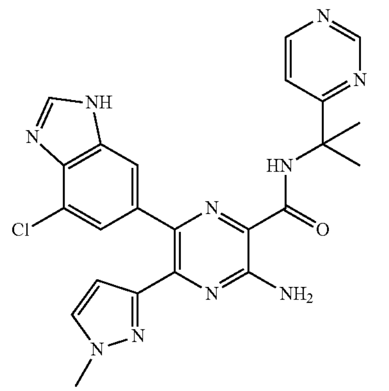 [SMILES: Cn1ccc(-c2nc(N)c(C(=O)NC(C)(C)c3ccncn3)nc2-c2cc(Cl)c3nc[nH]c3c2)n1] |
| 169 | 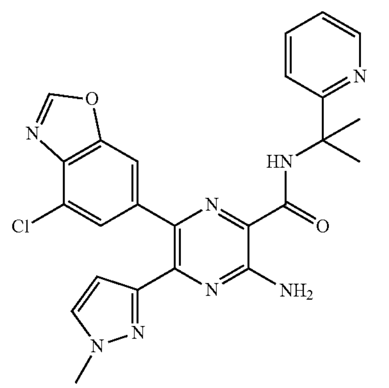 [SMILES: Cn1ccc(-c2nc(N)c(C(=O)NC(C)(C)c3ccccn3)nc2-c2cc(Cl)c3ncoc3c2)n1] |
| 170 | 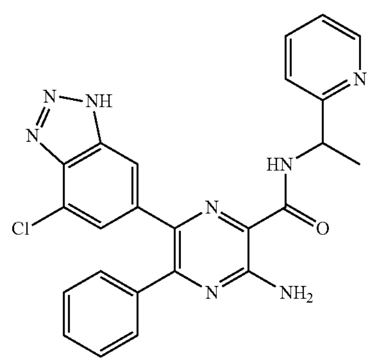 [SMILES: CC(NC(=O)c1nc(-c2cc(Cl)c3nn[nH]c3c2)c(-c2ccccc2)nc1N)c1ccccn1] |
| 171 | 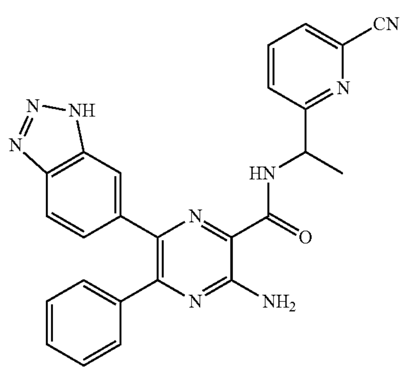 [SMILES: CC(NC(=O)c1nc(-c2ccc3nn[nH]c3c2)c(-c2ccccc2)nc1N)c1cccc(C#N)n1] |

TABLE 1-continued

| Compd No. | Structure |
|---|---|
| 172 | 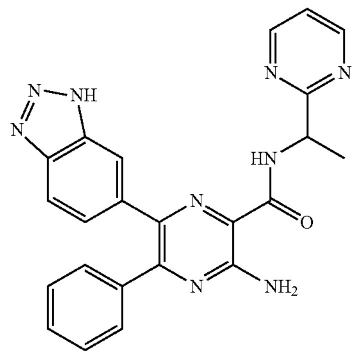 [SMILES: CC(NC(=O)c1nc(-c2ccc3nn[nH]c3c2)c(-c2ccccc2)nc1N)c1ncccn1] |
| 173 | 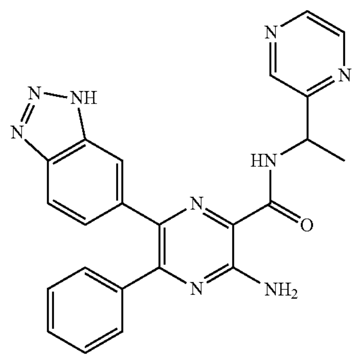 [SMILES: CC(NC(=O)c1nc(-c2ccc3nn[nH]c3c2)c(-c2ccccc2)nc1N)c1cnccn1] |
| 174 | 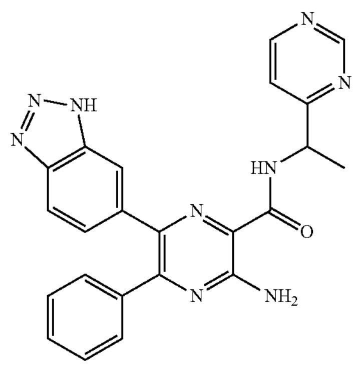 [SMILES: CC(NC(=O)c1nc(-c2ccc3nn[nH]c3c2)c(-c2ccccc2)nc1N)c1ccncn1] |
| 175 | 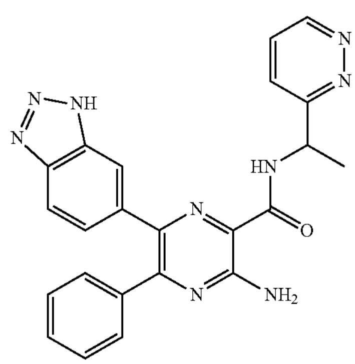 [SMILES: CC(NC(=O)c1nc(-c2ccc3nn[nH]c3c2)c(-c2ccccc2)nc1N)c1cccnn1] |

TABLE 1-continued
| Compd No. | Structure |
|---|---|
| 176 | 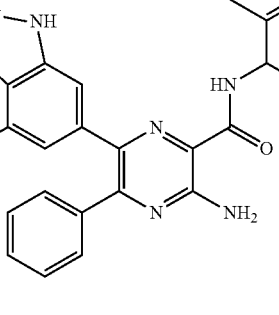 |
| 177 | 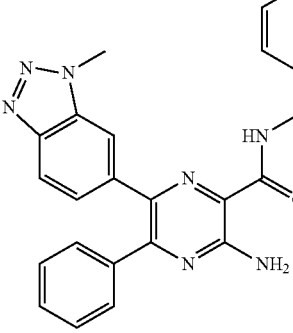 |
| 178 | 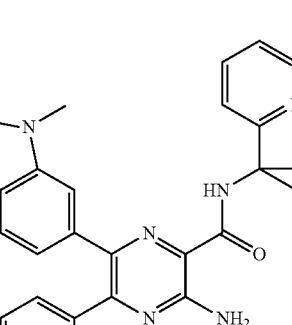 |
| 179 | 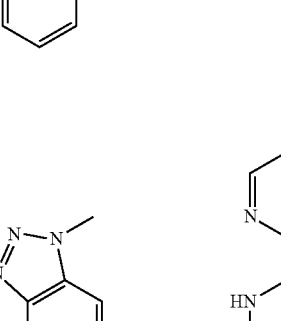 |

TABLE 1-continued
| Compd No. | Structure |
|---|---|
| 180 | 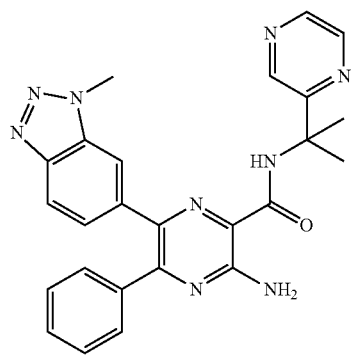 [SMILES: Cn1nnc2ccc(-c3nc(C(=O)NC(C)(C)c4cnccn4)c(N)nc3-c3ccccc3)cc21] |
| 181 | 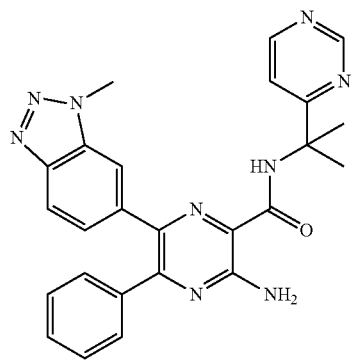 [SMILES: Cn1nnc2ccc(-c3nc(C(=O)NC(C)(C)c4ccncn4)c(N)nc3-c3ccccc3)cc21] |
| 182 | 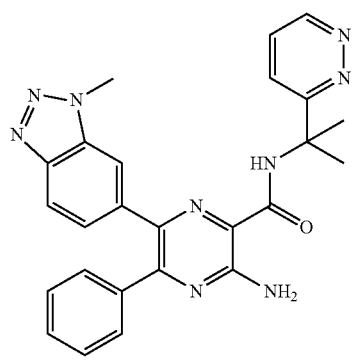 [SMILES: Cn1nnc2ccc(-c3nc(C(=O)NC(C)(C)c4cccnn4)c(N)nc3-c3ccccc3)cc21] |
| 183 | 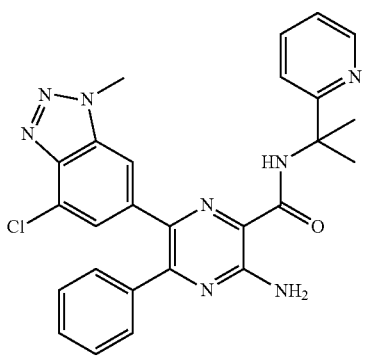 [SMILES: Cn1nnc2c(Cl)cc(-c3nc(C(=O)NC(C)(C)c4ccccn4)c(N)nc3-c3ccccc3)cc21] |

TABLE 1-continued
| Compd No. | Structure |
|---|---|
| 184 | 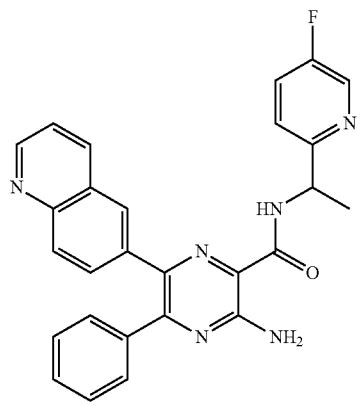 [SMILES: CC(NC(=O)c1nc(-c2ccc3ncccc3c2)c(-c2ccccc2)nc1N)c1ccc(F)cn1] |
| 185 | 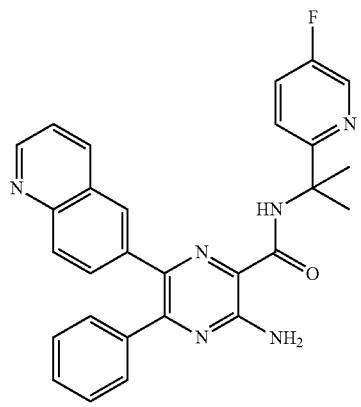 [SMILES: CC(C)(NC(=O)c1nc(-c2ccc3ncccc3c2)c(-c2ccccc2)nc1N)c1ccc(F)cn1] |
| 186 | 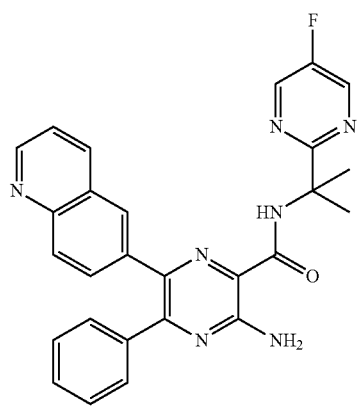 [SMILES: CC(C)(NC(=O)c1nc(-c2ccc3ncccc3c2)c(-c2ccccc2)nc1N)c1ncc(F)cn1] |

TABLE 1-continued
| Compd No. | Structure |
|---|---|
| 187 | 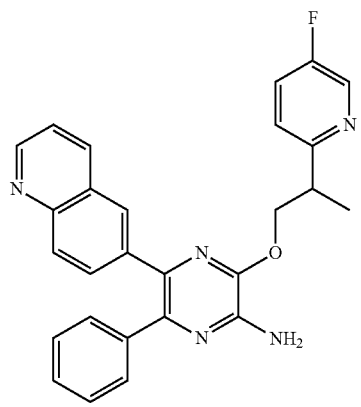 [SMILES: CC(COc1nc(-c2ccc3ncccc3c2)c(-c2ccccc2)nc1N)c1ccc(F)cn1] |
| 188 | 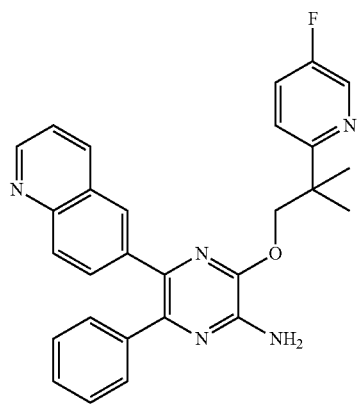 [SMILES: CC(C)(COc1nc(-c2ccc3ncccc3c2)c(-c2ccccc2)nc1N)c1ccc(F)cn1] |
| 189 | 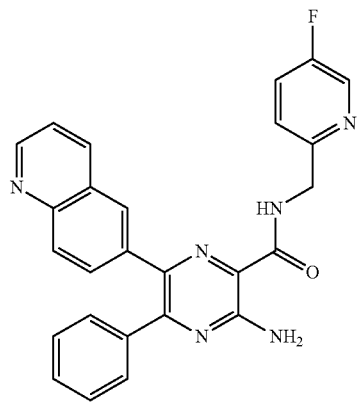 |

TABLE 1-continued
| Compd No. | Structure |
|---|---|
| 190 | 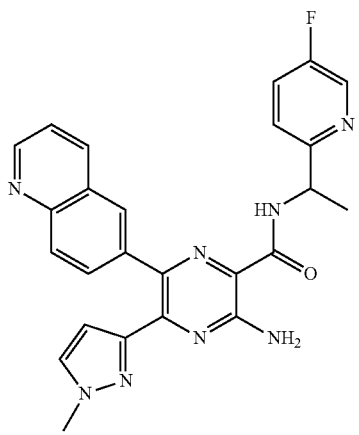 [SMILES: CC(NC(=O)c1nc(-c2ccc3ncccc3c2)c(-c2ccn(C)n2)nc1N)c1ccc(F)cn1] |
| 191 | 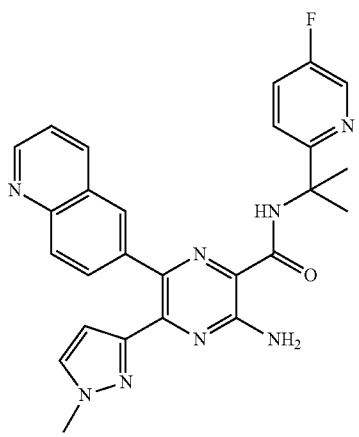 [SMILES: Cn1ccc(-c2nc(N)c(C(=O)NC(C)(C)c3ccc(F)cn3)nc2-c2ccc3ncccc3c2)n1] |
| 192 | 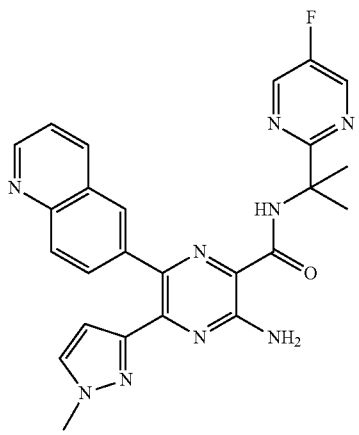 [SMILES: Cn1ccc(-c2nc(N)c(C(=O)NC(C)(C)c3ncc(F)cn3)nc2-c2ccc3ncccc3c2)n1] |

TABLE 1-continued
| Compd No. | Structure |
|---|---|
| 193 | 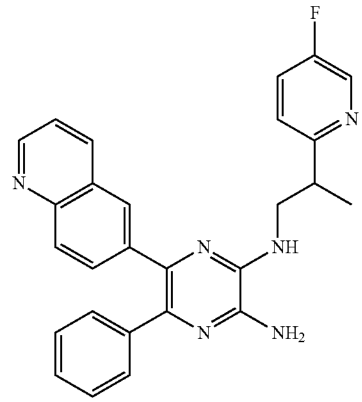 [SMILES: CC(CNc1nc(-c2ccc3ncccc3c2)c(-c2ccccc2)nc1N)c1ccc(F)cn1] |
| 194 | 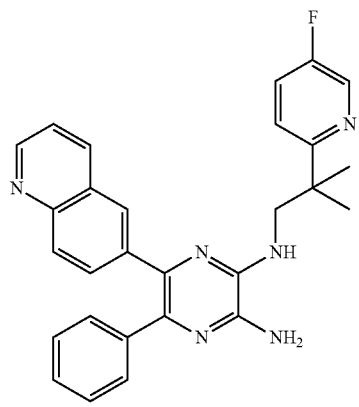 [SMILES: CC(C)(CNc1nc(-c2ccc3ncccc3c2)c(-c2ccccc2)nc1N)c1ccc(F)cn1] |
| 195 | 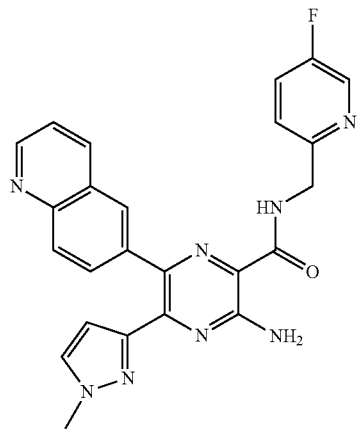 [SMILES: Cn1ccc(-c2nc(N)c(C(=O)NCc3ccc(F)cn3)nc2-c2ccc3ncccc3c2)n1] |

TABLE 1-continued
| Compd No. | Structure |
|---|---|
| 196 | 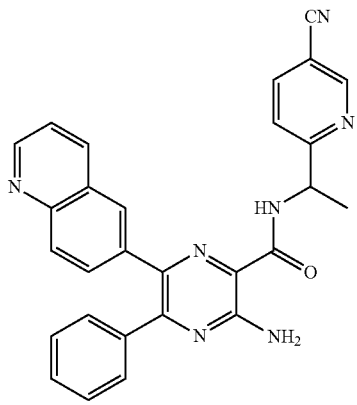 [SMILES: CC(NC(=O)c1nc(-c2ccc3ncccc3c2)c(-c2ccccc2)nc1N)c1ccc(C#N)cn1] |
| 197 | 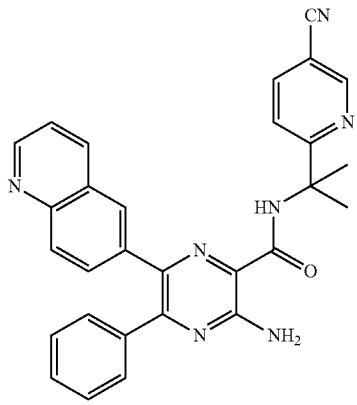 [SMILES: CC(C)(NC(=O)c1nc(-c2ccc3ncccc3c2)c(-c2ccccc2)nc1N)c1ccc(C#N)cn1] |
| 198 | 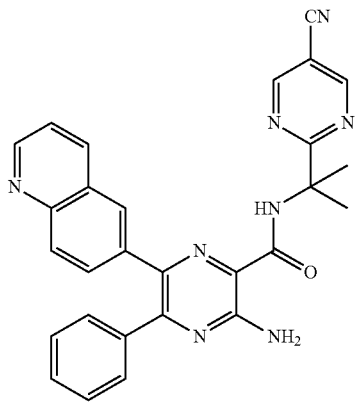 [SMILES: CC(C)(NC(=O)c1nc(-c2ccc3ncccc3c2)c(-c2ccccc2)nc1N)c1ncc(C#N)cn1] |

TABLE 1-continued
| Compd No. | Structure |
|---|---|
| 199 | 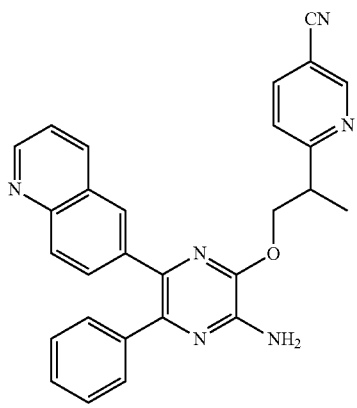 [SMILES: CC(COc1nc(-c2ccc3ncccc3c2)c(-c2ccccc2)nc1N)c1ccc(C#N)cn1] |
| 200 | 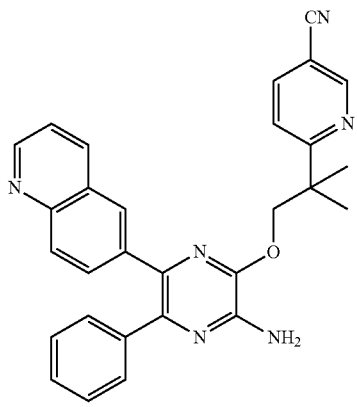 [SMILES: CC(C)(COc1nc(-c2ccc3ncccc3c2)c(-c2ccccc2)nc1N)c1ccc(C#N)cn1] |
| 201 | 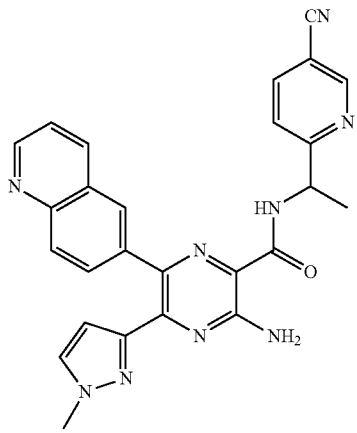 [SMILES: CC(NC(=O)c1nc(-c2ccc3ncccc3c2)c(-c2ccn(C)n2)nc1N)c1ccc(C#N)cn1] |

TABLE 1-continued
| Compd No. | Structure |
|---|---|
| 202 | 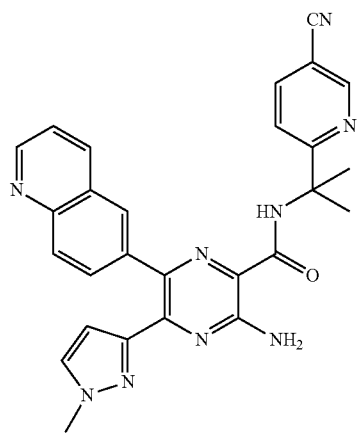 [SMILES: Cn1ccc(-c2nc(N)c(C(=O)NC(C)(C)c3ccc(C#N)cn3)nc2-c2ccc3ncccc3c2)n1] |
| 203 | 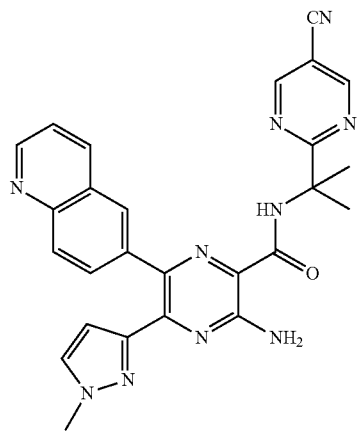 |
| 204 | 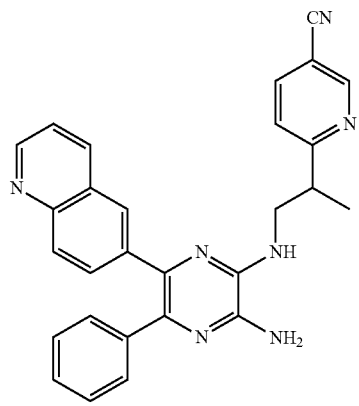 [SMILES: CC(CNc1nc(-c2ccc3ncccc3c2)c(-c2ccccc2)nc1N)c1ccc(C#N)cn1] |

TABLE 1-continued
| Compd No. | Structure |
|---|---|
| 205 | 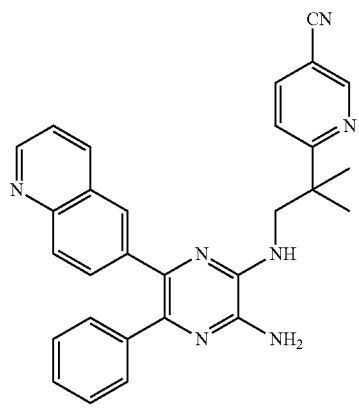 [SMILES: CC(C)(CNc1nc(-c2ccc3ncccc3c2)c(-c2ccccc2)nc1N)c1ccc(C#N)cn1] |
| 206 | 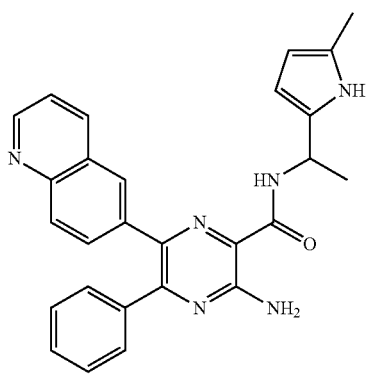 |
| 207 | 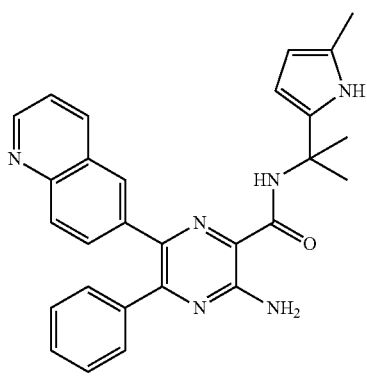 [SMILES: Cc1ccc(C(C)(C)NC(=O)c2nc(-c3ccc4ncccc4c3)c(-c3ccccc3)nc2N)[nH]1] |
| 208 | 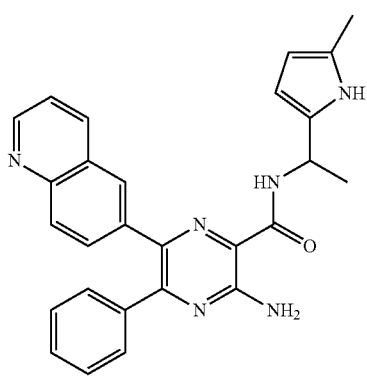 [SMILES: Cc1ccc(C(C)NC(=O)c2nc(-c3ccc4ncccc4c3)c(-c3ccccc3)nc2N)[nH]1] |

TABLE 1-continued
| Compd No. | Structure |
|---|---|
| 209 | 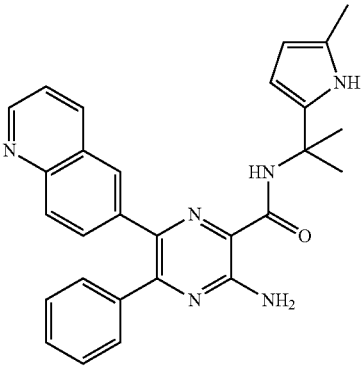 [SMILES: Cc1ccc(C(C)(C)NC(=O)c2nc(-c3ccc4ncccc4c3)c(-c3ccccc3)nc2N)[nH]1] |
| 210 | 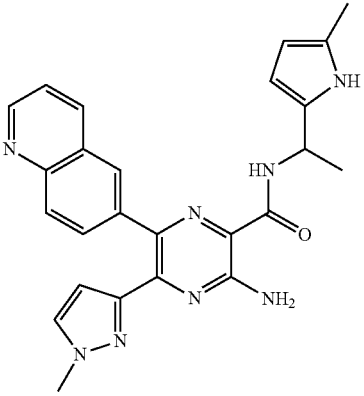 [SMILES: Cc1ccc(C(C)NC(=O)c2nc(-c3ccc4ncccc4c3)c(-c3ccn(C)n3)nc2N)[nH]1] |
| 211 | 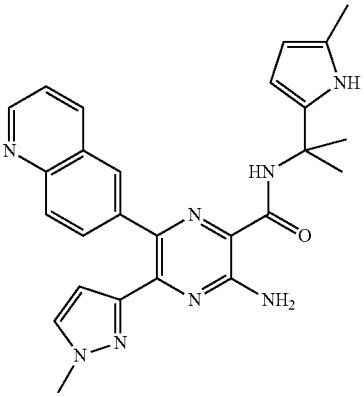 [SMILES: Cc1ccc(C(C)(C)NC(=O)c2nc(-c3ccc4ncccc4c3)c(-c3ccn(C)n3)nc2N)[nH]1] |
| 212 | 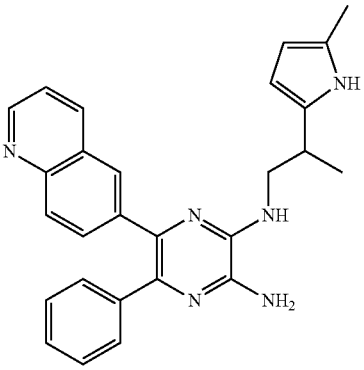 [SMILES: Cc1ccc(C(C)CNc2nc(-c3ccc4ncccc4c3)c(-c3ccccc3)nc2N)[nH]1] |

TABLE 1-continued
| Compd No. | Structure |
|---|---|
| 213 | 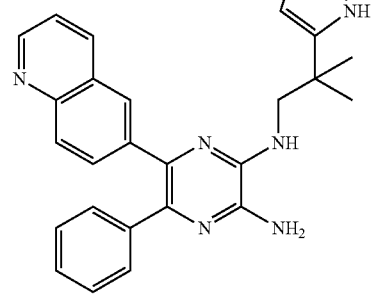 |
| 214 | 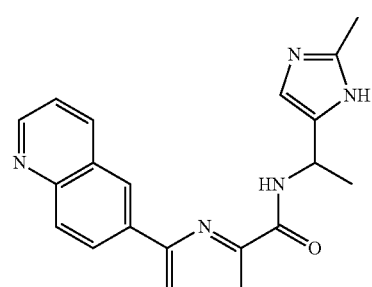 |
| 215 | 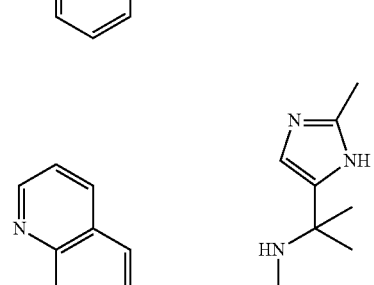 |
| 216 | 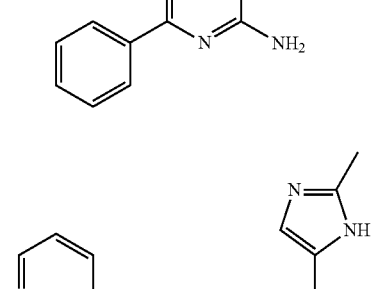 |

TABLE 1-continued
| Compd No. | Structure |
|---|---|
| 217 | 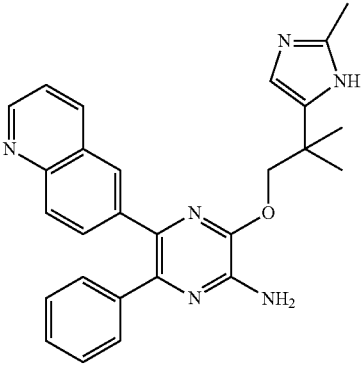 [SMILES: Cc1ncc(C(C)(C)COc2nc(-c3ccc4ncccc4c3)c(-c3ccccc3)nc2N)[nH]1] |
| 218 | 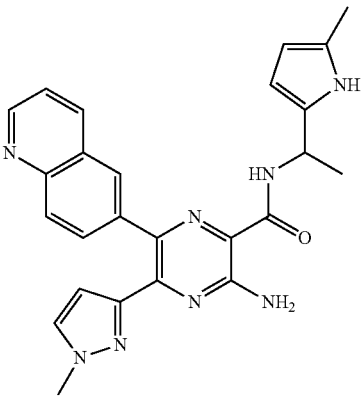 [SMILES: Cc1ccc(C(C)NC(=O)c2nc(-c3ccc4ncccc4c3)c(-c3ccn(C)n3)nc2N)[nH]1] |
| 219 | 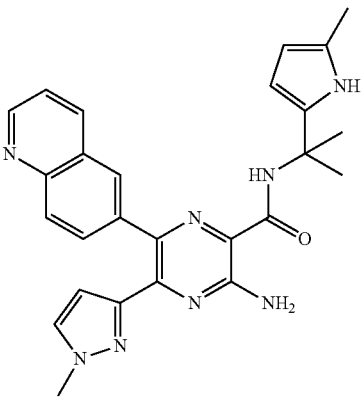 [SMILES: Cc1ccc(C(C)(C)NC(=O)c2nc(-c3ccc4ncccc4c3)c(-c3ccn(C)n3)nc2N)[nH]1] |
| 220 | 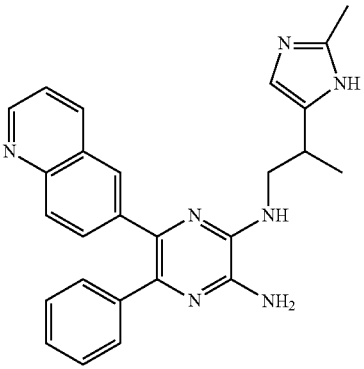 [SMILES: Cc1ncc(C(C)CNc2nc(-c3ccc4ncccc4c3)c(-c3ccccc3)nc2N)[nH]1] |

TABLE 1-continued
| Compd No. | Structure |
|---|---|
| 221 | 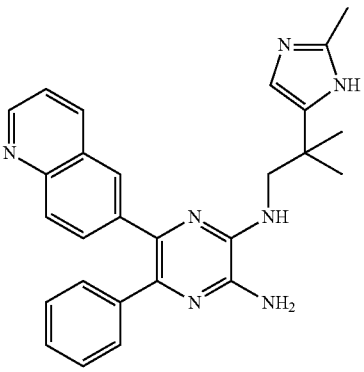 [SMILES: Cc1ncc(C(C)(C)CNc2nc(-c3ccc4ncccc4c3)c(-c3ccccc3)nc2N)[nH]1] |
| 222 | 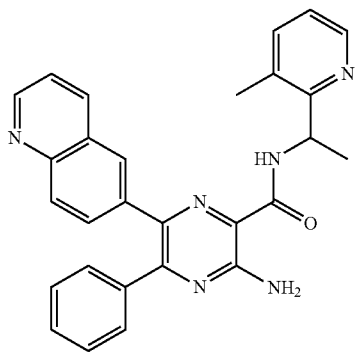 [SMILES: Cc1cccnc1C(C)NC(=O)c1nc(-c2ccc3ncccc3c2)c(-c2ccccc2)nc1N] |
| 223 | 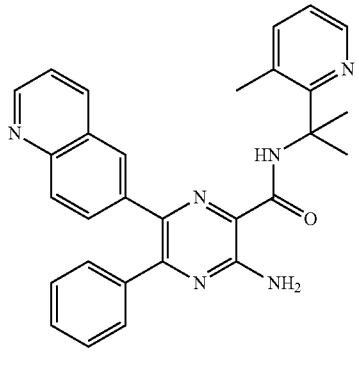 |
| 224 | 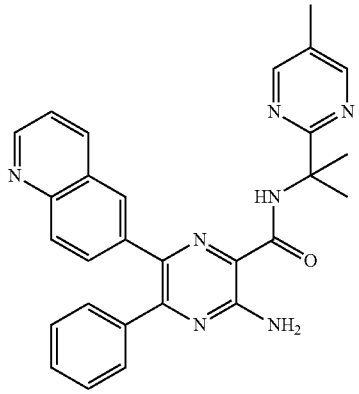 [SMILES: Cc1cnc(C(C)(C)NC(=O)c2nc(-c3ccc4ncccc4c3)c(-c3ccccc3)nc2N)nc1] |

TABLE 1-continued

| Compd No. | Structure |
|---|---|
| 225 | 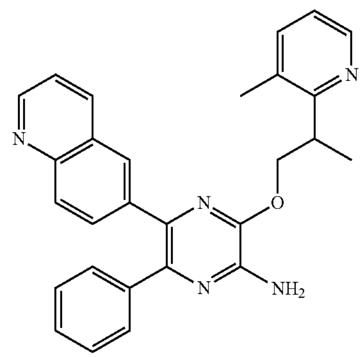 [SMILES: Cc1cccnc1C(C)COc1nc(-c2ccc3ncccc3c2)c(-c2ccccc2)nc1N] |
| 226 | 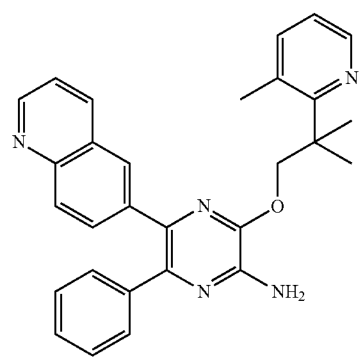 [SMILES: Cc1cccnc1C(C)(C)COc1nc(-c2ccc3ncccc3c2)c(-c2ccccc2)nc1N] |
| 227 | 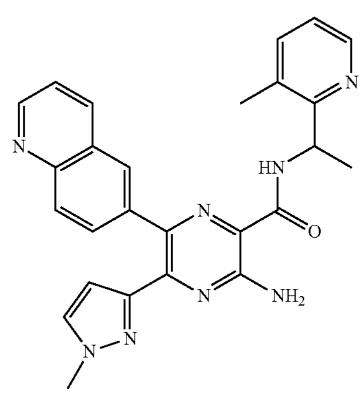 [SMILES: Cc1cccnc1C(C)NC(=O)c1nc(-c2ccc3ncccc3c2)c(-c2ccn(C)n2)nc1N] |
| 228 | 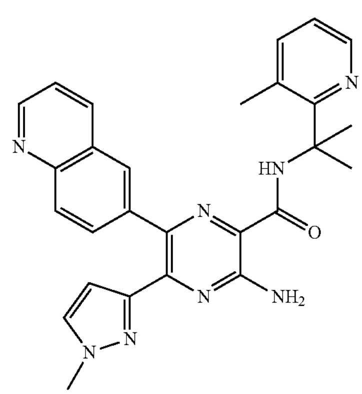 [SMILES: Cc1cccnc1C(C)(C)NC(=O)c1nc(-c2ccc3ncccc3c2)c(-c2ccn(C)n2)nc1N] |

TABLE 1-continued
| Compd No. | Structure |
|---|---|
| 229 | 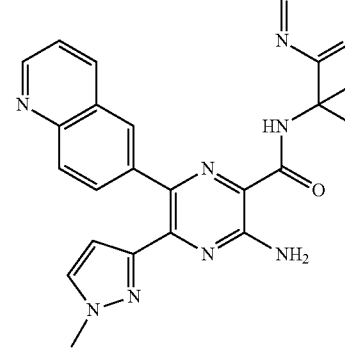 |
| 230 | 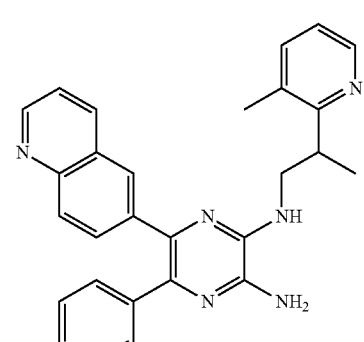 |
| 231 | 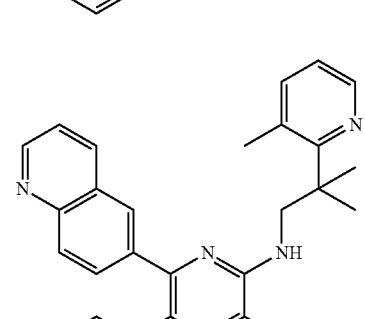 |
| 232 | 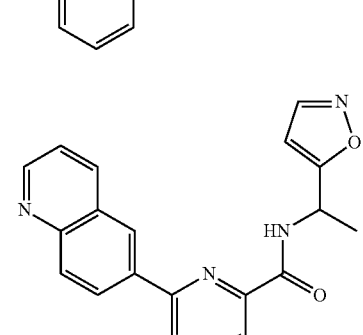 |

TABLE 1-continued

| Compd No. | Structure |
|---|---|
| 233 | 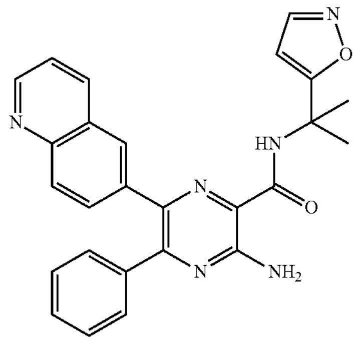 [SMILES: CC(C)(NC(=O)c1nc(-c2ccc3ncccc3c2)c(-c2ccccc2)nc1N)c1ccno1] |
| 234 | 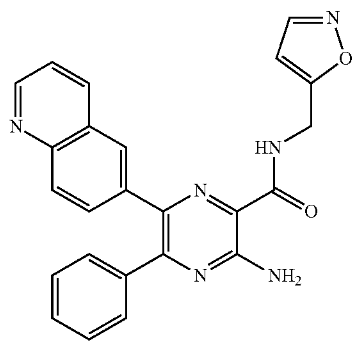 [SMILES: Nc1nc(-c2ccccc2)c(-c2ccc3ncccc3c2)nc1C(=O)NCc1ccno1] |
| 235 | 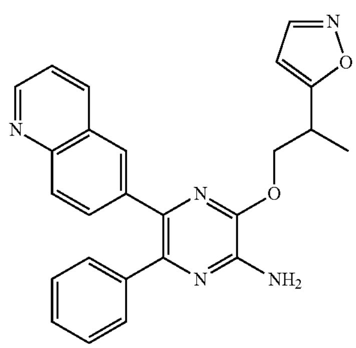 [SMILES: CC(COc1nc(-c2ccc3ncccc3c2)c(-c2ccccc2)nc1N)c1ccno1] |
| 236 | 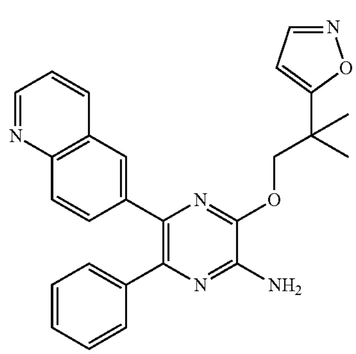 [SMILES: CC(C)(COc1nc(-c2ccc3ncccc3c2)c(-c2ccccc2)nc1N)c1ccno1] |

TABLE 1-continued
| Compd No. | Structure |
|---|---|
| 237 | 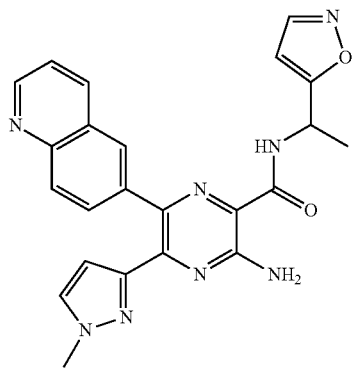 [SMILES: CC(NC(=O)c1nc(-c2ccc3ncccc3c2)c(-c2ccn(C)n2)nc1N)c1ccno1] |
| 238 | 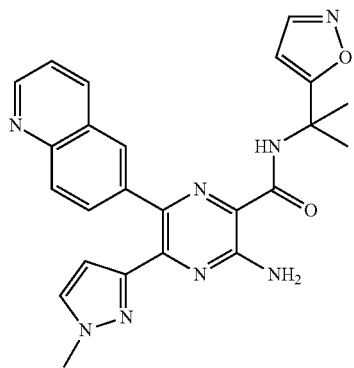 [SMILES: Cn1ccc(-c2nc(N)c(C(=O)NC(C)(C)c3ccno3)nc2-c2ccc3ncccc3c2)n1] |
| 239 | 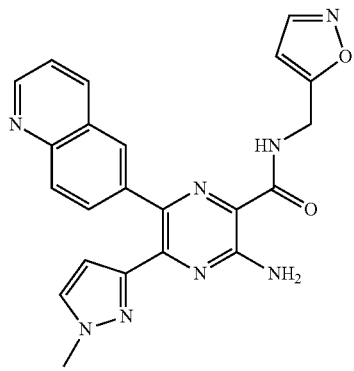 |
| 240 | 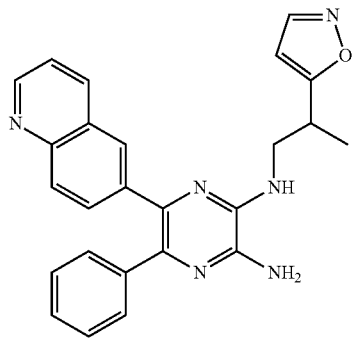 |

TABLE 1-continued

| Compd No. | Structure |
|---|---|
| 241 | 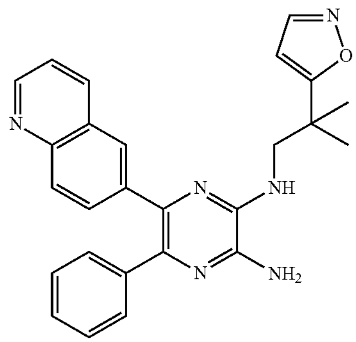 [SMILES: CC(C)(CNc1nc(-c2ccc3ncccc3c2)c(-c2ccccc2)nc1N)c1ccno1] |
| 242 | 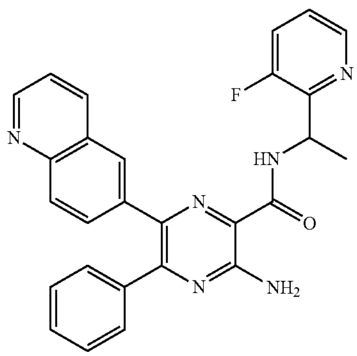 [SMILES: CC(NC(=O)c1nc(-c2ccc3ncccc3c2)c(-c2ccccc2)nc1N)c1ncccc1F] |
| 243 | 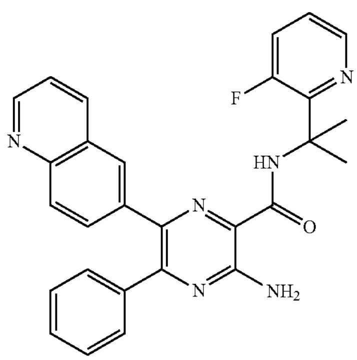 |
| 244 | 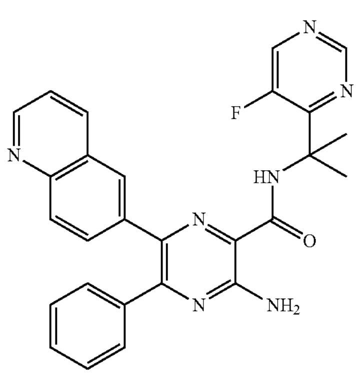 [SMILES: CC(C)(NC(=O)c1nc(-c2ccc3ncccc3c2)c(-c2ccccc2)nc1N)c1ncncc1F] |

TABLE 1-continued
| Compd No. | Structure |
|---|---|
| 245 | 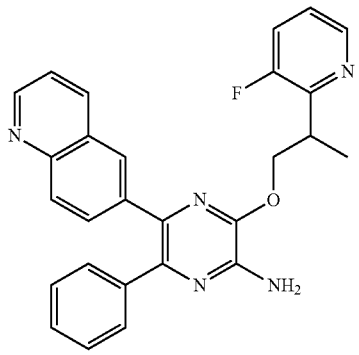 [SMILES: CC(COc1nc(-c2ccc3ncccc3c2)c(-c2ccccc2)nc1N)c1ncccc1F] |
| 246 | 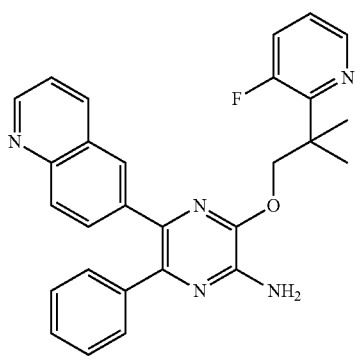 [SMILES: CC(C)(COc1nc(-c2ccc3ncccc3c2)c(-c2ccccc2)nc1N)c1ncccc1F] |
| 247 | 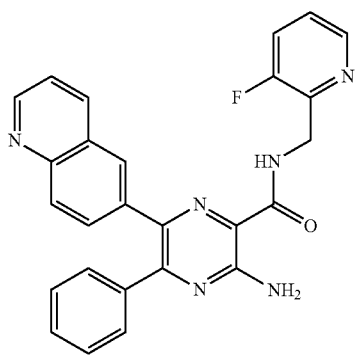 [SMILES: Nc1nc(-c2ccccc2)c(-c2ccc3ncccc3c2)nc1C(=O)NCc1ncccc1F] |
| 248 | 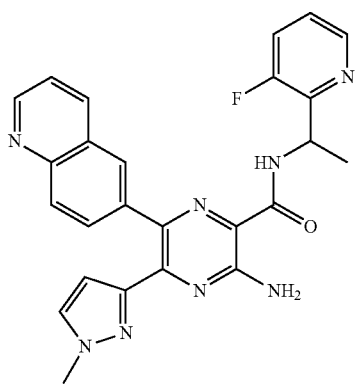 [SMILES: CC(NC(=O)c1nc(-c2ccc3ncccc3c2)c(-c2ccn(C)n2)nc1N)c1ncccc1F] |

TABLE 1-continued

| Compd No. | Structure |
|---|---|
| 249 | 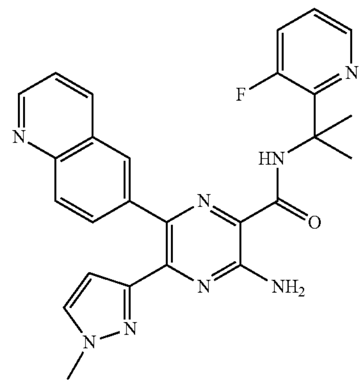 [SMILES: Cn1ccc(-c2nc(N)c(C(=O)NC(C)(C)c3ncccc3F)nc2-c2ccc3ncccc3c2)n1] |
| 250 | 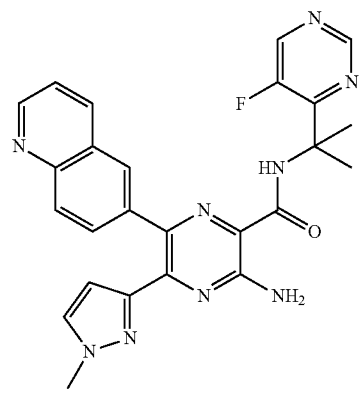 [SMILES: Cn1ccc(-c2nc(N)c(C(=O)NC(C)(C)c3ncncc3F)nc2-c2ccc3ncccc3c2)n1] |
| 251 | 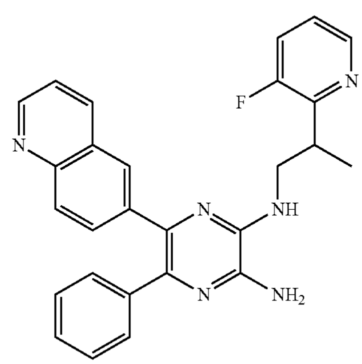 [SMILES: CC(CNc1nc(-c2ccc3ncccc3c2)c(-c2ccccc2)nc1N)c1ncccc1F] |
| 252 | 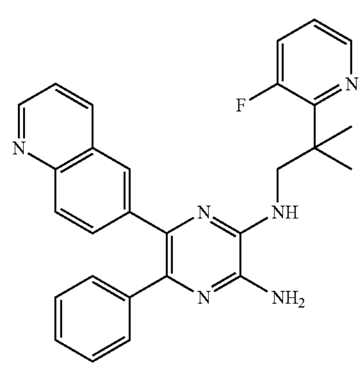 [SMILES: CC(C)(CNc1nc(-c2ccc3ncccc3c2)c(-c2ccccc2)nc1N)c1ncccc1F] |

TABLE 1-continued
| Compd No. | Structure |
|---|---|
| 253 | 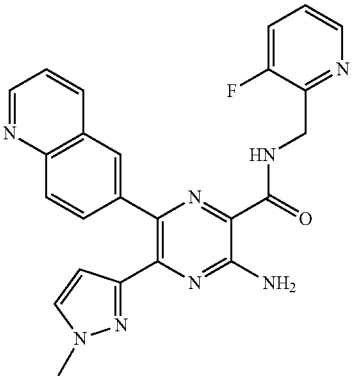 [SMILES: Cn1ccc(-c2nc(N)c(C(=O)NCc3ncccc3F)nc2-c2ccc3ncccc3c2)n1] |
| 254 | 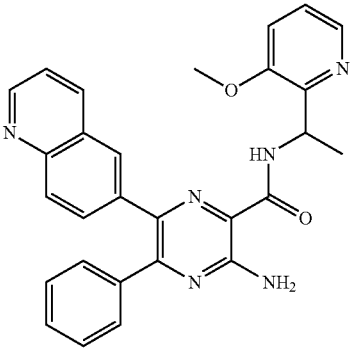 [SMILES: COc1cccnc1C(C)NC(=O)c1nc(-c2ccc3ncccc3c2)c(-c2ccccc2)nc1N] |
| 255 | 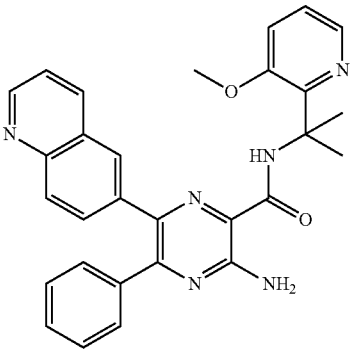 [SMILES: COc1cccnc1C(C)(C)NC(=O)c1nc(-c2ccc3ncccc3c2)c(-c2ccccc2)nc1N] |
| 256 | 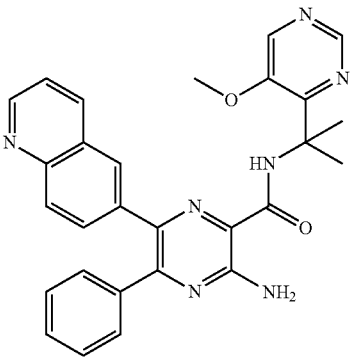 [SMILES: COc1cncnc1C(C)(C)NC(=O)c1nc(-c2ccc3ncccc3c2)c(-c2ccccc2)nc1N] |

TABLE 1-continued
| Compd No. | Structure |
|---|---|
| 257 | 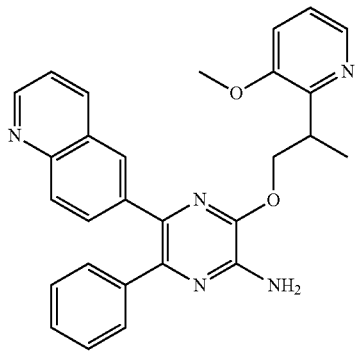 [SMILES: COc1cccnc1C(C)COc1nc(-c2ccc3ncccc3c2)c(-c2ccccc2)nc1N] |
| 258 | 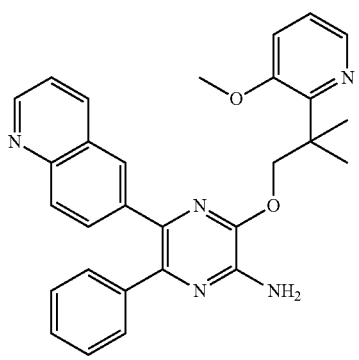 [SMILES: COc1cccnc1C(C)(C)COc1nc(-c2ccc3ncccc3c2)c(-c2ccccc2)nc1N] |
| 259 | 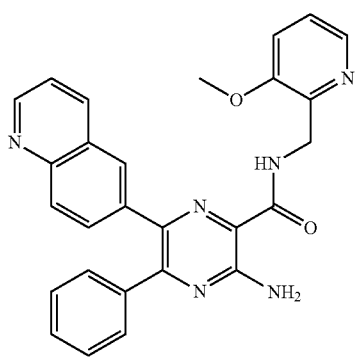 [SMILES: COc1cccnc1CNC(=O)c1nc(-c2ccc3ncccc3c2)c(-c2ccccc2)nc1N] |
| 260 | 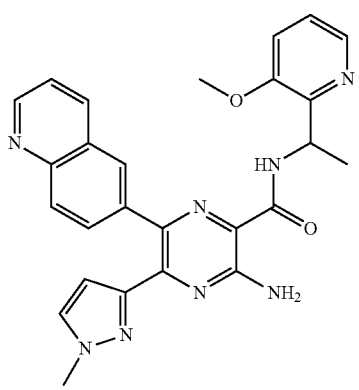 [SMILES: COc1cccnc1C(C)NC(=O)c1nc(-c2ccc3ncccc3c2)c(-c2ccn(C)n2)nc1N] |

TABLE 1-continued

| Compd No. | Structure |
|---|---|
| 261 | 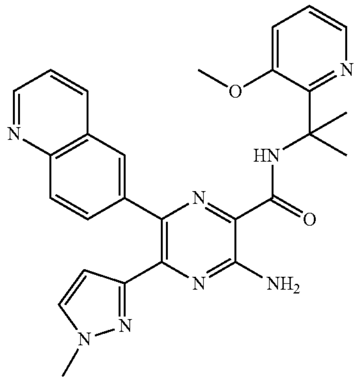 [SMILES: COc1cccnc1C(C)(C)NC(=O)c1nc(-c2ccc3ncccc3c2)c(-c2ccn(C)n2)nc1N] |
| 262 | 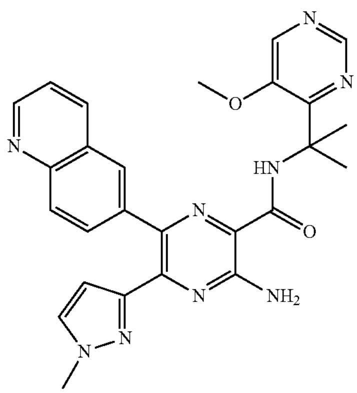 [SMILES: COc1cncnc1C(C)(C)NC(=O)c1nc(-c2ccc3ncccc3c2)c(-c2ccn(C)n2)nc1N] |
| 263 | 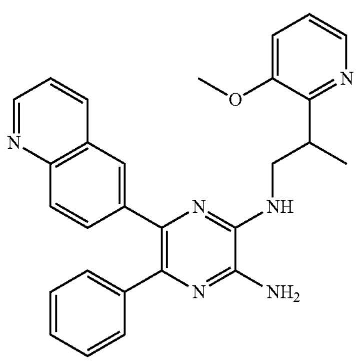 [SMILES: COc1cccnc1C(C)CNc1nc(-c2ccc3ncccc3c2)c(-c2ccccc2)nc1N] |
| 264 | 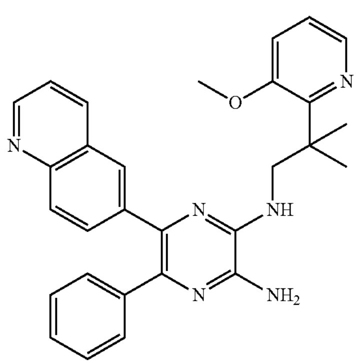 [SMILES: COc1cccnc1C(C)(C)CNc1nc(-c2ccc3ncccc3c2)c(-c2ccccc2)nc1N] |

TABLE 1-continued
| Compd No. | Structure |
|---|---|
| 265 | 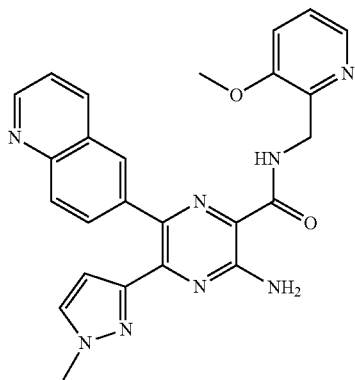 [SMILES: COc1cccnc1CNC(=O)c1nc(-c2ccc3ncccc3c2)c(-c2ccn(C)n2)nc1N] |
| 266 | 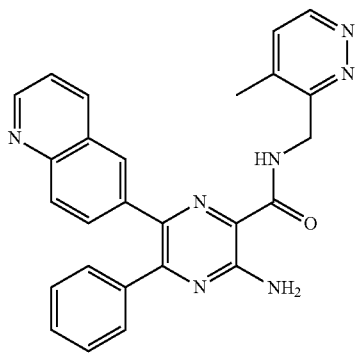 [SMILES: Cc1ccnnc1CNC(=O)c1nc(-c2ccc3ncccc3c2)c(-c2ccccc2)nc1N] |
| 267 | 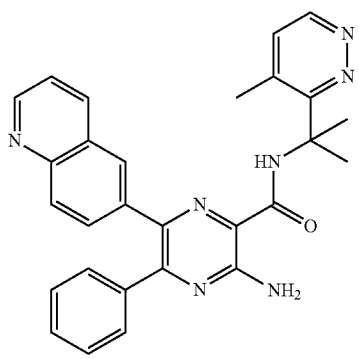 [SMILES: Cc1ccnnc1C(C)(C)NC(=O)c1nc(-c2ccc3ncccc3c2)c(-c2ccccc2)nc1N] |
| 268 | 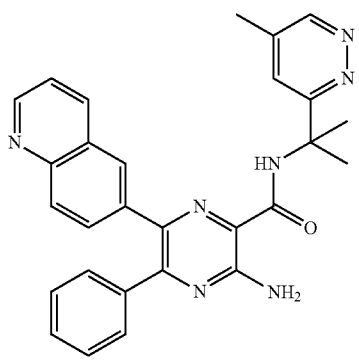 [SMILES: Cc1cnnc(C(C)(C)NC(=O)c2nc(-c3ccc4ncccc4c3)c(-c3ccccc3)nc2N)c1] |

TABLE 1-continued

| Compd No. | Structure |
|---|---|
| 269 | 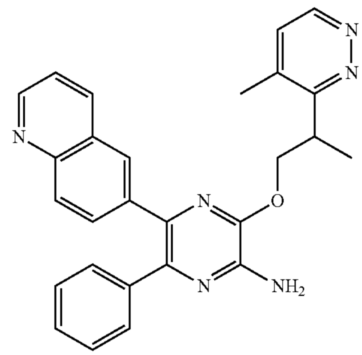 [SMILES: Cc1ccnnc1C(C)COc1nc(-c2ccc3ncccc3c2)c(-c2ccccc2)nc1N] |
| 270 | 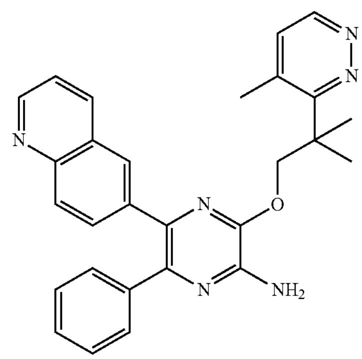 [SMILES: Cc1ccnnc1C(C)(C)COc1nc(-c2ccc3ncccc3c2)c(-c2ccccc2)nc1N] |
| 271 | 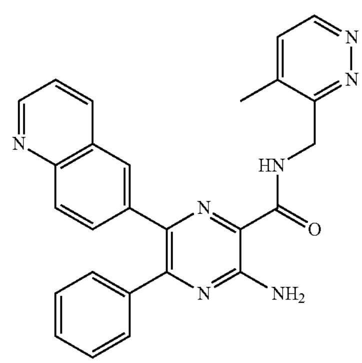 [SMILES: Cc1ccnnc1CNC(=O)c1nc(-c2ccc3ncccc3c2)c(-c2ccccc2)nc1N] |
| 272 | 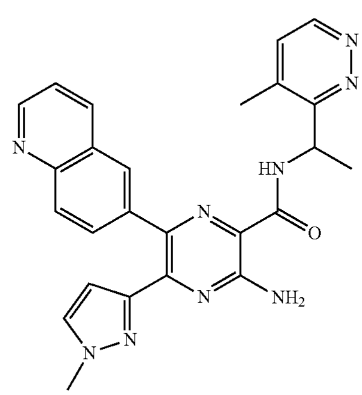 [SMILES: Cc1ccnnc1C(C)NC(=O)c1nc(-c2ccc3ncccc3c2)c(-c2ccn(C)n2)nc1N] |

TABLE 1-continued

| Compd No. | Structure |
|---|---|
| 273 | 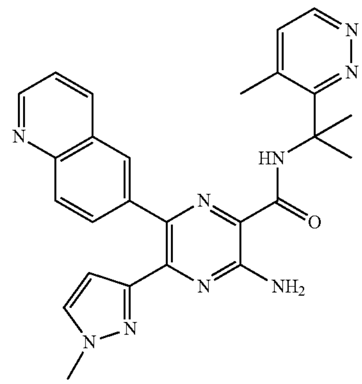 [SMILES: Cc1ccnnc1C(C)(C)NC(=O)c1nc(-c2ccc3ncccc3c2)c(-c2ccn(C)n2)nc1N] |
| 274 | 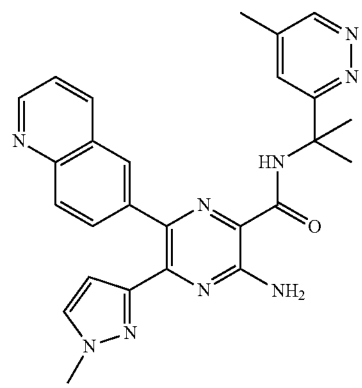 [SMILES: Cc1cnnc(C(C)(C)NC(=O)c2nc(-c3ccc4ncccc4c3)c(-c3ccn(C)n3)nc2N)c1] |
| 275 | 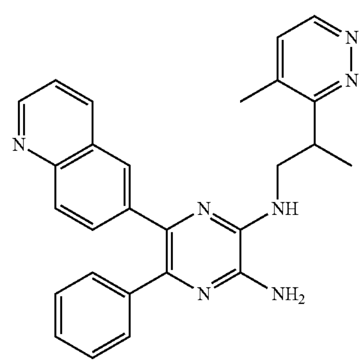 [SMILES: Cc1ccnnc1C(C)CNc1nc(-c2ccc3ncccc3c2)c(-c2ccccc2)nc1N] |
| 276 | 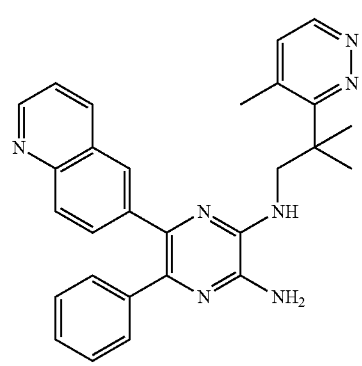 [SMILES: Cc1ccnnc1C(C)(C)CNc1nc(-c2ccc3ncccc3c2)c(-c2ccccc2)nc1N] |

TABLE 1-continued
| Compd No. | Structure |
| --- | --- |
| 277 | 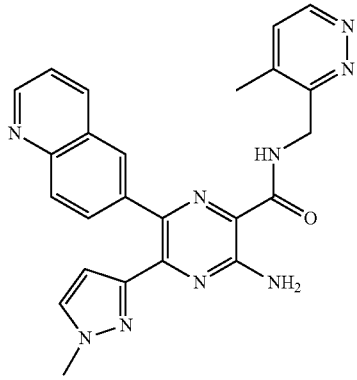 [SMILES: Cc1ccnnc1CNC(=O)c1nc(-c2ccc3ncccc3c2)c(-c2ccn(C)n2)nc1N] |
| 278 | 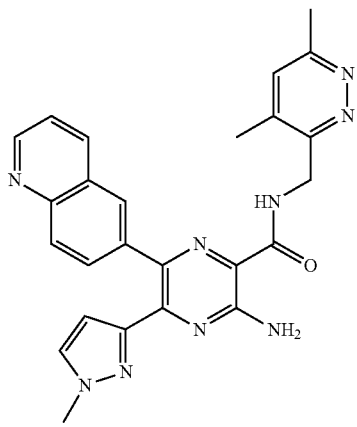 [SMILES: Cc1cc(C)c(CNC(=O)c2nc(-c3ccc4ncccc4c3)c(-c3ccn(C)n3)nc2N)nn1] |
| 279 | 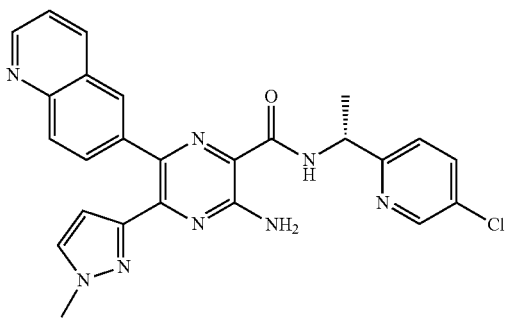 [SMILES: C[C@@H](NC(=O)c1nc(-c2ccc3ncccc3c2)c(-c2ccn(C)n2)nc1N)c1ccc(Cl)cn1] |
| 280 | 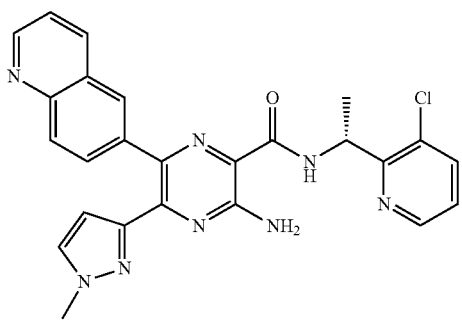 [SMILES: C[C@@H](NC(=O)c1nc(-c2ccc3ncccc3c2)c(-c2ccn(C)n2)nc1N)c1ncccc1Cl] |

TABLE 1-continued

| Compd No. | Structure |
|---|---|
| 281 | 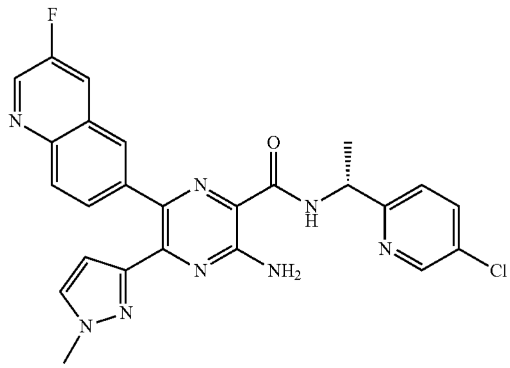 [SMILES: C[C@@H](NC(=O)c1nc(-c2ccc3ncc(F)cc3c2)c(-c2ccn(C)n2)nc1N)c1ccc(Cl)cn1] |
| 282 | 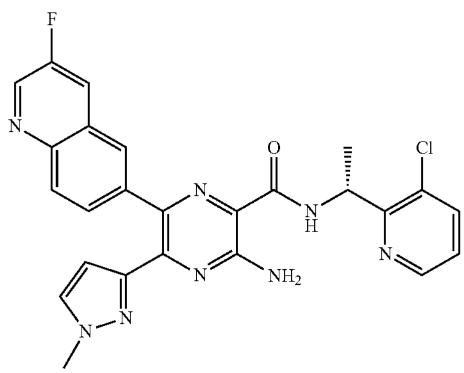 [SMILES: C[C@@H](NC(=O)c1nc(-c2ccc3ncc(F)cc3c2)c(-c2ccn(C)n2)nc1N)c1ncccc1Cl] |
| 283 | 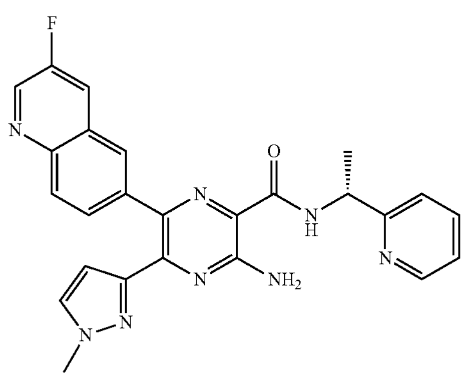 [SMILES: C[C@@H](NC(=O)c1nc(-c2ccc3ncc(F)cc3c2)c(-c2ccn(C)n2)nc1N)c1ccccn1] |
| 284 | 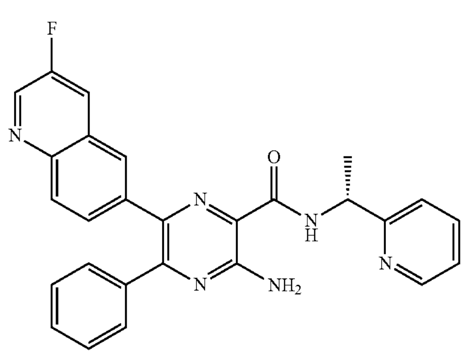 [SMILES: C[C@@H](NC(=O)c1nc(-c2ccc3ncc(F)cc3c2)c(-c2ccccc2)nc1N)c1ccccn1] |

TABLE 1-continued

| Compd No. | Structure |
|---|---|
| 285 | 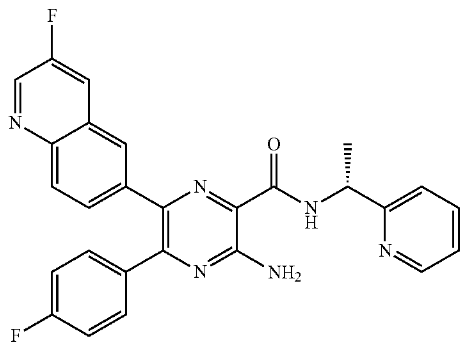 [SMILES: C[C@@H](NC(=O)c1nc(-c2ccc3ncc(F)cc3c2)c(-c2ccc(F)cc2)nc1N)c1ccccn1] |
| 286 | 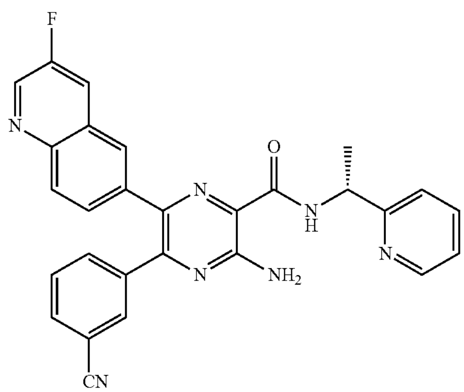 [SMILES: C[C@@H](NC(=O)c1nc(-c2ccc3ncc(F)cc3c2)c(-c2cccc(C#N)c2)nc1N)c1ccccn1] |
| 287 | 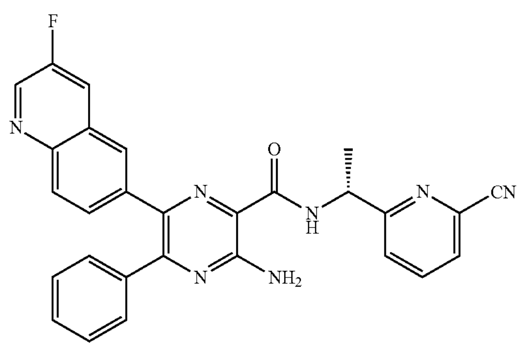 [SMILES: C[C@@H](NC(=O)c1nc(-c2ccc3ncc(F)cc3c2)c(-c2ccccc2)nc1N)c1cccc(C#N)n1] |
| 288 | 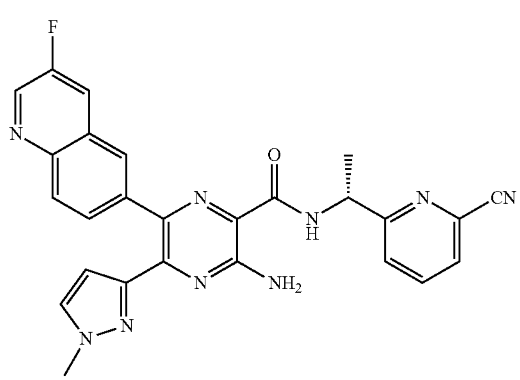 [SMILES: C[C@@H](NC(=O)c1nc(-c2ccc3ncc(F)cc3c2)c(-c2ccn(C)n2)nc1N)c1cccc(C#N)n1] |

TABLE 1-continued

| Compd No. | Structure |
|---|---|
| 289 | 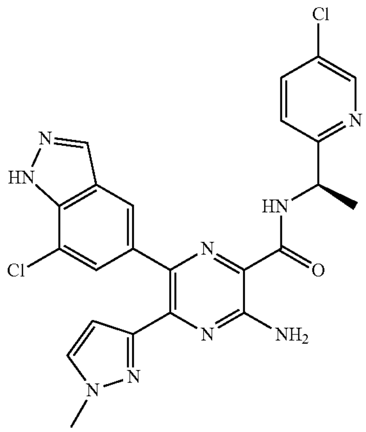 [SMILES: C[C@@H](NC(=O)c1nc(-c2cc(Cl)c3[nH]ncc3c2)c(-c2ccn(C)n2)nc1N)c1ccc(Cl)cn1] |
| 290 | 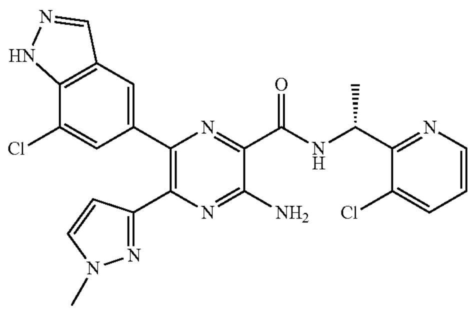 [SMILES: C[C@@H](NC(=O)c1nc(-c2cc(Cl)c3[nH]ncc3c2)c(-c2ccn(C)n2)nc1N)c1ncccc1Cl] |
| 291 | 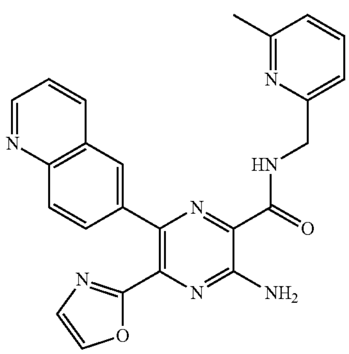 [SMILES: Cc1cccc(CNC(=O)c2nc(-c3ccc4ncccc4c3)c(-c3ncco3)nc2N)n1] |
| 292 | 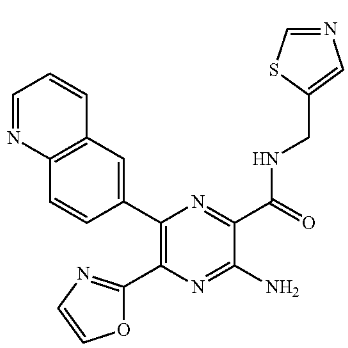 [SMILES: Nc1nc(-c2ncco2)c(-c2ccc3ncccc3c2)nc1C(=O)NCc1cncs1] |

TABLE 1-continued

| Compd No. | Structure |
|---|---|
| 293 | 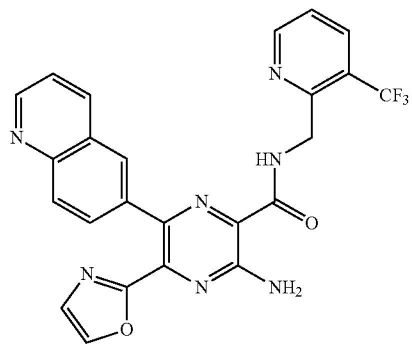 [SMILES: Nc1nc(-c2ncco2)c(-c2ccc3ncccc3c2)nc1C(=O)NCc1ncccc1C(F)(F)F] |
| 294 | 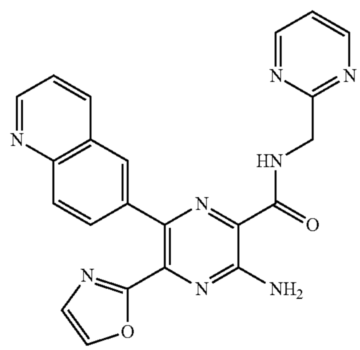 [SMILES: Nc1nc(-c2ncco2)c(-c2ccc3ncccc3c2)nc1C(=O)NCc1ncccn1] |
| 295 | 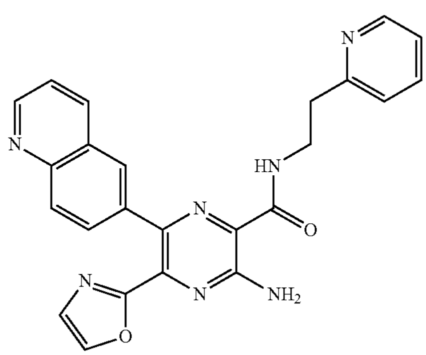 [SMILES: Nc1nc(-c2ncco2)c(-c2ccc3ncccc3c2)nc1C(=O)NCCc1ccccn1] |
| 296 | 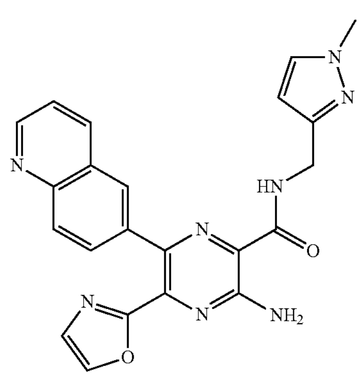 [SMILES: Cn1ccc(CNC(=O)c2nc(-c3ccc4ncccc4c3)c(-c3ncco3)nc2N)n1] |

TABLE 1-continued

| Compd No. | Structure |
|---|---|
| 297 | 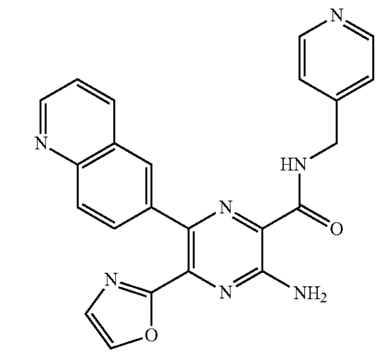 [SMILES: Nc1nc(-c2ncco2)c(-c2ccc3ncccc3c2)nc1C(=O)NCc1ccncc1] |
| 298 | 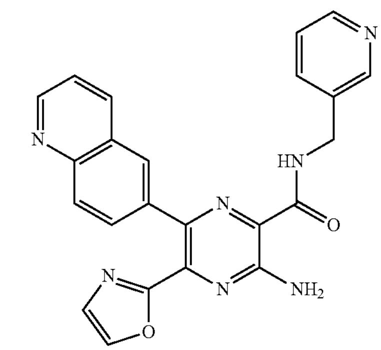 [SMILES: Nc1nc(-c2ncco2)c(-c2ccc3ncccc3c2)nc1C(=O)NCc1cccnc1] |
| 299 | 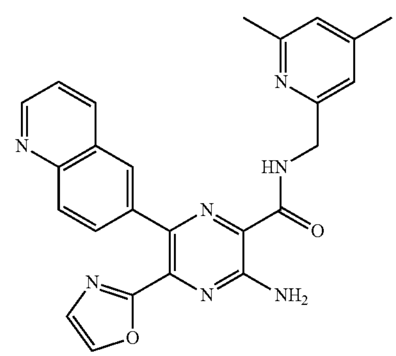 [SMILES: Cc1cc(C)nc(CNC(=O)c2nc(-c3ccc4ncccc4c3)c(-c3ncco3)nc2N)c1] |
| 300 | 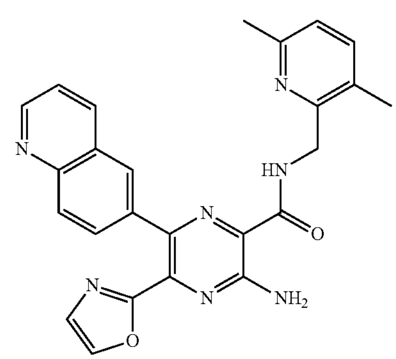 [SMILES: Cc1ccc(C)c(CNC(=O)c2nc(-c3ccc4ncccc4c3)c(-c3ncco3)nc2N)n1] |

TABLE 1-continued

| Compd No. | Structure |
|---|---|
| 301 | 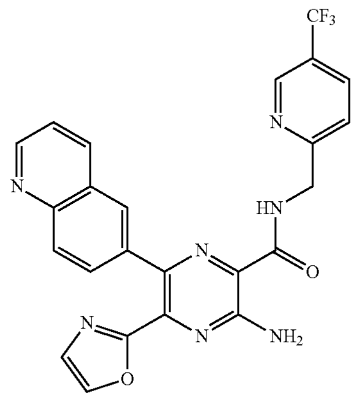 |
| 302 | 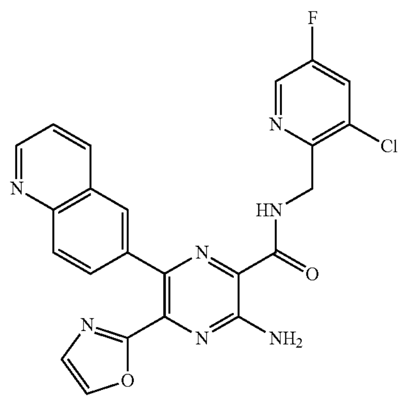 [SMILES: Nc1nc(-c2ncco2)c(-c2ccc3ncccc3c2)nc1C(=O)NCc1ncc(F)cc1Cl] |
| 303 | 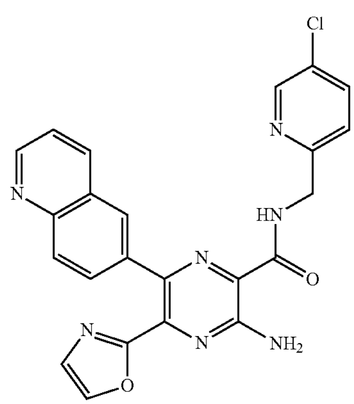 [SMILES: Nc1nc(-c2ncco2)c(-c2ccc3ncccc3c2)nc1C(=O)NCc1ccc(Cl)cn1] |
| 304 | 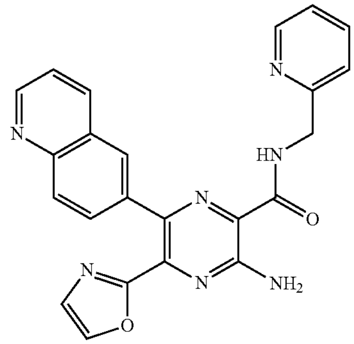 [SMILES: Nc1nc(-c2ncco2)c(-c2ccc3ncccc3c2)nc1C(=O)NCc1ccccn1] |

TABLE 1-continued

| Compd No. | Structure |
|---|---|
| 305 | 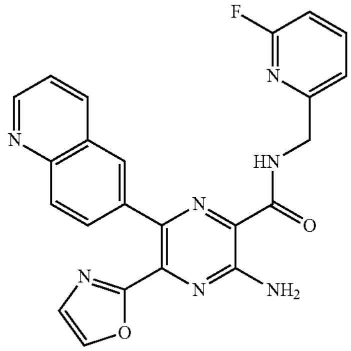 [SMILES: Nc1nc(-c2ncco2)c(-c2ccc3ncccc3c2)nc1C(=O)NCc1cccc(F)n1] |
| 306 | 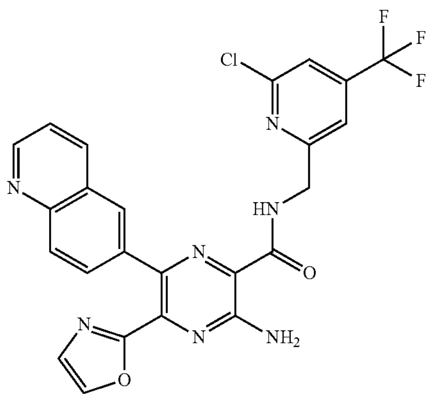 [SMILES: Nc1nc(-c2ncco2)c(-c2ccc3ncccc3c2)nc1C(=O)NCc1cc(C(F)(F)F)cc(Cl)n1] |
| 307 | 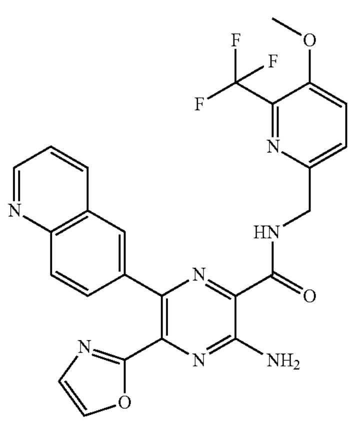 [SMILES: COc1ccc(CNC(=O)c2nc(-c3ccc4ncccc4c3)c(-c3ncco3)nc2N)nc1C(F)(F)F] |
| 308 | 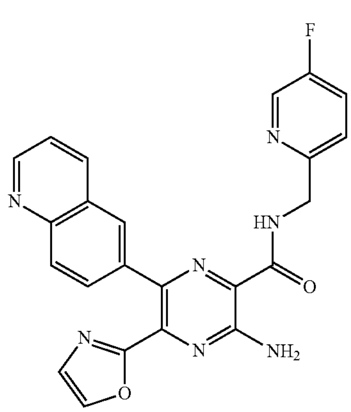 |

TABLE 1-continued

| Compd No. | Structure |
|---|---|
| 309 | 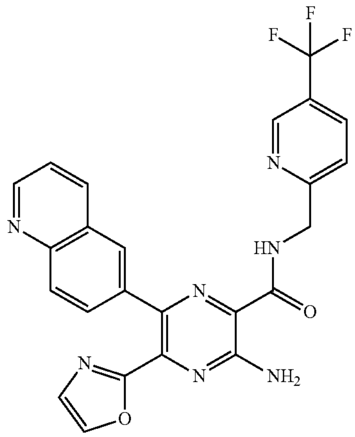 [SMILES: Nc1nc(-c2ncco2)c(-c2ccc3ncccc3c2)nc1C(=O)NCc1ccc(C(F)(F)F)cn1] |
| 310 | 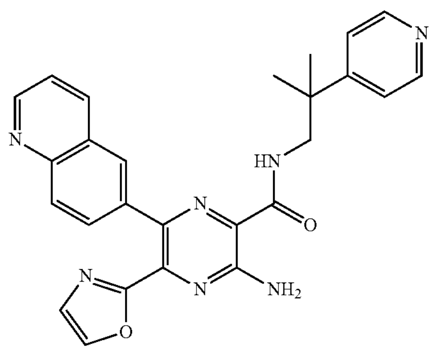 [SMILES: CC(C)(CNC(=O)c1nc(-c2ccc3ncccc3c2)c(-c2ncco2)nc1N)c1ccncc1] |
| 311 | 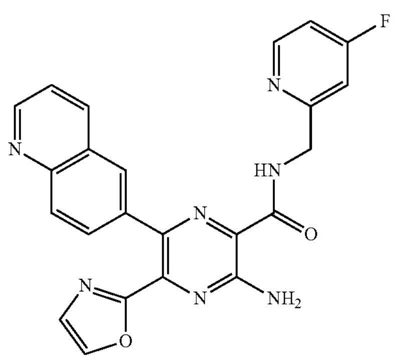 [SMILES: Nc1nc(-c2ncco2)c(-c2ccc3ncccc3c2)nc1C(=O)NCc1cc(F)ccn1] |
| 312 | 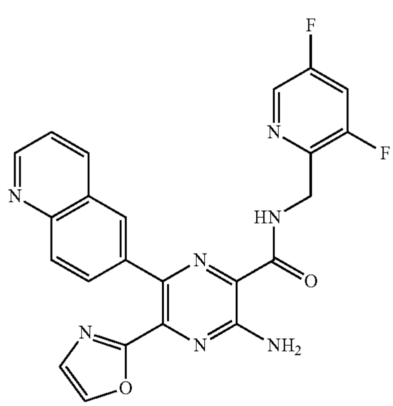 [SMILES: Nc1nc(-c2ncco2)c(-c2ccc3ncccc3c2)nc1C(=O)NCc1ncc(F)cc1F] |

TABLE 1-continued

| Compd No. | Structure |
|---|---|
| 313 | 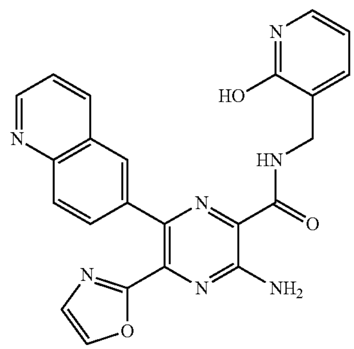 [SMILES: Nc1nc(-c2ncco2)c(-c2ccc3ncccc3c2)nc1C(=O)NCc1cccnc1O] |
| 314 | 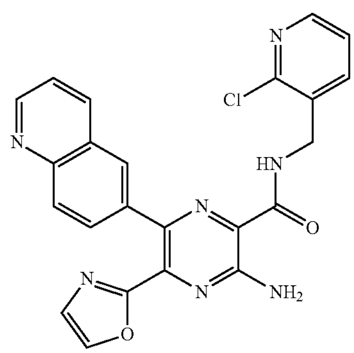 [SMILES: Nc1nc(-c2ncco2)c(-c2ccc3ncccc3c2)nc1C(=O)NCc1cccnc1Cl] |
| 315 | 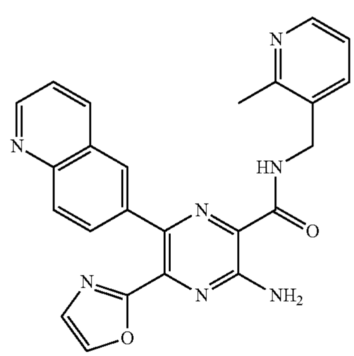 [SMILES: Cc1ncccc1CNC(=O)c1nc(-c2ccc3ncccc3c2)c(-c2ncco2)nc1N] |
| 316 | 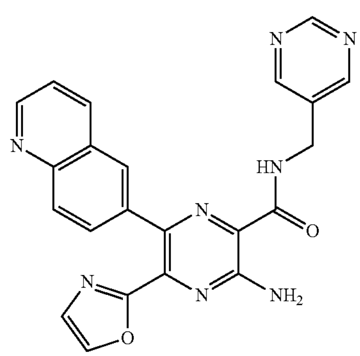 [SMILES: Nc1nc(-c2ncco2)c(-c2ccc3ncccc3c2)nc1C(=O)NCc1cncnc1] |

TABLE 1-continued
| Compd No. | Structure |
|---|---|
| 317 | 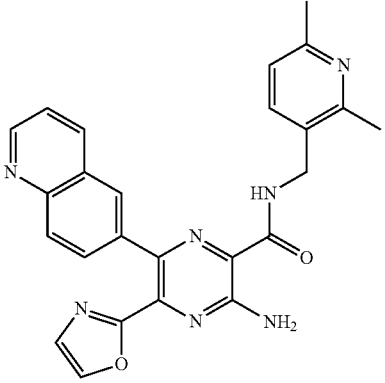 [SMILES: Cc1ccc(CNC(=O)c2nc(-c3ccc4ncccc4c3)c(-c3ncco3)nc2N)c(C)n1] |
| 318 | 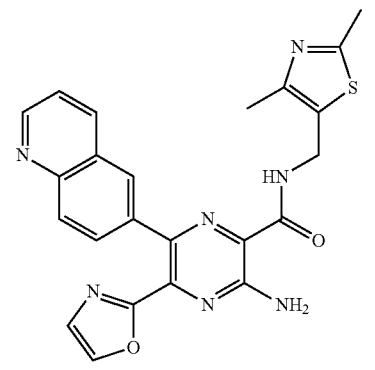 [SMILES: Cc1nc(C)c(CNC(=O)c2nc(-c3ccc4ncccc4c3)c(-c3ncco3)nc2N)s1] |
| 319 | 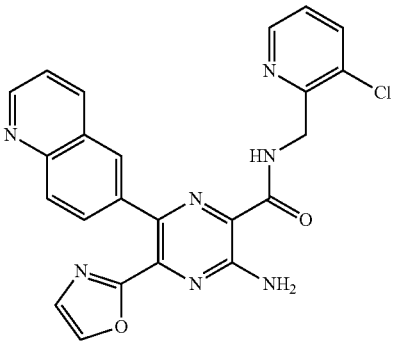 [SMILES: Nc1nc(-c2ncco2)c(-c2ccc3ncccc3c2)nc1C(=O)NCc1ncccc1Cl] |
| 320 | 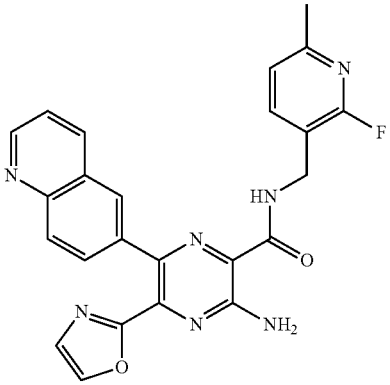 [SMILES: Cc1ccc(CNC(=O)c2nc(-c3ccc4ncccc4c3)c(-c3ncco3)nc2N)c(F)n1] |

TABLE 1-continued

| Compd No. | Structure |
|---|---|
| 321 | 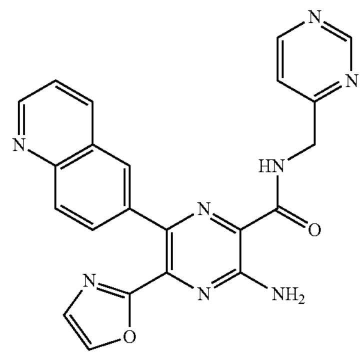 [SMILES: Nc1nc(-c2ncco2)c(-c2ccc3ncccc3c2)nc1C(=O)NCc1ccncn1] |
| 322 | 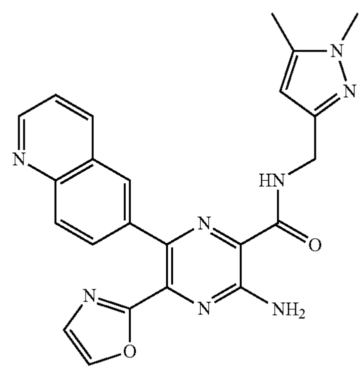 [SMILES: Cc1cc(CNC(=O)c2nc(-c3ccc4ncccc4c3)c(-c3ncco3)nc2N)nn1C] |
| 323 | 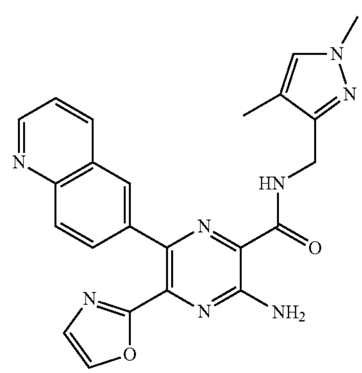 [SMILES: Cc1cn(C)nc1CNC(=O)c1nc(-c2ccc3ncccc3c2)c(-c2ncco2)nc1N] |
| 324 | 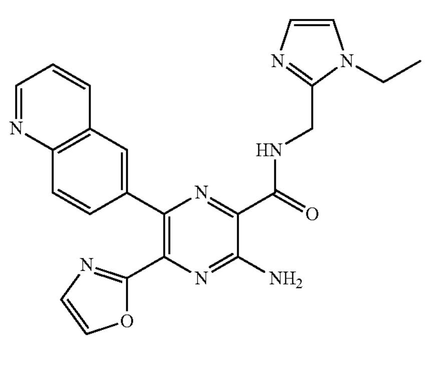 [SMILES: CCn1ccnc1CNC(=O)c1nc(-c2ccc3ncccc3c2)c(-c2ncco2)nc1N] |

TABLE 1-continued
| Compd No. | Structure |
|---|---|
| 325 | 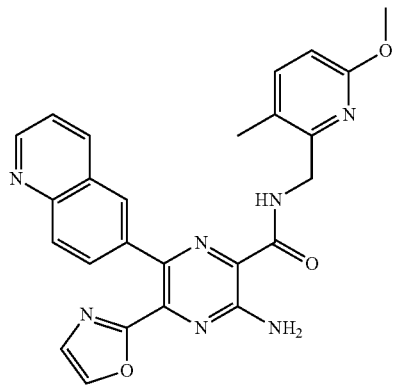 [SMILES: COc1ccc(C)c(CNC(=O)c2nc(-c3ccc4ncccc4c3)c(-c3ncco3)nc2N)n1] |
| 326 | 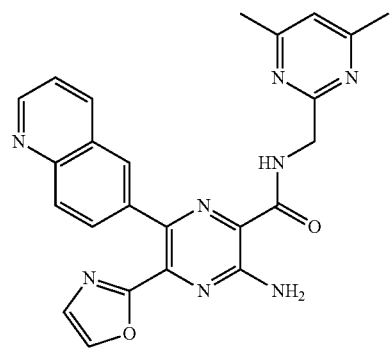 [SMILES: Cc1cc(C)nc(CNC(=O)c2nc(-c3ccc4ncccc4c3)c(-c3ncco3)nc2N)n1] |
| 327 | 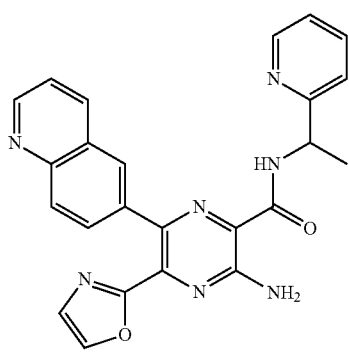 [SMILES: CC(NC(=O)c1nc(-c2ccc3ncccc3c2)c(-c2ncco2)nc1N)c1ccccn1] |
| 328 | 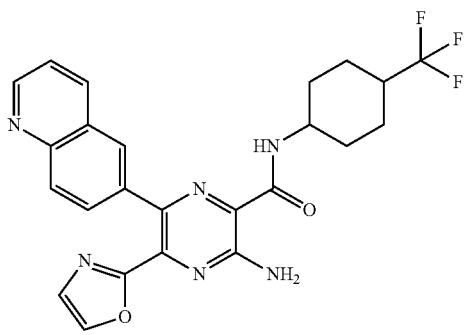 [SMILES: Nc1nc(-c2ncco2)c(-c2ccc3ncccc3c2)nc1C(=O)NC1CCC(C(F)(F)F)CC1] |

TABLE 1-continued
| Compd No. | Structure |
|---|---|
| 329 | 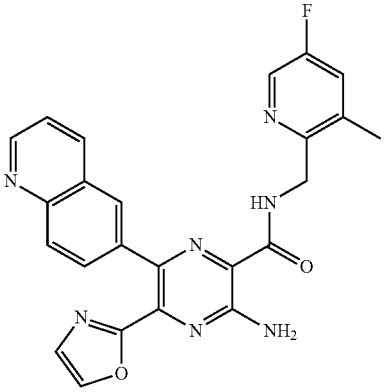 [SMILES: Cc1cc(F)cnc1CNC(=O)c1nc(-c2ccc3ncccc3c2)c(-c2ncco2)nc1N] |
| 330 | 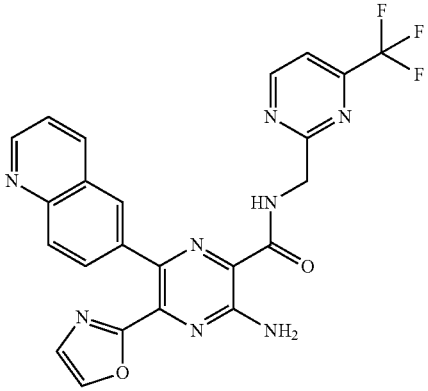 [SMILES: Nc1nc(-c2ncco2)c(-c2ccc3ncccc3c2)nc1C(=O)NCc1nccc(C(F)(F)F)n1] |
| 331 | 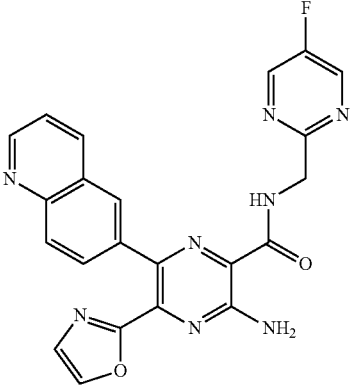 [SMILES: Nc1nc(-c2ncco2)c(-c2ccc3ncccc3c2)nc1C(=O)NCc1ncc(F)cn1] |
| 332 | 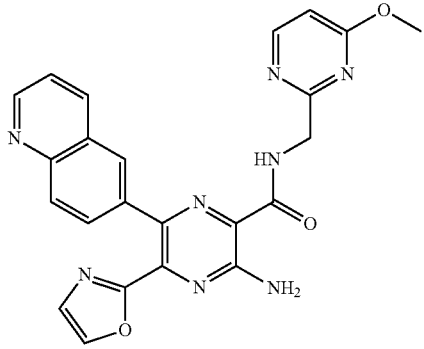 [SMILES: COc1ccnc(CNC(=O)c2nc(-c3ccc4ncccc4c3)c(-c3ncco3)nc2N)n1] |

TABLE 1-continued
| Compd No. | Structure |
|---|---|
| 333 | 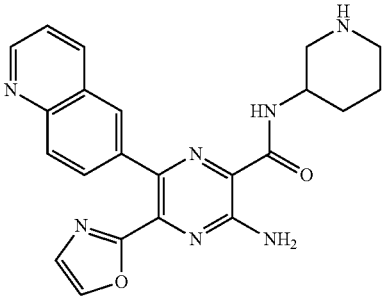 [SMILES: Nc1nc(-c2ncco2)c(-c2ccc3ncccc3c2)nc1C(=O)NC1CCCNC1] |
| 334 | 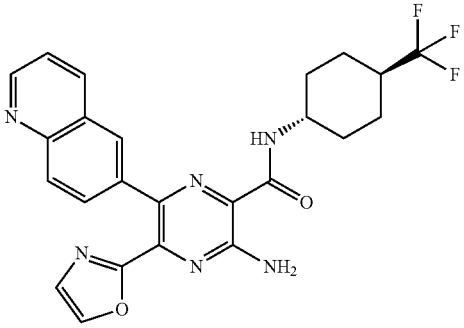 [SMILES: Nc1nc(-c2ncco2)c(-c2ccc3ncccc3c2)nc1C(=O)N[C@H]1CC[C@H](C(F)(F)F)CC1] |
| 335 | 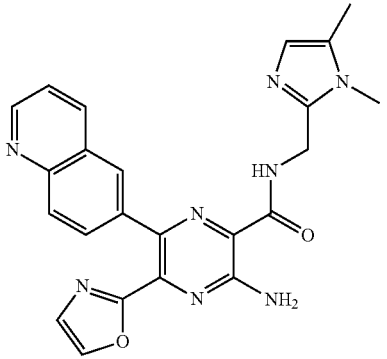 [SMILES: Cc1cnc(CNC(=O)c2nc(-c3ccc4ncccc4c3)c(-c3ncco3)nc2N)n1C] |
| 336 | 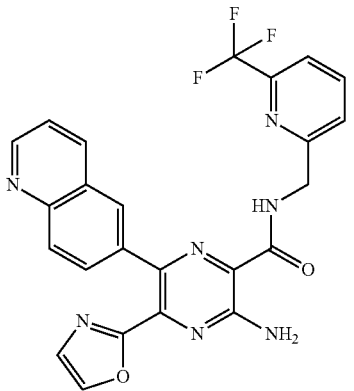 [SMILES: Nc1nc(-c2ncco2)c(-c2ccc3ncccc3c2)nc1C(=O)NCc1cccc(C(F)(F)F)n1] |

TABLE 1-continued
| Compd No. | Structure |
|---|---|
| 337 | 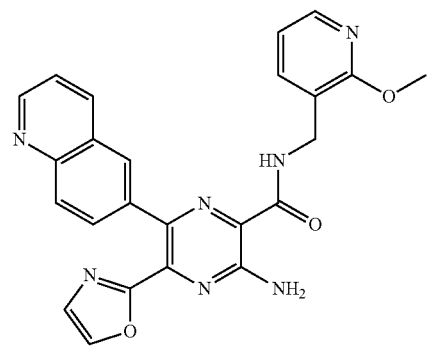 [SMILES: COc1ncccc1CNC(=O)c1nc(-c2ccc3ncccc3c2)c(-c2ncco2)nc1N] |
| 338 | 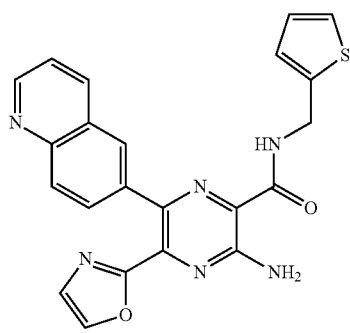 [SMILES: Nc1nc(-c2ncco2)c(-c2ccc3ncccc3c2)nc1C(=O)NCc1cccs1] |
| 339 | 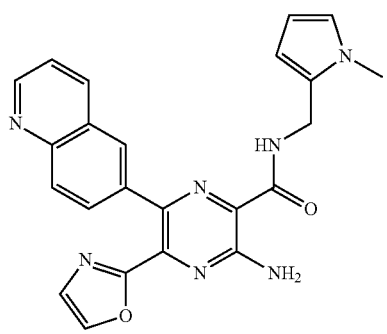 [SMILES: Cn1cccc1CNC(=O)c1nc(-c2ccc3ncccc3c2)c(-c2ncco2)nc1N] |
| 340 | 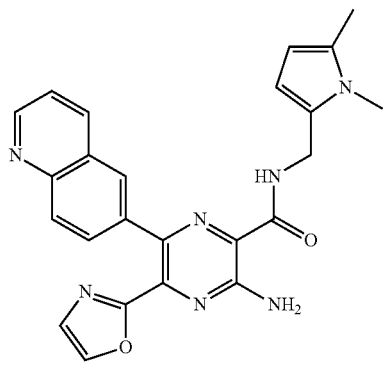 [SMILES: Cc1ccc(CNC(=O)c2nc(-c3ccc4ncccc4c3)c(-c3ncco3)nc2N)n1C] |

TABLE 1-continued
| Compd No. | Structure |
|---|---|
| 341 | 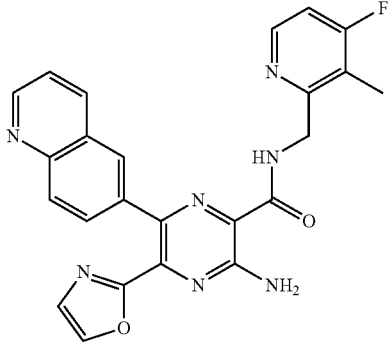 [SMILES: Cc1c(F)ccnc1CNC(=O)c1nc(-c2ccc3ncccc3c2)c(-c2ncco2)nc1N] |
| 342 | 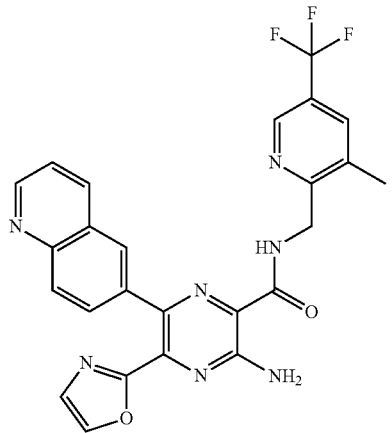 [SMILES: Cc1cc(C(F)(F)F)cnc1CNC(=O)c1nc(-c2ccc3ncccc3c2)c(-c2ncco2)nc1N] |
| 343 | 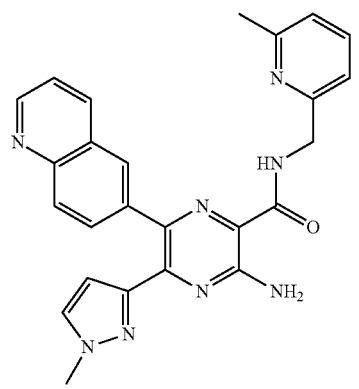 [SMILES: Cc1cccc(CNC(=O)c2nc(-c3ccc4ncccc4c3)c(-c3ccn(C)n3)nc2N)n1] |
| 344 | 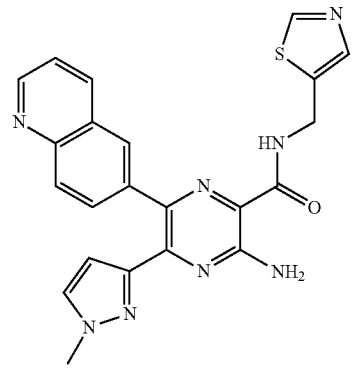 [SMILES: Cn1ccc(-c2nc(N)c(C(=O)NCc3cncs3)nc2-c2ccc3ncccc3c2)n1] |

TABLE 1-continued

| Compd No. | Structure |
|---|---|
| 345 | 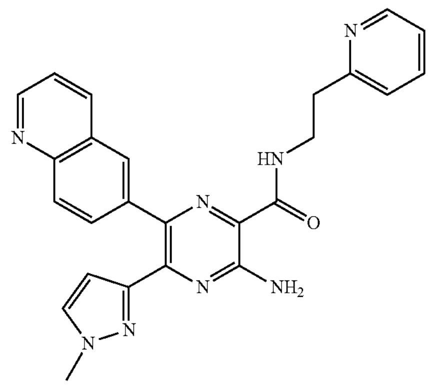 [SMILES: Cn1ccc(-c2nc(N)c(C(=O)NCCc3ccccn3)nc2-c2ccc3ncccc3c2)n1] |
| 346 | 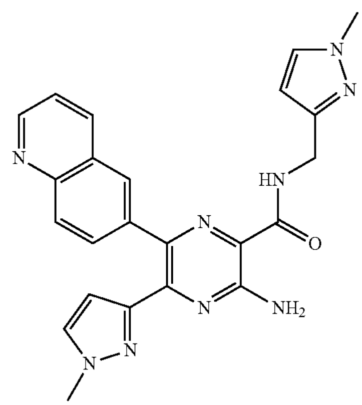 [SMILES: Cn1ccc(CNC(=O)c2nc(-c3ccc4ncccc4c3)c(-c3ccn(C)n3)nc2N)n1] |
| 347 | 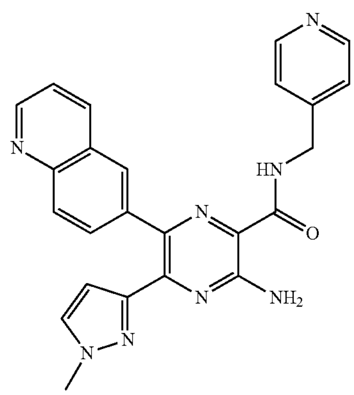 [SMILES: Cn1ccc(-c2nc(N)c(C(=O)NCc3ccncc3)nc2-c2ccc3ncccc3c2)n1] |
| 348 | 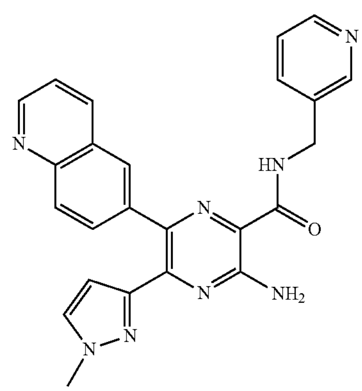 [SMILES: Cn1ccc(-c2nc(N)c(C(=O)NCc3cccnc3)nc2-c2ccc3ncccc3c2)n1] |

TABLE 1-continued
| Compd No. | Structure |
|---|---|
| 349 | 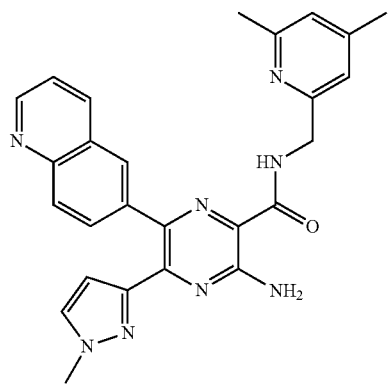 [SMILES: Cc1cc(C)nc(CNC(=O)c2nc(-c3ccc4ncccc4c3)c(-c3ccn(C)n3)nc2N)c1] |
| 350 | 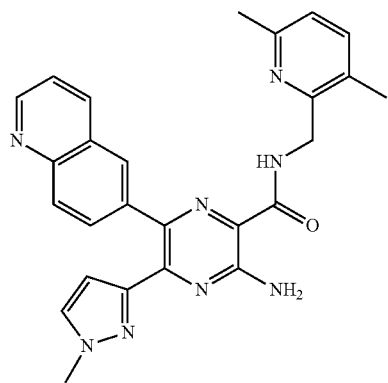 [SMILES: Cc1ccc(C)c(CNC(=O)c2nc(-c3ccc4ncccc4c3)c(-c3ccn(C)n3)nc2N)n1] |
| 351 | 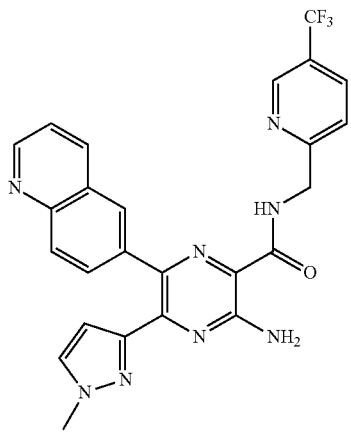 [SMILES: Cn1ccc(-c2nc(N)c(C(=O)NCc3ccc(C(F)(F)F)cn3)nc2-c2ccc3ncccc3c2)n1] |

TABLE 1-continued

| Compd No. | Structure |
|---|---|
| 352 | (structure) |
| 353 | (structure) |
| 354 | (structure) |

TABLE 1-continued

| Compd No. | Structure |
|---|---|
| 355 | 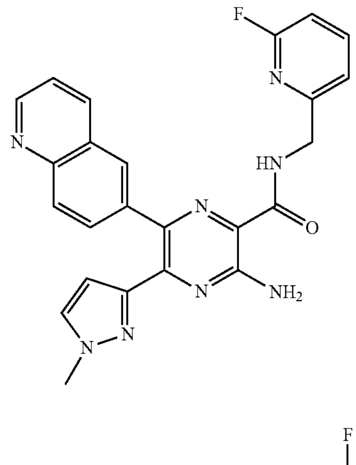 |
| 356 | 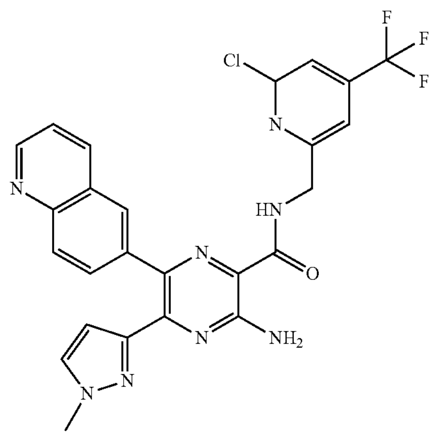 [SMILES: Cn1ccc(-c2nc(N)c(C(=O)NCC3=CC(C(F)(F)F)=CC(Cl)N3)nc2-c2ccc3ncccc3c2)n1] |
| 357 | 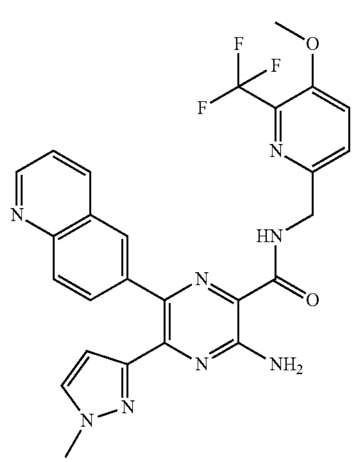 [SMILES: COc1ccc(CNC(=O)c2nc(-c3ccc4ncccc4c3)c(-c3ccn(C)n3)nc2N)nc1C(F)(F)F] |

TABLE 1-continued
| Compd No. | Structure |
|---|---|
| 358 | 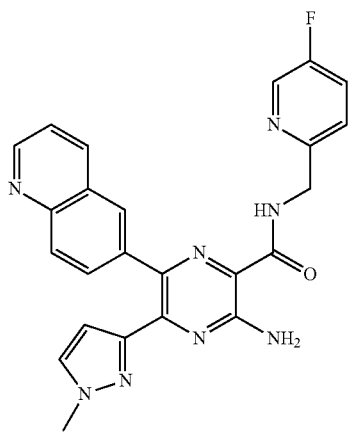 [SMILES: Cn1ccc(-c2nc(N)c(C(=O)NCc3ccc(F)cn3)nc2-c2ccc3ncccc3c2)n1] |
| 359 | 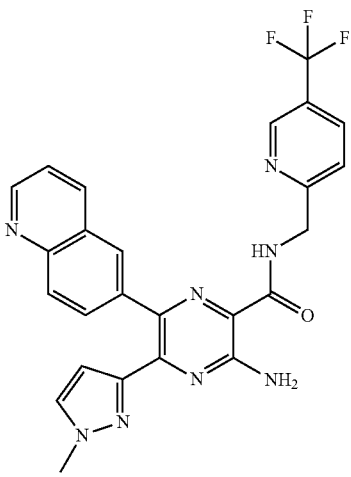 [SMILES: Cn1ccc(-c2nc(N)c(C(=O)NCc3ccc(C(F)(F)F)cn3)nc2-c2ccc3ncccc3c2)n1] |
| 360 | 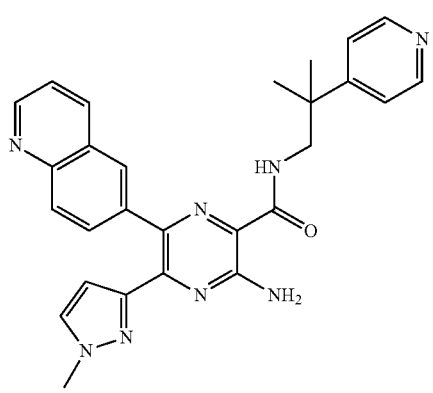 [SMILES: Cn1ccc(-c2nc(N)c(C(=O)NCC(C)(C)c3ccncc3)nc2-c2ccc3ncccc3c2)n1] |

TABLE 1-continued

| Compd No. | Structure |
|---|---|
| 361 | 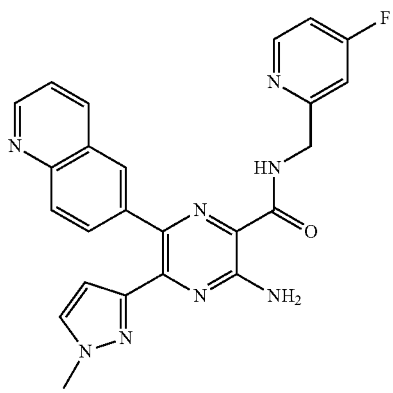 [SMILES: Cn1ccc(-c2nc(N)c(C(=O)NCc3cc(F)ccn3)nc2-c2ccc3ncccc3c2)n1] |
| 362 | 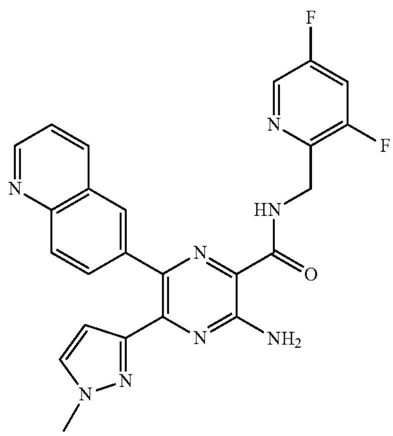 [SMILES: Cn1ccc(-c2nc(N)c(C(=O)NCc3ncc(F)cc3F)nc2-c2ccc3ncccc3c2)n1] |
| 363 | 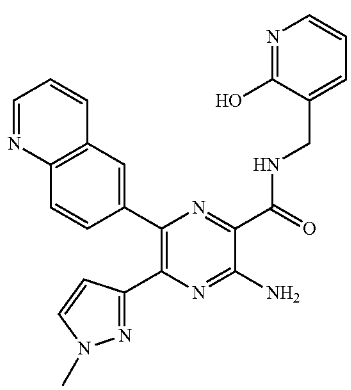 [SMILES: Cn1ccc(-c2nc(N)c(C(=O)NCc3cccnc3O)nc2-c2ccc3ncccc3c2)n1] |
| 364 | 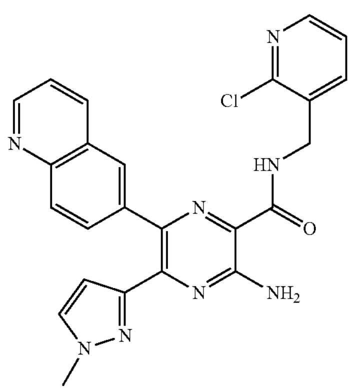 [SMILES: Cn1ccc(-c2nc(N)c(C(=O)NCc3cccnc3Cl)nc2-c2ccc3ncccc3c2)n1] |

TABLE 1-continued
| Compd No. | Structure |
|---|---|
| 365 | 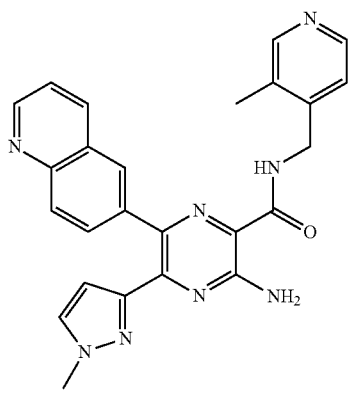 [SMILES: Cc1cnccc1CNC(=O)c1nc(-c2ccc3ncccc3c2)c(-c2ccn(C)n2)nc1N] |
| 366 | 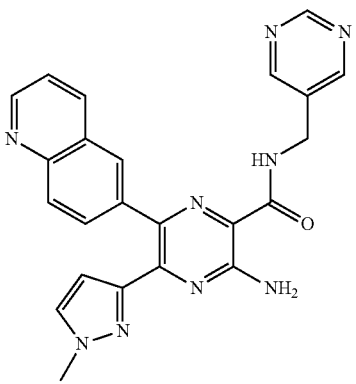 [SMILES: Cn1ccc(-c2nc(N)c(C(=O)NCc3cncnc3)nc2-c2ccc3ncccc3c2)n1] |
| 367 | 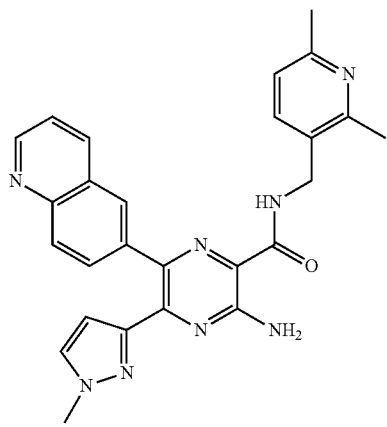 [SMILES: Cc1ccc(CNC(=O)c2nc(-c3ccc4ncccc4c3)c(-c3ccn(C)n3)nc2N)c(C)n1] |

TABLE 1-continued
| Compd No. | Structure |
|---|---|
| 368 | 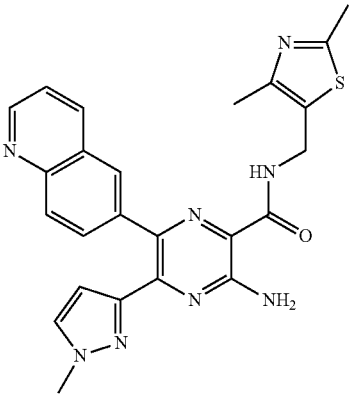 [SMILES: Cc1nc(C)c(CNC(=O)c2nc(-c3ccc4ncccc4c3)c(-c3ccn(C)n3)nc2N)s1] |
| 369 | 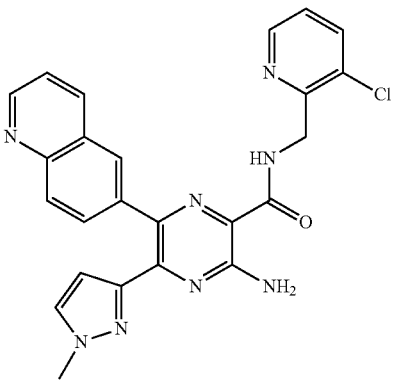 [SMILES: Cn1ccc(-c2nc(N)c(C(=O)NCc3ncccc3Cl)nc2-c2ccc3ncccc3c2)n1] |
| 370 | 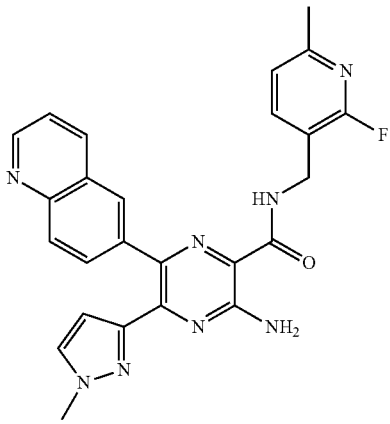 [SMILES: Cc1ccc(CNC(=O)c2nc(-c3ccc4ncccc4c3)c(-c3ccn(C)n3)nc2N)c(F)n1] |
| 371 | 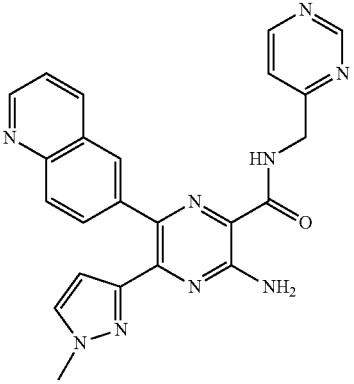 [SMILES: Cn1ccc(-c2nc(N)c(C(=O)NCc3ccncn3)nc2-c2ccc3ncccc3c2)n1] |

TABLE 1-continued
| Compd No. | Structure |
|---|---|
| 372 | 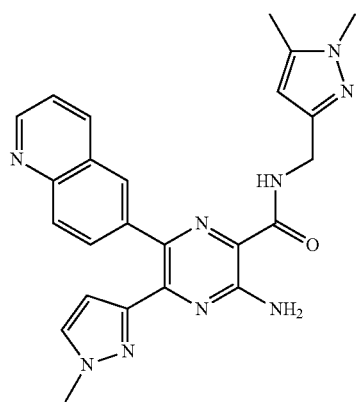 [SMILES: Cc1cc(CNC(=O)c2nc(-c3ccc4ncccc4c3)c(-c3ccn(C)n3)nc2N)nn1C] |
| 373 | 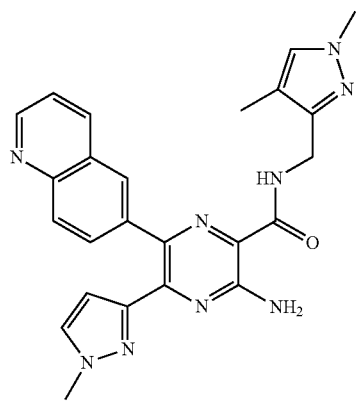 [SMILES: Cc1cn(C)nc1CNC(=O)c1nc(-c2ccc3ncccc3c2)c(-c2ccn(C)n2)nc1N] |
| 374 | 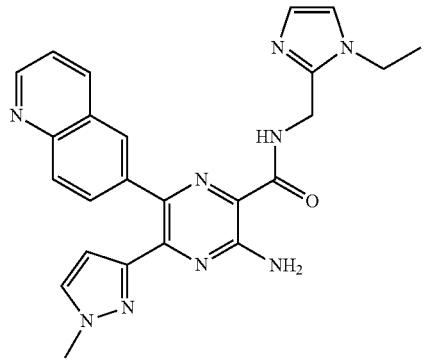 [SMILES: CCn1ccnc1CNC(=O)c1nc(-c2ccc3ncccc3c2)c(-c2ccn(C)n2)nc1N] |

TABLE 1-continued
| Compd No. | Structure |
|---|---|
| 375 | 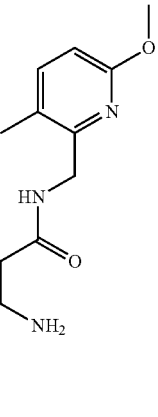 |
| 376 | 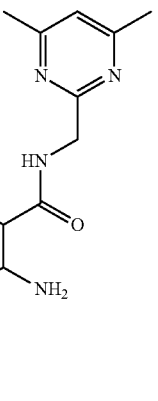 |
| 377 | 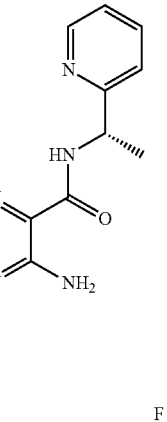 |
| 378 | 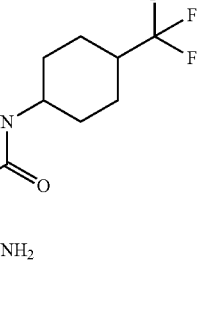 |

TABLE 1-continued
| Compd No. | Structure |
|---|---|
| 379 | 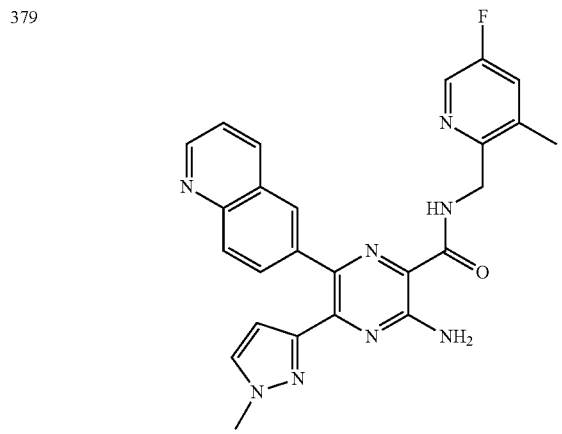 |
| 380 | 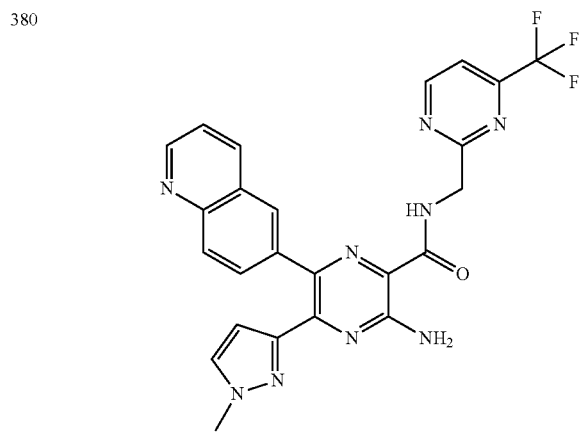 |
| 381 | 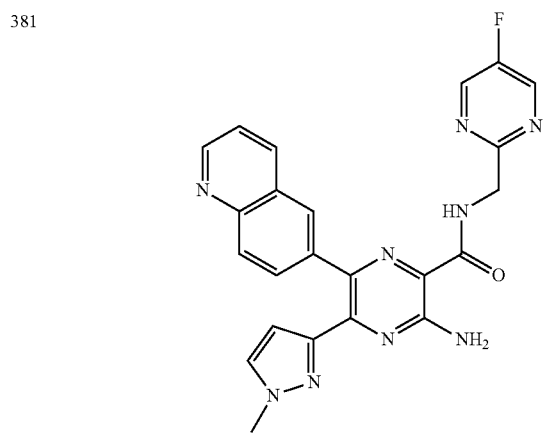 |

TABLE 1-continued

| Compd No. | Structure |
|---|---|
| 382 | 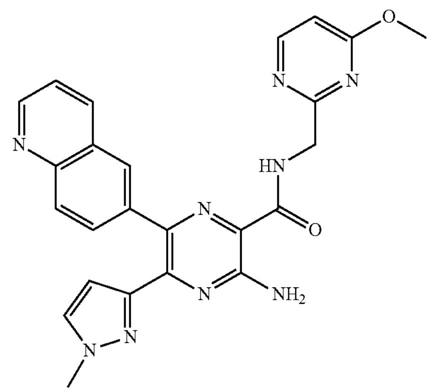 [SMILES: COc1ccnc(CNC(=O)c2nc(-c3ccc4ncccc4c3)c(-c3ccn(C)n3)nc2N)n1] |
| 383 | 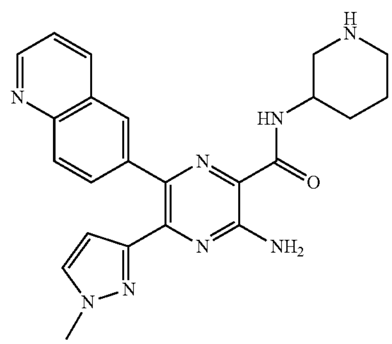 [SMILES: Cn1ccc(-c2nc(N)c(C(=O)NC3CCCNC3)nc2-c2ccc3ncccc3c2)n1] |
| 384 | 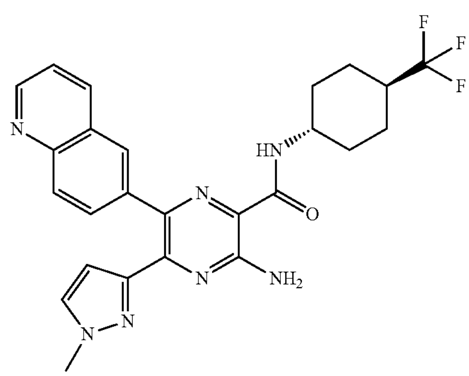 [SMILES: Cn1ccc(-c2nc(N)c(C(=O)N[C@H]3CC[C@H](C(F)(F)F)CC3)nc2-c2ccc3ncccc3c2)n1] |
| 385 | 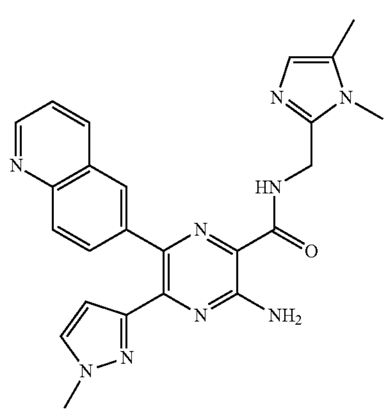 [SMILES: Cc1cnc(CNC(=O)c2nc(-c3ccc4ncccc4c3)c(-c3ccn(C)n3)nc2N)n1C] |

TABLE 1-continued
| Compd No. | Structure |
|---|---|
| 386 | 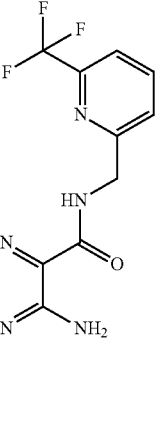 |
| 387 | 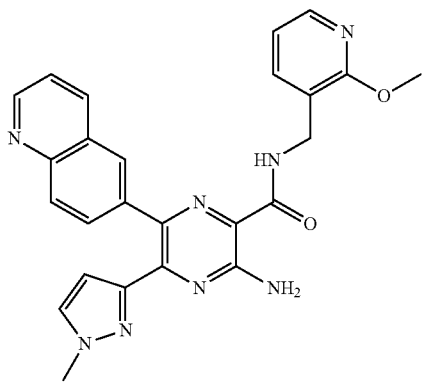 [SMILES: COc1ncccc1CNC(=O)c1nc(-c2ccc3ncccc3c2)c(-c2ccn(C)n2)nc1N] |
| 388 | 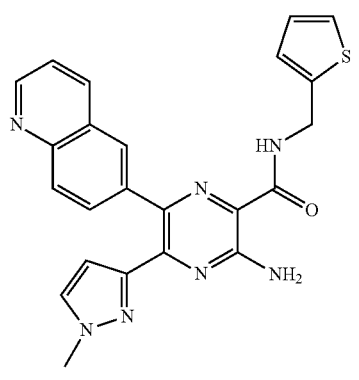 [SMILES: Cn1ccc(-c2nc(N)c(C(=O)NCc3cccs3)nc2-c2ccc3ncccc3c2)n1] |
| 389 | 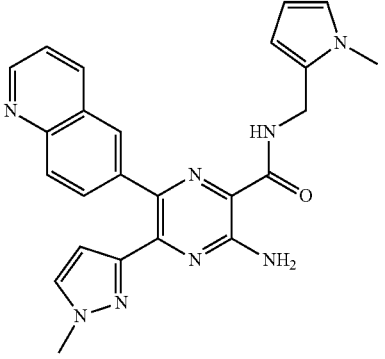 [SMILES: Cn1ccc(-c2nc(N)c(C(=O)NCc3cccn3C)nc2-c2ccc3ncccc3c2)n1] |

TABLE 1-continued

| Compd No. | Structure |
|---|---|
| 390 | 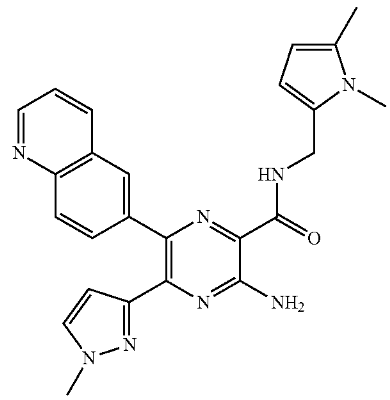 [SMILES: Cc1ccc(CNC(=O)c2nc(-c3ccc4ncccc4c3)c(-c3ccn(C)n3)nc2N)n1C] |
| 391 | 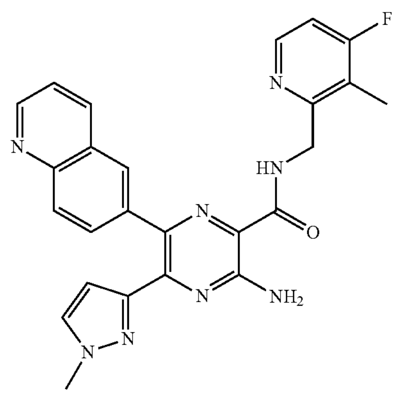 [SMILES: Cc1c(F)ccnc1CNC(=O)c1nc(-c2ccc3ncccc3c2)c(-c2ccn(C)n2)nc1N] |
| 392 | 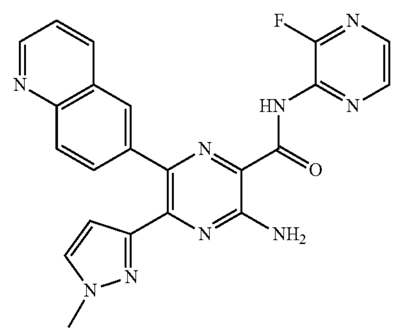 [SMILES: Cn1ccc(-c2nc(N)c(C(=O)Nc3nccnc3F)nc2-c2ccc3ncccc3c2)n1] |
| 393 | 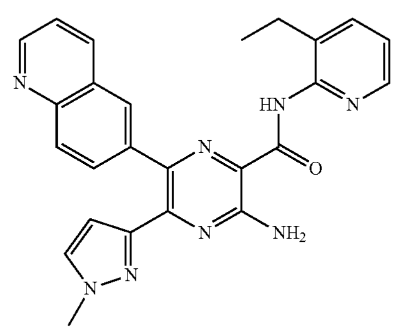 [SMILES: CCc1cccnc1NC(=O)c1nc(-c2ccc3ncccc3c2)c(-c2ccn(C)n2)nc1N] |

TABLE 1-continued

| Compd No. | Structure |
|---|---|
| 394 | 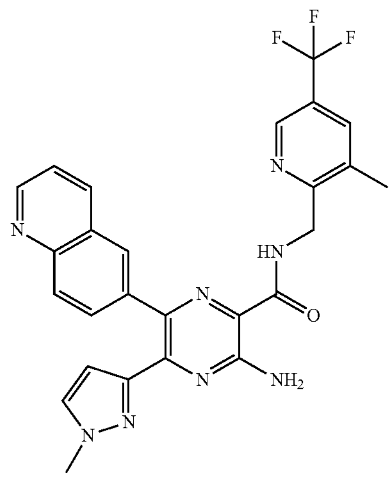 [SMILES: Cc1cc(C(F)(F)F)cnc1CNC(=O)c1nc(-c2ccc3ncccc3c2)c(-c2ccn(C)n2)nc1N] |
| 395 | 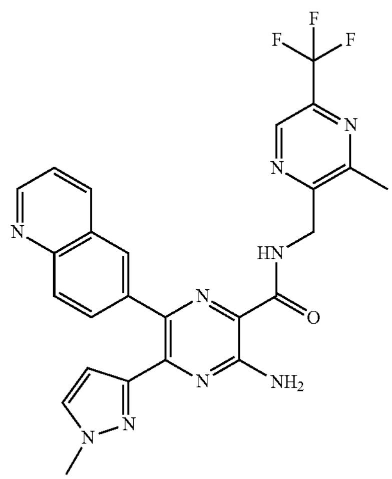 [SMILES: Cc1nc(C(F)(F)F)cnc1CNC(=O)c1nc(-c2ccc3ncccc3c2)c(-c2ccn(C)n2)nc1N] |
| 396 | 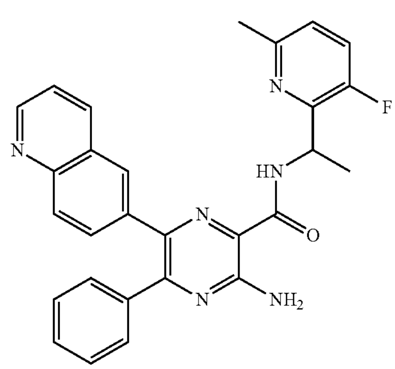 [SMILES: Cc1ccc(F)c(C(C)NC(=O)c2nc(-c3ccc4ncccc4c3)c(-c3ccccc3)nc2N)n1] |

TABLE 1-continued
| Compd No. | Structure |
|---|---|
| 397 | 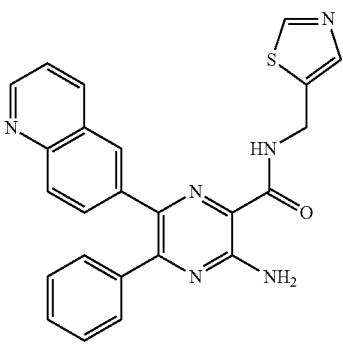 [SMILES: Nc1nc(-c2ccccc2)c(-c2ccc3ncccc3c2)nc1C(=O)NCc1cncs1] |
| 398 | 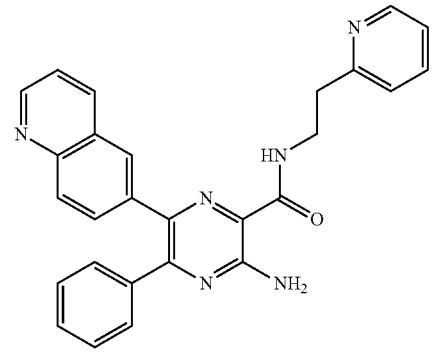 [SMILES: Nc1nc(-c2ccccc2)c(-c2ccc3ncccc3c2)nc1C(=O)NCCc1ccccn1] |
| 399 | 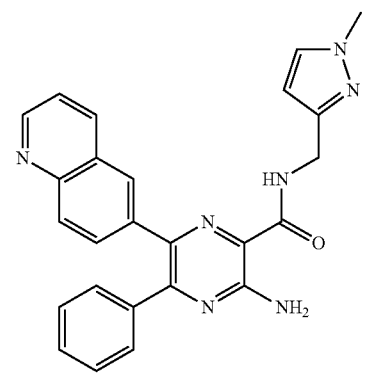 [SMILES: Cn1ccc(CNC(=O)c2nc(-c3ccc4ncccc4c3)c(-c3ccccc3)nc2N)n1] |
| 400 | 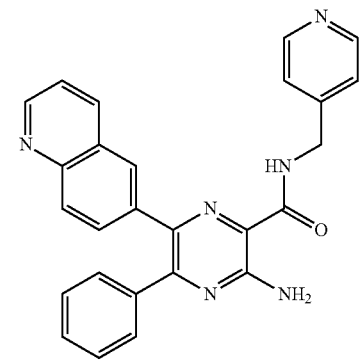 [SMILES: Nc1nc(-c2ccccc2)c(-c2ccc3ncccc3c2)nc1C(=O)NCc1ccncc1] |

TABLE 1-continued

| Compd No. | Structure |
|---|---|
| 401 | 3-amino-6-(quinolin-6-yl)-5-phenyl-N-(pyridin-3-ylmethyl)pyrazine-2-carboxamide |
| 402 | 3-amino-N-((4,6-dimethylpyridin-2-yl)methyl)-6-(quinolin-6-yl)-5-phenylpyrazine-2-carboxamide |
| 403 | 3-amino-N-((3,6-dimethylpyridin-2-yl)methyl)-6-(quinolin-6-yl)-5-phenylpyrazine-2-carboxamide |
| 404 | 3-amino-6-(quinolin-6-yl)-5-phenyl-N-((5-(trifluoromethyl)pyridin-2-yl)methyl)pyrazine-2-carboxamide |

TABLE 1-continued
| Compd No. | Structure |
|---|---|
| 405 | 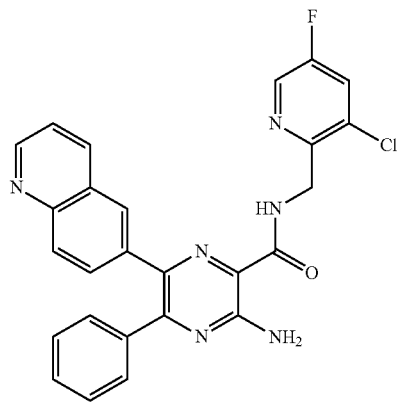 [SMILES: Nc1nc(-c2ccccc2)c(-c2ccc3ncccc3c2)nc1C(=O)NCc1ncc(F)cc1Cl] |
| 406 | 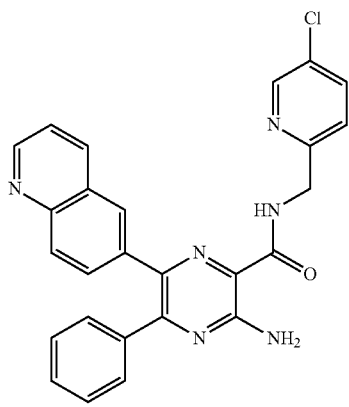 [SMILES: Nc1nc(-c2ccccc2)c(-c2ccc3ncccc3c2)nc1C(=O)NCc1ccc(Cl)cn1] |
| 407 | 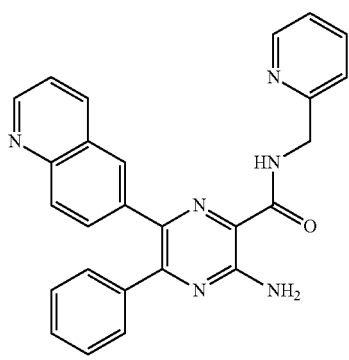 [SMILES: Nc1nc(-c2ccccc2)c(-c2ccc3ncccc3c2)nc1C(=O)NCc1ccccn1] |
| 408 | 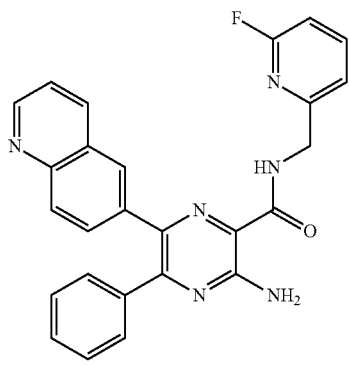 [SMILES: Nc1nc(-c2ccccc2)c(-c2ccc3ncccc3c2)nc1C(=O)NCc1cccc(F)n1] |

TABLE 1-continued
| Compd No. | Structure |
|---|---|
| 409 | 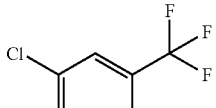 |
| 410 | 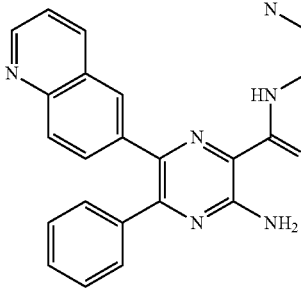 |
| 411 | 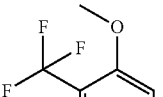 |

TABLE 1-continued

| Compd No. | Structure |
|---|---|
| 412 | 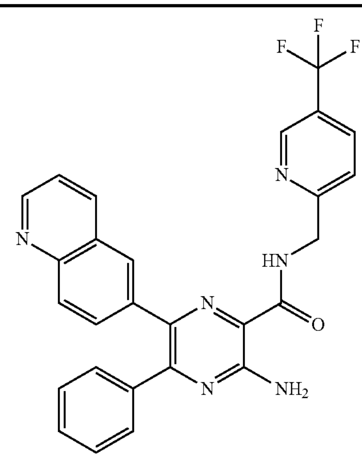 |
| 413 | 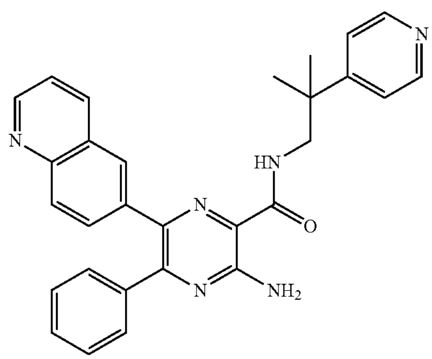 [SMILES: CC(C)(CNC(=O)c1nc(-c2ccc3ncccc3c2)c(-c2ccccc2)nc1N)c1ccncc1] |
| 414 | 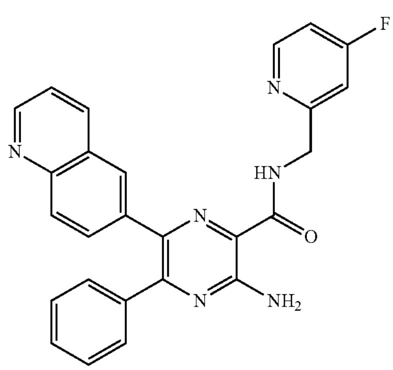 [SMILES: Nc1nc(-c2ccccc2)c(-c2ccc3ncccc3c2)nc1C(=O)NCc1cc(F)ccn1] |
| 415 | 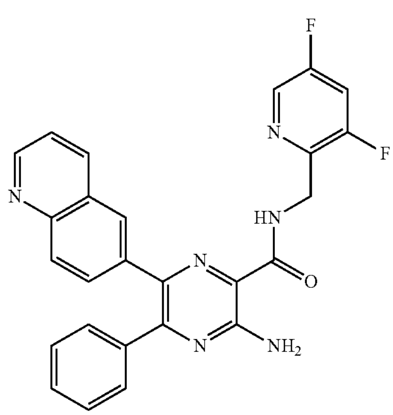 [SMILES: Nc1nc(-c2ccccc2)c(-c2ccc3ncccc3c2)nc1C(=O)NCc1ncc(F)cc1F] |

TABLE 1-continued
| Compd No. | Structure |
|---|---|
| 416 | 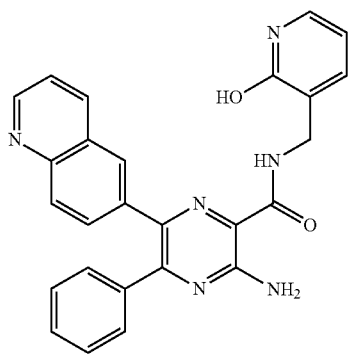 [SMILES: Nc1nc(-c2ccccc2)c(-c2ccc3ncccc3c2)nc1C(=O)NCc1cccnc1O] |
| 417 | 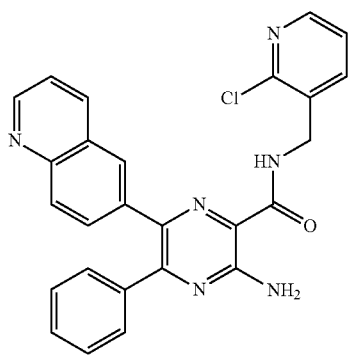 |
| 418 | 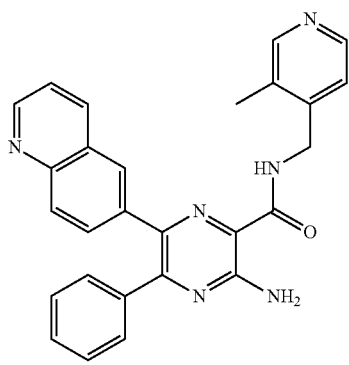 [SMILES: Cc1cnccc1CNC(=O)c1nc(-c2ccc3ncccc3c2)c(-c2ccccc2)nc1N] |
| 419 | 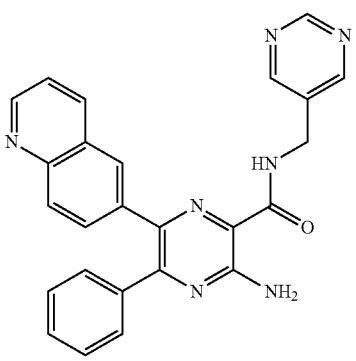 [SMILES: Nc1nc(-c2ccccc2)c(-c2ccc3ncccc3c2)nc1C(=O)NCc1cncnc1] |

TABLE 1-continued
| Compd No. | Structure |
|---|---|
| 420 | 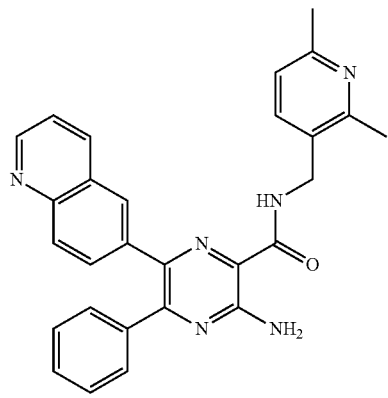 [SMILES: Cc1ccc(CNC(=O)c2nc(-c3ccc4ncccc4c3)c(-c3ccccc3)nc2N)c(C)n1] |
| 421 | 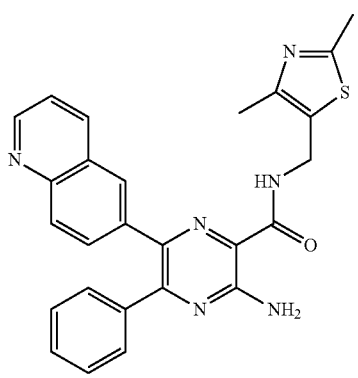 [SMILES: Cc1nc(C)c(CNC(=O)c2nc(-c3ccc4ncccc4c3)c(-c3ccccc3)nc2N)s1] |
| 422 | 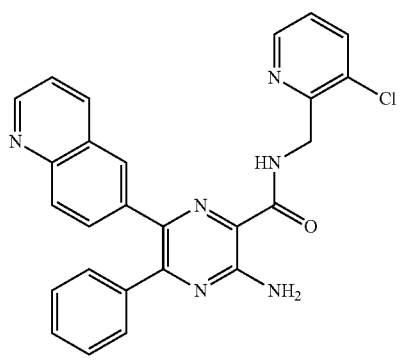 [SMILES: Nc1nc(-c2ccccc2)c(-c2ccc3ncccc3c2)nc1C(=O)NCc1ncccc1Cl] |
| 423 | 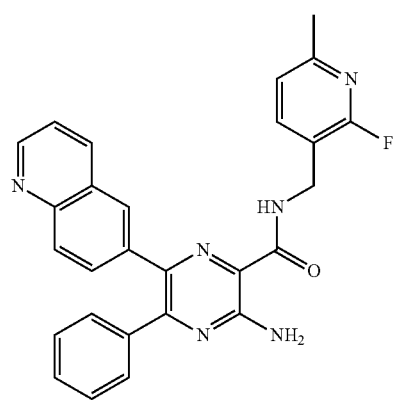 [SMILES: Cc1ccc(CNC(=O)c2nc(-c3ccc4ncccc4c3)c(-c3ccccc3)nc2N)c(F)n1] |

TABLE 1-continued
| Compd No. | Structure |
|---|---|
| 424 | 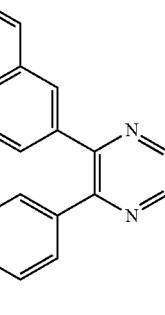 |
| 425 | 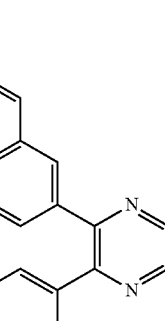 |
| 426 | 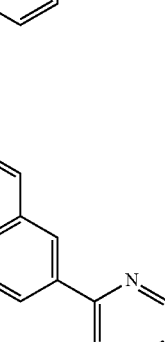 |
| 427 | 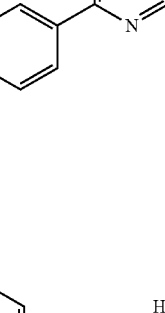 |

TABLE 1-continued
| Compd No. | Structure |
|---|---|
| 428 | 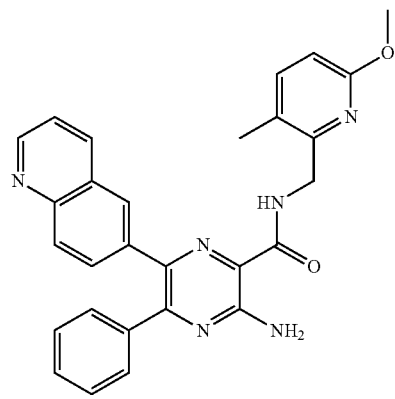 [SMILES: COc1ccc(C)c(CNC(=O)c2nc(-c3ccc4ncccc4c3)c(-c3ccccc3)nc2N)n1] |
| 429 | 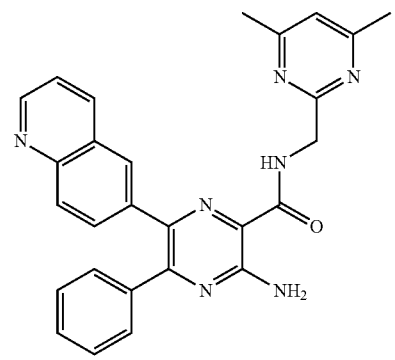 [SMILES: Cc1cc(C)nc(CNC(=O)c2nc(-c3ccc4ncccc4c3)c(-c3ccccc3)nc2N)n1] |
| 430 | 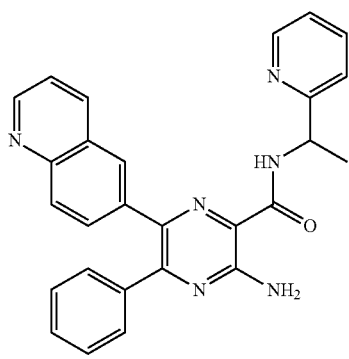 [SMILES: CC(NC(=O)c1nc(-c2ccc3ncccc3c2)c(-c2ccccc2)nc1N)c1ccccn1] |
| 431 | 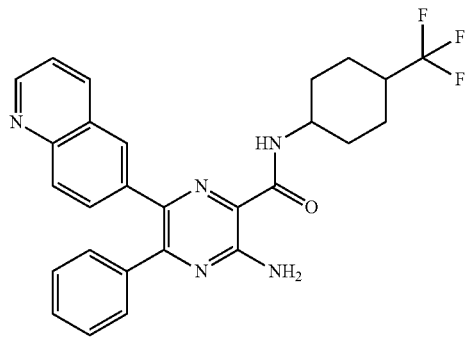 [SMILES: Nc1nc(-c2ccccc2)c(-c2ccc3ncccc3c2)nc1C(=O)NC1CCC(C(F)(F)F)CC1] |

TABLE 1-continued
| Compd No. | Structure |
|---|---|
| 432 | 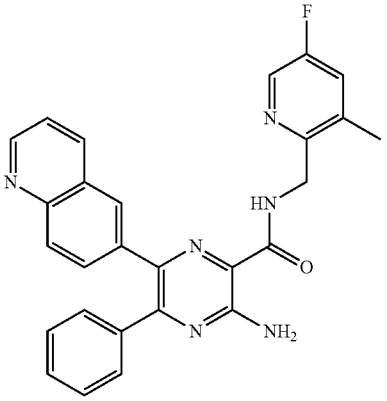 [SMILES: Cc1cc(F)cnc1CNC(=O)c1nc(-c2ccc3ncccc3c2)c(-c2ccccc2)nc1N] |
| 433 | 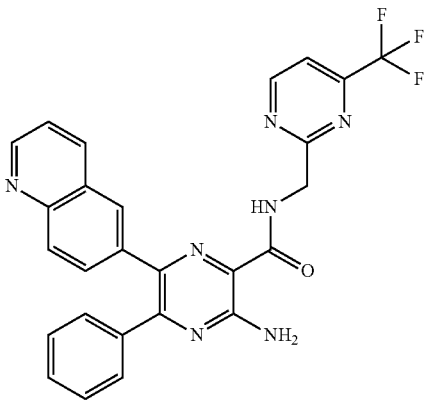 [SMILES: Nc1nc(-c2ccccc2)c(-c2ccc3ncccc3c2)nc1C(=O)NCc1nccc(C(F)(F)F)n1] |
| 434 | 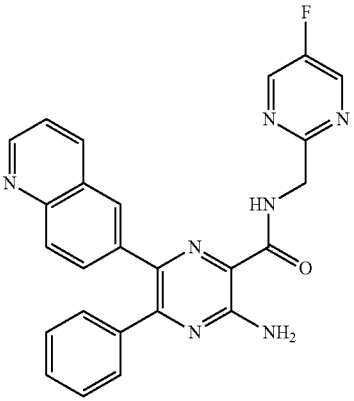 [SMILES: Nc1nc(-c2ccccc2)c(-c2ccc3ncccc3c2)nc1C(=O)NCc1ncc(F)cn1] |
| 435 | 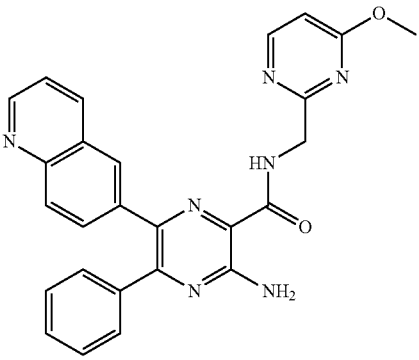 [SMILES: COc1ccnc(CNC(=O)c2nc(-c3ccc4ncccc4c3)c(-c3ccccc3)nc2N)n1] |

TABLE 1-continued
| Compd No. | Structure |
|---|---|
| 436 | 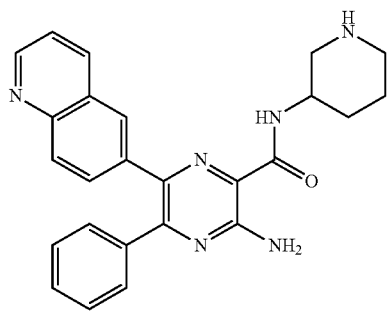 [SMILES: Nc1nc(-c2ccccc2)c(-c2ccc3ncccc3c2)nc1C(=O)NC1CCCNC1] |
| 437 | 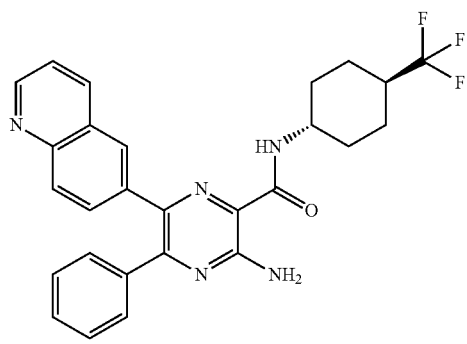 [SMILES: Nc1nc(-c2ccccc2)c(-c2ccc3ncccc3c2)nc1C(=O)N[C@H]1CC[C@H](C(F)(F)F)CC1] |
| 438 | 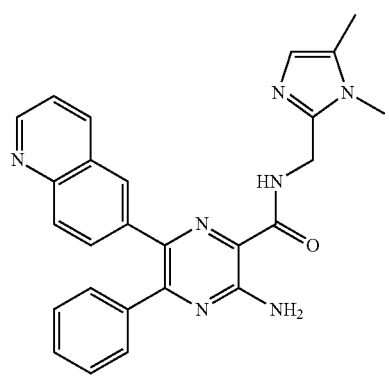 [SMILES: Cc1cnc(CNC(=O)c2nc(-c3ccc4ncccc4c3)c(-c3ccccc3)nc2N)n1C] |
| 439 | 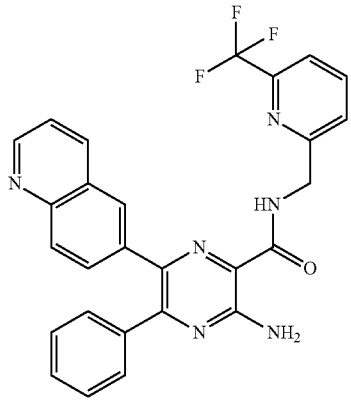 [SMILES: Nc1nc(-c2ccccc2)c(-c2ccc3ncccc3c2)nc1C(=O)NCc1cccc(C(F)(F)F)n1] |

TABLE 1-continued

| Compd No. | Structure |
|---|---|
| 440 | 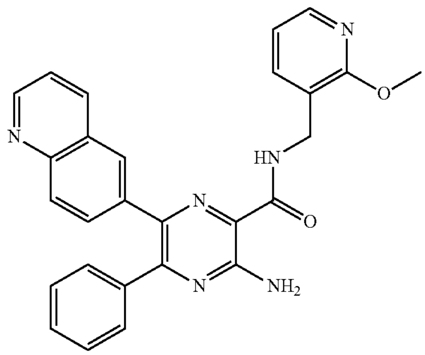 [SMILES: COc1ncccc1CNC(=O)c1nc(-c2ccc3ncccc3c2)c(-c2ccccc2)nc1N] |
| 441 | 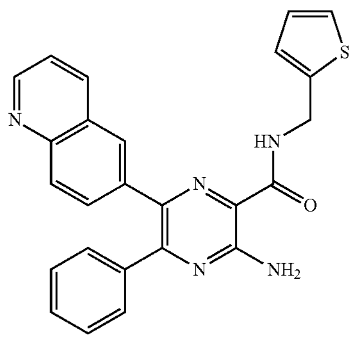 [SMILES: Nc1nc(-c2ccccc2)c(-c2ccc3ncccc3c2)nc1C(=O)NCc1cccs1] |
| 442 | 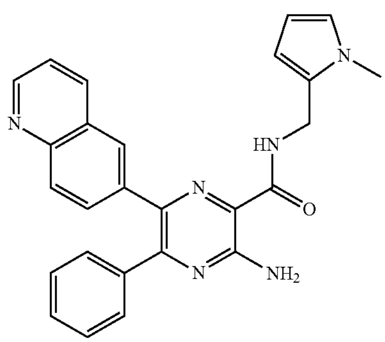 [SMILES: Cn1cccc1CNC(=O)c1nc(-c2ccc3ncccc3c2)c(-c2ccccc2)nc1N] |
| 443 | 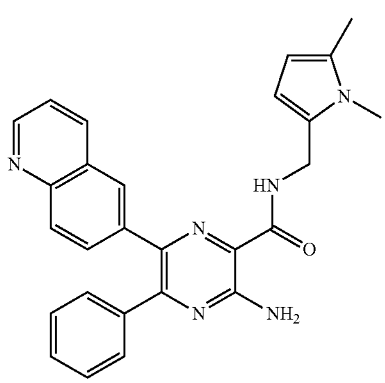 [SMILES: Cc1ccc(CNC(=O)c2nc(-c3ccc4ncccc4c3)c(-c3ccccc3)nc2N)n1C] |

TABLE 1-continued

| Compd No. | Structure |
|---|---|
| 444 | 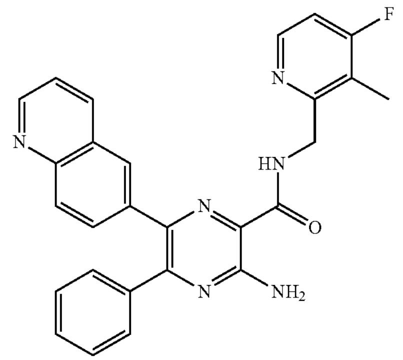 [SMILES: Cc1c(F)ccnc1CNC(=O)c1nc(-c2ccc3ncccc3c2)c(-c2ccccc2)nc1N] |
| 445 | 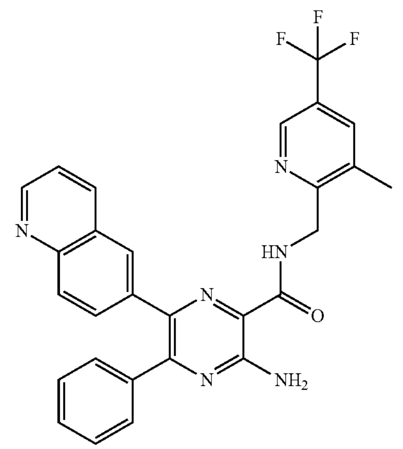 [SMILES: Cc1cc(C(F)(F)F)cnc1CNC(=O)c1nc(-c2ccc3ncccc3c2)c(-c2ccccc2)nc1N] |
| 446 | 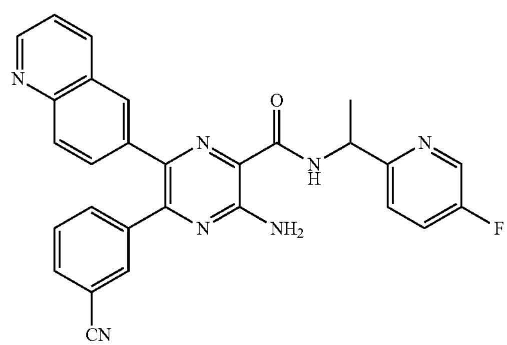 [SMILES: CC(NC(=O)c1nc(-c2ccc3ncccc3c2)c(-c2cccc(C#N)c2)nc1N)c1ccc(F)cn1] |
| 447 | 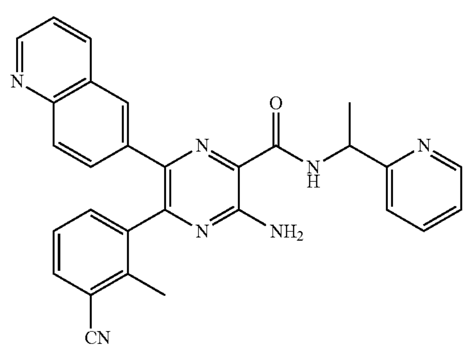 [SMILES: Cc1c(C#N)cccc1-c1nc(N)c(C(=O)NC(C)c2ccccn2)nc1-c1ccc2ncccc2c1] |

TABLE 1-continued
| Compd No. | Structure |
|---|---|
| 448 | 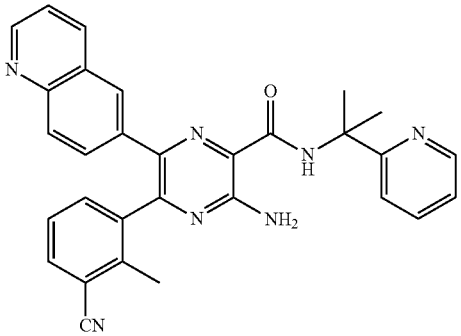 |
| 449 | 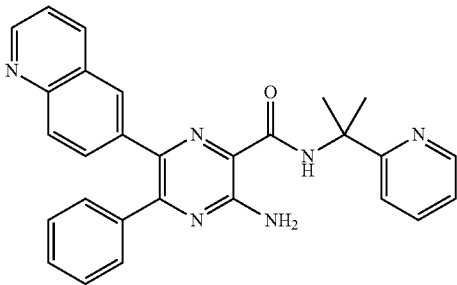 [SMILES: CC(C)(NC(=O)c1nc(-c2ccc3ncccc3c2)c(-c2ccccc2)nc1N)c1ccccn1] |
| 450 | 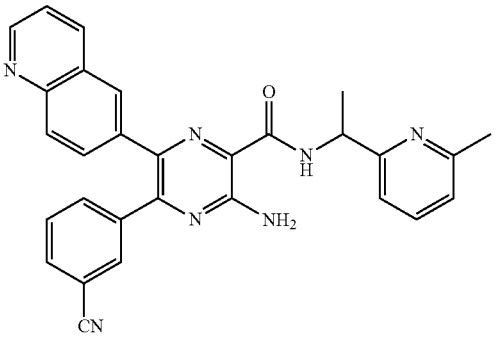 [SMILES: Cc1cccc(C(C)NC(=O)c2nc(-c3ccc4ncccc4c3)c(-c3cccc(C#N)c3)nc2N)n1] |
| 451 | 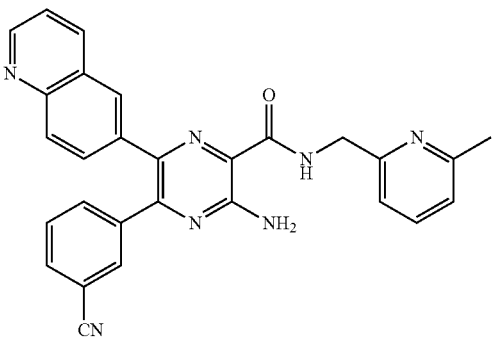 [SMILES: Cc1cccc(CNC(=O)c2nc(-c3ccc4ncccc4c3)c(-c3cccc(C#N)c3)nc2N)n1] |

TABLE 1-continued

| Compd No. | Structure |
|---|---|
| 452 | 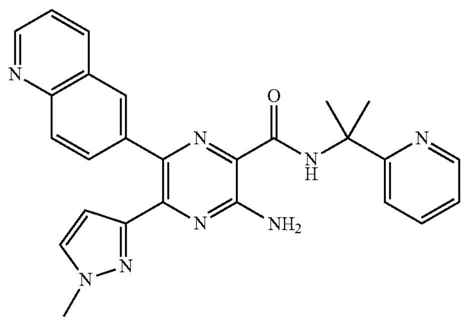 |
| 453 | 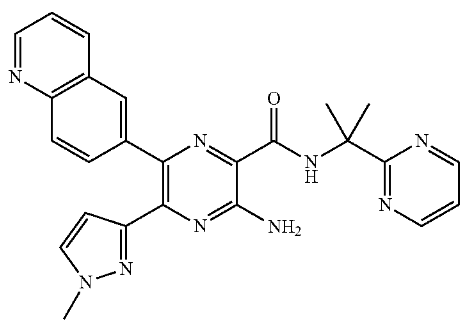 [SMILES: Cn1ccc(-c2nc(N)c(C(=O)NC(C)(C)c3ncccn3)nc2-c2ccc3ncccc3c2)n1] |
| 454 | 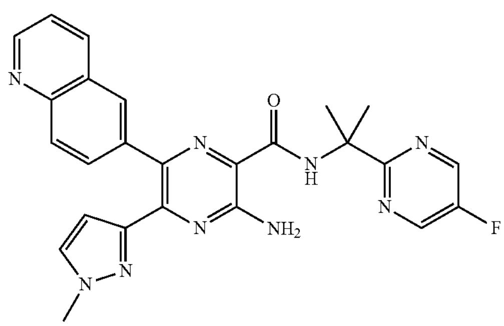 [SMILES: Cn1ccc(-c2nc(N)c(C(=O)NC(C)(C)c3ncc(F)cn3)nc2-c2ccc3ncccc3c2)n1] |
| 455 | 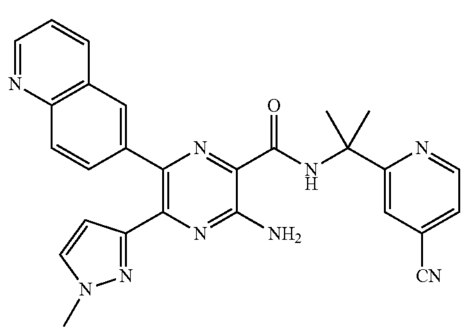 [SMILES: Cn1ccc(-c2nc(N)c(C(=O)NC(C)(C)c3cc(C#N)ccn3)nc2-c2ccc3ncccc3c2)n1] |

TABLE 1-continued
| Compd No. | Structure |
|---|---|
| 456 | 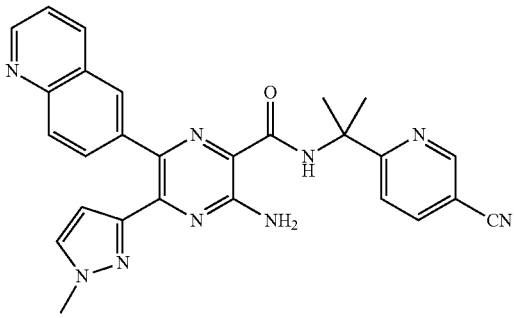 [SMILES: Cn1ccc(-c2nc(N)c(C(=O)NC(C)(C)c3ccc(C#N)cn3)nc2-c2ccc3ncccc3c2)n1] |
| 457 | 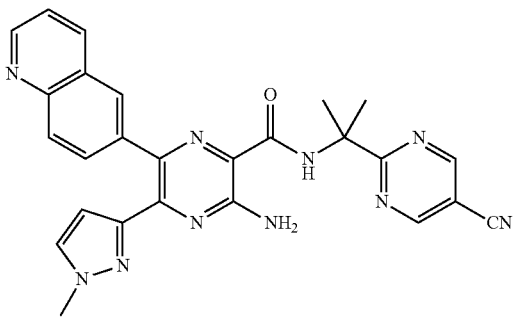 [SMILES: Cn1ccc(-c2nc(N)c(C(=O)NC(C)(C)c3ncc(C#N)cn3)nc2-c2ccc3ncccc3c2)n1] |
| 458 | 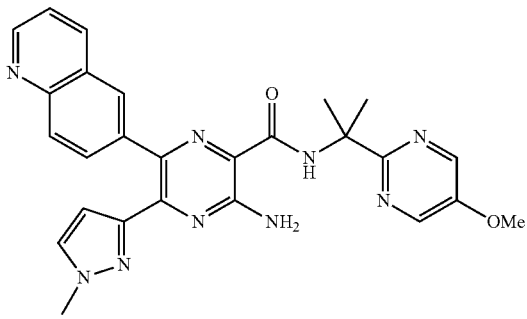 [SMILES: COc1cnc(C(C)(C)NC(=O)c2nc(-c3ccc4ncccc4c3)c(-c3ccn(C)n3)nc2N)nc1] |
| 459 | 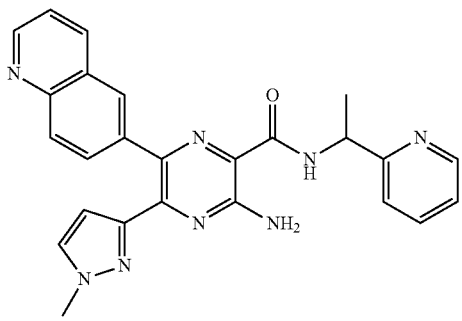 |

TABLE 1-continued
| Compd No. | Structure |
|---|---|
| 460 | 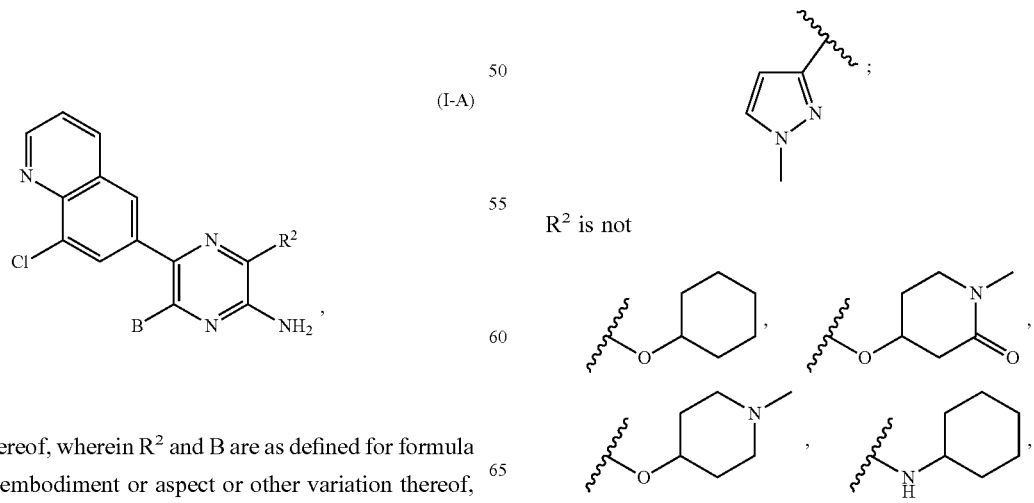 |
| 461 | 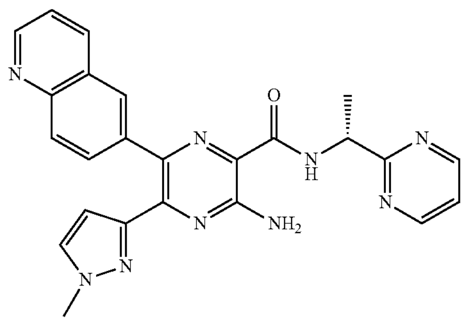 [SMILES: CC(NC(=O)c1nc(-c2ccc3ncccc3c2)c(-c2ccn(C)n2)nc1N)c1ncccn1] |
| 462 | 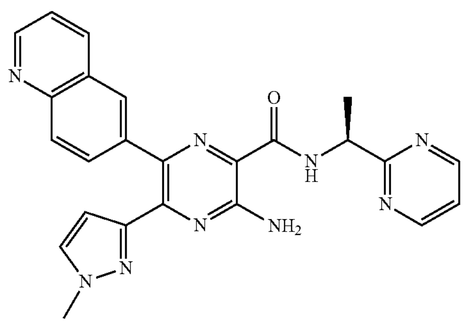 [SMILES: C[C@H](NC(=O)c1nc(-c2ccc3ncccc3c2)c(-c2ccn(C)n2)nc1N)c1ncccn1] |
In some embodiments, the compound of formula (I) is of formula (I-A):
(I-A)
or a salt thereof, wherein $R^2$ and B are as defined for formula (I) or any embodiment or aspect or other variation thereof, wherein
(i) when B is
$R^2$ is not
;

-continued
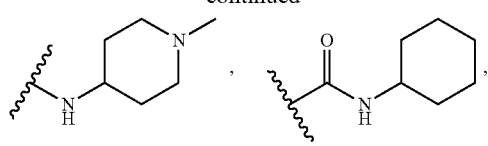
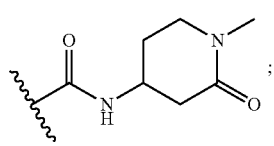
and
(ii) when B is
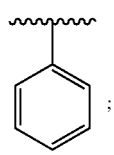
;
R² is not
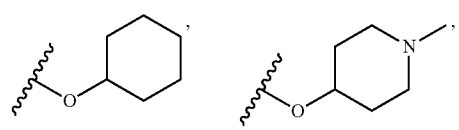
In some embodiments, the compound of formula (I) is of formula (I-B):
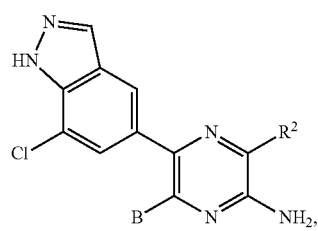
(I-B)
or a salt thereof, wherein R² and B are as defined for formula (I) or any embodiment or aspect or other variation thereof, wherein
(i) when B is
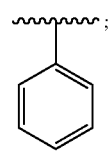 [SMILES: *c1ccccc1]
;
R² is not
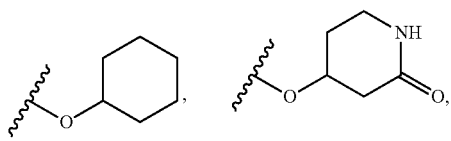
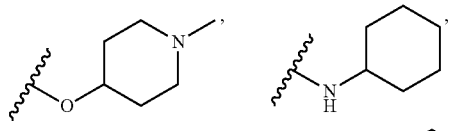
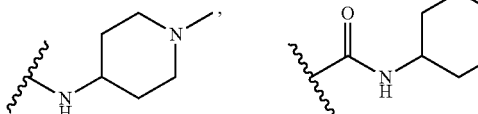
In some embodiments of the compound of formula (I),
(i) when the compound is of formula (I-A) and B is
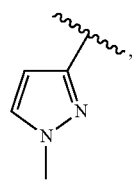 [SMILES: *c1ccn(C)n1]
,
R² is not
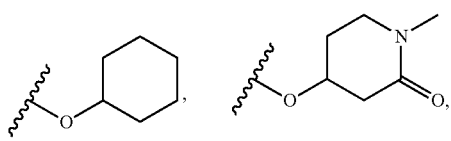
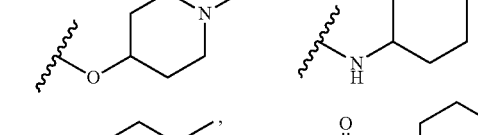
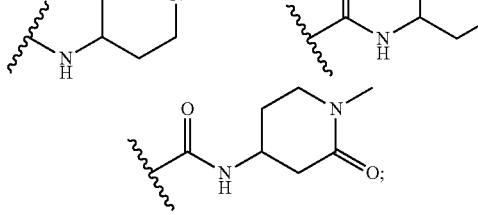

(ii) when the compound is of formula (I-A), and B is

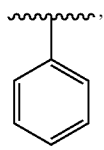 [SMILES: *c1ccccc1]

$R^2$ is not

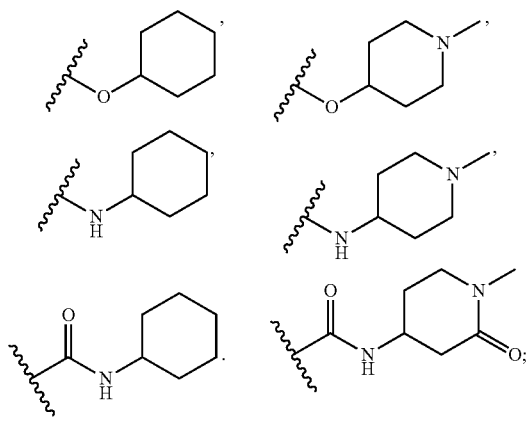

and (iii) when the compound is of formula (I-B), and B is

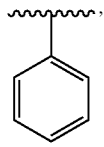

$R^2$ is not

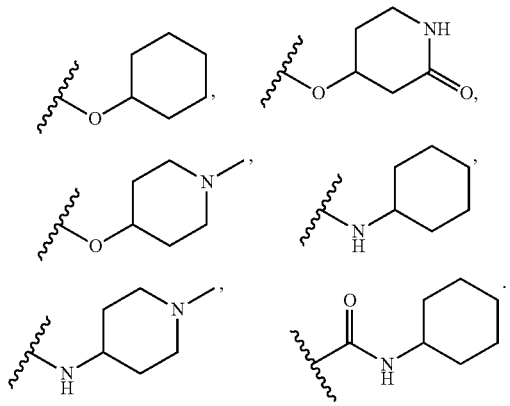

In some embodiments of the compound of any formulae disclosed herein (e.g., formulae (IIIa), (IIIb), (IIIc), (IIIc-1), (IIIc-2), (IIId), (IIIe), (IIIf), (IIIg), (IVa), (IVb), (IVc), (IVc-1), (IVc-2)), (i) when the compound is of formula (I-A) and B is

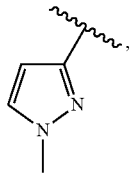 [SMILES: *c1ccn(C)n1]

$R^2$ is not

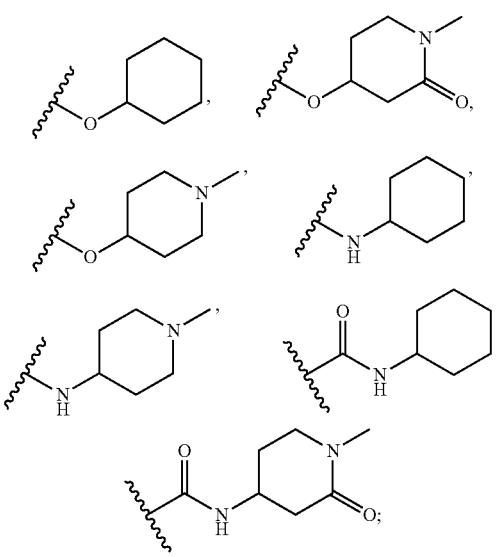

(ii) when the compound is of formula (I-A), and B is

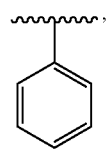

$R^2$ is not

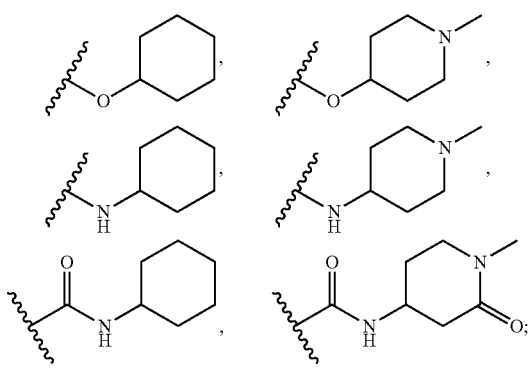

and (iii) when the compound is of formula (I-B), and B is

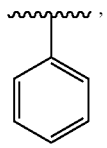 [SMILES: *c1ccccc1], $R^2$ is not

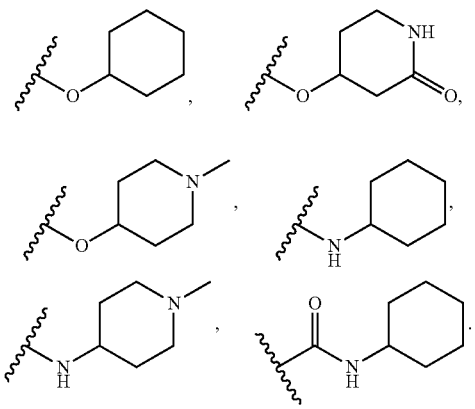

In some embodiments of formula (I) as disclosed herein, the compound is other than the compounds in Table 1X.

In some embodiments, the compound of formula (II) is of formula (II-A):

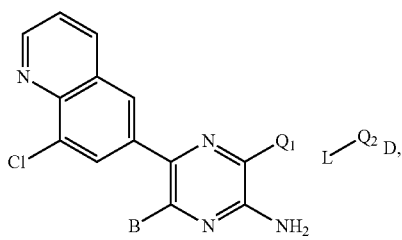
(II-A)

or a salt thereof, wherein $Q_1$, $Q_2$, L, D and B are as defined for formula (I) or any embodiment or aspect or other variation thereof, wherein (i) when B is

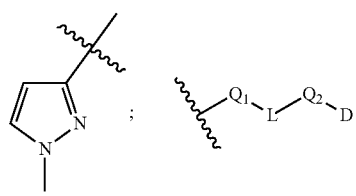

is not

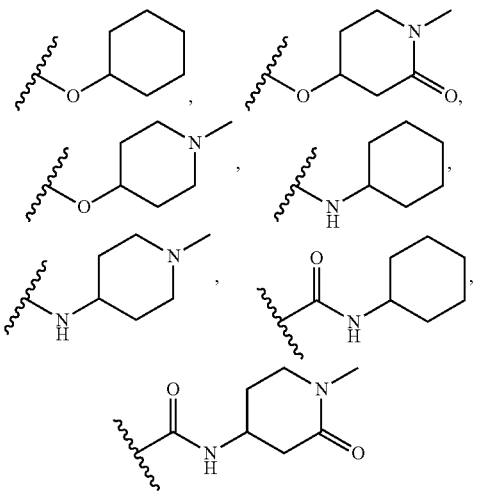

and
(ii) when B is

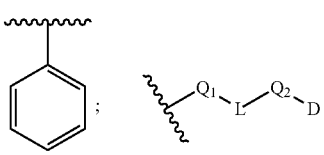

is not

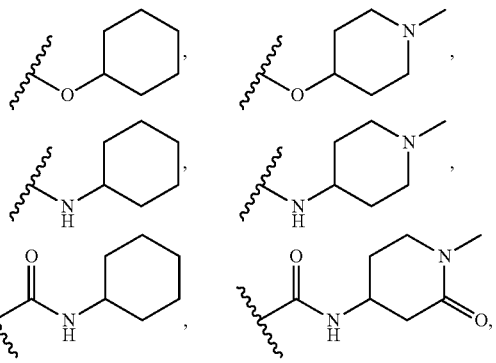

In some embodiments, the compound of formula (II) is of formula (II-B):

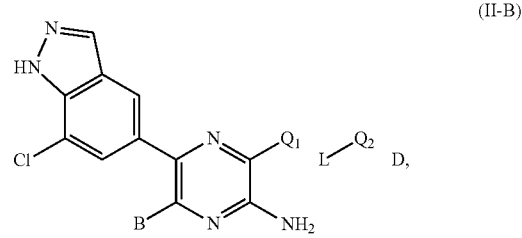
(II-B)

or a salt thereof, wherein $Q_1$, $Q_2$, L, D and B are as defined for formula (I) or any embodiment or aspect or other variation thereof, wherein (i) when B is

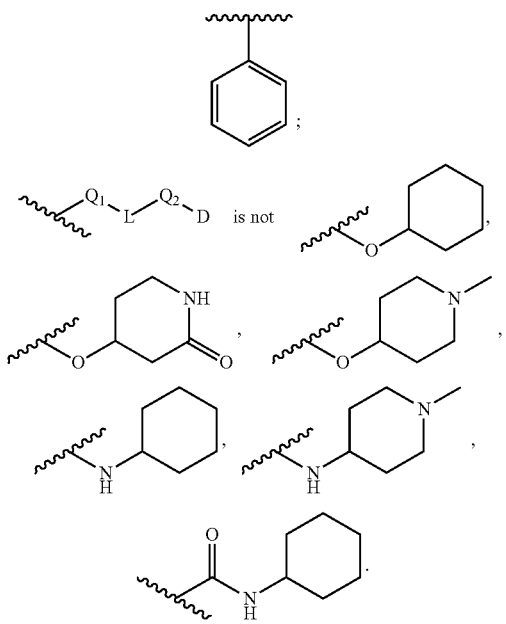

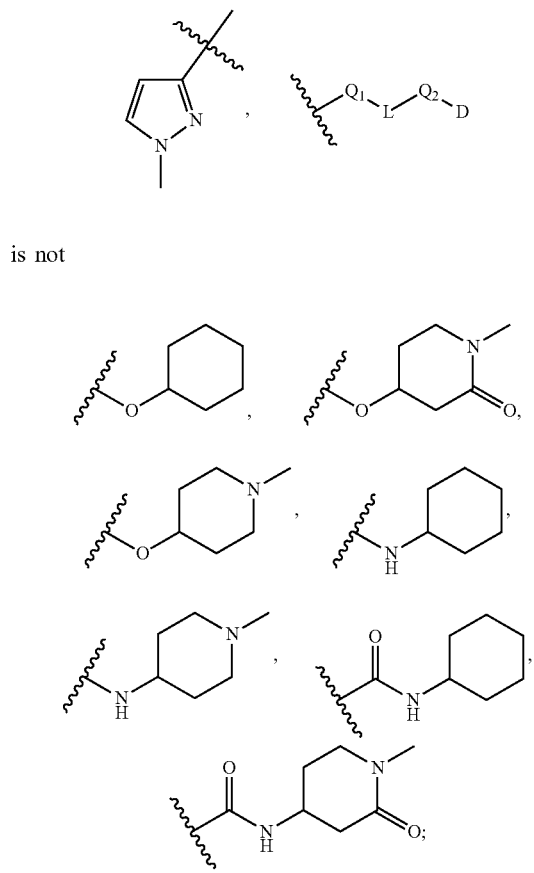

In some embodiments of the compound of formula (II), (i) when the compound is of formula (II-A) and B is (ii) when the compound is of formula (II-A), and B is

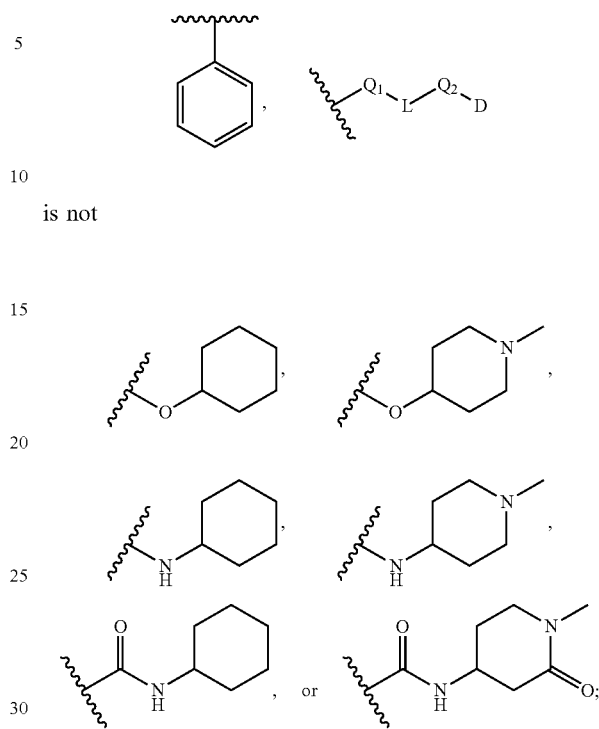

and (iii) when the compound is of formula (II-B), and B is

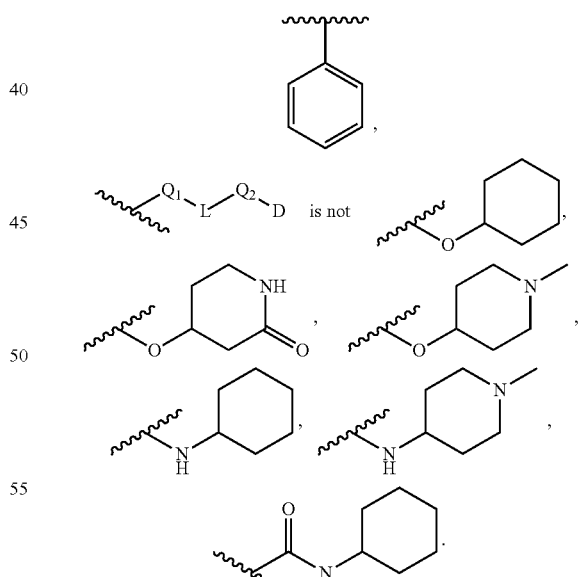

In some embodiments of formula (II) as disclosed herein, the compound is other than the compounds in Table 1X.

In some embodiments of a compound of formula (I) or (II), the compound is other than the compounds in Table 1X, a tautomer or isomer thereof, and a salt of any of the foregoing.

TABLE 1X

Compound Name 3-amino-5-(5-methylfuran-2-yl)-N-((6-methylpyridin-2-yl)methyl)-6-(quinolin-6-yl)pyrazine-2-carboxamide
3-amino-N-((6-methylpyridin-2-yl)methyl)-5-phenyl-6-(quinolin-6-yl)pyrazine-2-carboxamide
5-(8-chloroquinolin-6-yl)-6-(1-methyl-1H-pyrazol-3-yl)-3-(2-(4-methylpiperazin-1-yl)ethoxy)pyrazin-2-amine
5-(8-chloroquinolin-6-yl)-3-(2-(diethylamino)ethoxy)-6-(1-methyl-1H-pyrazol-3-yl)pyrazin-2-amine
6-(7-chloro-1H-indazol-5-yl)-5-(1-methyl-1H-pyrazol-3-yl)-N2-(morpholinomethyl)pyrazine-2,3-diamine
6-(5-amino-3-(1-methyl-1H-pyrazol-3-yl)-6-(((l-methyl-1H-pyrrol-2-yl)methyl)amino)pyrazin-2-yl)isoquinolin-1(2H)-one
3-amino-6-(8-chloroquinolin-6-yl)-5-(3-methyl-1H-pyrazol-1-yl)-N-((5-methylpyridin-2-yl)methyl)pyrazine-2-carboxamide
3-amino-6-(7-chloro-1H-indazol-5-yl)-5-(3-methyl-1H-pyrazol-1-yl)-N-(morpholinomethyl)pyrazine-2-carboxamide
3-amino-6-(8-chloroquinolin-6-yl)-5-(1-methyl-1H-pyrazol-3-yl)-N-((2-oxopiperidin-4-yl)methyl)pyrazine-2-carboxamide
3-amino-6-(8-chloroquinolin-6-yl)-N-(2-(3-hydroxypyrrolidin-1-yl)ethyl)-5-(2-oxopyridin-1(2H)-yl)pyrazine-2-carboxamide
6-(7-chloro-1H-benzo[d]imidazol-5-yl)-5-(5-methylisothiazol-3-yl)-N2-((tetrahydro-2H-pyran-4-yl)methyl)pyrazine-2,3-diamine
6-(5-amino-3-(1-methyl-1H-pyrazol-3-yl)-6-(((1-methyl-1H-pyrrol-2-yl)methyl)amino)pyrazin-2-yl)-8-methylisoquinolin-1(2H)-one
3-amino-6-(8-chloroquinolin-6-yl)-5-(3-methyl-1H-pyrrol-1-yl)-N-((5-methylpyridin-2-yl)methyl)pyrazine-2-carboxamide
3-amino-6-(7-chloro-1H-benzo[d]imidazol-5-yl)-5-(3-methyl-1H-pyrazol-1-yl)-N-(morpholinomethyl)pyrazine-2-carboxamide
3-amino-6-(8-chloroquinolin-6-yl)-5-(1-methyl-1H-pyrrol-3-yl)-N-((2-oxopiperazin-1-yl)methyl)pyrazine-2-carboxamide
3-amino-6-(8-chloro-1,2,3,4-tetrahydroquinolin-6-yl)-N-((3-hydroxypyrrolidin-1-yl)methyl)-5-(2-oxopyridin-1(2H)-yl)pyrazine-2-carboxamide
6-(8-chloroquinolin-6-yl)-N2-(2-(diethylamino)ethyl)-5-(3-methyl-1H-pyrazol-1-yl)pyrazine-2,3-diamine
6-(8-chloroquinolin-6-yl)-N2-(2-(diethylamino)ethyl)-5-(2-methylthiazol-5-yl)pyrazine-2,3-diamine
6-(7-chloro-1H-indazol-5-yl)-N2-(2-(diethylamino)ethyl)-5-(1-methyl-1H-pyrazol-3-yl)pyrazine-2,3-diamine
6-(4-chlorobenzo[d]thiazol-6-yl)-N2-(2-(diethylamino)ethyl)-5-(1-methyl-1H-pyrazol-3-yl)pyrazine-2,3-diamine
6-(4-chlorobenzo1H-pyrazol-3-yl)pyrazine-2,3-diamine
5-(8-chloroquinolin-6-yl)-3-(2-(diethylamino)ethoxy)-6-(1-methyl-1H-pyrazol-3-yl)pyrazin-2-amine
5-(8-chloroquinolin-6-yl)-3-(cyclopropylmethoxy)-6-(1-methyl-1H-pyrazol-3-yl)pyrazin-2-amine
5-(8-chloroquinolin-6-yl)-3-(cyclobutylmethoxy)-6-(1-methyl-1H-pyrazol-3-yl)pyrazin-2-amine
5-(8-chloroquinolin-6-yl)-3-(2-cyclopentylethoxy)-6-(1-methyl-1H-pyrazol-3-yl)pyrazin-2-amine
5-(8-chloroquinolin-6-yl)-3-(cyclohexylmethoxy)-6-(1-methyl-1H-pyrazol-3-yl)pyrazin-2-amine
5-(8-chloroquinolin-6-yl)-6-(1-methyl-1H-pyrazol-3-yl)-3-((1-methylpyrrolidin-3-yl)methoxy)pyrazin-2-amine
3-(2-(azetidin-1-yl)ethoxy)-5-(8-chloroquinolin-6-yl)-6-(1-methyl-1H-pyrazol-3-yl)pyrazin-2-amine
5-(8-chloroquinolin-6-yl)-6-(1-methyl-1H-pyrazol-3-yl)-3-(2-(pyrrolidin-1-yl)ethoxy)pyrazin-2-amine
5-(8-chloroquinolin-6-yl)-6-(1-methyl-1H-pyrazol-3-yl)-3-((1-methylpiperidin-4-yl)methoxy)pyrazin-2-amine
5-(8-chloroquinolin-6-yl)-6-(1-methyl-1H-pyrazol-3-yl)-3-(2-(3-(trifluoromethyl)-1H-pyrrol-1-yl)ethoxy)pyrazin-2-amine
5-(8-chloroquinolin-6-yl)-6-(1-methyl-1H-pyrazol-3-yl)-3-(pyridin-3-ylmethoxy)pyrazin-2-amine
5-(8-chloroquinolin-6-yl)-6-(1-methyl-1H-pyrazol-3-yl)-3-((6-(methylamino)pyridin-3-yl)methoxy)pyrazin-2-amine
6-(8-chloroquinolin-6-yl)-N2-(2-(diethylamino)ethyl)-5-(1-methyl-1H-pyrazol-3-yl)pyrazine-2,3-diamine
6-(8-chloroquinolin-6-yl)-N2-(cyclopropylmethyl)-5-(1-methyl-1H-pyrazol-3-yl)pyrazine-2,3-diamine
6-(8-chloroquinolin-6-yl)-N2-(cyclobutylmethyl)-5-(1-methyl-1H-pyrazol-3-yl)pyrazine-2,3-diamine
6-(8-chloroquinolin-6-yl)-N2-(2-cyclopentylethyl)-5-(1-methyl-1H-pyrazol-3-yl)pyrazine-2,3-diamine
6-(8-chloroquinolin-6-yl)-N2-(cyclohexylmethyl)-5-(1-methyl-1H-pyrazol-3-yl)pyrazine-2,3-diamine
1-(2-((3-amino-6-(8-chloroquinolin-6-yl)-5-(1-methyl-1H-pyrazol-3-yl)pyrazin-2-yl)amino)ethyl)piperidin-4-ol
N2-(2-(azetidin-1-yl)ethyl)-6-(8-chloroquinolin-6-yl)-5-(1-methyl-1H-pyrazol-3-yl)pyrazine-2,3-diamine
6-(8-chloroquinolin-6-yl)-5-(1-methyl-1H-pyrazol-3-yl)-N2-(2-(pyrrolidin-1-yl)ethyl)pyrazine-2,3-diamine
6-(8-chloroquinolin-6-yl)-5-(1-methyl-1H-pyrazol-3-yl)-N2-((4-methylpiperazin-1-yl)methyl)pyrazine-2,3-diamine
6-(8-chloroquinolin-6-yl)-5-(1-methyl-1H-pyrazol-3-yl)-N2-(2-(3-(trifluoromethyl)-1H-pyrrol-1-yl)ethyl)pyrazine-2,3-diamine
6-(8-chloroquinolin-6-yl)-5-(1-methyl-1H-pyrazol-3-yl)-N2-(pyridin-3-ylmethyl)pyrazine-2,3-diamine
6-(8-chloroquinolin-6-yl)-5-(1-methyl-1H-pyrazol-3-yl)-N2-((6-(methylamino)pyridin-3-yl)methyl)pyrazine-2,3-diamine
3-amino-6-(8-chloroquinolin-6-yl)-N-(2-(diethylamino)ethyl)-5-(1-methyl-1H-pyrazol-3-yl)pyrazine-2-carboxamide
3-amino-6-(8-chloroquinolin-6-yl)-N-(cyclopropylmethyl)-5-(1-methyl-1H-pyrazol-3-yl)pyrazine-2-carboxamide
3-amino-6-(8-chloroquinolin-6-yl)-N-((3-hydroxycyclobutyl)methyl)-5-(1-methyl-1H-pyrazol-3-yl)pyrazine-2-carboxamide
3-amino-6-(8-chloroquinolin-6-yl)-N-(cyclopentylmethyl)-5-(1-methyl-1H-pyrazol-3-yl)pyrazine-2-carboxamide
3-amino-6-(8-chloroquinolin-6-yl)-N-(cyclohexylmethyl)-5-(1-methyl-1H-pyrazol-3-yl)pyrazine-2-carboxamide
3-amino-6-(8-chloroquinolin-6-yl)-5-(1-methyl-1H-pyrazol-3-yl)-N-((5-oxopyrrolidin-3-yl)methyl)pyrazine-2-carboxamide
3-amino-6-(8-chloroquinolin-6-yl)-N-((3-hydroxyazetidin-1-yl)methyl)-5-(1-methyl-1H-pyrazol-3-yl)pyrazine-2-carboxamide
3-amino-6-(8-chloroquinolin-6-yl)-5-(1-methyl-1H-pyrazol-3-yl)-N-(2-(2-oxopyrrolidin-1-yl)ethyl)pyrazine-2-carboxamide
3-amino-6-(8-chloroquinolin-6-yl)-5-(1-methyl-1H-pyrazol-3-yl)-N-((1-methylpiperidin-4-yl)methyl)pyrazine-2-carboxamide
3-amino-6-(8-chloroquinolin-6-yl)-5-(1-methyl-1H-pyrazol-3-yl)-N-((1-methyl-1H-pyrrol-3-yl)methyl)pyrazine-2-carboxamide
ethyl 6-((3-amino-6-(8-chloroquinolin-6-yl)-5-(1-methyl-1H-pyrazol-3-yl)pyrazine-2-carboxamido)methyl)nicotinate
5-(8-chloroquinolin-6-yl)-3-((diethylamino)methoxy)-6-phenylpyrazin-2-amine
5-(8-chloroquinolin-6-yl)-3-(cyclopropylmethoxy)-6-phenylpyrazin-2-amine
5-(8-chloroquinolin-6-yl)-3-(cyclobutylmethoxy)-6-phenylpyrazin-2-amine
5-(8-chloroquinolin-6-yl)-3-(2-cyclopentylethoxy)-6-phenylpyrazin-2-amine
5-(8-chloroquinolin-6-yl)-3-(cyclohexylmethoxy)-6-phenylpyrazin-2-amine
4-(((3-amino-6-(8-chloroquinolin-6-yl)-5-phenylpyrazin-2-yl)oxy)methyl)-1-methylpyrrolidin-2-one
5-(8-chloroquinolin-6-yl)-3-((1-methylazetidin-3-yl)methoxy)-6-phenylpyrazin-2-amine
5-(8-chloroquinolin-6-yl)-6-phenyl-3-(2-(pyrrolidin-l-yl)ethoxy)pyrazin-2-amine
5-(8-chloroquinolin-6-yl)-3-((1-methylpiperidin-4-yl)methoxy)-6-phenylpyrazin-2-amine
5-(8-chloroquinolin-6-yl)-6-phenyl-3-(2-(3-(trifluoromethyl)-1H-pyrrol-1-yl)ethoxy)pyrazin-2-amine
5-(8-chloroquinolin-6-yl)-6-phenyl-3-(pyridin-3-ylmethoxy)pyrazin-2-amine
5-(8-chloroquinolin-6-yl)-3-((6-(methylamino)pyridin-3-yl)methoxy)-6-phenylpyrazin-2-amine
6-(8-chloroquinolin-6-yl)-N2-(2-(diethylamino)ethyl)-5-phenylpyrazine-2,3-diamine
6-(8-chloroquinolin-6-yl)-N2-(cyclopropylmethyl)-5-phenylpyrazine-2,3-diamine
6-(8-chloroquinolin-6-yl)-N2-(cyclobutylmethyl)-5-phenylpyrazine-2,3-diamine
6-(8-chloroquinolin-6-yl)-N2-(2-cyclopentylethyl)-5-phenylpyrazine-2,3-diamine
6-(8-chloroquinolin-6-yl)-N2-(cyclohexylmethyl)-5-phenylpyrazine-2,3-diamine
4-(((3-amino-6-(8-chloroquinolin-6-yl)-5-phenylpyrazin-2-yl)amino)methyl)pyrrolidin-2-one
N2-(2-(azetidin-l-yl)ethyl)-6-(8-chloroquinolin-6-yl)-5-phenylpyrazine-2,3-diamine
6-(8-chloroquinolin-6-yl)-5-phenyl-N2-(2-(pyrrolidin-l-yl)ethyl)pyrazine-2,3-diamine
6-(8-chloroquinolin-6-yl)-N2-((1-methylpiperidin-4-yl)methyl)-5-phenylpyrazine-2,3-diamine TABLE 1X-continued Compound Name 6-(8-chloroquinolin-6-yl)-5-phenyl-N2-(2-(3-(trifluoromethyl)-1H-pyrrol-1-yl)ethyl)pyrazine-2,3-diamine
6-(8-chloroquinolin-6-yl)-5-phenyl-N2-(pyridin-3-ylmethyl)pyrazine-2,3-diamine
6-(8-chloroquinolin-6-yl)-N2-((6-(methylamino)pyridin-3-yl)methyl)-5-phenylpyrazine-2,3-diamine
3-amino-6-(8-chloroquinolin-6-yl)-N-(2-(diethylamino)ethyl)-5-phenylpyrazine-2-carboxamide
3-amino-6-(8-chloroquinolin-6-yl)-N-(cyclopropylmethyl)-5-phenylpyrazine-2-carboxamide
3-amino-6-(8-chloroquinolin-6-yl)-N-((3-hydroxycyclobutyl)methyl)-5-phenylpyrazine-2-carboxamide
3-amino-6-(8-chloroquinolin-6-yl)-N-(cyclopentylmethyl)-5-phenylpyrazine-2-carboxamide
3-amino-6-(8-chloroquinolin-6-yl)-N-(cyclohexylmethyl)-5-phenylpyrazine-2-carboxamide
3-amino-6-(8-chloroquinolin-6-yl)-N-(morpholinomethyl)-5-phenylpyrazine-2-carboxamide
3-amino-6-(8-chloroquinolin-6-yl)-N-(2-(3-hydroxyazetidin-1-yl)ethyl)-5-phenylpyrazine-2-carboxamide
3-amino-6-(8-chloroquinolin-6-yl)-N-(2-(2-oxopyrrolidin-1-yl)ethyl)-5-phenylpyrazine-2-carboxamide
3-amino-6-(8-chloroquinolin-6-yl)-N-((1-methylpiperidin-4-yl)methyl)-5-phenylpyrazine-2-carboxamide
3-amino-6-(8-chloroquinolin-6-yl)-N-((1-methyl-1H-pyrrol-3-yl)methyl)-5-phenylpyrazine-2-carboxamide
ethyl 6-((3-amino-6-(8-chloroquinolin-6-yl)-5-phenylpyrazine-2-carboxamido)methyl)nicotinate
5-(7-chloro-1H-indazol-5-yl)-3-(2-(diethylamino)ethoxy)-6-phenylpyrazin-2-amine
5-(7-chloro-1H-indazol-5-yl)-3-(cyclopropylmethoxy)-6-phenylpyrazin-2-amine
5-(7-chloro-1H-indazol-5-yl)-3-(cyclobutylmethoxy)-6-phenylpyrazin-2-amine
5-(7-chloro-1H-indazol-5-yl)-3-(2-cyclopentylethoxy)-6-phenylpyrazin-2-amine
5-(7-chloro-1H-indazol-5-yl)-3-(cyclohexylmethoxy)-6-phenylpyrazin-2-amine
5-(7-chloro-1H-indazol-5-yl)-3-((3-methylimidazolidin-1-yl)methoxy)-6-phenylpyrazin-2-amine
5-(7-chloro-1H-indazol-5-yl)-3-((1-methylazetidin-3-yl)methoxy)-6-phenylpyrazin-2-amine
5-(7-chloro-1H-indazol-5-yl)-6-phenyl-3-(2-(pyrrolidin-1-yl)ethoxy)pyrazin-2-amine
5-(7-chloro-1H-indazol-5-yl)-3-((1-methylpiperidin-4-yl)methoxy)-6-phenylpyrazin-2-amine
5-(7-chloro-1H-indazol-5-yl)-6-phenyl-3-(2-(3-(trifluoromethyl)-1H-pyrrol-1-yl)ethoxy)pyrazin-2-amine
5-(7-chloro-1H-indazol-5-yl)-6-phenyl-3-(pyridin-3-ylmethoxy)pyrazin-2-amine
5-(7-chloro-1H-indazol-5-yl)-3-((6-(methylamino)pyridin-3-yl)methoxy)-6-phenylpyrazin-2-amine
6-(7-chloro-1H-indazol-5-yl)-N2-(2-(diethylamino)ethyl)-5-phenylpyrazine-2,3-diamine
6-(7-chloro-1H-indazol-5-yl)-N2-(cyclopropylmethyl)-5-phenylpyrazine-2,3-diamine
6-(7-chloro-1H-indazol-5-yl)-N2-(cyclobutylmethyl)-5-phenylpyrazine-2,3-diamine
6-(7-chloro-1H-indazol-5-yl)-N2-(2-cyclopentylethyl)-5-phenylpyrazine-2,3-diamine
6-(7-chloro-1H-indazol-5-yl)-N2-(cyclohexylmethyl)-5-phenylpyrazine-2,3-diamine
6-(7-chloro-1H-indazol-5-yl)-N2-((3-methylimidazolidin-1-yl)methyl)-5-phenylpyrazine-2,3-diamine
N2-(2-(azetidin-1-yl)ethyl)-6-(7-chloro-1H-indazol-5-yl)-5-phenylpyrazine-2,3-diamine
6-(7-chloro-1H-indazol-5-yl)-5-phenyl-N2-(2-(pyrrolidin-1-yl)ethyl)pyrazine-2,3-diamine
6-(7-chloro-1H-indazol-5-yl)-N2-((1-methylpiperidin-4-yl)methyl)-5-phenylpyrazine-2,3-diamine
6-(7-chloro-1H-indazol-5-yl)-5-phenyl-N2-(2-(3-(trifluoromethyl)-1H-pyrrol-1-yl)ethyl)pyrazine-2,3-diamine
6-(7-chloro-1H-indazol-5-yl)-5-phenyl-N2-(pyridin-3-ylmethyl)pyrazine-2,3-diamine
6-(7-chloro-1H-indazol-5-yl)-N2-((6-(methylamino)pyridin-3-yl)methyl)-5-phenylpyrazine-2,3-diamine
3-amino-6-(7-chloro-1H-indazol-5-yl)-N-(1-methyl-2-oxopiperidin-4-yl)-5-phenylpyrazine-2-carboxamide TABLE 1X-continued Compound Name 3-amino-6-(7-chloro-1H-indazol-5-yl)-N-(2-(diethylamino)ethyl)-5-phenylpyrazine-2-carboxamide
3-amino-6-(7-chloro-1H-indazol-5-yl)-N-(cyclopropylmethyl)-5-phenylpyrazine-2-carboxamide
3-amino-6-(7-chloro-1H-indazol-5-yl)-N-((3-hydroxycyclobutyl)methyl)-5-phenylpyrazine-2-carboxamide
3-amino-6-(7-chloro-1H-indazol-5-yl)-N-(cyclopentylmethyl)-5-phenylpyrazine-2-carboxamide
3-amino-6-(7-chloro-1H-indazol-5-yl)-N-(cyclohexylmethyl)-5-phenylpyrazine-2-carboxamide
3-amino-6-(7-chloro-1H-indazol-5-yl)-5-phenyl-N-((tetrahydro-2H-pyran-4-yl)methyl)pyrazine-2-carboxamide
3-amino-6-(7-chloro-1H-indazol-5-yl)-N-(2-(3-hydroxyazetidin-1-yl)ethyl)-5-phenylpyrazine-2-carboxamide
3-amino-6-(7-chloro-1H-indazol-5-yl)-N-((2-oxopyrrolidin-3-yl)methyl)-5-phenylpyrazine-2-carboxamide
3-amino-6-(7-chloro-1H-indazol-5-yl)-N-((1-methylpiperidin-4-yl)methyl)-5-phenylpyrazine-2-carboxamide
3-amino-6-(7-chloro-1H-indazol-5-yl)-N-((1-methyl-1H-pyrazol-3-yl)methyl)-5-phenylpyrazine-2-carboxamide
ethyl 6-((3-amino-6-(7-chloro-1H-indazol-5-yl)-5-phenylpyrazine-2-carboxamido)methyl)nicotinate In another aspect, also provided herein is a compound of the formula (III):

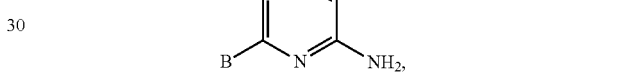

or a tautomer or isomer thereof, or a pharmaceutically acceptable salt of any of the foregoing, wherein:

A is 9- or 10-membered bicyclic heteroaryl or a 9- or 10-membered bicylic heterocylyl, each of A is optionally substituted by $R^a$;

B is a phenyl substituted with 1 to 3 $R^a$ groups which may be the same or different, wherein at least one $R^a$ group is —CN, and $R^a$ is halogen, oxo, —CF$_3$, —OH, —OCH$_3$, —CN, —C(O)OCH$_3$, —C(O)OC$_2$H$_5$, —NH$_2$, —NHCH$_3$ or C$_1$-C$_6$ alkyl optionally substituted by halogen, —OH or oxo.

In some embodiments of the compounds of formula (III), A is selected from the group consisting of

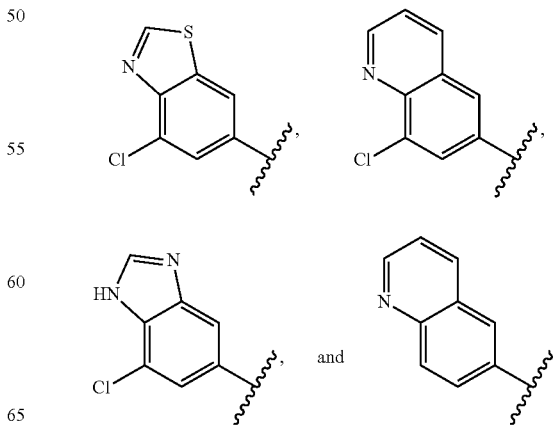

In some embodiments of the compounds of formula (III), B is selected from the group consisting of

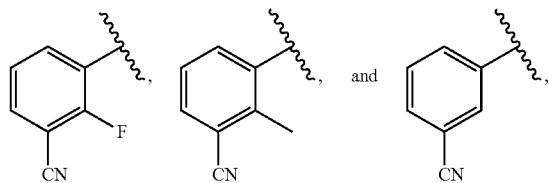

It is understood that each A may be combined with each B the same as if each and every combination of A and/or B were specifically and individually listed. For example, in some embodiments, B is

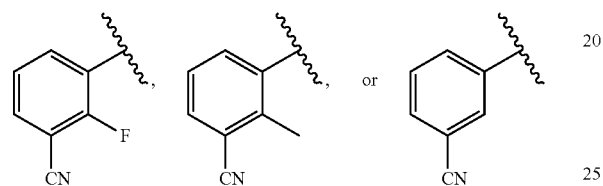

in formula (III), wherein A is as defined herein.

Representative compounds of formula (III) are listed in Table 2. In some embodiments, provided herein are compounds described in Table 2, including pharmaceutically acceptable salts thereof, and uses thereof. It is understood that individual enantiomers and diastereomers if not depicted and their corresponding structures can be readily determined therefrom.

TABLE 2

| Compd No. | Structure |
|---|---|
| 2-1 | |
| 2-2 | |
| 2-3 | 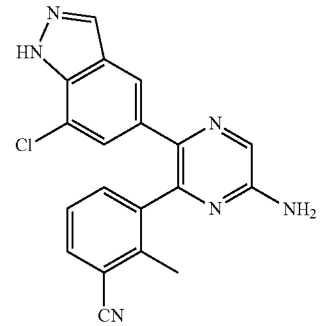 [SMILES: Cc1c(C#N)cccc1-c1nc(N)cnc1-c1cc(Cl)c2[nH]ncc2c1] |
| 2-4 | 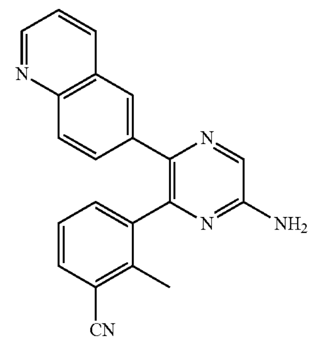 [SMILES: Cc1c(C#N)cccc1-c1nc(N)cnc1-c1ccc2ncccc2c1] |
| 2-5 | 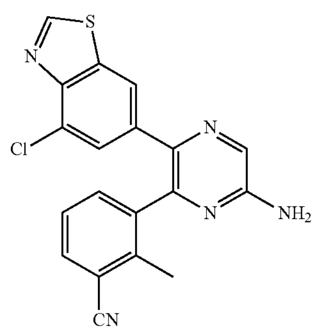 [SMILES: Cc1c(C#N)cccc1-c1nc(N)cnc1-c1cc(Cl)c2ncsc2c1] |
| 2-6 | 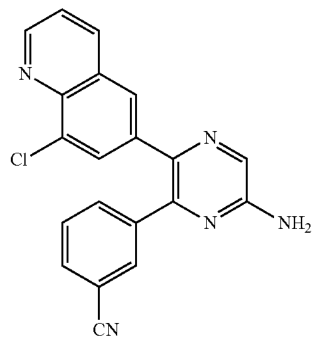 [SMILES: N#Cc1cccc(-c2nc(N)cnc2-c2cc(Cl)c3ncccc3c2)c1] |

TABLE 2-continued

| Compd No. | Structure |
|---|---|
| 2-7 | (structure) |
| 2-8 | (structure) |
| 2-9 | (structure) |
| 2-10 | (structure) |
| 2-11 | (structure) |
| 2-12 | (structure) |
| 2-13 | (structure) |

The embodiments and variations described herein are suitable for compounds of any formulae detailed herein, where applicable.

Representative examples of compounds detailed herein, including intermediates and final compounds according to the present disclosure are depicted herein. It is understood that in one aspect, any of the compounds may be used in the methods detailed herein, including, where applicable, intermediate compounds that may be isolated and administered to an individual.

The compounds depicted herein may be present as salts even if salts are not depicted and it is understood that the present disclosure embraces all salts and solvates of the compounds depicted here, as well as the non-salt and non-solvate form of the compound, as is well understood by the skilled artisan. In some embodiments, the salts of the compounds provided herein are pharmaceutically acceptable salts. Where one or more tertiary amine moiety is present in the compound, the N-oxides are also provided and described.

Where tautomeric forms may be present for any of the compounds described herein, each and every tautomeric form is intended even though only one or some of the tautomeric forms may be explicitly depicted. The tautomeric forms specifically depicted may or may not be the predominant forms in solution or when used according to the methods described herein.

The present disclosure also includes any or all of the stereochemical forms, including any enantiomeric or diastereomeric forms of the compounds described. The structure or name is intended to embrace all possible stereoisomers of a compound depicted, and each unique stereoisomer has a compound number bearing a suffix "a", "b", etc. All forms of the compounds are also embraced by the invention, such as crystalline or non-crystalline forms of the compounds. Compositions comprising a compound of the invention are also intended, such as a composition of substantially pure compound, including a specific stereochemical form thereof, or a composition comprising mixtures of compounds of the invention in any ratio, including two or more stereochemical forms, such as in a racemic or non-racemic mixture.

The invention also intends isotopically-labeled and/or isotopically-enriched forms of compounds described herein. The compounds herein may contain unnatural proportions of atomic isotopes at one or more of the atoms that constitute such compounds. In some embodiments, the compound is isotopically-labeled, such as an isotopically-labeled compound of formulae (I), (II) or (III), or variations thereof described herein, where a fraction of one or more atoms are replaced by an isotope of the same element. Exemplary isotopes that can be incorporated into compounds of the invention include isotopes of hydrogen, carbon, nitrogen, oxygen, phosphorus, sulfur, chlorine, such as $^{2}H$, $^{3}H$, $^{11}C$, $^{13}C$, $^{14}C$ $^{13}N$, $^{15}O$, $^{17}O$, $^{32}P$, $^{35}S$, $^{18}F$, $^{36}Cl$. Certain isotope labeled compounds (e.g. $^{3}H$ and $^{14}C$) are useful in compound or substrate tissue distribution study. Incorporation of heavier isotopes such as deuterium ($^{2}H$) can afford certain therapeutic advantages resulting from greater metabolic stability, for example, increased in vivo half-life, or reduced dosage requirements and, hence may be preferred in some instances.

Isotopically-labeled compounds of the present invention can generally be prepared by standard methods and techniques known to those skilled in the art or by procedures similar to those described in the accompanying Examples substituting appropriate isotopically-labeled reagents in place of the corresponding non-labeled reagent.

The invention also includes any or all metabolites of any of the compounds described. The metabolites may include any chemical species generated by a biotransformation of any of the compounds described, such as intermediates and products of metabolism of the compound, such as would be generated in vivo following administration to a human.

Articles of manufacture comprising a compound described herein, or a salt or solvate thereof, in a suitable container are provided. The container may be a vial, jar, ampoule, preloaded syringe, i.v. bag, and the like.

Preferably, the compounds detailed herein are orally bioavailable. However, the compounds may also be formulated for parenteral (e.g., intravenous) administration.

One or several compounds described herein can be used in the preparation of a medicament by combining the compound or compounds as an active ingredient with a pharmacologically acceptable carrier, which are known in the art. Depending on the therapeutic form of the medication, the carrier may be in various forms. In one variation, the manufacture of a medicament is for use in any of the methods disclosed herein, e.g., for the treatment of cancer.

General Synthetic Methods

The compounds of the invention may be prepared by a number of processes as generally described below and more specifically in the Examples hereinafter (such as the schemes provided in the Examples below). In the following process descriptions, the symbols when used in the formulae depicted are to be understood to represent those groups described above in relation to the formulae herein.

Where it is desired to obtain a particular enantiomer of a compound, this may be accomplished from a corresponding mixture of enantiomers using any suitable conventional procedure for separating or resolving enantiomers. Thus, for example, diastereomeric derivatives may be produced by reaction of a mixture of enantiomers, e.g., a racemate, and an appropriate chiral compound. The diastereomers may then be separated by any convenient means, for example by crystallization and the desired enantiomer recovered. In another resolution process, a racemate may be separated using chiral High Performance Liquid Chromatography. Alternatively, if desired a particular enantiomer may be obtained by using an appropriate chiral intermediate in one of the processes described.

Chromatography, recrystallization and other conventional separation procedures may also be used with intermediates or final products where it is desired to obtain a particular isomer of a compound or to otherwise purify a product of a reaction.

Solvates and/or polymorphs of a compound provided herein, or a pharmaceutically acceptable salt thereof are also contemplated. Solvates contain either stoichiometric or non-stoichiometric amounts of a solvent and are often formed during the process of crystallization.

Hydrates are formed when the solvent is water, or alcoholates are formed when the solvent is alcohol. Polymorphs include the different crystal packing arrangements of the same elemental composition of a compound. Polymorphs usually have different X-ray diffraction patterns, infrared spectra, melting points, density, hardness, crystal shape, optical and electrical properties, stability, and/or solubility. Various factors such as the recrystallization solvent, rate of crystallization, and storage temperature may cause a single crystal form to dominate.

In some embodiments, compounds of the formula (I) may be synthesized according to Scheme 1. In some embodiments, compounds of the formula (I) may be synthesized according to Scheme 1, 2 or 3.

Scheme 1.

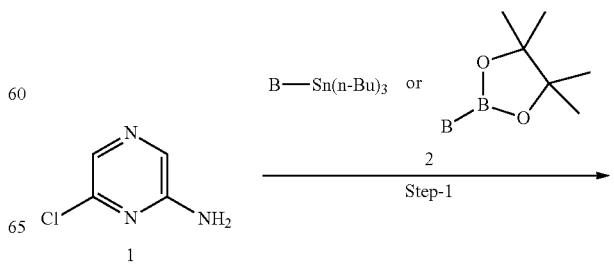

347
-continued
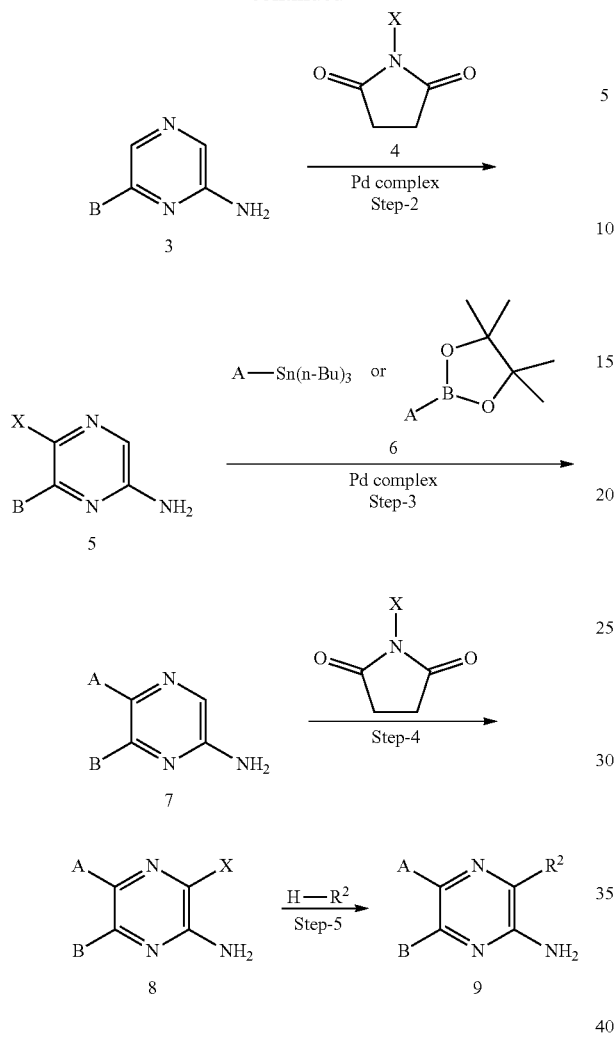
wherein A, B and R² are as defined for formula (I), or any variation thereof detailed herein; and X is a leaving group (e.g., alkoxy or halogen).
Scheme 2.
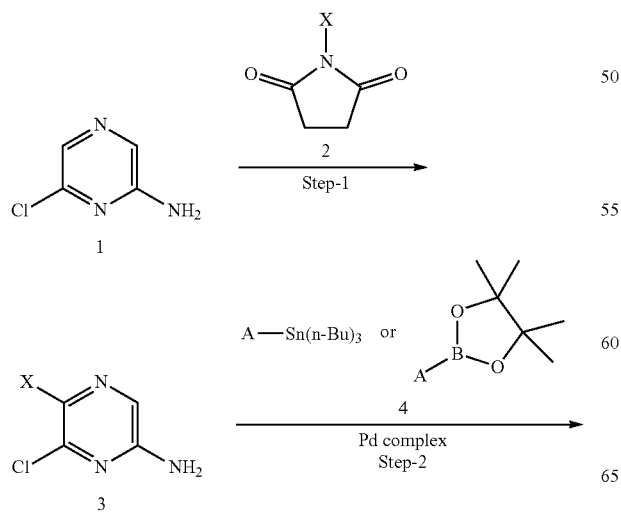
348
-continued
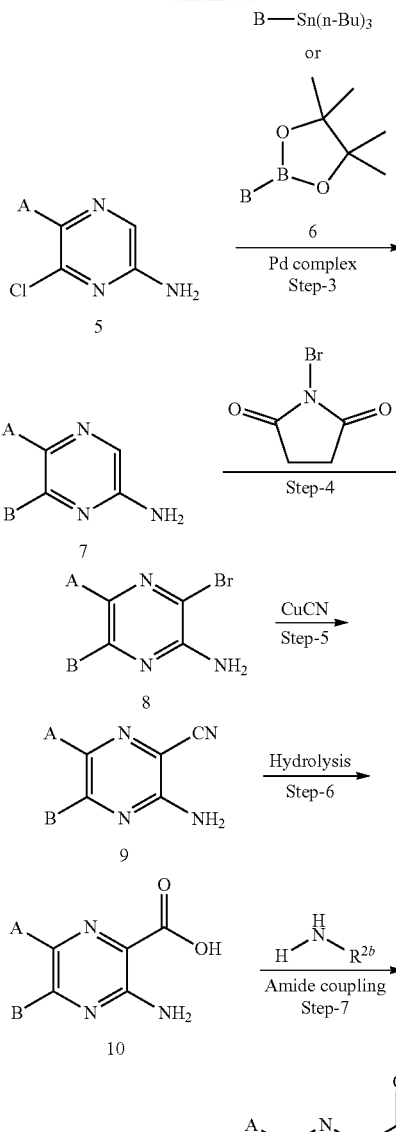
wherein A, B and R²ᵇ are as defined for formula (I), or any variation thereof detailed herein; and X is a leaving group (e.g., alkoxy or halogen).
Scheme 3.
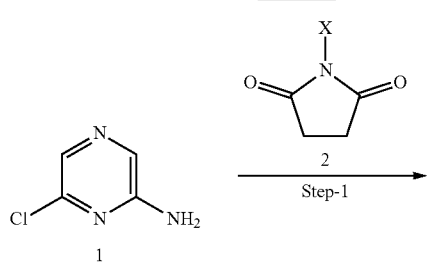

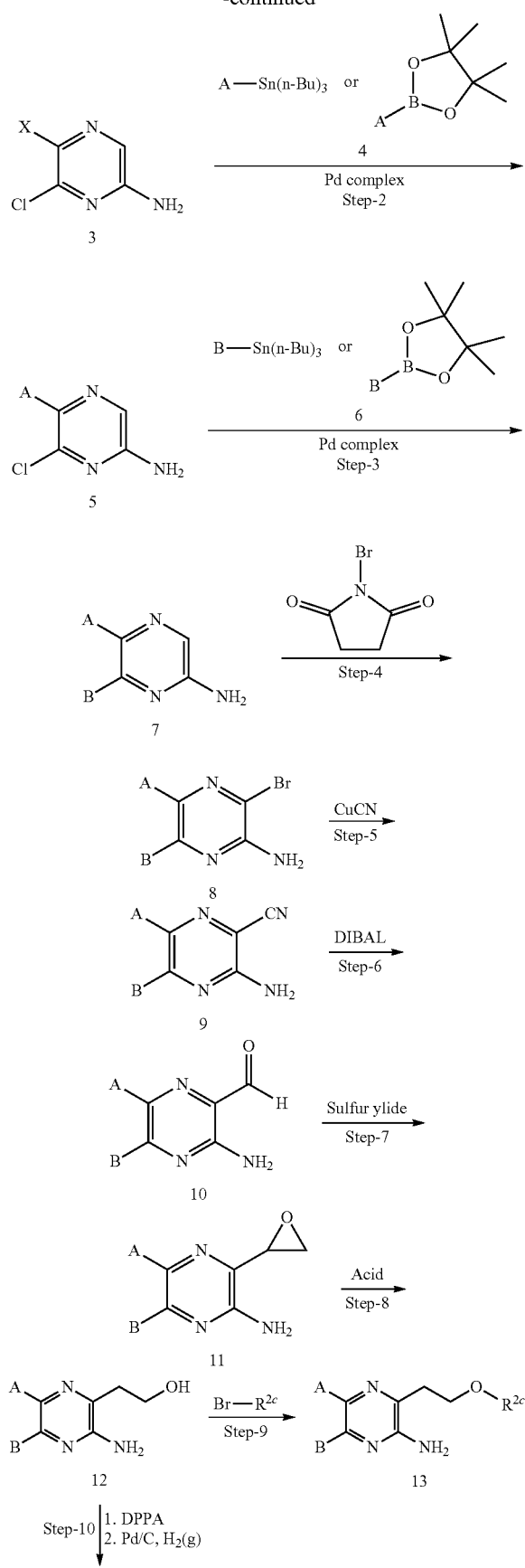
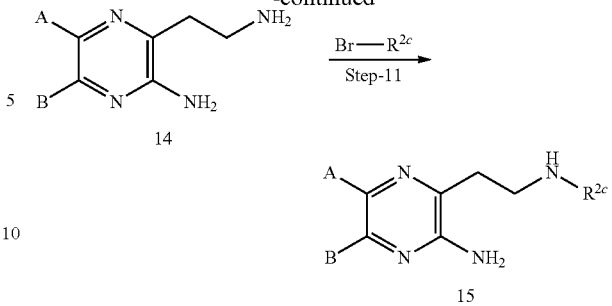

wherein A, B and $R^2$ are as defined for formula (I), or any variation thereof detailed herein; and X is a leaving group (e.g., alkoxy or halogen).

Pharmaceutical Compositions and Formulations

Pharmaceutical compositions of any of the compounds detailed herein are embraced by this disclosure. Thus, the present disclosure includes pharmaceutical compositions comprising a compound as detailed herein or a pharmaceutically acceptable salt thereof and a pharmaceutically acceptable carrier or excipient. In one aspect, the pharmaceutically acceptable salt is an acid addition salt, such as a salt formed with an inorganic or organic acid. Pharmaceutical compositions may take a form suitable for oral, buccal, parenteral, nasal, topical or rectal administration or a form suitable for administration by inhalation.

A compound as detailed herein may in one aspect be in a purified form and compositions comprising a compound in purified forms are detailed herein. Compositions comprising a compound as detailed herein or a salt thereof are provided, such as compositions of substantially pure compounds. In some embodiments, a composition containing a compound as detailed herein or a salt thereof is in substantially pure form.

In one variation, the compounds herein are synthetic compounds prepared for administration to an individual. In another variation, compositions are provided containing a compound in substantially pure form. In another variation, the present disclosure embraces pharmaceutical compositions comprising a compound detailed herein and a pharmaceutically acceptable carrier. In another variation, methods of administering a compound are provided. The purified forms, pharmaceutical compositions and methods of administering the compounds are suitable for any compound or form thereof detailed herein.

A compound detailed herein or salt thereof may be formulated for any available delivery route, including an oral, mucosal (e.g., nasal, sublingual, vaginal, buccal or rectal), parenteral (e.g., intramuscular, subcutaneous or intravenous), topical or transdermal delivery form. A compound or salt thereof may be formulated with suitable carriers to provide delivery forms that include, but are not limited to, tablets, caplets, capsules (such as hard gelatin capsules or soft elastic gelatin capsules), cachets, troches, lozenges, gums, dispersions, suppositories, ointments, cataplasms (poultices), pastes, powders, dressings, creams, solutions, patches, aerosols (e.g., nasal spray or inhalers), gels, suspensions (e.g., aqueous or non-aqueous liquid suspensions, oil-in-water emulsions or water-in-oil liquid emulsions), solutions and elixirs.

One or several compounds described herein or a salt thereof can be used in the preparation of a formulation, such as a pharmaceutical formulation, by combining the compound or compounds, or a salt thereof, as an active ingredient with a pharmaceutically acceptable carrier, such as those mentioned above. Depending on the therapeutic form of the system (e.g., transdermal patch vs. oral tablet), the carrier may be in various forms. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants. Formulations comprising the compound may also contain other substances which have valuable therapeutic properties. Pharmaceutical formulations may be prepared by known pharmaceutical methods. Suitable formulations can be found, e.g., in Remington's Pharmaceutical Sciences, Mack Publishing Company, Philadelphia, Pa., 20 ed. (2000), which is incorporated herein by reference.

Compounds as described herein may be administered to individuals in a form of generally accepted oral compositions, such as tablets, coated tablets, and gel capsules in a hard or in soft shell, emulsions or suspensions. Examples of carriers, which may be used for the preparation of such compositions, are lactose, corn starch or its derivatives, talc, stearate or its salts, etc. Acceptable carriers for gel capsules with soft shell are, for instance, plant oils, wax, fats, semisolid and liquid poly-ols, and so on. In addition, pharmaceutical formulations may contain preservatives, solubilizers, stabilizers, re-wetting agents, emulgators, sweeteners, dyes, adjusters, and salts for the adjustment of osmotic pressure, buffers, coating agents or antioxidants.

Any of the compounds described herein can be formulated in a tablet in any dosage form described, for example, a compound as described herein or a pharmaceutically acceptable salt thereof can be formulated as a 10 mg tablet.

Compositions comprising a compound provided herein are also described. In one variation, the composition comprises a compound or salt thereof and a pharmaceutically acceptable carrier or excipient. In another variation, a composition of substantially pure compound is provided.

Methods of Use

Compounds and compositions detailed herein, such as a pharmaceutical composition containing a compound of any formula provided herein or a salt thereof and a pharmaceutically acceptable carrier or excipient, may be used in methods of administration and treatment as provided herein. The compounds and compositions may also be used in in vitro methods, such as in vitro methods of administering a compound or composition to cells for screening purposes and/or for conducting quality control assays.

Provided herein is a method of treating a disease in an individual comprising administering an effective amount of a compound of formulae (I), (II) or (III), or any embodiment, variation or aspect thereof (collectively, a compound of formulae (I), (II) or (III), or the present compounds or the compounds detailed or described herein) or a pharmaceutically acceptable salt thereof, to the individual. In some embodiments, provided herein is a method of treating a disease mediated by a G protein coupled receptor signaling pathway in an individual comprising administering an effective amount of a compound of formulae (I), (II) or (III), or a pharmaceutically acceptable salt thereof, to the individual. In some embodiments, the disease is mediated by a class A G protein coupled receptor. In some embodiments, the disease is mediated by a class B G protein coupled receptor. In some embodiments, the disease is mediated by a class C G protein coupled receptor. In some embodiments, the G protein coupled receptor is a purinergic G protein receptor.

In some embodiments, the G protein coupled receptor is an adenosine receptor, such as any of the $A_1$, $A_{2A}$, $A_{2B}$, and $A_3$ receptors.

The present compounds or salts thereof are believed to be effective for treating a variety of diseases and disorders. For example, in some embodiments, the present compositions may be used to treat a proliferative disease, such as cancer. In some embodiments the cancer is a solid tumor. In some embodiments the cancer is any of adult and pediatric oncology, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

In some embodiments, the present compounds or salts thereof are used in treatment of tumors which produce high levels of ATP and/or adenosine. For example, in some embodiments the extracellular concentration of adenosine is 10-20 times higher in the tumor compared to adjacent tissue. In some embodiments, the present compounds or salts thereof are used in treatment of tumors that express high levels of an ectonucleotidase. In some embodiments, the ectonucleotidase is CD39. In some embodiments, the ectonucleotidase is CD73.

Also provided herein is a method of enhancing an immune response in an individual in need thereof comprising administering an effective amount of a compound of formulae (I), (II) or (III), or a pharmaceutically acceptable salt thereof, to the individual. Adenosine receptors are known to play an immunosuppressive role in cancer biology. High levels of adenosine present in the tumor microenvironment bind to adenosine receptors on immune cells to provide an immunosuppressive microenvironment. Specifically, binding of adenosine to the $A_{2A}$ receptor provides an immunosuppressive signal that inhibits T cell proliferation, cytokine production and cytotoxicity. The $A_{2A}$ receptor signaling has been implicated in adenosine-mediated inhibition of NK cell cytotoxicity, NKT cell cytokine production and CD40L upregulation. Therefore, use of an $A_{2A}$ receptor antagonist, such as those provided herein, may reverse the immunosuppressive effect of adenosine on immune cells. In some embodiments, the immune response is enhanced by a compound of formulae (I), (II) or (III) or a salt thereof enhancing activity of natural killer (NK) cells. In some embodiments, the present compounds or salts thereof increase NK cell-mediated cytotoxicity. In some embodiments, the immune response is enhanced by enhancing the activity of CD8+ T cells. In some embodiments, the present compounds or salts thereof cause an inflammatory response in the tumor microenvironment.

The present disclosure further provides a method of increasing the activity of a natural killer cell in an individual comprising administering an effective amount of a compound of formulae (I), (II) or (III), or a pharmaceutically acceptable salt thereof, to the individual. In some of these embodiments, the present compounds or salts thereof increase NK cell-mediated cytotoxicity. In some embodiments, a compound of formulae (I), (II) or (III) or a salt thereof increases the number of NK cells.

A compound of formulae (I), (II) or (III) or a salt thereof may be useful for modulating the activity of G protein receptor coupled signaling pathway proteins. In some embodiments, a compound of formulae (I), (II) or (III) or a salt thereof activates a G protein receptor coupled signaling pathway protein (i.e. is an agonist of a G protein receptor). In some embodiments, a compound of formulae (I), (II) or (III) or a salt thereof inhibits a G protein receptor coupled signaling pathway protein (i.e., is a G protein receptor antagonist). In some embodiments, a compound of formulae (I), (II) or (III) or a salt thereof is an adenosine receptor antagonist. In some embodiments, a compound of formulae (I), (II) or (III) or a salt thereof is an antagonist of any of the $A_1$, $A_{2A}$, $A_{2B}$, and $A_3$ receptors.

Accordingly, also provided herein is a method of modulating the activity of an $A_{2A}$ receptor in an individual comprising administering an effective amount of a compound of formulae (I), (II) or (III), or a pharmaceutically acceptable salt thereof to an individual. In some embodiments a compound of formulae (I), (II) or (III) or a salt thereof is an $A_{2A}$ receptor antagonist. In some embodiments, a compound of formulae (I), (II) or (III) or a salt thereof reduces $A_{2A}$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formulae (I), (II) or (III) or a salt thereof reduces $A_{2A}$ receptor signaling by 40-99%, 50-99%, 60-99%, 70-99%, 80-99%, 90-99%, or 95-99%. In some of these embodiments, a compound of formulae (I), (II) or (III) or a salt thereof binds to the $A_{2A}$ receptor with an $IC_{50}$ of less than 1 µM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, [compound x] binds to the $A_{2A}$ receptor with an $IC_{50}$ of 500 nM to 100 pM, 400 nM to 100 pM, 300 nM to 100 pM, 200 nM to 100 pM, or 100 nM to 100 pM.

Also provided herein is a method of modulating the activity of an $A_{2B}$ receptor in an individual comprising administering an effective amount of a compound of formulae (I), (II) or (III), or a pharmaceutically acceptable salt thereof to an individual. In some embodiments a compound of formulae (I), (II) or (III) or a salt thereof is an $A_{2B}$ receptor antagonist. In some embodiments, a compound of formulae (I), (II) or (III) or a salt thereof reduces $A_{2B}$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formulae (I), (II) or (III) or a salt thereof reduces $A_{2B}$ receptor signaling by 40-99%, 50-99%, 60-99%, 70-99%, 80-99%, 90-99%, or 95-99%. In some of these embodiments, a compound of formulae (I), (II) or (III) or a salt thereof binds to the $A_{2B}$ receptor with an $IC_{50}$ of less than 1 pM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, a compound of formulae (I), (II) or (III) or a salt thereof binds to the $A_{2B}$ receptor with an $IC_{50}$ of 500 nM to 100 pM, 400 nM to 100 pM, 300 nM to 100 pM, 200 nM to 100 pM, or 100 nM to 100 pM.

Also provided herein is a method of modulating the activity of an $A_3$ receptor in an individual comprising administering an effective amount of a compound of formulae (I), (II) or (III), or a pharmaceutically acceptable salt thereof to an individual. In some embodiments a compound of formulae (I), (II) or (III) or a salt thereof is an $A_3$ receptor antagonist. In some embodiments, a compound of formulae (I), (II) or (III) or a salt thereof reduces $A_3$ receptor signaling by at least 10%, 20%, 30%, 40%, 50%, 60%, 70%, 80%, 90%, 91%, 92%, 93%, 94%, 95%, 96%, 97%, 98%, or 99%. In some embodiments, a compound of formulae (I), (II) or (III) or a salt thereof reduces $A_3$ receptor signaling by 40-99%, 50-99%, 60-99%, 70-99%, 80-99%, 90-99%, or 95-99%. In some of these embodiments, a compound of formulae (I), (II) or (III) or a salt thereof binds to the $A_3$ receptor with an $IC_{50}$ of less than 1 pM, less than 900 nM, less than 800 nM, less than 700 nM, less than 600 nM, less than 500 nM, less than 400 nM, less than 300 nM, less than 200 nM, less than 100 nM, less than 10 nM, less than 1 nM or less than 100 pM. In some embodiments, a compound of formulae (I), (II) or (III) or a salt thereof binds to the $A_3$ receptor with an $IC_{50}$ of 500 nM to 100 pM, 400 nM to 100 pM, 300 nM to 100 pM, 200 nM to 100 pM, or 100 nM to 100 pM.

In some embodiments, the present invention comprises a method of inhibiting tumor metastasis in an individual in need thereof comprising administering a compound of formulae (I), (II) or (III), or a pharmaceutically acceptable salt thereof, to the individual. In some embodiments, the metastasis is to the lung, liver, lymph node, bone, adrenal gland, brain, peritoneum, muscle, or vagina. In some embodiments, a compound of formulae (I), (II) or (III) or a salt thereof inhibits metastasis of melanoma cells. In some embodiments, the present disclosure includes a method of delaying tumor metastasis comprising administering a compound of formulae (I), (II) or (III), or a pharmaceutically acceptable salt thereof, to the individual. In some of these embodiments, the time to metastasis is delayed by 1 month, 2 months 3 months, 4 months, 5 months, 6 months, 12 months, or more, upon treatment with the compounds of the present invention.

In some embodiments, a compound of formulae (I), (II) or (III) or a salt thereof is used to treat an individual having a proliferative disease, such as cancer as described herein. In some embodiments, the individual is at risk of developing a proliferative disease, such as cancer. In some of these embodiments, the individual is determined to be at risk of developing cancer based upon one or more risk factors. In some of these embodiments, the risk factor is a family history and/or gene associated with cancer. In some embodiments, the individual has a cancer that expresses a high level of a nucleotide metabolizing enzyme. In some embodiments, the nucleotide metabolizing enzyme is a nucleotidase, such as CD73 (ecto-5'-nucleotidase, Ecto5'NTase). In some of these embodiments, the individual has a cancer that expresses a high level of a nucleotidase, such as CD73. In any of these embodiments, the nucleotide metabolizing enzyme is an ecto-nucleotidase. In some embodiments, the ecto-nucleotidase degrades adenosine monophosphate. In some embodiments, the nucleotide metabolizing enzyme is CD39 (ecto-nucleoside triphosphate diphosphohydrolase 1, E-NTPDase1). In some of these embodiments, the individual has a cancer that expresses a high level of CD39. In some embodiments, the individual has a cancer that expresses a high level of an adenosine receptor, such as the $A_{2A}$ receptor.

Combination Therapy

As provided herein, the presently disclosed compounds or a salt thereof may activate the immune system by modulating the activity of a G protein coupled receptor signaling pathway, for example acting as an $A_{2A}$ receptor antagonist, which results in significant anti-tumor effects. Accordingly, the present compounds or a salt thereof may be used in combination with other anti-cancer agents to enhance tumor immunotherapy. In some embodiments, provided herein is a method of treating a disease mediated by a G protein coupled receptor signaling pathway in an individual comprising administering an effective amount of a compound of formulae (I), (II) or (III), or a pharmaceutically acceptable salt thereof, and an additional therapeutic agent to the individual. In some embodiments, the disease mediated by a G protein coupled receptor signaling pathway is a proliferative disease such as cancer.

In some embodiments, the additional therapeutic agent is a cancer immunotherapy. In some embodiments, the additional therapeutic agent is an immunostimulatory agent. In some embodiments, the additional therapeutic agent targets a checkpoint protein. In some embodiments, the additional therapeutic agent is effective to stimulate, enhance or improve an immune response against a tumor.

In another aspect, provided herein is a combination therapy in which a compound of formulae (I), (II) or (III) is coadministered (which may be separately or simultaneously) with one or more additional agents that are effective in stimulating immune responses to thereby further enhance, stimulate or upregulate immune responses in a subject. For example, provided is a method for stimulating an immune response in a subject comprising administering to the subject a compound of formulae (I), (II) or (III) or a salt thereof and one or more immunostimulatory antibodies, such as an anti-PD-1 antibody, an anti-PD-L1 antibody and/or an anti-CTLA-4 antibody, such that an immune response is stimulated in the subject, for example to inhibit tumor growth. In one embodiment, the subject is administered a compound of formulae (I), (II) or (III) or a salt thereof and an anti-PD-1 antibody. In another embodiment, provided is a method for stimulating an immune response in a subject comprising administering to the subject a compound of formulae (I), (II) or (III) or a salt thereof and one or more immunostimulatory antibodies or immunotherapy like Chimeric antigen receptor (CAR) T-cell therapy; immunostimulatory antibodies such as an anti-PD-1 antibody, an anti-PD-L1 antibody and/or an anti-CTLA-4 antibody, such that an immune response is stimulated in the subject, for example to inhibit tumor growth. In another embodiment, the subject is administered a compound of formulae (I), (II) or (III) or a salt thereof and an anti-PD-L1 antibody. In yet another embodiment, the subject is administered a compound of formulae (I), (II) or (III) or a salt thereof and an anti-CTLA-4 antibody. In another embodiment, the immunostimulatory antibody (e.g., anti-PD-1, anti-PD-L1 and/or anti-CTLA-4 antibody) is a human antibody. Alternatively, the immunostimulatory antibody can be, for example, a chimeric or humanized antibody (e.g., prepared from a mouse anti-PD-1, anti-PD-L1 and/or anti-CTLA-4 antibody). In another embodiment, the subject is administered a compound of formulae (I), (II) or (III) or a salt thereof and CAR T-cells (genetically modified T cells).

In one embodiment, the present disclosure provides a method for treating a proliferative disease (e.g., cancer), comprising administering a compound of formulae (I), (II) or (III) or a salt thereof and an anti-PD-1 antibody to a subject. In further embodiments, a compound of formulae (I), (II) or (III) or a salt thereof is administered at a subtherapeutic dose, the anti-PD-1 antibody is administered at a subtherapeutic dose, or both are administered at a subtherapeutic dose. In another embodiment, the present disclosure provides a method for altering an adverse event associated with treatment of a hyperproliferative disease with an immunostimulatory agent, comprising administering a compound of formulae (I), (II) or (III) or a salt thereof and a subtherapeutic dose of anti-PD-1 antibody to a subject. In certain embodiments, the subject is human. In certain embodiments, the anti-PD-1 antibody is a human sequence monoclonal antibody In one embodiment, the present invention provides a method for treating a hyperproliferative disease (e.g., cancer), comprising administering a compound of formulae (I), (II) or (III) or a salt thereof and an anti-PD-L1 antibody to a subject. In further embodiments, a compound of formulae (I), (II) or (III) or a salt thereof is administered at a subtherapeutic dose, the anti-PD-L1 antibody is administered at a subtherapeutic dose, or both are administered at a subtherapeutic dose. In another embodiment, the present invention provides a method for altering an adverse event associated with treatment of a hyperproliferative disease with an immunostimulatory agent, comprising administering a compound of formulae (I), (II) or (III) or a salt thereof and a subtherapeutic dose of anti-PD-L1 antibody to a subject. In certain embodiments, the subject is human. In certain embodiments, the anti-PD-L1 antibody is a human sequence monoclonal antibody.

In certain embodiments, the combination of therapeutic agents discussed herein can be administered concurrently as a single composition in a pharmaceutically acceptable carrier, or concurrently as separate compositions each in a pharmaceutically acceptable carrier. In another embodiment, the combination of therapeutic agents can be administered sequentially. For example, an anti-CTLA-4 antibody and a compound of formulae (I), (II) or (III) or a salt thereof can be administered sequentially, such as anti-CTLA-4 antibody being administered first and a compound of formulae (I), (II) or (III) or a salt thereof second, or a compound of formulae (I), (II) or (III) or a salt thereof being administered first and anti-CTLA-4 antibody second. Additionally, or alternatively, an anti-PD-1 antibody and a compound of formulae (I), (II) or (III) or a salt thereof can be administered sequentially, such as anti-PD-1 antibody being administered first and a compound of formulae (I), (II) or (III) or a salt thereof second, or a compound of formulae (I), (II) or (III) or a salt thereof being administered first and anti-PD-1 antibody second. Additionally, or alternatively, an anti-PD-L1 antibody and a compound of formulae (I), (II) or (III) or a salt thereof can be administered sequentially, such as anti-PD-L1 antibody being administered first and a compound of formulae (I), (II) or (III) or a salt thereof second, or a compound of formulae (I), (II) or (III) or a salt thereof being administered first and anti-PD-L1 antibody second.

Furthermore, if more than one dose of the combination therapy is administered sequentially, the order of the sequential administration can be reversed or kept in the same order at each time point of administration, sequential administrations can be combined with concurrent administrations, or any combination thereof.

Optionally, the combination of a compound of formulae (I), (II) or (III) or a salt thereof can be further combined with an immunogenic agent, such as cancerous cells, purified tumor antigens (including recombinant proteins, peptides, and carbohydrate molecules), cells, and cells transfected with genes encoding immune stimulating cytokines.

A compound of formulae (I), (II) or (III) or a salt thereof can also be further combined with standard cancer treatments. For example, a compound of formulae (I), (II) or (III) or a salt thereof can be effectively combined with chemotherapeutic regimes. In these instances, it is possible to reduce the dose of other chemotherapeutic reagent administered with the combination of the instant disclosure (Mokyr et al. (1998) *Cancer Research* 58: 5301-5304). Other combination therapies with a compound of formulae (I), (II) or (III) or a salt thereof include radiation, surgery, or hormone deprivation. Angiogenesis inhibitors can also be combined with a compound of formulae (I), (II) or (III) or a salt thereof. Inhibition of angiogenesis leads to tumor cell death, which can be a source of tumor antigen fed into host antigen presentation pathways.

In another example, a compound of formulae (I), (II) or (III) or a salt thereof can be used in conjunction with anti-neoplastic antibodies. By way of example and not wishing to be bound by theory, treatment with an anti-cancer antibody or an anti-cancer antibody conjugated to a toxin can lead to cancer cell death (e.g., tumor cells) which would potentiate an immune response mediated by CTLA-4, PD-1, PD-L1 or a compound of formulae (I), (II) or (III) or a salt thereof. In an exemplary embodiment, a treatment of a hyperproliferative disease (e.g., a cancer tumor) can include an anti-cancer antibody in combination with a compound of formulae (I), (II) or (III) or a salt thereof and anti-CTLA-4 and/or anti-PD-1 and/or anti-PD-L1 antibodies, concurrently or sequentially or any combination thereof, which can potentiate anti-tumor immune responses by the host. Other antibodies that can be used to activate host immune responsiveness can be further used in combination with a compound of formulae (I), (II) or (III) or a salt thereof.

In some embodiments, a compound of formulae (I), (II) or (III) or a salt thereof can be combined with an anti-CD73 therapy, such as an anti-CD73 antibody.

In some embodiments, a compound of formulae (I), (II) or (III) or a salt thereof can be combined with an anti-CD39 therapy, such as an anti-CD39 antibody.

In yet further embodiments, a compound of formulae (I), (II) or (III) or a salt thereof is administered in combination another G protein receptor antagonist, such as an adenosine $A_1$ and/or $A_3$ antagonist.

Dosing and Method of Administration

The dose of a compound administered to an individual (such as a human) may vary with the particular compound or salt thereof, the method of administration, and the particular disease, such as type and stage of cancer, being treated. In some embodiments, the amount of the compound or salt thereof is a therapeutically effective amount.

The effective amount of the compound may in one aspect be a dose of between about 0.01 and about 100 mg/kg. Effective amounts or doses of the compounds of the invention may be ascertained by routine methods, such as modeling, dose escalation, or clinical trials, taking into account routine factors, e.g., the mode or route of administration or drug delivery, the pharmacokinetics of the agent, the severity and course of the disease to be treated, the subject's health status, condition, and weight. An exemplary dose is in the range of about from about 0.7 mg to 7 g daily, or about 7 mg to 350 mg daily, or about 350 mg to 1.75 g daily, or about 1.75 to 7 g daily.

Any of the methods provided herein may in one aspect comprise administering to an individual a pharmaceutical composition that contains an effective amount of a compound provided herein or a salt thereof and a pharmaceutically acceptable excipient.

A compound or composition of the invention may be administered to an individual in accordance with an effective dosing regimen for a desired period of time or duration, such as at least about one month, at least about 2 months, at least about 3 months, at least about 6 months, or at least about 12 months or longer, which in some variations may be for the duration of the individual's life. In one variation, the compound is administered on a daily or intermittent schedule. The compound can be administered to an individual continuously (for example, at least once daily) over a period of time. The dosing frequency can also be less than once daily, e.g., about a once weekly dosing. The dosing frequency can be more than once daily, e.g., twice or three times daily. The dosing frequency can also be intermittent, including a 'drug holiday' (e.g., once daily dosing for 7 days followed by no doses for 7 days, repeated for any 14 day time period, such as about 2 months, about 4 months, about 6 months or more). Any of the dosing frequencies can employ any of the compounds described herein together with any of the dosages described herein.

The compounds provided herein or a salt thereof may be administered to an individual via various routes, including, e.g., intravenous, intramuscular, subcutaneous, oral and transdermal. A compound provided herein can be administered frequently at low doses, known as 'metronomic therapy,' or as part of a maintenance therapy using compound alone or in combination with one or more additional drugs. Metronomic therapy or maintenance therapy can comprise administration of a compound provided herein in cycles. Metronomic therapy or maintenance therapy can comprise intra-tumoral administration of a compound provided herein.

In one aspect, the invention provides a method of treating cancer in an individual by parenterally administering to the individual (e.g., a human) an effective amount of a compound or salt thereof. In some embodiments, the route of administration is intravenous, intra-arterial, intramuscular, or subcutaneous. In some embodiments, the route of administration is oral. In still other embodiments, the route of administration is transdermal.

The invention also provides compositions (including pharmaceutical compositions) as described herein for the use in treating, preventing, and/or delaying the onset and/or development of cancer and other methods described herein. In certain embodiments, the composition comprises a pharmaceutical formulation which is present in a unit dosage form.

Also provided are articles of manufacture comprising a compound of the disclosure or a salt thereof, composition, and unit dosages described herein in suitable packaging for use in the methods described herein. Suitable packaging is known in the art and includes, for example, vials, vessels, ampules, bottles, jars, flexible packaging and the like. An article of manufacture may further be sterilized and/or sealed.

Kits

The present disclosure further provides kits for carrying out the methods of the invention, which comprises one or more compounds described herein or a composition comprising a compound described herein. The kits may employ any of the compounds disclosed herein. In one variation, the kit employs a compound described herein or a pharmaceutically acceptable salt thereof. The kits may be used for any one or more of the uses described herein, and, accordingly, may contain instructions for the treatment of cancer.

Kits generally comprise suitable packaging. The kits may comprise one or more containers comprising any compound described herein. Each component (if there is more than one component) can be packaged in separate containers or some components can be combined in one container where cross-reactivity and shelf life permit.

The kits may be in unit dosage forms, bulk packages (e.g., multi-dose packages) or sub-unit doses. For example, kits may be provided that contain sufficient dosages of a compound as disclosed herein and/or a second pharmaceutically active compound useful for a disease detailed herein (e.g., hypertension) to provide effective treatment of an individual for an extended period, such as any of a week, 2 weeks, 3 weeks, 4 weeks, 6 weeks, 8 weeks, 3 months, 4 months, 5 months, 7 months, 8 months, 9 months, or more. Kits may also include multiple unit doses of the compounds and instructions for use and be packaged in quantities sufficient for storage and use in pharmacies (e.g., hospital pharmacies and compounding pharmacies).

The kits may optionally include a set of instructions, generally written instructions, although electronic storage media (e.g., magnetic diskette or optical disk) containing instructions are also acceptable, relating to the use of component(s) of the methods of the present invention. The instructions included with the kit generally include information as to the components and their administration to an individual.

The invention can be further understood by reference to the following examples, which are provided by way of illustration and are not meant to be limiting.

EXAMPLES

Synthetic Examples

Example S-1: Synthesis of N2-(2-(diethylamino)ethyl)-5-phenyl-6-(quinolin-6-yl)pyrazine-2,3-diamine (Compound No. 1)

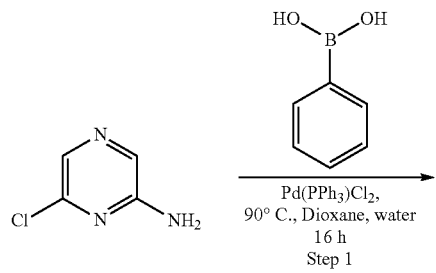

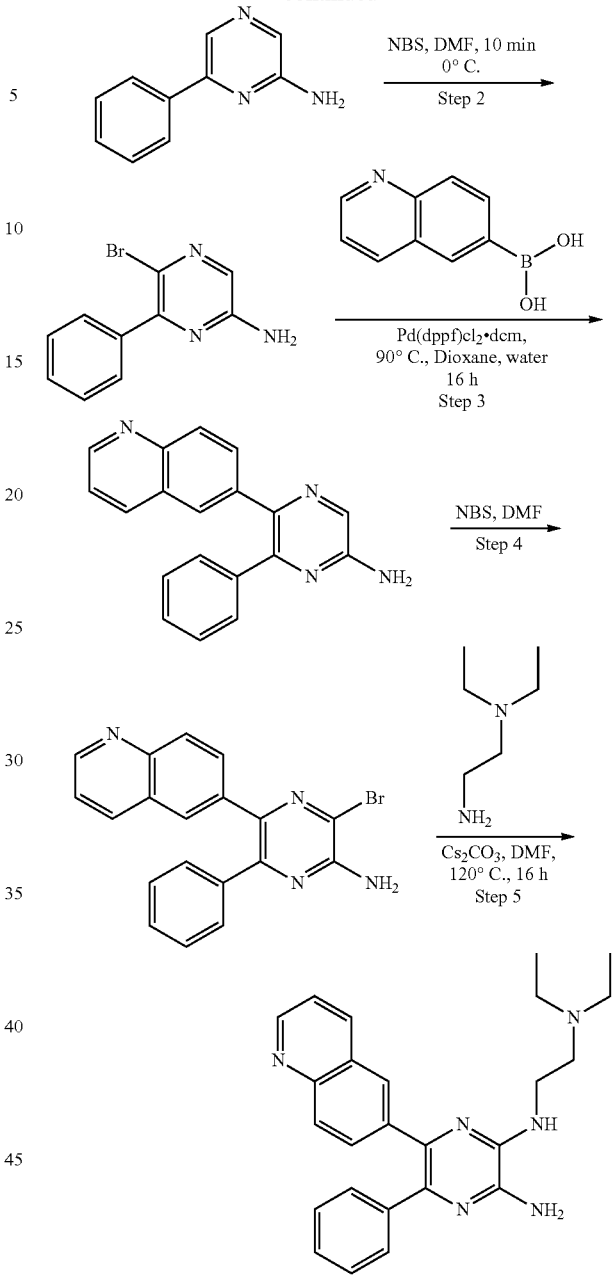

Step-1: Synthesis of 6-phenylpyrazin-2-amine

To a stirred solution of 6-chloropyrazin-2-amine (50 g, 0.3861 mol) in dioxane:water (400 mL: 100 mL) was added benzeneboronic acid (56.4 g, 0.46 mol). The reaction mixture was purged with nitrogen for 20 min then charged $Na_2CO_3$ (70.6 g, 0.57 mol) and $Pd(PPh_3)Cl_2$ (13.5 g, 0.01930 mol). The reaction mixture was again purged with nitrogen. The reaction mixture was stirred at RT for 10 min followed by heating at 90° C. for 16 h. The reaction was monitored by TLC and LCMS. The reaction mixture was filter through celite and distilled. The reaction was diluted with water and extracted with ethyl acetate (3×200 mL). The combined organic layers were washed (brine), dried (anhydrous $Na_2SO_4$) and concentrated under vacuum to get the solid which was purified by column chromatography over silica gel (100-200 mesh) [Ethyl acetate:Hexane (3:7) as eluent] to get the desired product (55 g, 83%). LCMS: 172 [M+1]+

Step-2: Synthesis of 5-bromo-6-phenylpyrazin-2-amine

To a stirred solution of 6-phenylpyrazin-2-amine (48 g, 0.2803 mol) in DMF was added NBS (49.9 g, 0.28 mol) at 0° C. under nitrogen atmosphere. The reaction mixture was stirred at RT for 16 h. The reaction was monitored by TLC and LCMS. The reaction was diluted with water and extracted with ethyl acetate (3×100 mL). The combined organic layers were washed (brine), dried (anhydrous $Na_2SO_4$) and concentrated under vacuum to get the solid which was purified by column chromatography silica gel (100-200 mesh) [Ethyl acetate:Hexane (1:4) as eluent] to get the desired product (38 g, 55%). LCMS: 252 [M+2]+

Step-3: synthesis of 6-phenyl-5-(quinolin-6-yl)pyrazin-2-amine

To a stirred solution of 5-bromo-6-phenylpyrazin-2-amine (38 g, 0.1519 mol) in dioxane:water (320 mL:80 mL) was added quinolin-6-ylboronic acid (46.4 g, 0.18 mol). The reaction mixture was purged with nitrogen for 20 min then charged with $Na_2CO_3$ (32.2 g, 0.3038 mol) and Pd(dppf)Cl$_2$ (6.19 g, 0.007 mol). The reaction mixture was again purged with nitrogen. The reaction mixture was stirred at RT for 10 min followed by heating at 90° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the solid which was purified by column chromatography over basic alumina [Ethyl acetate:Hexane (3:7) as eluent] to get the desired product (31 g, 68%). LCMS: 299 [M+1]+

Step-4: synthesis of 3-bromo-6-phenyl-5-(quinolin-6-yl)pyrazin-2-amine

To a stirred solution of 6-phenyl-5-(quinolin-6-yl) pyrazin-2-amine (21 g, 0.07 mol) in DMF was added NBS (12.5 g, 0.07 mol) at 0° C. under nitrogen atmosphere. The reaction mixture was stir at RT for 16h. The reaction was monitored by TLC and LCMS. The reaction was diluted with water and extracted with ethyl acetate (3×30 mL). The combined organic layers were washed (brine), dried (anhydrous $Na_2SO_4$) and concentrated under vacuum to get the solid which was purified by column chromatography over basic alumina [Ethyl acetate:Hexane (3:7) as eluent] to get the desired product (18 g, 69%). LCMS: 377 [M+1]+

Step-5: Synthesis of N2-(2-(diethylamino)ethyl)-5-phenyl-6-(quinolin-6-yl)pyrazine-2,3-diamine To a stirred solution of N1,N1-diethylethane-1,2-diamine (0.155 g, 1.32 mmol, 5.0 eq) in DMF (5 mL) was added $Cs_2CO_3$ (0.104 g, 0.31 mmol, 1.2 eq) and the mixture was stirred at RT for 15 min. To this mixture 3-bromo-6-phenyl-5-(quinolin-6-yl)pyrazin-2-amine (0.100 g, 0.26 mmol, 1.0 eq) was added and the resultant mixture was allowed to heat at 120° C. for 16 h. The progress of reaction was monitored by TLC. Upon completion, the mixture was diluted with water (40 mL), extracted with EtOAc (2×100 mL). The combined organic layers were washed with water (40 mL), brine (40 mL), dried over $Na_2SO_4$, filtered and concentrated under reduced pressure to afford a crude residue which was purified by reverse phase column chromatography to afford the desired product as an off-white solid (3 mg, 4%). LCMS: 413 [M+1]+; $^1$H NMR (400 MHz, DMSO-d$_6$) δ 8.82 (d, J=2.63 Hz, 2H), 8.10-8.21 (m, 2H), 7.93 (s, 1H), 7.87 (d, J=7.45 Hz, 1H), 7.79 (d, J=8.77 Hz, 1H), 7.58 (d, J=7.02 Hz, 1H), 7.40-7.51 (m, 2H), 7.13-7.31 (m, 5H), 6.82 (br s, 1H), 6.36 (br s, 2H), 3.71 (br s, 2H), 3.12 (br s, 2H), 2.98 (br s, 4H), 1.09 (t, J=7.02 Hz, 6H).

Example S-2: Synthesis of 3-amino-5-phenyl-N-(1-(pyridin-2-yl)ethyl)-6-(quinolin-6-yl)pyrazine-2-carboxamide (Compound No. 73)

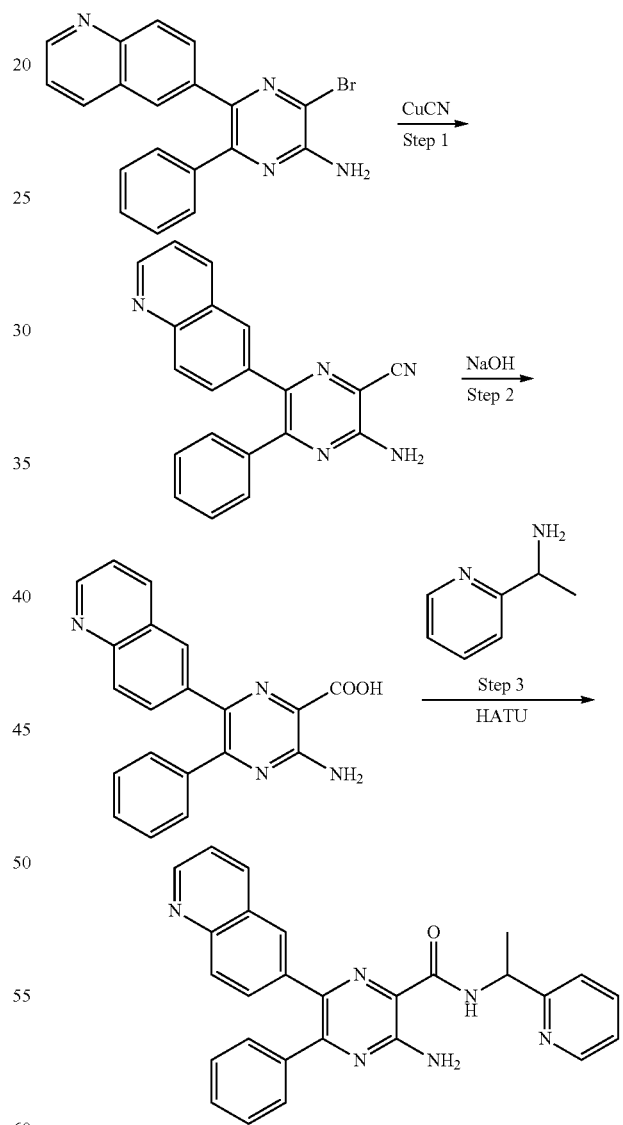

Step-1: Synthesis of 3-amino-5-phenyl-6-(quinolin-6-yl)pyrazine-2-carbonitrile

To a stirred solution of NaCN (1.56 g, 0.03 mol) and CuCN (5.7 g, 0.06 mol) in dry DMF (150 mL) was added 3-bromo-6-phenyl-5-(quinolin-6-yl)pyrazin-2-amine (12.0 g, 0.03 mol) at 120° C. The reaction mixture was stirred at 145° C. for 12h. The reaction was monitored by TLC and LCMS. The reaction was distilled. The crude product was poured in ice-water the solid precipitate out. The reaction mixture pH was adjusted with aqueous ammonia and extracted with ethyl acetate (3×100 mL). The combined organic layers were washed (brine), dried (anhydrous $Na_2SO_4$) and concentrated under vacuum to get the solid which was purified by column chromatography using basic alumina [Ethyl acetate:Hexane (1:1) as eluent] to get the desired product (3.8 g, 34%). LCMS: 324 [M+1]$^+$.

Step-2: Synthesis of 3-amino-5-phenyl-6-(quinolin-6-yl)pyrazine-2-carboxylic Acid To a stirred solution of 3-amino-5-phenyl-6-(quinolin-6-yl)pyrazine-2-carbonitrile (1 g, 3.08 mmol, 1 eq) in 1,4-dioxane (50 mL) and aqueous NaOH (10%, 50 mL) was heated at 100° C. for 48 h. Progress of reaction was monitored by LCMS. On completion of the reaction, the reaction mixture was concentrated under vacuum to get the solid residue which was diluted with water (15 mL) and acidified with 3N HCl solution (10 mL), and extracted with ethyl acetate (50 mL×2). Organic layer was washed with water (100 mL×2), dried over anhydrous $Na_2SO_4$ and concentrated under vacuum to get the solid residue which was used as such for next step without further purification (950 mg, 91%). LCMS: 343 [M+1]$^+$.

Step-3: Synthesis of 3-amino-5-phenyl-N-(1-(pyridin-2-yl)ethyl)-6-(quinolin-6-yl)pyrazine-2-carboxamide To a stirred solution of 3-amino-5-phenyl-6-(quinolin-6-yl)pyrazine-2-carboxylic acid (0.100 g, 0.30 mmol, 1 eq) and 1-(pyridin-2-yl)ethan-1-amine (0.07 g, 0.58 mmol, 2.0 eq) in DMF (2 mL), was added HOBT (0.06 g, 0.43 mmol, 1.5 eq), EDC.HCl (0.08 g, 0.43 mmol, 1.5 eq) and DIPEA (0.113 g, 0.87 mmol, 3.0 eq). The reaction mixture was allowed to stir at RT for 24 h. Progress of reaction was monitored by TLC and LCMS. On completion of the reaction, the reaction mixture was diluted with water (15 mL) and extracted with ethyl acetate (50 mL×2). Combined organic layer was washed with water (50 mL×2), dried over anhydrous $Na_2SO_4$ and concentrated under vacuum to get the solid residue which was purified by normal phase column chromatography to get the desired product (5 mg, 2%). LCMS: 447 [M+1]+; $^1$H NMR (400 MHz, DMSO-d$_6$) δ 9.18 (d, J=7.45 Hz, 1H), 9.02 (br s, 1H), 8.62 (br s, 2H), 8.52 (s, 1H), 8.14 (br s, 1H), 7.98 (d, J=8.77 Hz, 2H), 7.84 (d, J=8.77 Hz, 1H), 7.68 (br s, 3H), 7.26-7.44 (m, 5H), 5.29 (d, J=6.58 Hz, 1H), 1.59 (d, J=7.02 Hz, 3H).

Example-S-3: Synthesis of (S)-3-amino-5-phenyl-N-(1-(pyridin-2-yl)ethyl)-6-(quinolin-6-yl)pyrazine-2-carboxamide. (Compound No. 75)

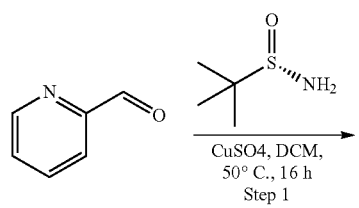

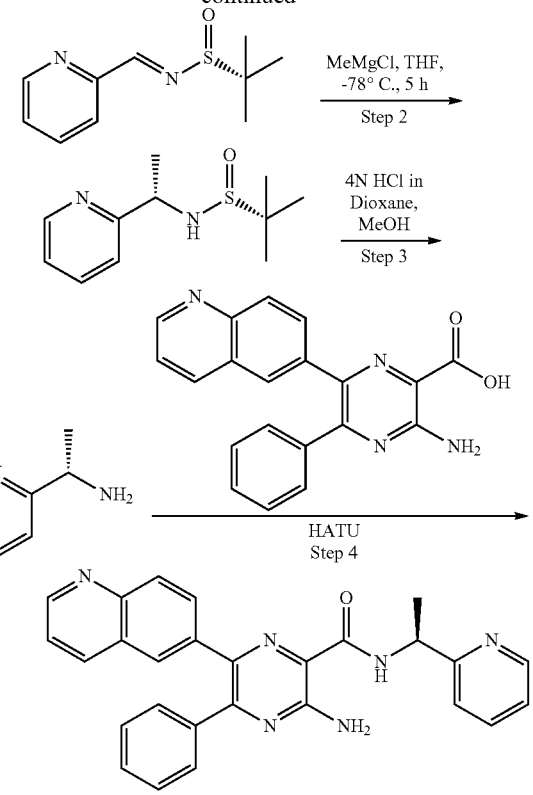

Step-1: Synthesis of (S, E)-2-methyl-N-(pyridin-2-ylmethylene)propane-2-sulfinamide To a stirred solution of pyridine-2-carboxaldehyde (1 g, 9.34 mmol, 1.0 eq) and copper(II) sulfate (2.98 g, 18.69 mmol, 2.0 eq) in dichloromethane (15 mL) was added (S)-2-methylpropane-2-sulfinamide (1.13 g, 9.34 mmol, 1.0 eq) at RT. The resulting mixture was heated at 50° C. for 16 h. Following this, reaction mixture was allowed to cool to room temperature, filtered through celite pad, the celite pad washed with dichloromethane (30 mL). The combined filtrate dried over anhydrous $Na_2SO_4$ and concentrated under vacuum to get the solid residue which was purified by flash column chromatography to get the desired product as white solid (1.2 g, 61%). LCMS: 211[M+1]$^+$ Step-2: Synthesis of (S)-2-methyl-N—((S)-1-(pyridin-2-yl)ethyl)propane-2-sulfinamide To a stirred solution of (S,E)-2-methyl-N-(pyridin-2-ylmethylene)propane-2-sulfinamide (1.0 g, 4.76 mmol, 1.0 eq) in tetrahydrofuran (15 mL) was added drop wise 3 M methylmagnesium bromide (2.38 mL, 7.14 mmol, 1.5 eq) at −78° C. The resulting mixture was stirred for 4 h at same temperature. The reaction was then quenched by careful addition of saturated $NH_4Cl$ (10 mL). The aqueous layer was separated and extracted with ethyl acetate (3×50 mL). The combined organic layers were dried over $Na_2SO_4$, filtered and concentrated to give crude solid residue which was purified by flash column chromatography to get the desired product as semi solid (0.72 g, 71%). LCMS: 227.0 [M+1]$^+$;

Step-3: Synthesis of (S)-1-(pyridin-2-yl)ethanamine

To a stirred solution of (S)-2-methyl-N—((S)-1-(pyridin-2-yl)ethyl)propane-2-sulfinamide (0.7 g, 3.09 mmol, 1.0 eq)

in methanol (5 mL) was added 4N HCl in dioxane (1.6 ml) at RT. The resulting mixture was stirred for 30 min. Following this the reaction mixture was evaporated under reduced pressure to get solid residue. The obtained solid was washed with diethyl ether, died under vacuum to get desired product as off white solid (0.35 g, 94%). LCMS: 123 [M+1]+

Step-4: Synthesis of (S)-3-amino-5-phenyl-N-(1-(pyridin-2-yl)ethyl)-6-(quinolin-6-yl)pyrazine-2-carboxamide To stirred solution of 3-amino-5-phenyl-6-(quinolin-6-yl)pyrazine-2-carboxylic acid (0.1 g, 0.29 mmol, 1.0 eq) in DMF (5.0 ml) was added (S)-1-(pyridin-2-yl)ethanamine (0.042 g, 0.35 mmol, 1.2 eq), DIPEA (0.15 mL, 0.87 mmol, 3 eq) and HATU (0.22 g, 0.58 mmol, 2 eq) at RT under inert condition. The resulting mixture stirred for 16h at same temperature. Following this, ice cold water (20 mL) was added and extracted with ethyl acetate (3×20 mL), the combined organic layer washed with brine solution (1×50 mL), dried over Na$_2$SO$_4$, filtered and distilled purified by column chromatography using basic alumina (18 mg, 14%). LCMS: 447 [M+1]+. $^1$H NMR (400 MHz, DMSO-d$_6$) δ 9.20 (d, J=7.45 Hz, 1H), 9.10 (d, J=3.51 Hz, 1H), 8.68 (d, J=3.51 Hz, 2H), 8.25 (br s, 1H), 8.13 (br s, 1H), 8.03 (d, J=8.77 Hz, 1H), 7.91 (d, J=8.77 Hz, 1H), 7.75-7.84 (m, 3H), 7.58 (br s, 1H), 7.35-7.43 (m, 3H), 7.28-7.35 (m, 2H), 5.28-5.38 (m, 1H), 2.87-2.97 (m, 1H), 1.62 (d, J=7.02 Hz, 3H), 1.16 (t, J=7.24 Hz, 1H).

Example-S-4: Synthesis of (R)-3-amino-5-phenyl-N-(1-(pyridin-2-yl)ethyl)-6-(quinolin-6-yl)pyrazine-2-carboxamide. (Compound No. 76)

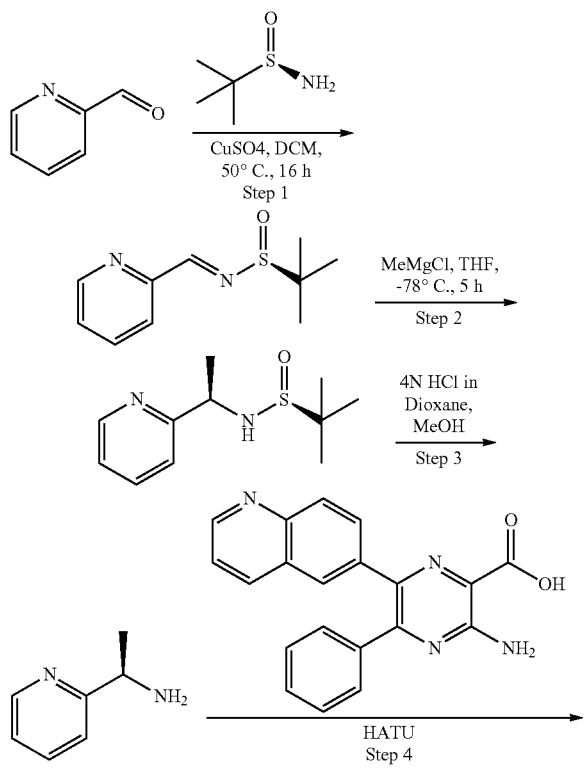

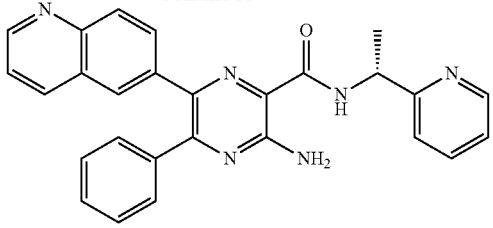

Step-1: Synthesis of 2-methyl-N—[(E)-pyridin-2-ylmethylidene]propane-2-sulfinamide To a stirred solution of pyridine-2-carboxaldehyde (1 g, 9.34 mmol, 1.0 eq) and copper(II) sulfate (2.98 g, 18.69 mmol, 2.0 eq) in dichloromethane (15 mL) was added (R)-2-methylpropane-2-sulfinamide (1.13 g, 9.34 mmol, 1.0 eq) at RT. The resulting mixture was heated at 50° C. for 16 h. Following this, reaction was allowed to cool to room temperature, filtered through celite pad, the celite pad washed with dichloromethane (30 mL). The combined filtrate dried over anhydrous Na$_2$SO$_4$ and concentrated under vacuum to get the solid residue which was purified by flash column chromatography to get the desired product as white solid (800 mg, 40%) LCMS: 210 [M+1]+

Step-2: Synthesis of 2-methyl-N-[(1R)-1-(pyridin-2-yl)ethyl]propane-2-sulfinamide To a stirred solution of 2-methyl-N—[(E)-pyridin-2-ylmethylidene]propane-2-sulfinamide (800 mg, 3.80 mmol, 1.0 eq) in tetrahydrofuran (10 mL) was added drop wise 3 M methylmagnesium bromide (2.5 mL, 7.61 mmol, 2.0 eq) at −78° C. The resulting mixture was stirred for 4 h at same temperature. The reaction was then quenched by addition of saturated NH$_4$Cl (10 mL). The aqueous layer was separated and extracted with ethyl acetate (3×50 mL). The combined organic layers were dried over Na$_2$SO$_4$, filtered and concentrated to give crude solid residue which was purified by flash column chromatography to get the desired product as semi solid (600 mg, 75%). LCMS: 227.0 [M+1]+

Step-3: Synthesis of (1R)-1-(pyridin-2-yl)ethanamine

To a stirred solution of 2-methyl-N-[(1R)-1-(pyridin-2-yl)ethyl]propane-2-sulfinamide (600 mg, 2.65 mmol, 1.0 eq) in methanol (10 mL) was added 4N HCl in dioxane (2.5 ml) at RT. The resulting mixture was stirred for 30 min. Following this the reaction mixture was evaporated under reduced pressure to get solid residue. The obtained solid was washed with diethyl ether, died under vacuum to get desired product as solid (0.35 g, 94%). LCMS: 123 [M+1]+

Step-4: Synthesis of (R)-3-amino-5-phenyl-N-(1-(pyridin-2-yl)ethyl)-6-(quinolin-6-yl)pyrazine-2-carboxamide To stirred solution of 3-amino-5-phenyl-6-(quinolin-6-yl)pyrazine-2-carboxylic acid (0.1 g, 0.29 mmol, 1.0 eq) in DMF (10 ml) was added (1R)-1-(pyridin-2-yl)ethanamine e (68 mg, 0.43 mmol, 1.5 eq), DIPEA (0.2 mL, 0.87 mmol, 3 eq) and HATU (220 mg, 0.58 mmol, 2 eq) at RT under inert condition. The resulting mixture stirred for 16h at same temperature. Following this, ice cold water (20 mL) was added and extracted with ethyl acetate (3×20 mL), the combined organic layer washed with brine solution (1×50 mL), dried over Na$_2$SO$_4$, filtered and distilled purified by reverse phase column chromatography to get the desired product (10 mg, 8%) LCMS: 447 [M+1]$^+$. $^1$H NMR (400 MHz, DMSO-d$_6$) δ 9.18 (d, J=8.33 Hz, 2H), 8.91 (d, J=2.63 Hz, 1H), 8.57 (d, J=5.26 Hz, 1H), 8.29 (d, J=7.45 Hz, 1H), 8.03 (br s, 1H), 7.92 (d, J=8.77 Hz, 1H), 7.82 (d, J=7.02 Hz, 2H), 7.73 (d, J=7.02 Hz, 1H), 7.50-7.57 (m, 2H), 7.38-7.42 (m, 2H), 7.28-7.38 (m, 4H), 5.22-5.27 (m, 2H), 2.87-2.97 (m, 4H), 1.55 (d, J=7.02 Hz, 3H), 1.16 (t, J=7.45 Hz, 4H).

Example S-5: Synthesis of 3-amino-5-phenyl-6-(quinolin-6-yl)-N-(2-(tetrahydro-2H-pyran-4-yl)ethyl)pyrazine-2-carboxamide. (Compound No. 89)

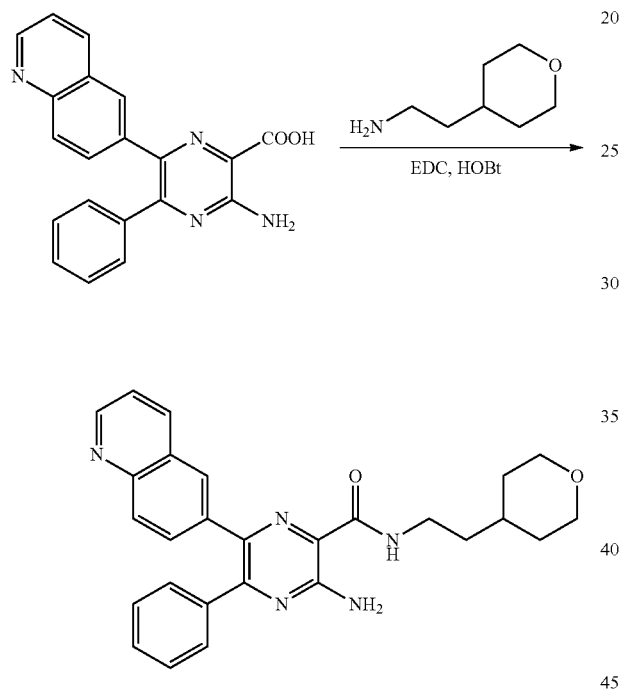

To a stirred solution of 3-amino-5-phenyl-6-(quinolin-6-yl)pyrazine-2-carboxylic acid (0.100 g, 0.30 mmol, 1 eq) and 2-(tetrahydro-2H-pyran-4-yl)ethan-1-amine (0.07 g, 0.58 mmol, 2.0 eq) in DMF (5 mL), was added HOBT (0.06 g, 0.43 mmol, 1.5 eq), EDC.HCl (0.08 g, 0.43 mmol, 1.5 eq) and DIPEA (0.113 g, 0.87 mmol, 3.0 eq). The reaction mixture was allowed to stir at RT for 24 h. Progress of reaction was monitored by TLC and LCMS. On completion of the reaction, the reaction mixture was diluted with water (15 mL) and extracted with ethyl acetate (50 mL×2). Combined organic layer were washed (brine), dried (anhydrous Na$_2$SO$_4$) and concentrated under vacuum to get the solid residue which was purified by reverse phase column chromatography to get the desired product (3 mg, 2%). LCMS: 454 [M+1]$^+$; $^1$H NMR (400 MHz, DMSO-d6) δ 8.84-8.90 (m, 1H), 8.74 (s, 1H), 8.43 (s, 1H), 8.21 (d, J=7.45 Hz, 1H), 8.03 (br s, 1H), 7.85 (d, J=8.33 Hz, 1H), 7.66-7.73 (m, 1H), 7.51 (dd, J=3.95, 8.33 Hz, 1H), 7.26-7.43 (m, 5H), 6.62 (s, 1H), 4.66 (s, 1H), 4.09 (s, 2H), 3.83 (d, J=7.89 Hz, 2H), 3.17 (d, J=4.39 Hz, 2H), 1.52 (d, J=7.45 Hz, 2H), 1.23 (br s, 4H).

Example-S-6: Synthesis of 3-(6-amino-3-(8-chloroquinolin-6-yl)pyrazin-2-yl)-2-methylbenzonitrile. (Compound No. 2-2)

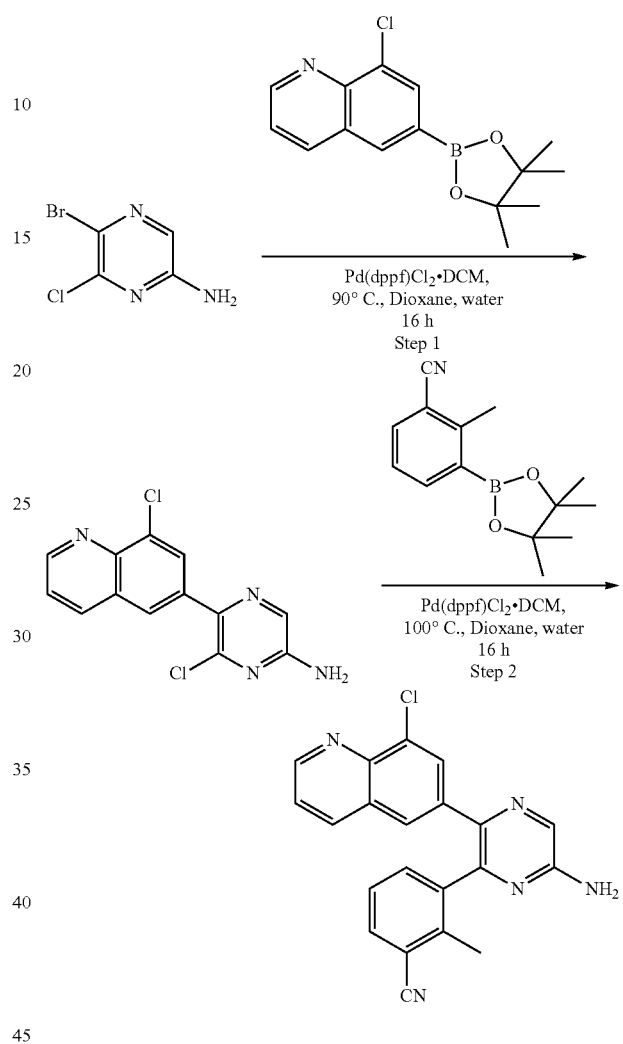

Step-1: Synthesis of 6-chloro-5-(8-chloroquinolin-6-yl)pyrazin-2-amine

To a stirred solution of 5-bromo-6-chloropyrazin-2-amine (4.0 g, 19.23 mmol, 1 eq) in dioxane:water (180 mL: 20 mL) was added 8-chloroquinolin-6-ylboronic acid (5.0 g, 17.30 mmol, 0.9 eq). The reaction mixture was purged with nitrogen for 20 min then charged with Na$_2$CO$_3$ (4.1 g, 39.0 mmol, 2.0 eq) and Pd(dppf)Cl$_2$.DCM (787 mg, 5 mol %). The reaction mixture was again purged with nitrogen. The reaction mixture was stirred at RT for 10 min followed by heating at 90° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous Na$_2$SO$_4$) and concentrated under vacuum to get the solid which was purified by reverse phase column chromatography to get the desired product (2.2 g, 78%). LCMS: 292 [M+1]$^+$ Step-2: Synthesis of 3-(6-amino-3-(8-chloroquinolin-6-yl)pyrazin-2-yl)-2-methylbenzonitrile To a stirred solution of 6-chloro-5-(8-chloroquinolin-6-yl)pyrazin-2-amine (0.100 g, 0.35 mmol, 1 eq) in dioxane: water (4 mL: 10 mL) was added 2-methyl-3-(4,4,5,5-tetramethyl-1,3,2-dioxaborolan-2-yl)benzonitrile (0.9 g, 0.31 mmol, 1.2 eq). The reaction mixture was purged with nitrogen for 20 min then charged with $Na_2CO_3$ (0.073 g, 0.69 mmol, 2.0 eq) and $Pd(dppf)Cl_2.DCM$ (14 mg, 5 mol %). The reaction mixture was again purged with nitrogen. The reaction mixture was stirred at RT for 10 min followed by heating at 100° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the solid which was purified by reverse phase column chromatography to get the desired product (0.05 g, 38%). LCMS: 372 [M+1]$^+$. $^1$H NMR (400 MHz, DMSO-d$_6$) 8.94 (dd, J=1.53, 4.17 Hz, 1H), 8.24 (dd, J=1.75, 8.33 Hz, 1H), 8.11 (s, 1H), 7.82 (d, J=6.58 Hz, 1H), 7.73 (d, J=1.75 Hz, 1H), 7.66 (d, J=1.75 Hz, 1H), 7.51-7.60 (m, 2H), 7.35-7.42 (m, 1H), 6.94 (s, 2H), 2.20 (s, 3H).

Example-S-7: Synthesis of 3-(6-amino-3-(8-chloroquinolin-6-yl)pyrazin-2-yl)-2-fluorobenzonitrile (Compound No. 2-10)

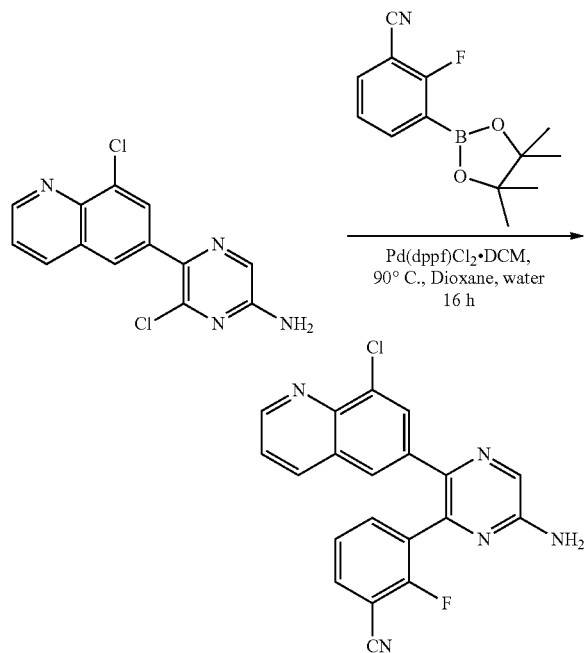

To a stirred solution of 6-chloro-5-(8-chloroquinolin-6-yl)pyrazin-2-amine (0.05 g, 0.18 mmol, 1 eq) in dioxane: water (4 mL: 10 mL) was added 2-fluoro-3-(4,4,5,5-tetramethyl-1,3,2-dioxaborolan-2-yl)benzonitrile (0.9 g, 0.15 mmol 1.2 eq). The reaction mixture was purged with nitrogen for 20 min then charged with $Na_2CO_3$ (0.073 g, 0.35 mmol, 2.0 eq) and $Pd(dppf)Cl_2.DCM$ (7 mg, 5 mol %). The reaction mixture was again purged with nitrogen. The reaction mixture was stirred at RT for 10 min followed by heating at 100° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the solid which was purified by reverse phase column chromatography to get the desired product (0.008 g, 12%). LCMS: 376 [M+1]$^+$. $^1$H NMR (400 MHz, DMSO-d$_6$) δ 8.93-8.99 (m, 1H), 8.30 (dd, J=1.53, 8.55 Hz, 1H), 8.12 (s, 1H), 7.98 (t, J=5.92 Hz, 1H), 7.88 (t, J=6.80 Hz, 1H), 7.83 (d, J=1.75 Hz, 1H), 7.75 (d, J=1.75 Hz, 1H), 7.59 (td, J=3.84, 8.11 Hz, 1H), 7.47 (t, J=7.67 Hz, 1H), 7.02 (s, 2H).

Example-S-8: Synthesis of 3-amino-N-((6-cyanopyridin-2-yl)methyl)-5-phenyl-6-(quinolin-6-yl)pyrazine-2-carboxamide (Compound No. 98)

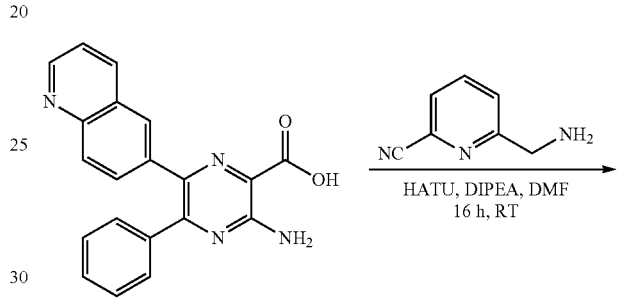

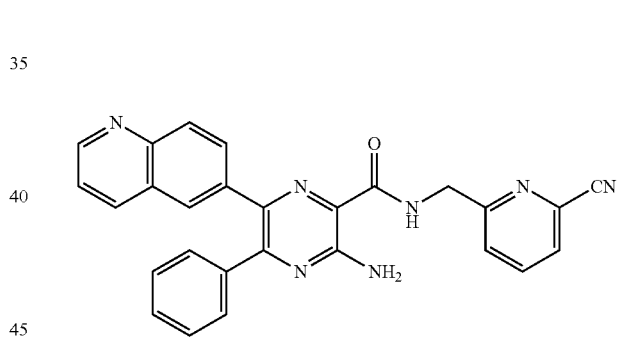

To a stirred solution of 3-amino-5-phenyl-6-(quinolin-6-yl)pyrazine-2-carboxylic acid (100 mg, 0.29 mmol, 1.0 eq) in DMF (10 mL) was added 6-(aminomethyl)pyridine-2-carbonitrile (58 mg, 0.43 mmol, 1.5 eq) and the mixture was stirred at RT for 5 min. To this mixture HATU (220 mg, 0.58 mmol, 2.0 eq) and DIPEA (108 mg, 0.87 mmol, 3.0 eq) was added and the resultant mixture was allowed to stir for 16 h. The progress of reaction was monitored by TLC. Upon completion, the mixture was diluted with water (40 mL), extracted with EtOAc (2×100 mL). The combined organic layers were washed with water (40 mL), brine (40 mL), dried over $Na_2SO_4$, filtered and concentrated under reduced pressure to afford a crude residue which was purified by reverse phase column chromatography to afford the desired product as an off-white solid (14 mg, 11%). LCMS: 458 [M+1]$^+$. $^1$H NMR (400 MHz, DMSO-d6) δ 9.50 (t, J=6.14 Hz, 1H), 8.87 (d, J=3.07 Hz, 1H), 8.21 (d, J=7.89 Hz, 1H), 8.00-8.08 (m, 2H), 7.95 (d, J=7.45 Hz, 1H), 7.86 (d, J=8.77 Hz, 1H), 7.68-7.77 (m, 3H), 7.50 (dd, J=4.39, 8.33 Hz, 1H), 7.27-7.45 (m, 5H), 4.69 (d, J=6.14 Hz, 2H).

Example S-9: Synthesis of 3-amino-5-phenyl-N-(2-(pyridin-2-yl)propan-2-yl)-6-(quinolin-6-yl)pyrazine-2-carboxamide: (Compound No. 108)

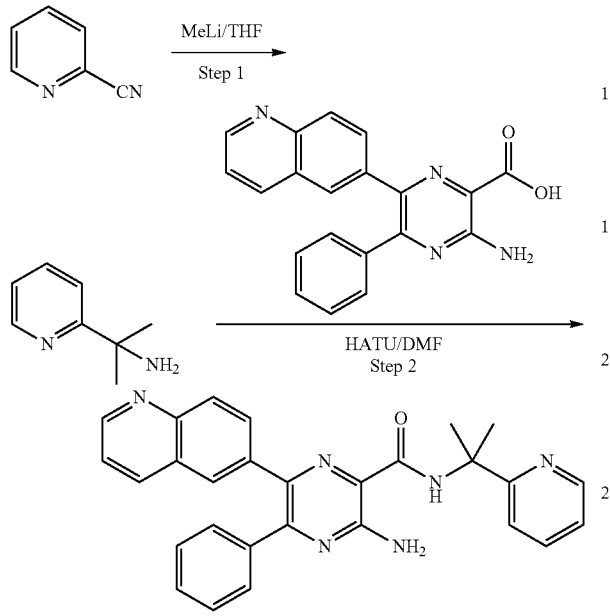

Step 1: Synthesis of 2-(pyridin-2-yl)propan-2-amine

To a stirred solution of anhydrous cerium (III) chloride (7.1 g, 0.0288 mmol, 3 eq) in THF (15 mL) was added methyl lithium (1.6 M, 18 mL, 0.0288 mmol, 3 eq) at −78° C. The reaction was allowed to stir at same temperature for 30 min. Picolinonitrile (1 g, 0.0096 mmol, 3 eq) in THF was added at −78° C. and reaction was allowed to stir at RT for 1 h. The reaction was cooled to −40° C., then charged with 10 mL ammonium hydroxide. The reaction was allowed to stir at RT for 16 h. The solid was filtered and wash with THF. The organic layer was concentrated under vacuum to get the title compound which was used directly for next step without further purification (0.460 g, Crude); LCMS: 137 [M+1]$^+$

Step 2: Synthesis of 3-amino-5-phenyl-N-(2-(pyridin-2-yl)propan-2-yl)-6-(quinolin-6-yl)pyrazine-2-carboxamide To a stirred solution of 3-amino-5-phenyl-6-(quinolin-6-yl)pyrazine-2-carboxylic acid (100 mg, 0.2924 mmol, 1.0 eq) and 2-(pyridin-2-yl)propan-2-amine (222 mg, 0.3508 mmol, 2 eq) in DMF (5 mL) was added DIPEA (0.150 mL, 0.8772 mmol, 3.0 eq) at 0° C. The reaction was allowed to stir at same temperature for 10 min. Then charged HATU (222 mg, 0.5848 mmol, 2.0 eq) and the reaction was allowed to stir at RT for 16 h. The reaction mixture was quenched with cold water (5 mL) then extracted using ethyl acetate (2×50 mL). The combined organic layers were washed with brine, dried (anhydrous sodium sulphate) and concentrated under vacuum to get the solid which was purified by SFC to get the title compound (8 mg, 6%). LCMS: 461 [M+1]$^+$; $^1$H NMR (400 MHz, DMSO-d$_6$) δ 10.08 (s, 1H), 8.89 (d, J=2.63 Hz, 1H), 8.57 (d, J=4.82 Hz, 1H), 8.26 (d, J=7.89 Hz, 1H), 8.05 (s, 1H), 7.94 (d, J=8.77 Hz, 1H), 7.84-7.92 (m, 1H), 7.75 (d, J=8.33 Hz, 2H), 7.67 (d, J=8.33 Hz, 2H), 7.53 (dd, J=3.95, 8.33 Hz, 2H), 7.41-7.49 (m, 2H), 7.30-7.41 (m, 4H), 1.80 (s, 6H).

Example S-10: Synthesis of 3-amino-N-(2-(diethylamino)ethyl)-5-phenyl-6-(quinolin-6-yl)pyrazine-2-carboxamide (Compound No. 107)

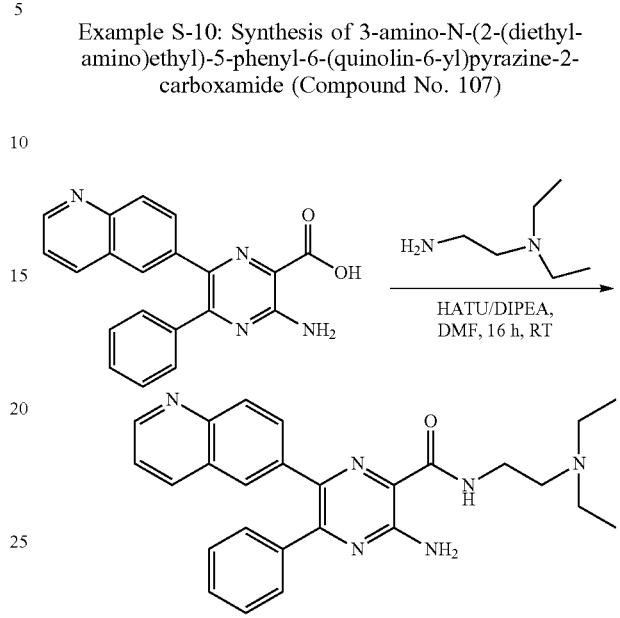

To a stirred solution of 3-amino-5-phenyl-6-(quinolin-6-yl)pyrazine-2-carboxylic acid (0.1 g, 0.29 mmol, 1.0 eq) in DMF (10 mL) was added N,N-diethylethane-1,2-diamine (51 mg, 0.43 mmol, 1.5 eq), DIPEA (0.2 mL, 0.87 mmol, 3 eq) and HATU (220 mg, 0.58 mmol, 2 eq) at RT under inert condition. The resulting mixture was stirred for 16 h at same temperature. Following this, ice cold water (20 mL) was added and extracted with ethyl acetate (3×20 mL), the combined organic layer washed with brine solution (1×50 mL), dried over Na$_2$SO$_4$, filtered and distilled purified by reverse phase column chromatography to get the desired product (8 mg, 7%). LCMS: 441 [M+1]$^+$; $^1$H NMR (DMSO-d6, 400 MHz) δ 8.87 (dd, J=4.2, 1.5 Hz, 1H), 8.70 (t, J=5.7 Hz, 1H), 8.19 (d, J=7.5 Hz, 1H), 7.99 (d, J=2.2 Hz, 1H), 7.85 (d, J=8.8 Hz, 1H), 7.65 (dd, J=8.8, 2.2 Hz, 1H), 7.51 (dd, J=8.3, 4.4 Hz, 1H), 7.26-7.43 (m, 5H), 3.36-3.43 (m, 3H), 2.60 (t, J=6.8 Hz, 3H), 2.52-2.56 (m, 7H), 0.97 (t, J=7.0 Hz, 6H).

Example S-11: Synthesis of (R)-3-amino-6-(8-chloroquinolin-6-yl)-5-(4-fluorophenyl)-N-(1-(pyridin-2-yl)ethyl)pyrazine-2-carboxamide (Compound No. 106)

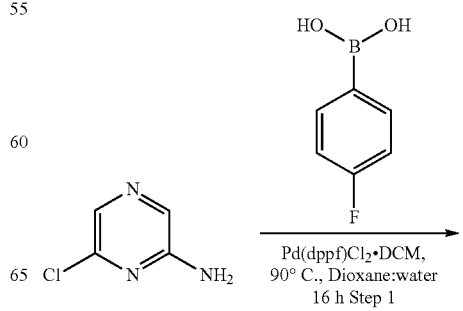

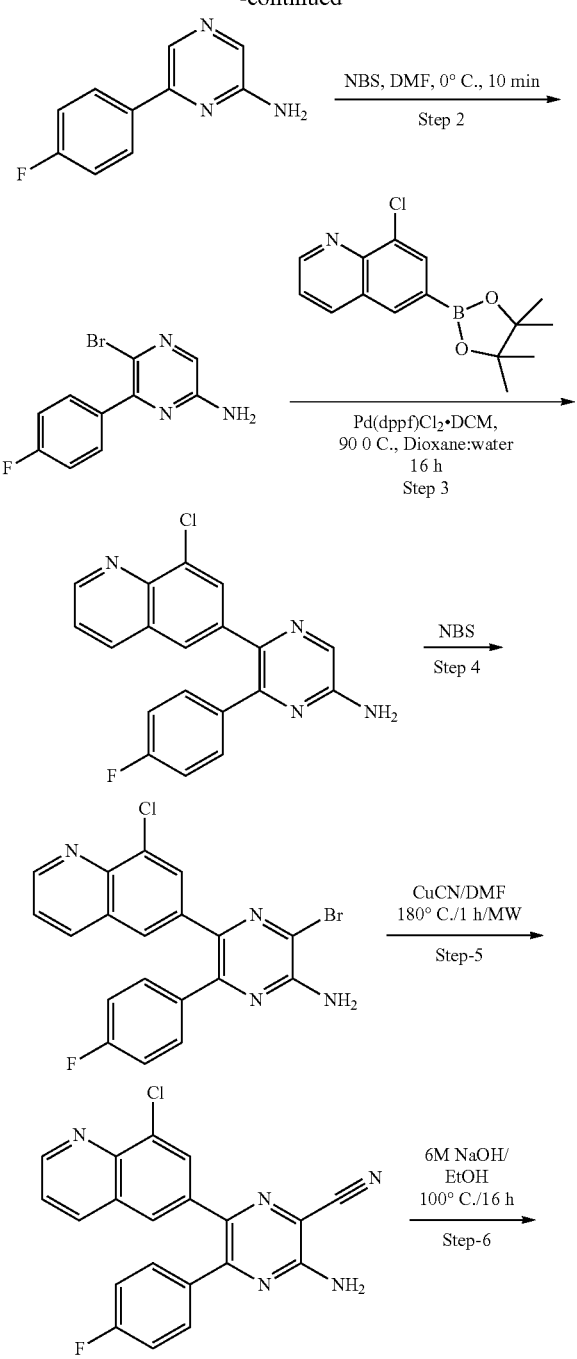

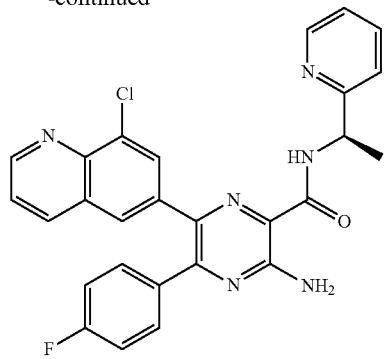

Step 1: Synthesis of 6-(4-fluorophenyl)pyrazin-2-amine

To a stirred solution of 6-chloropyrazin-2-amine (2 g, 15.50 mmol, 1 eq) in dioxane:water (50 mL: 10 mL) was added 4-fluorobenzeneboronic acid (2.8 g, 20.15 mmol, 1.3 eq). The reaction mixture was purged with nitrogen for 20 min then charged $K_2CO_3$ (4.2 g, 31.0 mmol, 2.0 eq) and Pd(dppf)Cl$_2$.DCM complex (632 mg, 0.77 mmol, 0.05 eq). The reaction mixture was again purged with nitrogen. The reaction mixture was stirred at RT for 10 min followed by heating at 90° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the solid which was purified by column chromatography over silica gel (100-200 mesh) [Ethyl acetate:Hexane (5:5) as eluent] to get the title compound (2 g, 68%). LCMS: 190 [M+1]$^+$.

Step 2: Synthesis of 5-bromo-6-(4-fluorophenyl)pyrazin-2-amine

To a stirred solution of 6-(4-fluorophenyl)pyrazin-2-amine (2 g, 10.50 mmol, 1.0 eq) in DMF (20 mL) was added NBS (1.9 g, 10.50 mmol, 1.0 eq) at 0° C. under nitrogen atmosphere. The reaction mixture was stirred at RT for 30 min. The reaction was monitored by TLC and LCMS. The reaction was diluted with water and extracted with ethyl acetate (3×100 mL). The combined organic layers were washed (brine), dried (anhydrous $Na_2SO_4$) and concentrated under vacuum to get the solid which was purified by column chromatography silica gel (100-200 mesh) [Ethyl acetate: Hexane (2:8) as eluent] to get the title compound (2.5 g, 89%). LCMS: 269 [M+1]$^+$.

Step 3: 5-(8-chloroquinolin-6-yl)-6-(4-fluorophenyl) pyrazin-2-amine

To a stirred solution of 5-bromo-6-(4-fluorophenyl) pyrazin-2-amine (4.5 g, 16.79 mmol, 1 eq) in dioxane:water (50 mL:10 mL) was added 8-chloroquinolin-6-ylboronic acid (5.8 g, 20.14 mmol 1.2 eq). The reaction mixture was purged with nitrogen for 20 min then charged with $K_2CO_3$ (4.6 g, 33.58 mmol, 2.0 eq) and Pd(dppf)Cl$_2$.DCM complex (685 mg, 0.83 mmol, 0.05 eq). The reaction mixture was again purged with nitrogen. The reaction mixture was stirred at RT for 10 min followed by heating at 90° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous Na$_2$SO$_4$) and concentrated under vacuum to get the solid which was purified by column chromatography over basic alumina [Ethyl acetate:Hexane (3:7) as eluent] to get the title compound (5 g, 86%). LCMS: 351 [M+1]$^+$.

Step 4: Synthesis of 3-bromo-5-(8-chloroquinolin-6-yl)-6-(4-fluorophenyl)pyrazin-2-amine To a stirred solution of 5-(8-chloroquinolin-6-yl)-6-(4-fluorophenyl)pyrazin-2-amine (1 g, 2.85 mmol, 1 eq) in DMF (20 mL) was added NBS (498 mg, 2.85 mmol, 1 e.q) at 0° C. under nitrogen atmosphere. The reaction mixture was stirred at RT for 30 min. The reaction was monitored by TLC and LCMS. The reaction was diluted with water and extracted with ethyl acetate (3×30 mL). The combined organic layers were washed (brine), dried (anhydrous Na$_2$SO$_4$) and concentrated under vacuum to get the solid which was purified by column chromatography [Ethyl acetate:Hexane (7:3) as eluent] to get the title compound (600 mg, 73%). LCMS: 429 [M+1]$^+$.

Step-5 Synthesis of 3-amino-6-(8-chloroquinolin-6-yl)-5-(4-fluorophenyl)pyrazine-2-carbonitrile To a stirred solution of 3-bromo-5-(8-chloroquinolin-6-yl)-6-(4-fluorophenyl)pyrazin-2-amine (500 mg, 1.16 mmol, 1.0 eq) in DMF (5 mL) was added cuprous cyanide (0.104 g, 3.50 mmol, 3.0 eq). The reaction mixture was allowed to heat at 150° C. for 1 h using microwave irradiation. The reaction mixture was allowed to cool to RT, diluted with aqueous ammonia (5 mL) and extracted using ethyl acetate (3×25 mL). The combined organic layers were washed (brine), dried (anhydrous Na$_2$SO$_4$) and concentrated under vacuum to get the solid which was purified by reverse phase column chromatography to get the title compound (0.20 g, 46%). LCMS: 376[M+1]$^+$.

Step-6 Synthesis of 3-amino-6-(8-chloroquinolin-6-yl)-5-(4-fluorophenyl)pyrazine-2-carboxylic acid To a stirred solution of 3-bromo-6-phenyl-5-(quinolin-6-yl)pyrazin-2-amine (0.2 g, 0.53 mmol, 1.0 eq) in ethanol (5 mL) was added 6M NaOH solution (5 mL). The resulting reaction mixture was heated at 100° C. for 16 h. The reaction mixture was allowed to cool to RT.

The solvent was evaporated under vacuum and acidified using 1N HCl to get the solid which was filtered and dried to get the title compound (0.20 g, 95%). LCMS: 394 [M+1]$^+$.

Step-7: (R)-3-amino-6-(8-chloroquinolin-6-yl)-5-(4-fluorophenyl)-N-(1-(pyridin-2-yl)ethyl)pyrazine-2-carboxamide To stirred solution of 3-amino-6-(8-chloroquinolin-6-yl)-5-(4-fluorophenyl)pyrazine-2-carboxylic acid (0.1 g, 0.25 mmol, 1.0 eq) in DMF (10 ml) was added (1R)-1-(pyridin-2-yl)ethanamine (47 mg, 0.43 mmol, 1.5 eq), DIPEA (0.2 mL, 0.75 mmol, 3 eq) and HATU (190 mg, 0.50 mmol, 2 eq) at RT under inert condition. The resulting mixture stirred for 16 h at same temperature. Following this, ice cold water (20 mL) was added and extracted with ethyl acetate (3×20 mL), the combined organic layer washed with brine solution (1×50 mL), dried over Na$_2$SO$_4$, filtered and distilled purified by reverse phase column chromatography to get the title compound (10 mg, 8%). LCMS: 499 [M+1]$^+$. $^1$H NMR (400 MHz, DMSO-d$_6$) δ 9.28 (d, J=7.9 Hz, 1H), 9.00 (d, J=3.1 Hz, 1H), 8.58 (d, J=3.9 Hz, 1H), 8.32 (d, J=7.9 Hz, 1H), 8.02 (s, 1H), 7.90 (s, 1H), 7.81 (t, J=6.8 Hz, 2H), 7.63 (dd, J=8.3, 3.9 Hz, 1H), 7.44-7.54 (m, 3H), 7.29-7.36 (m, 1H), 7.19 (t, J=8.8 Hz, 2H), 5.18-5.30 (m, 1H), 1.55 (d, J=7.0 Hz, 3H).

Example S-12: Synthesis of 3-(6-amino-3-(8-chloroquinolin-6-yl)pyrazin-2-yl)benzonitrile (Compound No. 2-6)

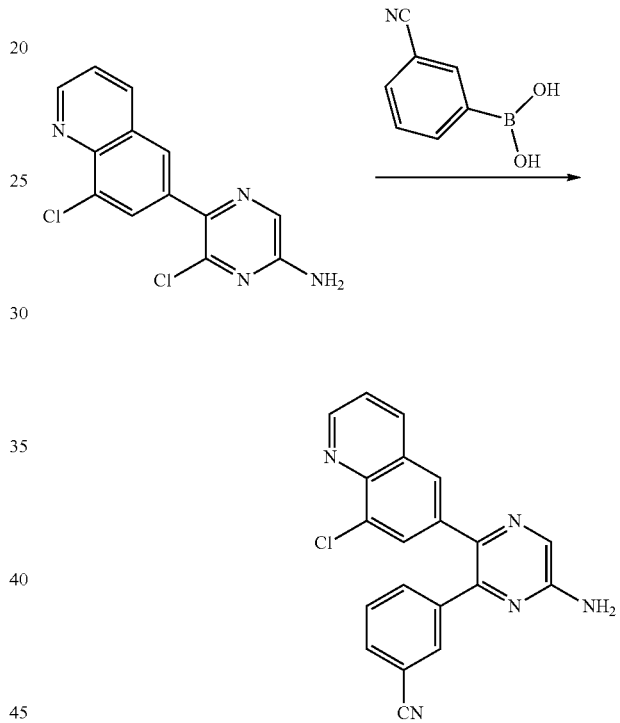

To a stirred solution of 6-chloro-5-(8-chloroquinolin-6-yl)pyrazin-2-amine (0.110 g 0.38 mmol, 1.0 eq) in dioxane (5 mL):water (1 mL) was added 3-cyanophenylboronic acid (0.103 g, 0.45 mmol, 1.2 eq), Na$_2$CO$_3$ (0.80 g, 0.76 mmol, 2.0 eq) and PdCl$_2$(dppf).DCM complex (0.015 g, 5 mol %). The reaction mixture was deoxygenated using N2 atmosphere and the reaction mixture was heated at 100° C. for 18 h. The reaction was monitored by TLC and LCMS. The reaction mixture was diluted with water (50 mL) and extracted using ethyl acetate (3×50 mL). The separated organic layer was dried over sodium sulfate and concentrated under reduced pressure. The crude product was purified by normal phase silica gel column chromatography to afford (0.015 g, 11%) the title compound. LCMS: 358 [M+1]$^1$; $^1$H NMR (400 MHz, DMSO-d$_6$) δ 8.97 (dd, J=1.53, 4.17 Hz, 1H), 8.31 (dd, J=1.75, 8.33 Hz, 1H), 8.06 (s, 1H), 7.91 (s, 1H), 7.76-7.85 (m, 3H), 7.54-7.63 (m, 2H), 7.42-7.51 (m, 1H), 6.94 (s, 2H).

Example S-13: Synthesis of Synthesis of 5-(6-amino-3-(8-chloroquinolin-6-yl)pyrazin-2-yl)-2-fluorobenzonitrile (Compound No. 2-13)

Example S-14: Synthesis of 3-amino-6-(8-chloroquinolin-6-yl)-N-((6-cyanopyridin-2-yl)methyl)-5-(4-fluorophenyl)pyrazine-2-carboxamide (Compound No. 105)

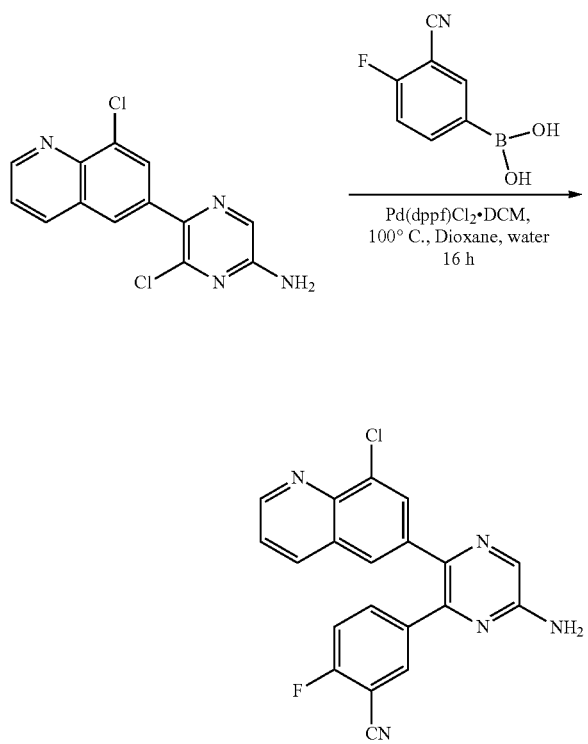

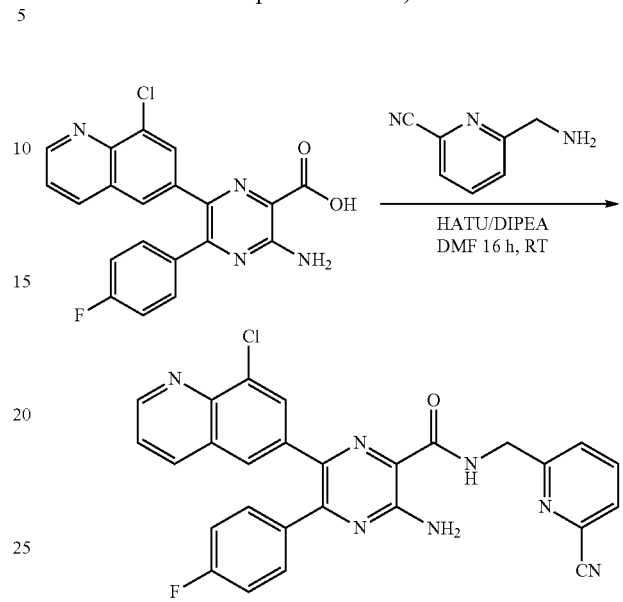

To a stirred solution of 6-chloro-5-(8-chloroquinolin-6-yl)pyrazin-2-amine (0.200 g, 0.68 mmol, 1 eq) in dioxane:water (8 mL: 2 mL) was added 3-cyano-4-fluorophenylboronic acid (0.136 g, 0.82 mmol 1.2 eq) The reaction mixture was purged with nitrogen for 20 min then charged with $Na_2CO_3$ (0.146 g, 1.38 mmol, 2.0 eq) and Pd(dppf)$Cl_2$.DCM complex (28 mg, 5 mol %). The reaction mixture was again purged with nitrogen. The reaction mixture was stirred at RT for 10 min followed by heating at 100° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the solid which was purified by reverse phase column chromatography to get the title compound (0.04 g, 15%). LCMS: 376 [M+1]$^+$; $^1$H NMR (400 MHz, DMSO-$d_6$) δ 8.92-9.02 (m, 1H), 8.33 (d, J=7.02 Hz, 1H), 8.06 (s, 1H), 8.01 (dd, J=2.19, 6.14 Hz, 1H), 7.81 (d, J=1.75 Hz, 1H), 7.85 (d, J=1.75 Hz, 1H), 7.57-7.70 (m, 2H), 7.43 (t, J=8.99 Hz, 1H), 6.94 (s, 2H).

To stirred solution of 3-amino-6-(8-chloroquinolin-6-yl)-5-(4-fluorophenyl)pyrazine-2-carboxylic acid (0.1 g, 0.25 mmol, 1.0 eq) in DMF (10 ml) was added 6-(aminomethyl)picolinonitrile (51 mg, 0.38 mmol, 1.5 eq), DIPEA (0.2 mL, 0.75 mmol, 3 eq) and HATU (190 mg, 0.50 mmol, 2 eq) at RT under inert condition. The resulting mixture stirred for 16h at same temperature. Following this, ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the desired product (10 mg, 7%) LCMS: 510 [M+1]$^+$. $^1$H NMR (400 MHz, DMSO-$d_6$) δ 9.54 (t, 1H), 8.98 (d, 1H), 8.28 (d, 1H), 8.00-8.05 (m, 2H), 7.91-7.96 (m, 2H), 7.71 (d, 1H), 7.61 (dd, 1H), 7.48 (dd, 5.5, 2H), 7.19 (t, 2H), 4.69 ppm (d, 2H).

Example S-15: Synthesis of (R)-3-amino-6-(7-chloro-1H-indazol-5-yl)-5-(4-fluorophenyl)-N-(1-(pyridin-2-yl)ethyl)pyrazine-2-carboxamide (Compound No. 104)

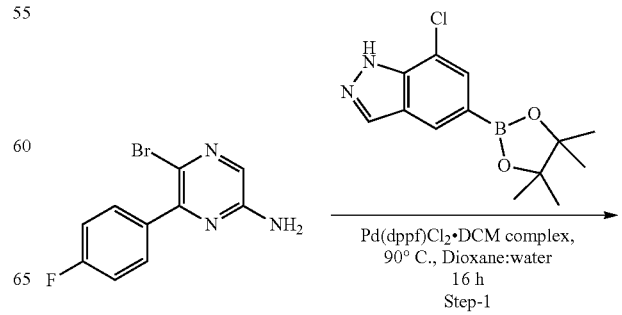

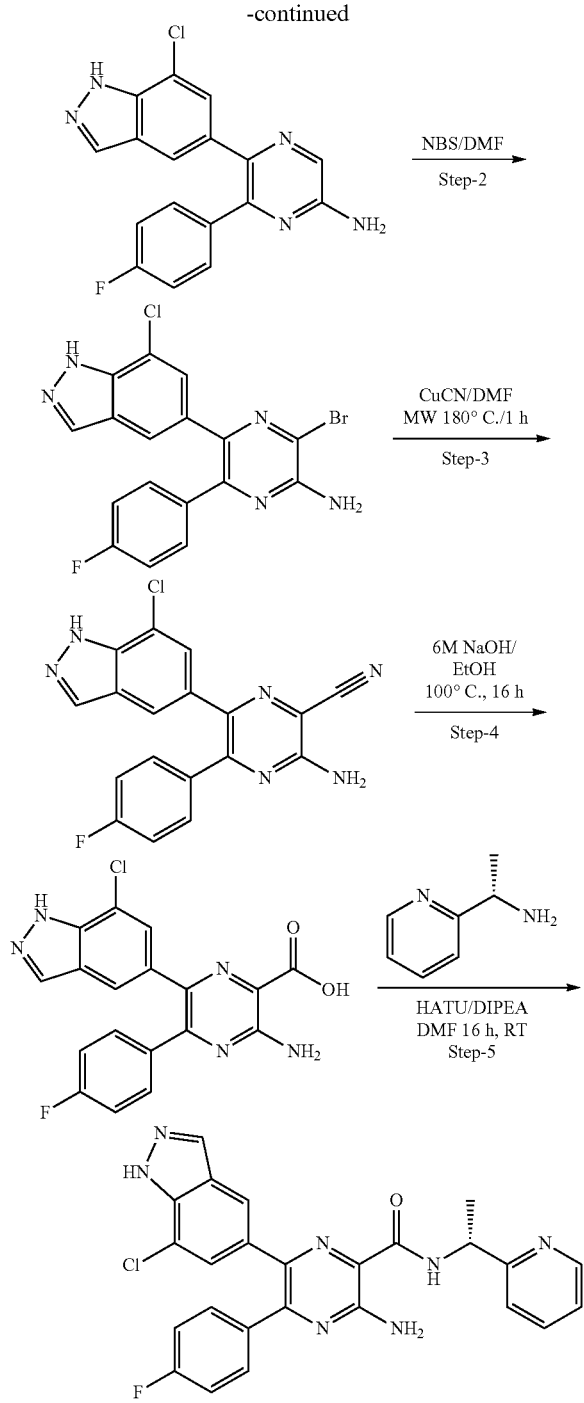

Step-1 Synthesis of 5-(7-chloro-1H-indazol-5-yl)-6-(4-fluorophenyl)pyrazin-2-amine To a stirred solution of 5-bromo-6-(4-fluorophenyl)pyrazin-2-amine (1.3 g, 4.84 mmol, 1.0 eq) in dioxane:water (50 mL:10 mL) was added 7-chloro-5-(4,4,5,5-tetramethyl-1,3,2-dioxaborolan-2-yl)-1H-indazole (1.6 g, 5.80 mmol, 1.2 eq). The reaction mixture was purged with nitrogen for 20 min then charged with K$_2$CO$_3$ (1.3 g 9.63 mmol, 2.0 eq) and Pd(dppf)Cl$_2$.DCM complex (197 mg, 0.02 mmol, 0.05 eq). The reaction mixture was again purged with nitrogen. The reaction mixture was stirred at RT for 10 min followed by heating at 90° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous Na$_2$SO$_4$) and concentrated under vacuum to get the solid which was purified by column chromatography over silica gel (100-200 mesh) [Ethyl acetate:Hexane (5:5) as eluent] to get the title compound (300 mg, 18%). LCMS: 340 [M+1]$^+$.

Step-2 Synthesis of 3-bromo-5-(7-chloro-1H-indazol-5-yl)-6-(4-fluorophenyl)pyrazin-2-amine To a stirred solution of 5-(7-chloro-1H-indazol-5-yl)-6-(4-fluorophenyl)pyrazin-2-amine (533 mg, 1.45 mmol, 1 eq) in DMF (10 ml) was added NBS (259 mg, 1.45 mmol, 1.0 eq) at 0° C. Reaction mixture was stirred at 0° C. for 30 min. The reaction was monitored by TLC and LCMS and found to be complete after 30 min. The reaction mixture was quenched with cold water 10 mL and was extracted with EtOAc (2×20 ml). The resulting solution was concentrated under reduced pressure. The crude product was purified by normal phase silica gel column chromatography to get the title compound (483 mg, 73%) LCMS: 376[M+1]$^+$.

Step-3 Synthesis 3-amino-6-(7-chloro-1H-indazol-5-yl)-5-(4-fluorophenyl)pyrazine-2-carbonitrile To a stirred solution of 3-bromo-5-(7-chloro-1H-indazol-5-yl)-6-(4-fluorophenyl)pyrazin-2-amine (483 mg, 1.15 mmol, 1.0 eq) in DMF (10 mL) was added cuprous cyanide (206 mg, 2.30 mmol, 2.0 eq). The reaction mixture was allowed to stir at 150° C. for 1 h under microwave irradiation. The reaction mixture was allowed to cool to RT, diluted with aqueous ammonia (5 mL) and extracted using ethyl acetate (3×25 mL). The combined organic layers were washed (brine), dried (anhydrous Na$_2$SO$_4$) and concentrated under vacuum to get the solid which was purified by column chromatography to get the title compound (250 mg, 48%). LCMS: 336 [M+1]$^+$.

Step-4 Synthesis of 3-amino-6-(7-chloro-1H-indazol-5-yl)-5-(4-fluorophenyl)pyrazine-2-carboxylic Acid To a stirred solution of -amino-6-(7-chloro-1H-indazol-5-yl)-5-(4-fluorophenyl)pyrazine-2-carbonitrile (250 mg, 0.68 mmol, 1.0 eq) in ethanol (5 mL) was added 6M NaOH solution (5 mL). The resulting reaction mixture was heated at 100° C. for 16h. The reaction mixture was allowed to cool to RT. The solvent was evaporated under vacuum and acidified using 1N HCl to get the solid which was filtered and dried to get the title compound (100 mg, 38%) LCMS: 384(M+1)$^+$.

Step-5: (R)-3-amino-6-(7-chloro-1H-indazol-5-yl)-5-(4-fluorophenyl)-N-(1-(pyridin-2-yl)ethyl)pyrazine-2-carboxamide To stirred solution of 3-amino-6-(7-chloro-1H-indazol-5-yl)-5-(4-fluorophenyl)pyrazine-2-carboxylic acid (100 mg, 0.26 mmol, 1.0 eq) in DMF (10 ml) was added (1R)-1-(pyridin-2-yl)ethanamine (63 mg, 0.39 mmol, 1.5 eq), DIPEA (0.2 mL, 0.75 mmol, 3 eq) and HATU (190 mg, 0.50 mmol, 2 eq) at RT under inert condition. The resulting mixture stirred for 16 h at same temperature. Following this, ice cold water (20 mL) was added and extracted with ethyl acetate (3×20 mL), the combined organic layer washed with brine solution (1×50 mL), dried over Na₂SO₄, filtered and distilled purified by reverse phase column chromatography to get the title compound (10 mg, 8%) LCMS: 488[M+1]⁺; ¹H NMR (400 MHz, DMSO-d₆) δ 13.66 (br s, 1H), 9.20 (d, 1H), 8.57 (d, 1H), 8.18 (s, 1H), 7.78-7.83 (m, 1H), 7.69 (s, 1H), 7.47-7.52 (m, 2H), 7.43 (dd, 2H), 7.31 (dd, 2H), 7.17 (t, 2H), 5.19-5.25 (m, 1H), 1.53 (d, 3H)

Example S-16: Synthesis of 5-(8-chloroquinolin-6-yl)-6-(4-fluorophenyl)-3-(1-(pyridin-2-yl)ethoxy)pyrazin-2-amine (Compound No. 103)

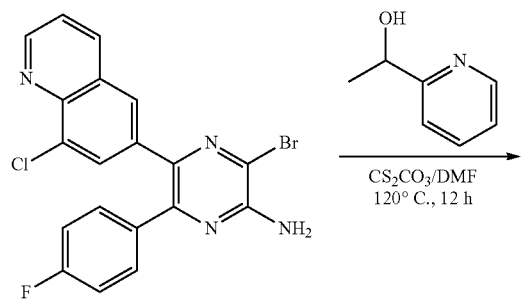

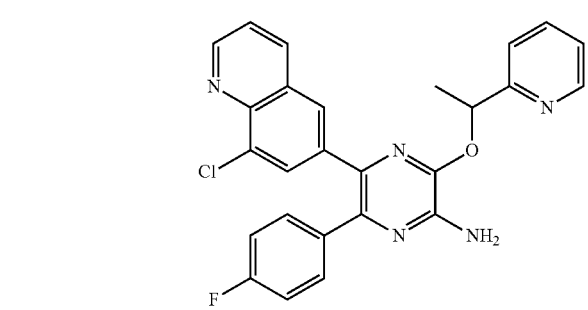

To a stirred solution of 3-bromo-5-(8-chloroquinolin-6-yl)-6-(4-fluorophenyl)pyrazin-2-amine (0.1 g, 0.23 mmol, 1.0 eq) in DMF (5 ml) was added Cs₂CO₃ (224 mg, 0.69 mmol, 3 eq) and it was stirred at RT for 5 min followed by the addition of 1-(pyridin-2-yl)ethanol (72 mg, 0.69 mmol, 2.5 eq) at RT under inert condition. The resulting mixture was stirred for 16 h at 120° C. Following this, ice cold water (20 mL) was added and extracted with ethyl acetate (3×20 mL), the combined organic layer washed with brine solution (1×50 mL), dried over Na₂SO₄, filtered and distilled purified by reverse phase column chromatography to get the title compound (20 mg, 18%). LCMS: 472 [M+1]⁺. ¹H NMR (400 MHz, DMSO-d₆) δ 8.93 (d, 1H), 8.58 (d, 1H), 8.19 (d, 1H), 7.84 (t, 1H), 7.64 (d, 1H), 7.52-7.61 (m, 3H), 7.26-7.37 (m, 3H), 7.11 (t, 2H), 6.83 (br s, 2H), 6.20-6.25 (m, 1H), 1.70 (d, J=6.6 Hz, 3H).

Example S-17: Synthesis of 3-amino-6-(8-chloroquinolin-6-yl)-N-(1-(6-cyanopyridin-2-yl)ethyl)-5-(4-fluorophenyl)pyrazine-2-carboxamide (Compound No. 102)

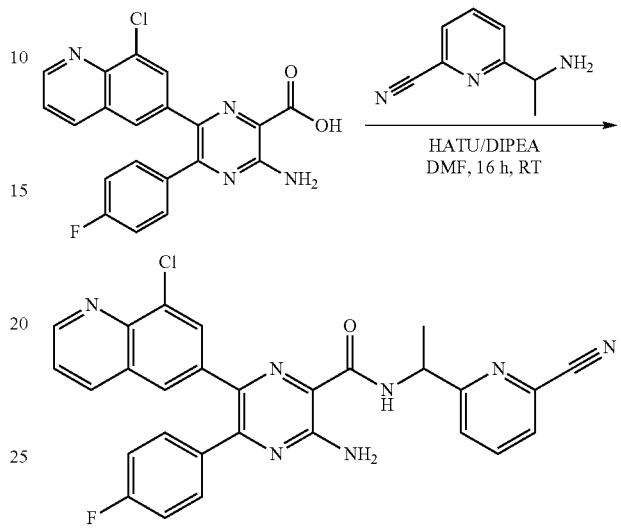

To the stirred solution of 3-amino-6-(8-chloroquinolin-6-yl)-5-(4-fluorophenyl)pyrazine-2-carboxylic acid (0.1 g, 0.25 mmol, 1.0 eq) in DMF (10 ml) was added 6-(1-aminoethyl)pyridine-2-carbonitrile (60 mg, 0.38 mmol, 1.5 eq), DIPEA (0.2 mL, 0.87 mmol, 3 eq) and HATU (190 mg, 0.50 mmol, 2 eq) at RT under inert condition. The resulting mixture stirred for 16 h at same temperature. The reaction was monitored by TLC and LCMS. ice cold water (20 mL) was added and extracted with ethyl acetate (3×20 mL), the combined organic layer washed with brine solution (1×50 mL), dried over Na₂SO₄, filtered and distilled purified by reverse phase column chromatography to get the title compound (20 mg, 15%) LCMS:524 [M+1]⁺; ¹H NMR (400 MHz, DMSO-d₆) δ 9.16 (d, 1H), 8.99 (dd, 1H), 8.34 (dd, 1H), 8.04-8.09 (m, 1H), 7.93-8.00 (m, 3H), 7.85 (d, 1H), 7.62 (dd, 1H), 7.46 (dd, 2H), 7.18 (t, 2H), 5.26-5.33 (m, 1H), 1.59 (d, 3H).

Example S-18: Synthesis of 3-amino-6-(8-chloroquinolin-6-yl)-5-(4-fluorophenyl)-N-(2-(tetrahydro-2H-pyran-4-yl)ethyl)pyrazine-2-carboxamide (Compound No. 101)

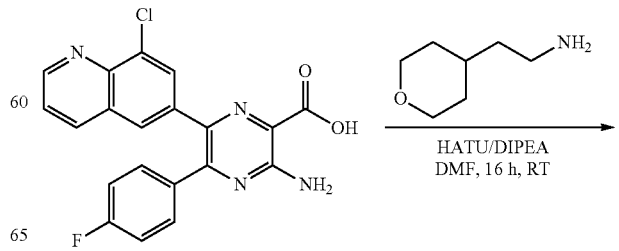

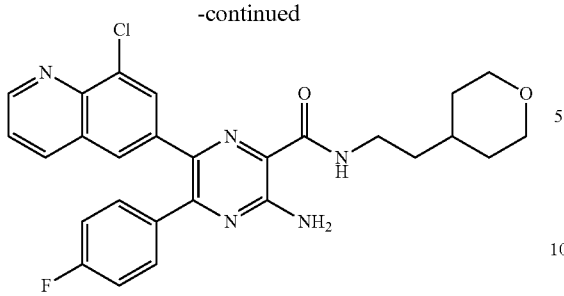

To the stirred solution of 3-amino-6-(8-chloroquinolin-6-yl)-5-(4-fluorophenyl)pyrazine-2-carboxylic acid (0.1 g, 0.25 mmol, 1.0 eq) in DMF (10 ml) was added 2-(tetrahydro-2H-pyran-4-yl)ethanamine (49 mg, 0.38 mmol, 1.5 eq), DIPEA (0.2 mL, 0.87 mmol, 3 eq) and HATU (220 mg, 0.58 mmol, 2 eq) at RT under inert condition. The resulting mixture stirred for 16h at same temperature. The reaction was monitored by TLC and LCMS.

Ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the title compound (80 mg, 62%), LCMS:506 [M+1]$^+$. $^1$H NMR (400 MHz, DMSO-d6) δ 8.99 (dd, 1H), 8.81 (t, 1H), 8.25-8.32 (m, 1H), 7.99 (d, 1H), 7.91 (d, 1H), 7.62 (dd, 1H), 7.46 (dd, 2H), 7.18 (t, 2H), 3.83 (d, 2H), 3.35-3.40 (m, 2H), 3.27 (t, 3H), 1.64 (d, 2H), 1.47-1.55 (m, 3H), 1.11-1.25 (m, 3H).

Example S-19: Synthesis of (R)-3-amino-6-(8-chloroquinolin-6-yl)-5-(1-methyl-1H-pyrazol-3-yl)-N-(1-(pyridin-2-yl)ethyl)pyrazine-2-carboxamide (Compound No. 100)

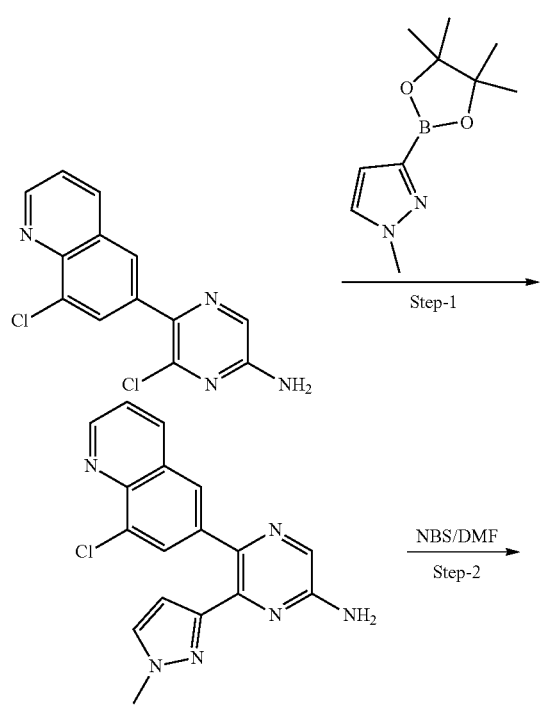

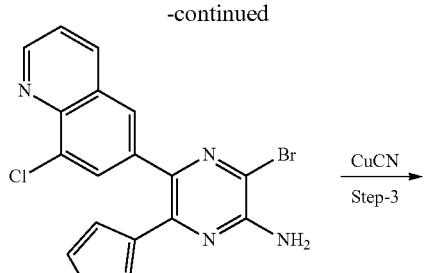

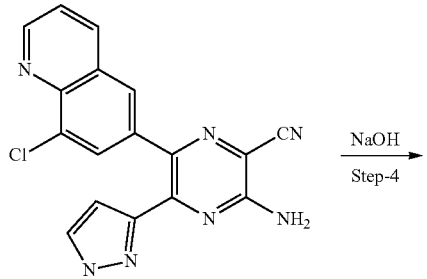

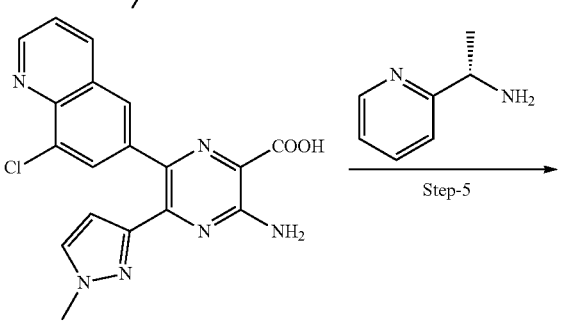

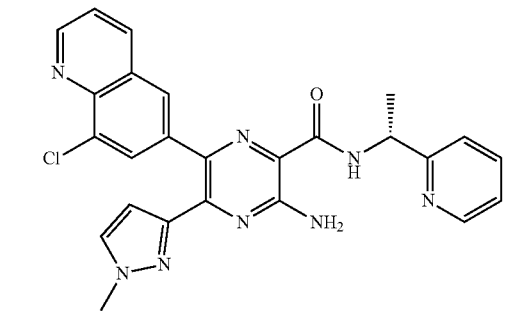

Step-1 Synthesis of 5-(8-chloroquinolin-6-yl)-6-(1-methyl-1H-pyrazol-3-yl)pyrazin-2-amine To a stirred solution of 6-chloro-5-(quinolin-6-yl)pyrazin-2-amine (1.0 g, 3.44 mmol, 1.0 eq) in dioxane:water (16 mL: 4 mL) was added 1-methyl-3-(4,4,5,5-tetramethyl-1,3,2-dioxaborolan-2-yl)-1H-pyrazole (0.860 g, 4.12 mmol, 1.2 eq). The reaction mixture was purged with nitrogen for 5 min then charged with $Na_2CO_3$ (0.73 g, 6.88 mmol, 2.0 eq) and Pd(dppf)Cl$_2$.DCM complex (0.080 g, 10 mol %). The reaction mixture was again purged with nitrogen. The reaction mixture was allowed to heat at 100° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum, to get the crude which was purified by normal phase silica-gel column chromatography to get the title compound (0.400 g, 34%). LCMS: 337[M+1]⁺.

Step-2 Synthesis of 3-bromo-5-(8-chloroquinolin-6-yl)-6-(1-methyl-1H-pyrazol-3-yl)pyrazin-2-amine To a stirred solution 5-(8-chloroquinolin-6-yl)-6-(1-methyl-1H-pyrazol-3-yl)pyrazin-2-amine (0.400 g, 1.18 mmol, 1 eq) in DMF (5 ml) was added NBS (210 mg, 1.18 mmol, 1.0 eq) at 0° C. Reaction mixture was stirred at 0° C. for 10 min. The reaction was monitored by TLC and LCMS and found to be complete after 10 min. The reaction mixture was quenched with cold water 10 mL and was extracted with EtOAc (3×20 mL). The resulting solution was concentrated under reduced pressure. The crude product was purified by normal phase column chromatography to get the title compound (0.300 g, 61%). LCMS: 415 [M+1]⁺.

Step-3 Synthesis of 3-amino-6-(8-chloroquinolin-6-yl)-5-(1-methyl-1H-pyrazol-3-yl)pyrazine-2-carbonitrile To a stirred solution of 3-bromo-5-(8-chloroquinolin-6-yl)-6-(1-methyl-1H-pyrazol-3-yl)pyrazin-2-amine (500 mg, 1.20 mmol, 1.0 eq) in DMF (10 mL) was added cuprous cyanide (120 mg, 1.35 mmol, 1.1 eq). The reaction mixture was allowed to stir at 120° C. for 45 min under microwave irradiation. The reaction mixture was allowed to cool to RT, diluted with aqueous ammonia (5 mL) and extracted using ethyl acetate (3×25 mL). The combined organic layers were washed (brine), dried (anhydrous Na₂SO₄) and concentrated under vacuum to get the solid which was purified by column chromatography to get the title compound (170 mg, 46%). LCMS: 362[M+1]⁺.

Step-4 Synthesis of 3-amino-6-(8-chloroquinolin-6-yl)-5-(1-methyl-1H-pyrazol-3-yl)pyrazine-2-carboxylic Acid To a stirred solution of 3-bromo-5-(8-chloroquinolin-6-yl)-6-(1-methyl-1H-pyrazol-3-yl)pyrazin-2-amine (170 mg, 0.48 mmol, 1.0 eq) in ethanol (5 mL) was added 6M NaOH solution (5 mL). The resulting reaction mixture was heated at 100° C. for 16 h.

The reaction mixture was allowed to cool to RT. The solvent was evaporated under vacuum and acidified using 1N HCl to get the solid which was filtered and dried to get the product as yellow solid (110 mg, 60%) LCMS: 381 [M+1]⁺.

Step-3 Synthesis of (R)-3-amino-6-(8-chloroquinolin-6-yl)-5-(1-methyl-1H-pyrazol-3-yl)-N-(1-(pyridin-2-yl)ethyl)pyrazine-2-carboxamide To a stirred solution of 3-amino-6-(8-chloroquinolin-6-yl)-5-(1-methyl-1H-pyrazol-3-yl)pyrazine-2-carboxylic acid (50 mg, 0.13 mmol, 1 eq) in DMF (4 mL) was added (1R)-1-(pyridin-2-yl)ethanamine (23 mg, 0.19 mmol, 1.2 eq), DIPEA (0.1 mL, 0.39 mmol, 3 eq) and HATU (95 mg, 0.26 mmol, 2 eq) at RT under inert condition. The resulting mixture stirred for 16 h at same temperature. The reaction was monitored by TLC and LCMS. Ice cold water (20 mL) was added and extracted with ethyl acetate (3×20 mL), the combined organic layer washed with brine solution (1×50 mL), dried over Na₂SO₄, filtered and distilled purified by reverse phase column chromatography to get the desired product (0.005 g, 8%). LCMS: 485 [M+1]⁺; ¹H NMR (400 MHz, D₂O) δ 9.17 (d, J=7.45 Hz, 1H), 9.02 (dd, J=1.32, 3.95 Hz, 1H), 8.60 (d, J=4.82 Hz, 1H), 8.38-8.49 (m, 1H), 8.07 (d, J=1.75 Hz, 1H), 8.00 (d, J=1.32 Hz, 1H), 7.93 (br s, 1H), 7.63-7.72 (m, 2H), 7.60 (d, J=7.89 Hz, 1H), 7.42 (br s, 1H), 6.35 (d, J=2.19 Hz, 1H), 5.17-5.32 (m, 1H), 3.64-3.76 (m, 3H), 1.56 (d, J=7.02 Hz, 3H).

Example S-20: Synthesis of 3-(6-amino-3-(7-chloro-1H-indazol-5-yl)pyrazin-2-yl)benzonitrile (Compound No. 2-7)

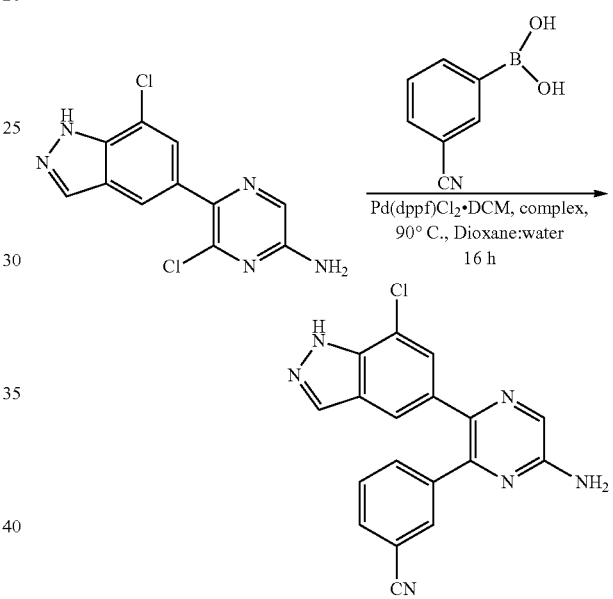

To a stirred solution of 6-chloro-5-(7-chloro-1H-indazol-5-yl)pyrazin-2-amine (160 mg, 0.57 mmol, 1 eq) in dioxane:water (10 mL: 5 mL) was added 3-cyanobenzeneboronic acid (197 mg, 0.86 mmol, 1.5 eq). The reaction mixture was purged with nitrogen for 20 min then charged K₂CO₃ (157 mg 1.14 mmol, 2.0 eq) and Pd(dppf)Cl₂.DCM complex (23 mg, 0.02 mmol, 0.05 eq). The reaction mixture was again purged with nitrogen. The reaction mixture was stirred at RT for 10 min followed by heating at 90° C. for 16 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous Na₂SO₄) and concentrated under vacuum to get the crude which was purified by reverse phase column chromatography to get the title compound (50 mg, 25%). LCMS: 347[M+1]⁺; ¹H NMR (DMSO-d6 400 MHz): δ 13.60 (br s, 1H), 8.10 (s, 1H), 8.01 (s, 1H), 7.84 (s, 1H), 7.78 (d, 1H), 7.52-7.56 (m, 2H), 7.41-7.47 (m, 2H), 7.35 (s, 1H), 6.75 (s, 2H).

Example S-21: Synthesis of 3-amino-6-(8-chloro-quinolin-6-yl)-N-(1-(6-cyanopyridin-2-yl)ethyl)-5-(1-methyl-1H-pyrazol-3-yl)pyrazine-2-carboxamide (Compound No. 99)

Example S-22: Synthesis of (R)-5-(3-cyanophenyl)-N-(1-(pyridin-2-yl)ethyl)-6-(quinolin-6-yl)pyrazine-2-carboxamide (Compound No. 109)

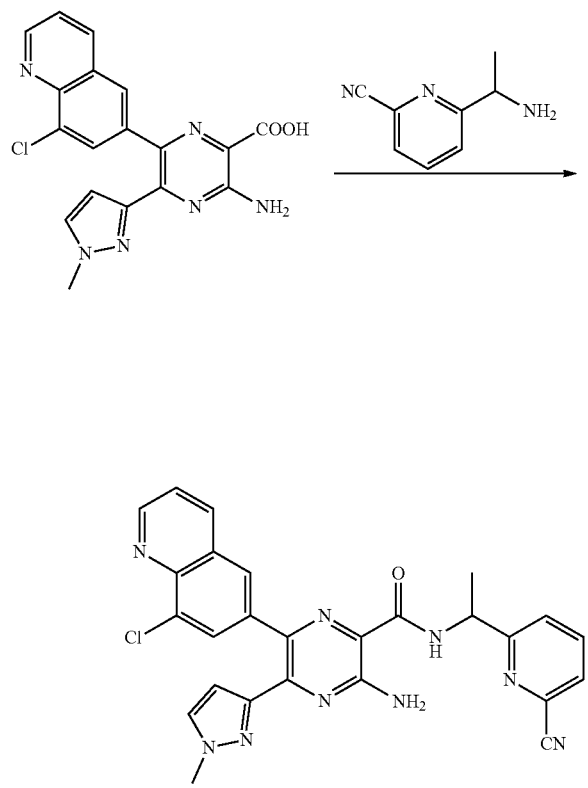

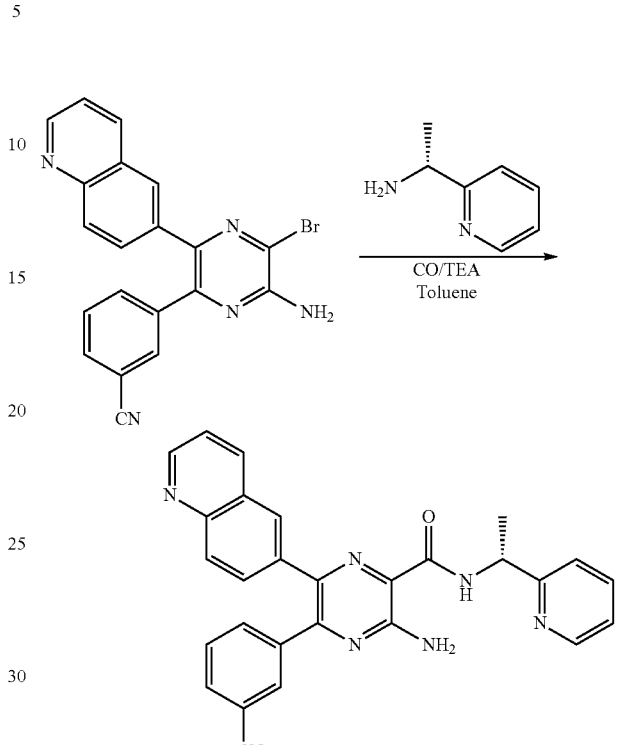

To a stirred solution of 3-amino-6-(8-chloroquinolin-6-yl)-5-(1-methyl-1H-pyrazol-3-yl)pyrazine-2-carboxylic acid (50 mg, 0.13 mmol, 1 eq) in DMF (4 mL) was added 6-(1-aminoethyl)picolinonitrile (27 mg, 0.19 mmol, 1.2 eq), DIPEA (0.1 mL, 0.39 mmol, 3 eq) and HATU (95 mg, 0.26 mmol, 2 eq) at RT under inert condition. The resulting mixture stirred for 16 h at same temperature. The reaction was monitored by TLC and LCMS. Ice cold water (20 mL) was added and extracted with ethyl acetate (3×20 mL), the combined organic layer was washed with brine solution (1×50 mL), dried over $Na_2SO_4$, filtered and distilled under vacuum to get the crude which was purified by reverse phase column chromatography to get the title compound (0.003 g, 5%). LCMS: 510 [M+1]$^+$; $^1$H NMR (400 MHz, METHANOL-$d_4$) δ 8.91-8.97 (m, 1H), 8.48 (d, J=8.33 Hz, 1H), 8.13 (s, 1H), 7.98 (t, J=7.89 Hz, 1H), 7.90 (d, J=1.75 Hz, 1H), 7.77 (t, J=7.67 Hz, 2H), 7.63 (dd, J=4.39, 8.33 Hz, 1H), 7.56 (d, J=2.19 Hz, 1H), 6.31 (d, J=2.19 Hz, 1H), 5.34 (dd, J=6.80, 13.81 Hz, 1H), 3.82 (s, 3H), 1.62 (d, J=7.02 Hz, 3H)

To a solution of 3-(6-amino-5-bromo-3-(quinolin-6-yl)pyrazin-2-yl)benzonitrile (200 mg 0.49 mmol, 1 eq) in toluene (10 mL) was added (R)-1-(pyridin-2-yl)ethanamine (72 mg, 0.59 mmol, 1.2 eq), TEA (0.210 mL, 1.49 mol, 3.0 eq) in autoclave. The reaction mixture was deoxygenated using $N_2$ atmosphere for 10 min, then charged Palladium Acetate (6 mg, 0.025 mmol, 0.05 eq) and Xanthphos (28 mg, 0.049 mmol, 0.1 eq). The reaction mixture was heated at 90° C. for 16 h under carbon monoxide. The reaction was monitored by TLC and LCMS. The reaction mixture was filter through celite. The reaction mixture was diluted with water (50 mL) and extracted using ethyl acetate (3×50 mL). The separated organic layer was dried over sodium sulphate and concentrated under reduced pressure. The crude product was purified by normal phase silica-gel column chromatography followed by HPLC purification to get the title compound (4 mg, 2%). LCMS: 481 [M+1]$^+$; $^1$H NMR (400 MHz, DMSO-$d_6$) δ 10.06 (br s, 1H) 9.21 (d, J=7.89 Hz, 1H) 8.99 (br s, 1H) 8.61 (d, J=4.82 Hz, 1H) 8.45 (d, J=8.33 Hz, 1H) 8.09 (d, J=1.75 Hz, 1H) 8.01 (d, J=8.77 Hz, 1H) 7.91-7.94 (m, 1H) 7.81-7.87 (m, 2H) 7.57-7.69 (m, 3H) 7.37-7.51 (m, 2H) 5.26-5.36 (m, 1H) 1.58 (d, J=7.02 Hz, 3H).

Example S-23: Synthesis of (R)-3-amino-5-(1-methyl-1H-pyrazol-3-yl)-N-(1-(pyridin-2-yl)ethyl)-6-(quinolin-6-yl)pyrazine-2-carboxamide (Compound No. 110)

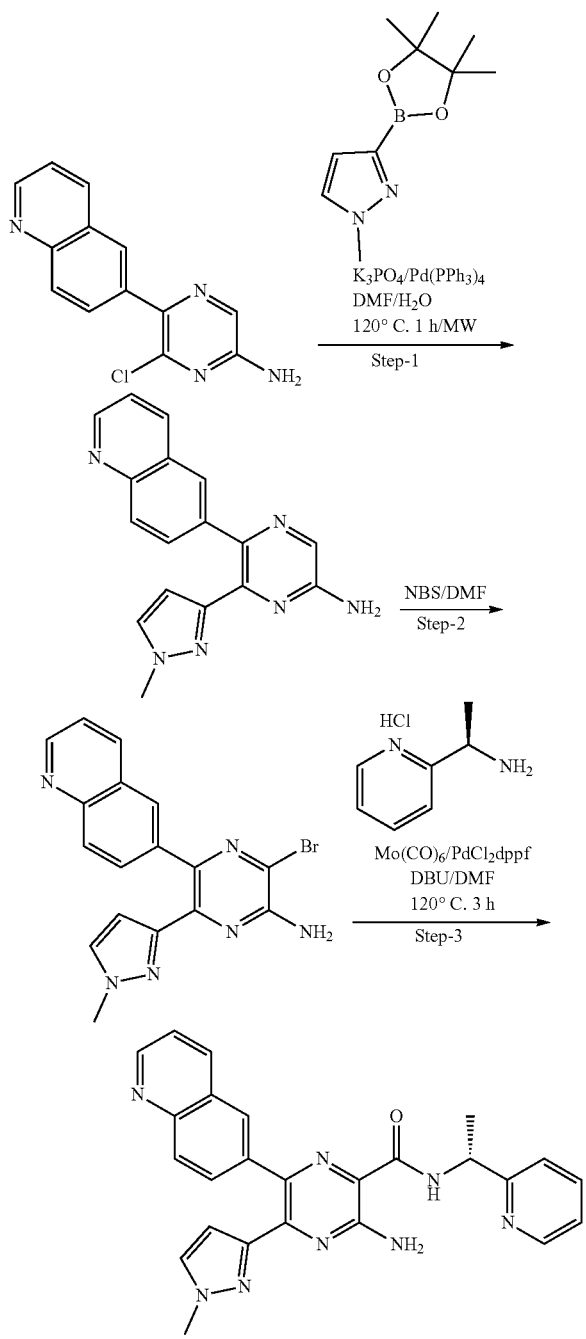

Step-1: Synthesis of 6-(1-methyl-1H-pyrazol-3-yl)-5-(quinolin-6-yl)pyrazin-2-amine To a stirred solution of 6-chloro-5-(quinolin-6-yl)pyrazin-2-amine (500 mg, 1.95 mmol, 1 eq) in DMF:water (10 mL:5 mL) was added 1-methyl-3-(4,4,5,5-tetramethyl-1,3,2-dioxaborolan-2-yl)-1H-pyrazole (487 mg, 2.34 mmol, 1.2 eq). The reaction mixture was purged with nitrogen for 5 min then charged with $K_3PO_4$ (1.2 g, 5.85 mmol, 3.0 eq) and Pd(PPh$_3$)$_4$(90 mg, 0.07 mmol, 0.04 eq). The reaction mixture was again purged with nitrogen. The reaction mixture was stirred at RT for 10 min followed by heating at 120° C. for 1 h using microwave irradiation. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the crude which was purified by column chromatography to get the title compound (226 mg, 34%). LCMS: 303 [M+1]$^+$.

Step-2: Synthesis of 3-bromo-6-(1-methyl-1H-pyrazol-3-yl)-5-(quinolin-6-yl)pyrazin-2-amine To a stirred solution 6-(1-methyl-1H-pyrazol-3-yl)-5-(quinolin-6-yl)pyrazin-2-amine (226 mg, 0.74 mmol, 1 eq) in DMF (10 ml) was added NBS (133 mg, 0.61 mmol, 1.0 eq) at 0° C. Reaction mixture was stirred at 0° C. for 10 min. The reaction was monitored by TLC and LCMS and found to be complete after 10 min. The reaction mixture was quenched with cold water 10 mL and was extracted with EtOAc (3×20 mL). The resulting solution was concentrated under reduced pressure. The crude product was purified by normal phase silica gel column chromatography to get the title compound. (189 mg, 66%). LCMS: 381[M+1]$^+$.

Step-3 Synthesis of (R)-3-amino-5-(1-methyl-1H-pyrazol-3-yl)-N-(1-(pyridin-2-yl)ethyl)-6-(quinolin-6-yl)pyrazine-2-carboxamide To a stirred solution of 3-bromo-6-(1-methyl-1H-pyrazol-3-yl)-5-(quinolin-6-yl)pyrazin-2-amine (189 mg, 0.49 mmol, 1 eq) in DMF (10 mL) was added (R)-1-(pyridin-2-yl)ethanamine (121 mg, 0.99 mmol, 1.2 eq). The reaction mixture was purged with nitrogen for 5 min then charged with Mo(CO)$_6$ (48 mg, 0.18 mmol, 0.37 eq) and PdCl$_2$dppf (18 mg, 0.02 mmol, 0.05 eq). The reaction mixture was again purged with nitrogen for 5 min and then stirred at RT for 1 h followed by the addition of DBU (0.2 mL, 1.07 mmol, 2.2 eq). The reaction mixture was stirred at RT for 5 min and then heated at 120° C. for 3h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the crude which was purified by reverse phase column chromatography to get the title compound (30 mg, 9.0%). LCMS: 451[M+1]$^+$; $^1$H NMR (DMSO-d6, 400 MHz) δ 9.08 (d, 1H), 8.90 (d, 1H), 8.53 (d, 1H), 8.35 (d, 1H), 8.07-8.13 (m, 1H), 7.95 (d, 1H), 7.70-7.83 (m, 3H), 7.64 (d, 2H), 7.54 (dd, 1H), 7.47 (d, 1H), 7.29 (dd, 1H), 6.19 (d, 1H), 5.22 (d, 1H), 3.71 (s, 3H) 1.52 (d, 3H).

Example S-24: Synthesis of 3-amino-N-(1-(6-cyanopyridin-2-yl)ethyl)-5-phenyl-6-(quinolin-6-yl)pyrazine-2-carboxamide (Compound No. 111), (R)-3-amino-N-(1-(6-cyanopyridin-2-yl)ethyl)-5-phenyl-6-(quinolin-6-yl)pyrazine-2-carboxamide (Compound No. 115) and (S)-3-amino-N-(1-(6-cyanopyridin-2-yl)ethyl)-5-phenyl-6-(quinolin-6-yl)pyrazine-2-carboxamide (Compound No. 116)

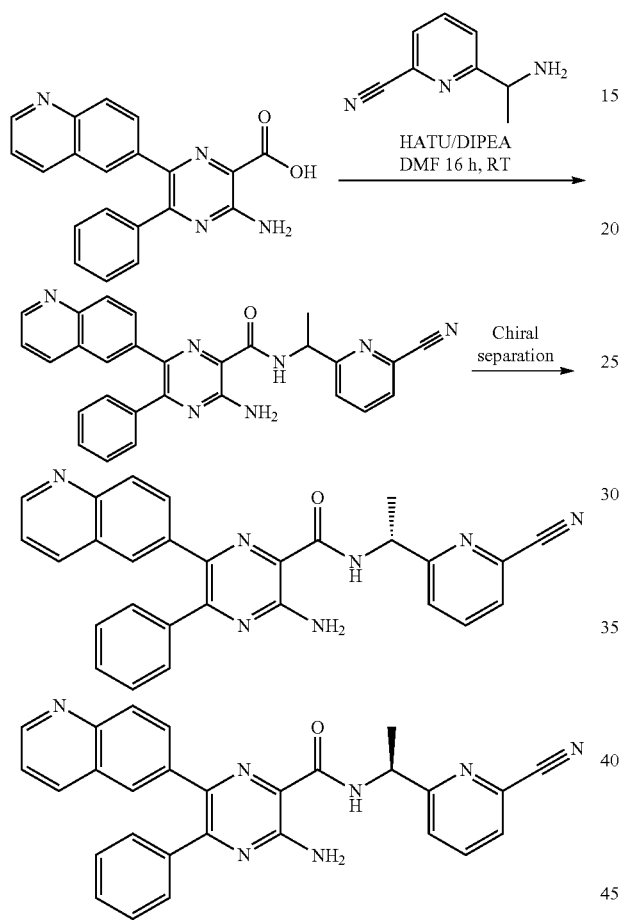

To the stirred solution 3-amino-5-phenyl-6-(quinolin-6-yl)pyrazine-2-carboxylic acid (0.1 g, 0.29 mmol, 1.0 eq) in DMF (10 ml) was added 6-(1-aminoethyl)pyridine-2-carbonitrile (86 mg, 0.58 mmol, 2.0 eq), DIPEA (0.2 mL, 0.87 mmol, 3 eq) and HATU (220 mg, 0.58 mmol, 2 eq) at RT under inert condition. The resulting mixture stirred for 16 h at same temperature. The reaction was monitored by TLC and LCMS. Ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the title compound (4 mg, 3.0%). The title compound was purified by chiral HPLC to get the two enantiomers (R)-3-amino-N-(1-(6-cyanopyridin-2-yl)ethyl)-5-phenyl-6-(quinolin-6-yl)pyrazine-2-carboxamide and (S)-3-amino-N-(1-(6-cyanopyridin-2-yl)ethyl)-5-phenyl-6-(quinolin-6-yl)pyrazine-2-carboxamide. LCMS:472 [M+1]$^+$; $^1$H NMR (DMSO-d6, 400 MHz) δ 9.20 (d, 1H), 8.87 (s., 1H), 8.23 (d, 1H), 8.04-8.12 (m, 1H), 7.94-8.00 (m, 1H), 7.87 (d, 2H), 7.91 (d, 2H), 7.77 (d, 1H), 7.50 (dd, 2H), 7.41 (d, 1H), 7.32 (d, 1H), 7.36 (d, 1H), 5.26-5.32 (m, 1H), 1.57 (d, 3H).

Example S-25: Synthesis of (R)-3-amino-6-(7-chloro-1H-indazol-5-yl)-5-(1-methyl-1H-pyrazol-3-yl)-N-(1-(pyridin-2-yl)ethyl)pyrazine-2-carboxamide (Compound No. 112)

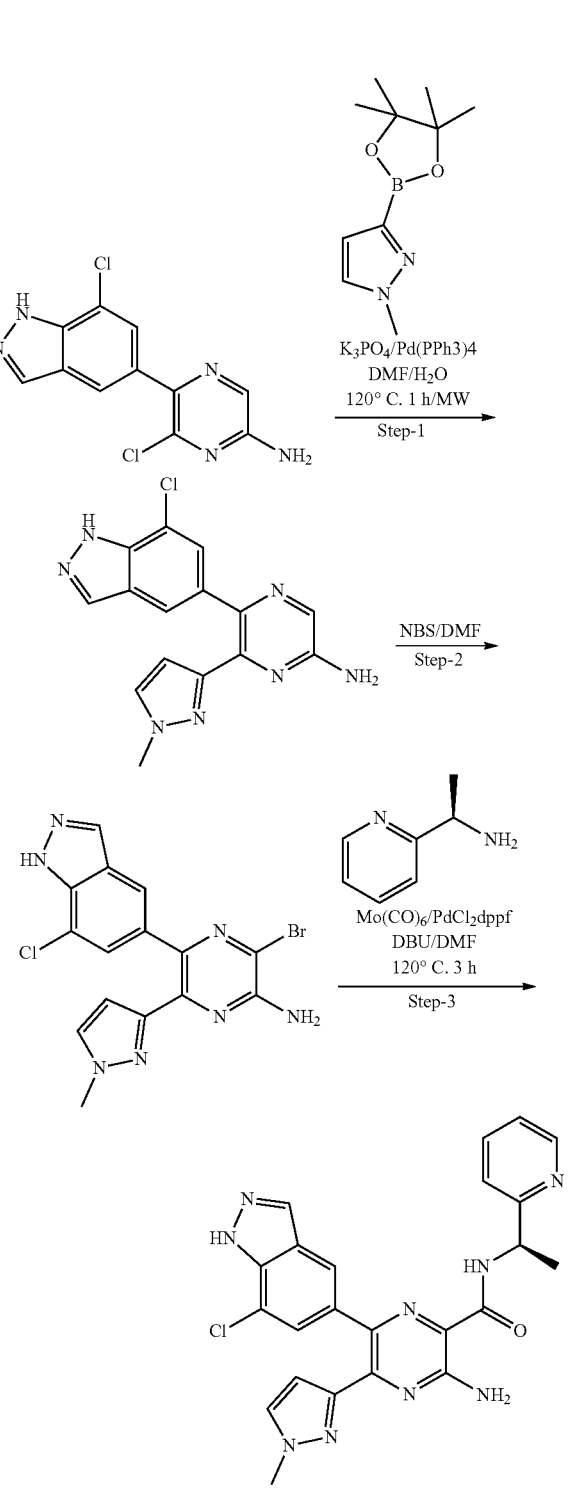

Step-1: Synthesis of 5-(7-chloro-1H-indazol-5-yl)-6-(4-fluorophenyl)pyrazin-2-amine To a stirred solution of 6-chloro-5-(7-chloro-1H-indazol-5-yl)pyrazin-2-amine (500 mg, 1.79 mmol, 1 eq) in DMF: water (10 mL: 5 mL) was added 1-methyl-3-(4,4,5,5-tetramethyl-1,3,2-dioxaborolan-2-yl)-1H-pyrazole (447 mg, 2.15 mmol, 1.2 eq). The reaction mixture was purged with nitrogen for 5 min then charged with $K_3PO_4$ (1.2 g, 5.37 mmol, 3.0 eq) and $Pd(PPh_3)_4$ (82 mg, 0.07 mmol, 0.04 eq). The reaction mixture was again purged with nitrogen. The reaction mixture was stirred at RT for 10 min followed by heating at 120° C. for 1 h using microwave irradiation. The reaction was monitored by TLC and LCMS. The reaction mixture was filtered through celite and concentrated under vacuum. The reaction was diluted with water and extracted with ethyl acetate (3×200 mL). The combined organic layers were washed (brine), dried (anhydrous $Na_2SO_4$) and concentrated under vacuum to get the crude which was purified by column chromatography to get the title compound (200 mg, 34%). LCMS: 326 [M+1]$^+$.

Step-2: Synthesis of 3-bromo-5-(7-chloro-1H-indazol-5-yl)-6-(1-methyl-1H-pyrazol-3-yl)pyrazin-2-amine To a stirred solution of 5-(7-chloro-1H-indazol-5-yl)-6-(4-fluorophenyl)pyrazin-2-amine (200 mg, 0.61 mmol, 1 eq) in DMF (10 ml) was added NBS (109 mg, 0.61 mmol, 1.0 eq) at 0° C. Reaction mixture was stirred at 0° C. for 10 min. The reaction was monitored by TLC and LCMS and found to be complete after 10 min. The reaction mixture was quenched with cold water (10 mL) and was extracted with EtOAc (3×20 mL). The resulting solution was concentrated under reduced pressure. The crude product was purified by normal phase silica-gel column chromatography to get the title compound. (138 mg, 55%). LCMS: 404 [M+1]$^+$.

Step-3: Synthesis of (R)-3-amino-6-(7-chloro-1H-indazol-5-yl)-5-(1-methyl-1H-pyrazol-3-yl)-N-(1-(pyridin-2-yl)ethyl)pyrazine-2-carboxamide To a stirred solution of 3-bromo-5-(7-chloro-1H-indazol-5-yl)-6-(1-methyl-1H-pyrazol-3-yl)pyrazin-2-amine (138 mg, 0.34 mmol, 1 eq) in DMF (10 mL) was added (1R)-1-(pyridin-2-yl)ethanamine (83 mg, 2.15 mmol, 1.2 eq). The reaction mixture was purged with nitrogen for 5 min then charged with $Mo(CO)_6$ (33 mg, 0.12 mmol, 0.37 eq) and $PdCl_2$dppf (12 mg, 0.01 mmol, 0.05 eq). The reaction mixture was again purged with nitrogen for 5 min and then stirred at RT for 1 h followed by the addition of DBU (0.1 mL, 0.74 mmol, 2.2 eq). The reaction mixture was stirred at RT for 5 min and then heated at 120° C. for 3h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the crude which was purified by reverse phase column chromatography to get the title compound (20 mg, 12%). LCMS: 474 [M+1]$^+$; $^1$H NMR (DMSO-d6, 400 MHz): δ13.63 (br s, 1H), 9.10 (d, 1H), 8.55 (d, 1H), 8.21 (s, 1H), 7.75-7.83 (m, 2H), 7.64 (d, 2H), 7.46-7.54 (m, 2H), 7.24-7.35 (m, 1H), 6.14 (d, 1H), 5.16-5.24 (m, 1H), 3.74 (s, 3H), 1.51 (d, 3H).

Example S-26: Synthesis of (R)-3-amino-6-(8-chloroquinolin-6-yl)-5-phenyl-N-(1-(pyridin-2-yl)ethyl)pyrazine-2-carboxamide (Compound No. 113)

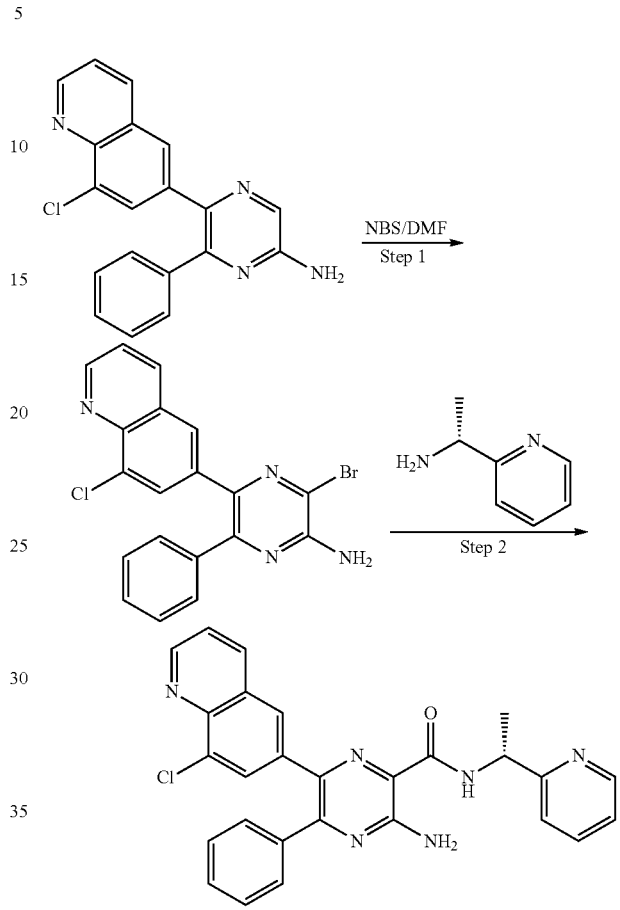

Step-1: Synthesis of 3-bromo-5-(8-chloroquinolin-6-yl)-6-phenylpyrazin-2-amine

To a solution of 5-(8-chloroquinolin-6-yl)-6-phenylpyrazin-2-amine (1.6 g, 4.81 mmol, 1 eq) in DMF (20 mL) was added N-bromosuccinimide (0.85 g, 4.81 mmol, 1 eq) at 0° C. The reaction mixture was stirred at same temperature for 2 h. The reaction was monitored by TLC. The reaction was added with water and the solid precipitates out. The solid was filtered and dried to use for next step without further purification (1.1 g, 55%). LCMS: 412[M+1]±

Step-2: Synthesis of (R)-3-amino-6-(8-chloroquinolin-6-yl)-N-(1-(6-cyanopyridin-2-yl)ethyl)-5-phenylpyrazine-2-carboxamide To a solution of 3-bromo-5-(8-chloroquinolin-6-yl)-6-phenylpyrazin-2-amine (200 mg, 0.48 mmol, 1 eq) in DMF (10 mL) was added (R)-6-(1-aminoethyl)picolinonitrile hydrochloride (92 mg, 0.58 mmol, 1.2 eq) The reaction mixture was deoxygenated using N2 atmosphere then charged $MO(CO)_6$ (51.3 mg, 0.19 mmol, 0.4 eq) and $PdCl_2$(dppf).DCM complex (20 mg, 0.024 mmol, 0.05 eq), deoxygenating was continued for further 20 min, and DBU (0.165 mL, 1.07 mmol, 2.2 eq) was charged and the reaction mixture was heated at 12.0° C. for 4 h. The reaction was monitored by TLC and LCMS. The reaction mixture was diluted with water (50 mL) and extracted using ethyl acetate (3×100 mL). The separated organic layer was dried over sodium sulfate and concentrated under reduced pressure. The crude product was purified by normal phase silica-gel column chromatography followed by HPLC purification to afford (40 mg, 17%) the title compound. LCMS: 481 [M+1]$^+$; $^1$H NMR (400 MHz, DMSO-$d_6$) δ 9.28 (d, J=7.9 Hz, 1H), 8.99 (d, J=3.9 Hz, 1H), 8.58 (d, J=3.5 Hz, 1H), 8.28 (d, J=7.0 Hz, 1H), 7.98 (d, J=1.8 Hz, 1H), 7.90 (d, J=1.8 Hz, 1H), 7.81 (dd, J=5.7, 7.5 Hz, 2H), 7.62 (dd, J=4.4, 8.3 Hz, 1H), 7.51 (d, J=7.9 Hz, 1H), 7.46-7.31 (m, 7H), 5.26-5.21 (m, 1H), 1.55 (d, J=6.6 Hz, 3H).

Example S-27: Synthesis of 3-amino-6-(8-chloro-quinolin-6-yl)-N-(1-(6-cyanopyridin-2-yl)ethyl)-5-phenylpyrazine-2-carboxamide (Compound No. 114), (R)-3-amino-6-(8-chloroquinolin-6-yl)-N-(1-(6-cyanopyridin-2-yl)ethyl)-5-phenylpyrazine-2-carboxamide (Compound No. 121) and (S)-3-amino-6-(8-chloroquinolin-6-yl)-N-(1-(6-cyanopyridin-2-yl)ethyl)-5-phenylpyrazine-2-carboxamide (Compound No. 122)

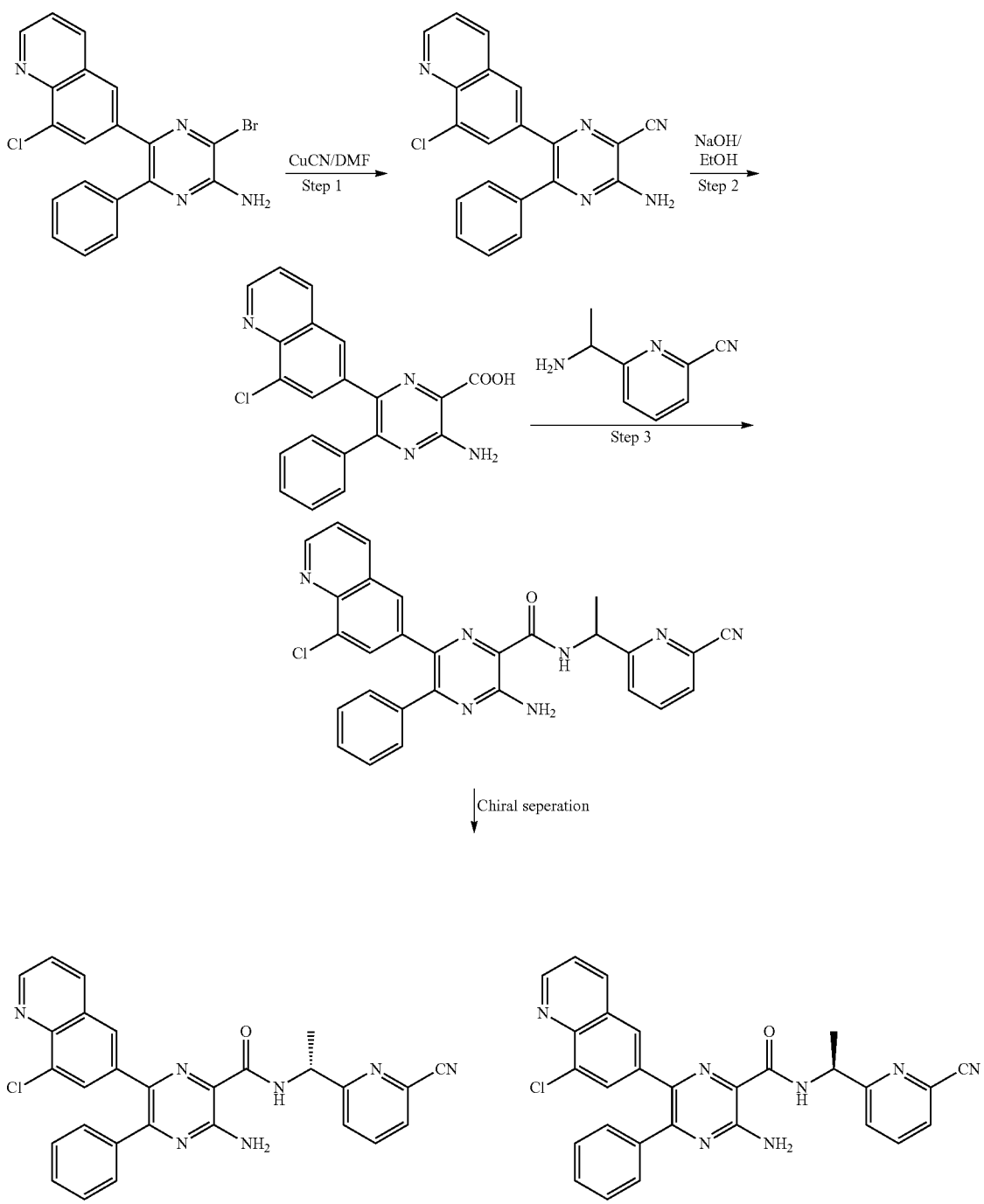

Step-1: Synthesis of 3-amino-6-(8-chloroquinolin-6-yl)-5-phenylpyrazine-2-carbonitrile To a stirred solution of CuI (554 mg, 2.92 mmol, 1.5 eq) and CuCN (384 mg, 4.28 mol, 2.2 eq) in dry DMF (150 mL) was added 3-bromo-5-(8-chloroquinolin-6-yl)-6-phenylpyrazin-2-amine (800 mg, 1.94 mmol, 1 eq) at 100° C. The reaction mixture was stirred at 120° C. for 12 h. The reaction was monitored by TLC and LCMS. The crude product was poured in ice-water the solid precipitate out. The reaction mixture PH was adjusted with aqueous ammonia until pH=9 then extracted with ethyl acetate (3×50 mL). The combined organic layers were washed (brine), dried (anhydrous $Na_2SO_4$) and concentrated under vacuum to get the solid which was purified by column chromatography using basic Alumina [Ethyl acetate:Hexane (5:5)] to get the title compound (400 mg, 57%). LCMS: 358 [M+1]$^+$

Step-2: Synthesis 3-amino-6-(8-chloroquinolin-6-yl)-5-phenylpyrazine-2-carboxylic Acid To a solution of 3-amino-6-(8-chloroquinolin-6-yl)-5-phenylpyrazine-2-carbonitrile (700 mg, 1.96 mmol, 1.0 eq) in ethanol (10 mL) was added aqueous NaOH (6M, 10 mL) at 0° C. The reaction mixture was stirred at 120° C. The reaction was monitored by TLC. The reaction was distilled then charged ice water then acidifies with dilute HCl solid precipitates out. The solid was filtered and dried to use it for next step without further purification (610 g, 82%). LCMS: 377 [M+1]$^+$.

Step-3: Synthesis of (R)-3-amino-6-(8-chloroquinolin-6-yl)-N-(1-(6-cyanopyridin-2-yl)ethyl)-5-phenylpyrazine-2-carboxamide To a stirred solution of 3-amino-6-(8-chloroquinolin-6-yl)-5-phenylpyrazine-2-carboxylic acid (200 mg, 0.53 mmol, 1.0 eq) in DMF (10 mL) was added 6-(1-aminoethyl)picolinonitrile (94 mg, 0.63 mmol, 1.2 eq) and the mixture was stirred at RT for 5 min. To this mixture HATU (404 mg, 1.06 mmol, 2.0 eq) and DIPEA (0.260 mL, 1.60 mmol, 3.0 eq) was added and the resultant mixture was allowed to stir for 16 h. The progress of reaction was monitored by TLC. Upon completion, the mixture was diluted with water (40 mL), extracted with EtOAc (2×100 mL). The combined organic layers were washed with water (40 mL), brine (40 mL), dried over $Na_2SO_4$, filtered and concentrated under reduced pressure to afford a crude residue which was purified by reverse phase column chromatography to afford the title compound (100 mg, 37%). The title compound was purified by chiral HPLC to get the two enantiomers (R)-3-amino-6-(8-chloroquinolin-6-yl)-N-(1-(6-cyanopyridin-2-yl)ethyl)-5-phenylpyrazine-2-carboxamide (4 mg) and (S)-3-amino-6-(8-chloroquinolin-6-yl)-N-(1-(6-cyanopyridin-2-yl)ethyl)-5-phenylpyrazine-2-carboxamide (7 mg). LCMS: 506 [M+1]$^+$; $^1$H NMR (400 MHz, DMSO-d$_6$) δ 9.17 (d, J=7.89 Hz, 1H), 8.96-9.02 (m, 1H), 8.31 (d, J=8.33 Hz, 1H), 8.05 (d, J=7.89 Hz, 1H), 7.93-8.02 (m, 2H), 7.90 (d, J=1.75 Hz, 1H), 7.85 (d, J=8.33 Hz, 1H), 7.61 (dd, J=3.95, 8.33 Hz, 1H), 7.28-7.46 (m, 5H), 5.29 (s, 1H), 1.59 (d, J=7.02 Hz, 3H)

Example S-28: Synthesis of (R)-3-amino-5-(3-cyanophenyl)-N-(1-(6-cyanopyridin-2-yl)ethyl)-6-(quinolin-6-yl)pyrazine-2-carboxamide (Compound No. 117) and (S)-3-amino-5-(3-cyanophenyl)-N-(1-(6-cyanopyridin-2-yl)ethyl)-6-(quinolin-6-yl)pyrazine-2-carboxamide (Compound No. 118)

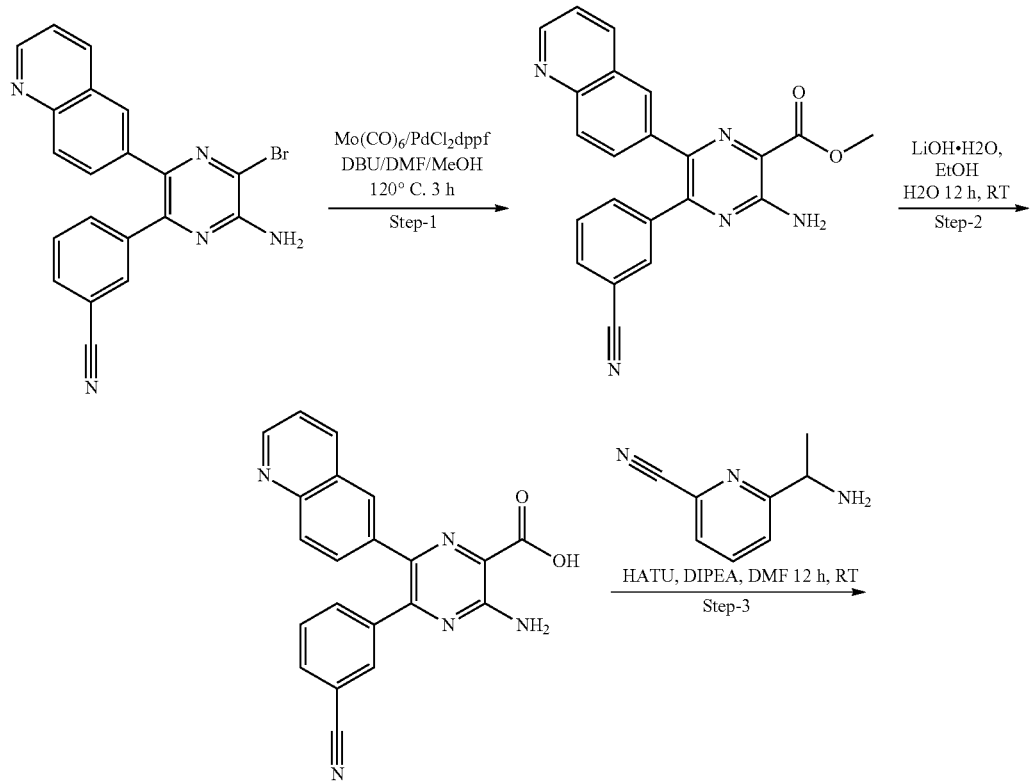

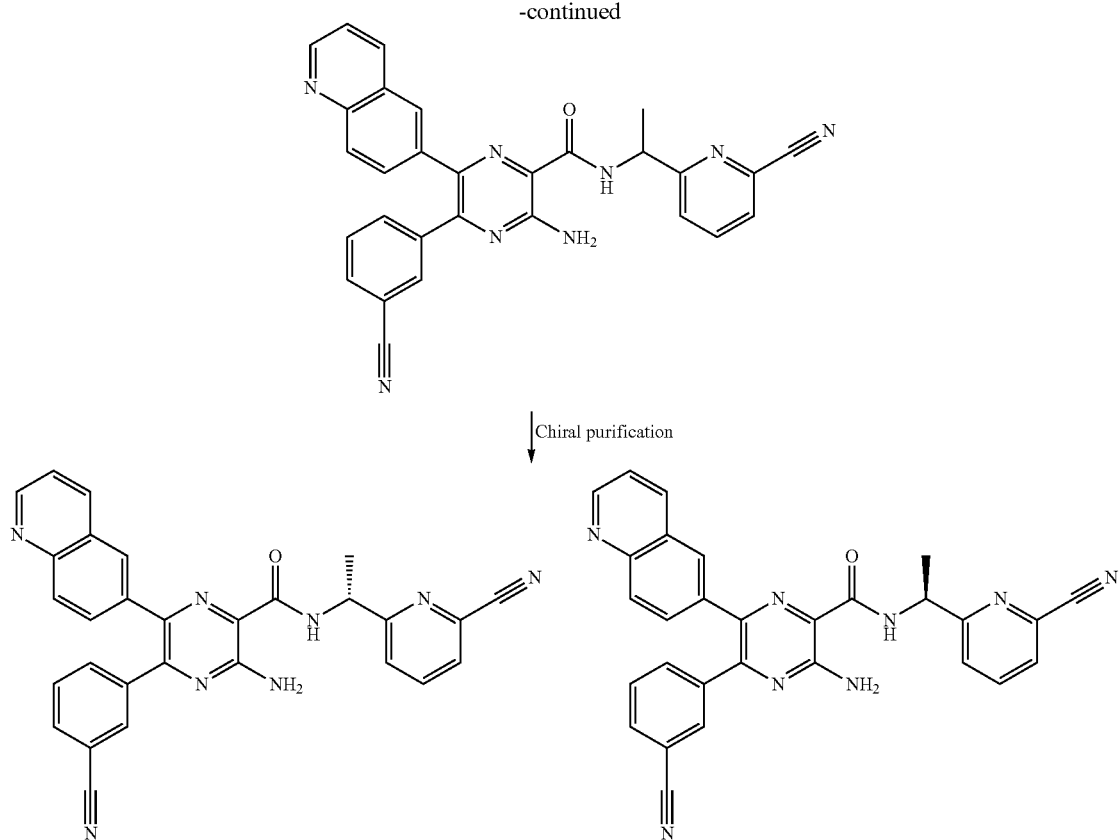

Step-1: Synthesis of methyl 3-amino-5-(3-cyano-phenyl)-6-(quinolin-6-yl)pyrazine-2-carboxylate To a stirred solution of 3-[6-amino-5-bromo-3-(quinolin-6-yl)pyrazin-2-yl]benzonitrile (700 mg, 1.74 mmol, 1.0 eq) in DMF (5 mL) and MeOH (10 mL). The reaction mixture was purged with nitrogen for 5 min then charged with Mo(CO)$_6$ (170 mg, 0.64 mmol, 0.37 eq) and PdCl$_2$dppf (63 mg, 0.08 mmol, 0.05 eq). The reaction mixture was again purged with nitrogen for 5 min and then stirred at RT for 1 h followed by the addition of DBU (0.6 mL, 3.82 mmol, 2.2 eq). The reaction mixture was stirred at RT for 5 min and then heated at 120° C. for 3h. The reaction was monitored by TLC and LCMS. The reaction mixture was filtered through celite and distilled to get the crude which was purified by column chromatography to get the desired product (200 mg, 22%). LCMS: 382 [M+1].+

Step-2: Synthesis of 3-amino-5-(3-cyanophenyl)-6-(quinolin-6-yl)pyrazine-2-carboxylic Acid To a stirred solution of methyl 3-amino-5-(3-cyanophenyl)-6-(quinolin-6-yl)pyrazine-2-carboxylate (200 mg, 0.52 mmol, 1.0 eq) in ethanol (5 mL) and THF (5 mL) was added LiOH.H$_2$O (88 mg, 2.09 mmol, 4.0 eq) dissolved in H$_2$O (2 mL). The resulting reaction mixture was stirred at RT for 16 h. The reaction mixture was allowed to cool to RT. The solvent was evaporated under vacuum and acidified using 1N HCl to get the solid which was filtered and dried to get the product (100 mg, 52%) LCMS: 368 [M+1]+.

Step-3: Synthesis of 3-amino-6-(8-chloroquinolin-6-yl)-5-phenyl-N-(1-(pyridin-2-yl)ethyl)pyrazine-2-carboxamide To stirred solution of of 3-amino-5-(3-cyanophenyl)-6-(quinolin-6-yl)pyrazine-2-carboxylic acid (100 mg, 0.27 mmol, 1.0 eq) in DMF (10 ml) was added (1R)-1-(pyridin-2-yl)ethanamine (80 mg, 0.54 mmol, 2.0 eq), DIPEA (0.2 mL, 0.81 mmol, 3 eq) and HATU (205 mg, 0.54 mmol, 2 eq) at RT under inert condition. The resulting mixture stirred for 16h at same temperature. Following this, ice cold water (20 mL) was added and extracted with ethyl acetate (3×20 mL), the combined organic layer washed with brine solution (1×50 mL), dried over Na$_2$SO$_4$, filtered and distilled purified by reverse phase column chromatography to get the title compound (50 mg) which was further purified by chiral purification to get the two enantiomers (R)-3-amino-5-(3-cyanophenyl)-N-(1-(6-cyanopyridin-2-yl)ethyl)-6-(quinolin-6-yl)pyrazine-2-carboxamide (10 mg, 7.0%) and (S)-3-amino-5-(3-cyanophenyl)-N-(1-(6-cyanopyridin-2-yl)ethyl)-6-(quinolin-6-yl)pyrazine-2-carboxamide (16 mg, 11.0%). LCMS: 497 [M+1]+; $^1$H NMR (DMSO-d6,400 MHz): δ 9.25 (d, 1H), 8.89 (d, 1H), 8.27 (d, 1H), 8.05-8.10 (m, 1H), 7.96-8.02 (m, 4H), 7.88-7.94 (m, 5H), 7.62 (d, 1H), 7.46-7.54 (m, 2H), 5.27-5.33 (m, 1H), 1.58 (d, 3H).

Example S-29: Synthesis of 3-amino-6-(8-chloro-quinolin-6-yl)-5-phenyl-N-(1-(pyridin-2-yl)ethyl) pyrazine-2-carboxamide (Compound No. 119), (R)-3-amino-6-(8-chloroquinolin-6-yl)-5-phenyl-N-(1-(pyridin-2-yl)ethyl)pyrazine-2-carboxamide (Compound No. 123) and (S)-3-amino-6-(8-chloro-quinolin-6-yl)-5-phenyl-N-(1-(pyridin-2-yl)ethyl) pyrazine-2-carboxamide (Compound No. 124)
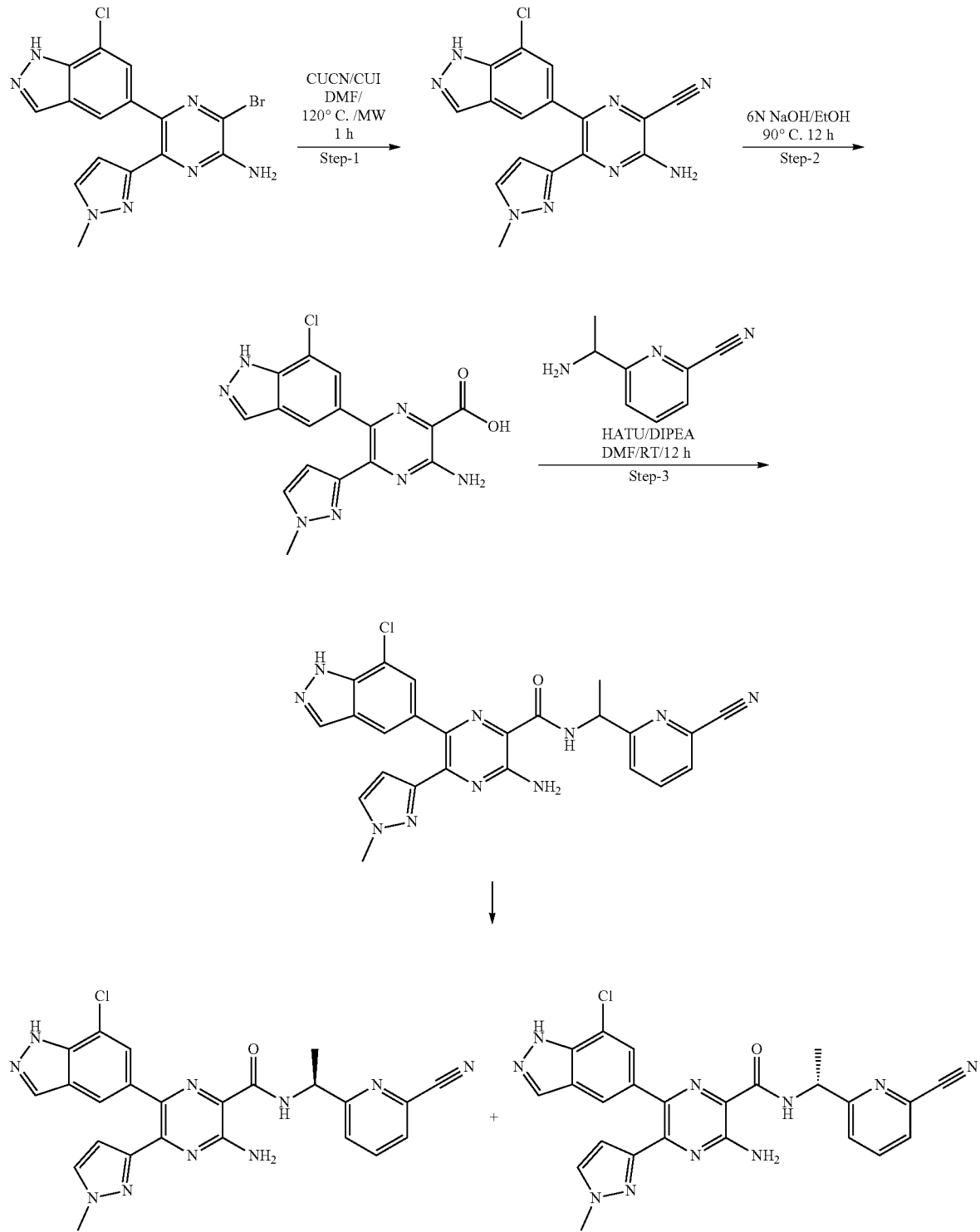

Step-1: Synthesis of 3-amino-6-(7-chloro-1H-indazol-5-yl)-5-(1-methyl-1H-pyrazol-3-yl)pyrazine-2-carbonitrile)

To a stirred solution of 3-bromo-5-(7-chloro-1H-indazol-5-yl)-6-(1-methyl-1H-pyrazol-3-yl)pyrazin-2-amine (500 mg, 1.24 mmol, 1.0 eq) in DMF (10 mL) was added cuprous cyanide (122 mg, 1.36 mmol, 1.1 eq) and copper iodide (354 mg, 1.86 mmol, 1.5 eq). The reaction mixture was allowed to stir at 120° C. for 45 mins under microwave irradiation. The reaction mixture was allowed to cool to RT, diluted with aqueous ammonia (5 mL) and extracted using ethyl acetate (3×25 mL). The combined organic layers were washed (brine), dried (anhydrous $Na_2SO_4$) and concentrated under vacuum to get the solid which was purified by column chromatography to get the desired product. (170 mg, 39%). LCMS: 351 [M+1]$^+$.

Step-2: Synthesis of 3-amino-6-(7-chloro-1H-indazol-5-yl)-5-(1-methyl-1H-pyrazol-3-yl)pyrazine-2-carboxylic Acid FK-GRF-633-84)

To a stirred solution of 3-amino-6-(7-chloro-1H-indazol-5-yl)-5-(1-methyl-1H-pyrazol-3-yl)pyrazine-2-carbonitrile (170 mg, 0.48 mmol, 1.0 eq) in ethanol (5 mL) was added 6M NaOH solution (5 mL). The resulting reaction mixture was heated at 100° C. for 16h. The reaction mixture was allowed to cool to RT. The solvent was evaporated under vacuum and acidified using 1N HCl to get the solid which was filtered and dried to get the product as yellow solid (120 mg, 67%). LCMS: 370 [M+1]$^+$.

Step-3: Synthesis of 3-amino-6-(8-chloroquinolin-6-yl)-5-phenyl-N-(1-(pyridin-2-yl)ethyl)pyrazine-2-carboxamide To stirred solution of 3-amino-6-(7-chloro-1H-indazol-5-yl)-5-(1-methyl-1H-pyrazol-3-yl)pyrazine-2-carboxylic acid (120 mg, 0.33 mmol, 1.0 eq) in DMF (10 ml) was added (1R)-1-(pyridin-2-yl)ethanamine (96 mg, 0.65 mmol, 2.0 eq), DIPEA (0.2 mL, 0.97 mmol, 3 eq) and HATU (247 mg, 0.65 mmol, 2 eq) at RT under inert condition. The resulting mixture stirred for 16 h at the same temperature. Following this, ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the title compound (26 mg, 21%). The title compound was purified by chiral HPLC to get the two enantiomers (R)-3-amino-6-(8-chloroquinolin-6-yl)-5-phenyl-N-(1-(pyridin-2-yl)ethyl)pyrazine-2-carboxamide and (S)-3-amino-6-(8-chloroquinolin-6-yl)-5-phenyl-N-(1-(pyridin-2-yl)ethyl)pyrazine-2-carboxamide LCMS: 49 [M+1]$^+$; $^1$H NMR (DMSO-d6, 400 MHz): δ 9.04 (d, 1H), 8.21 (s, 1H), 8.02-8.08 (m, 2H), 7.95 (d, 1H), 7.81-7.87 (m, 2H), 7.63 (d, 2H), 7.47 (s, 2H), 6.13 (d, 1H), 5.23-5.28 (m, 1H), 3.74 (s, 3H), 1.55 (d, 3H).

Example S-30: Synthesis of (3-amino-5-phenyl-N-(1-(pyrimidin-2-yl)ethyl)-6-(quinolin-6-yl)pyrazine-2-carboxamide (Compound No. 120), (R)-3-amino-5-phenyl-N-(1-(pyrimidin-2-yl)ethyl)-6-(quinolin-6-yl)pyrazine-2-carboxamide (Compound No. 125) and (S)-3-amino-5-phenyl-N-(1-(pyrimidin-2-yl)ethyl)-6-(quinolin-6-yl)pyrazine-2-carboxamide (Compound No. 126)

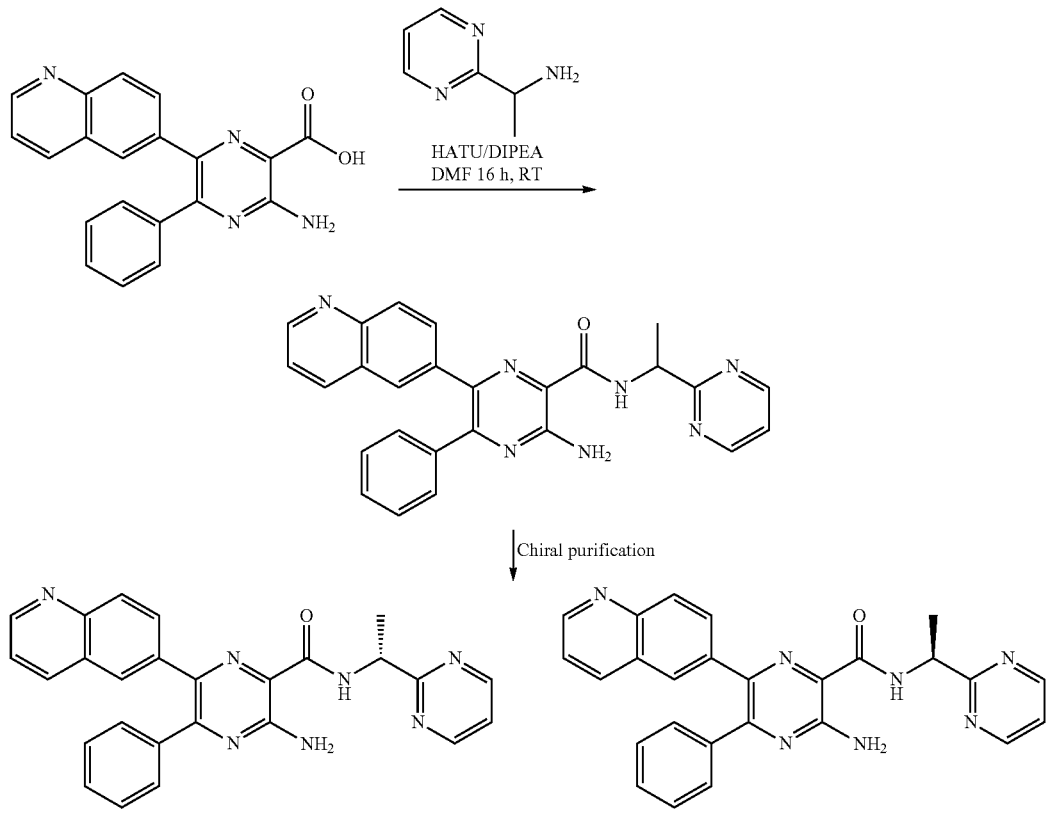

To the stirred solution 3-amino-5-phenyl-6-(quinolin-6-yl)pyrazine-2-carboxylic acid (0.2 g, 0.58 mmol, 1.0 eq) in DMF (10 ml) was added 1-(pyrimidin-2-yl)ethanamine (143 mg, 1.16 mmol, 2.0 eq), DIPEA (0.3 mL, 1.74 mmol, 3 eq) and HATU (440 mg, 1.16 mmol, 2 eq) at RT under inert condition. The resulting mixture stirred for 16h at same temperature. The reaction was monitored by TLC and LCMS. Ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the desired product (26 mg, 10%) LCMS: 448 [M+1]$^+$; $^1$H NMR (DMSO-d6, 400 MHz) δ 9.16 (d, 1H), 8.87-8.90 (m, 1H), 8.83 (d, 2H), 8.26 (d, 1H), 8.02 (d, 1H), 7.91-7.52 (m, 4H), 7.39-7.46 (m, 3H), 7.28-7.37 (m, 3H), 5.24 (dt, 1H), 1.60 (d, 3H).

Example S-31: Synthesis of 3-amino-N-(1-(6-cyanopyridin-2-yl)ethyl)-5-(1-methyl-1H-pyrazol-3-yl)-6-(quinolin-6-yl)pyrazine-2-carboxamide (Compound No. 127)

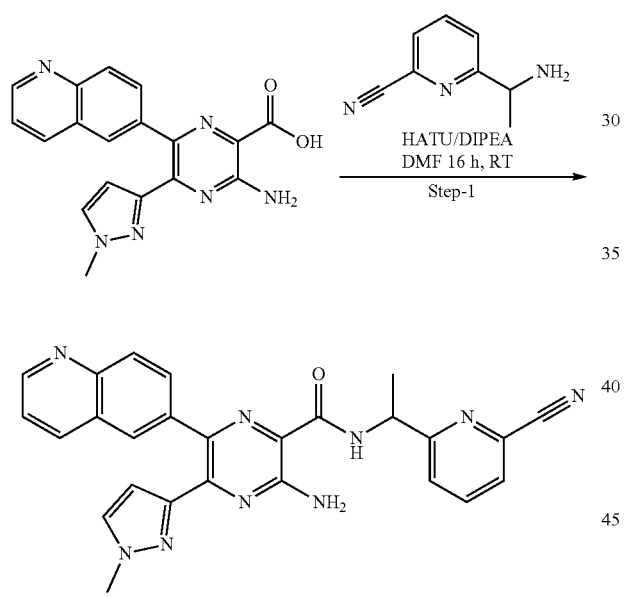

To the stirred solution 3-amino-5-(1-methyl-1H-pyrazol-3-yl)-6-(quinolin-6-yl)pyrazine-2-carboxylic acid (0.2 g, 0.57 mmol, 1.0 eq) in DMF (10 ml) was added 6-(1-aminoethyl)pyridine-2-carbonitrile (170 mg, 1.15 mmol, 2.0 eq), DIPEA (0.3 mL, 1.71 mmol, 3 eq) and HATU (433 mg, 1.15 mmol, 2 eq) at RT under inert condition. The resulting mixture stirred for 16 h at same temperature. The reaction was monitored by TLC and LCMS. Ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the title compound (7 mg, 3%). LCMS: 476 [M+1]$^+$. $^1$H NMR (DMSO-d6, 400 MHz): δ 9.10 (d, 1H), 8.97 (br s, 1H), 8.50 (br s, 1H), 8.18 (br s, 1H), 8.04-8.10 (m, 1H), 8.00 (d, 2H), 7.96 (d, 2H), 7.65-7.93 (m, 4H), 6.26 (br s, 1H), 5.20-5.29 (m, 1H), 3.71 (s, 3H), 1.55 (d, 0.3H).

Example S-32: Synthesis of (R)-3-amino-5-phenyl-N-(1-(pyrazin-2-yl)ethyl)-6-(quinolin-6-yl)pyrazine-2-carboxamide (Compound No. 128) and (S)-3-amino-5-phenyl-N-(1-(pyrazin-2-yl)ethyl)-6-(quinolin-6-yl)pyrazine-2-carboxamide (Compound No. 129)

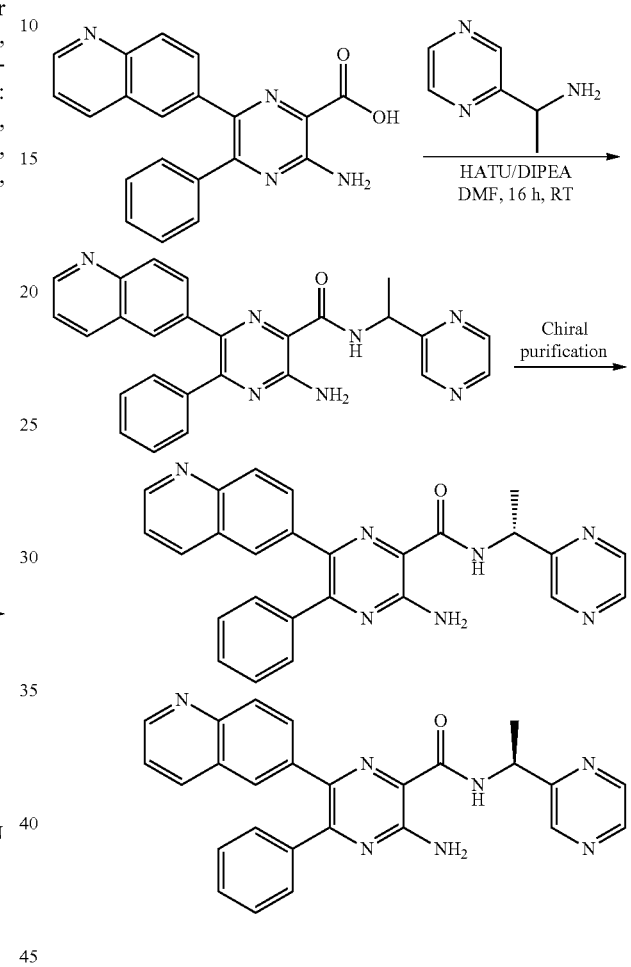

To the stirred solution 3-amino-5-phenyl-6-(quinolin-6-yl)pyrazine-2-carboxylic acid (0.2 g, 0.58 mmol, 1.0 eq) in DMF (10 mL) was added 1-(pyrazin-2-yl)ethanamine (143 mg, 1.16 mmol, 2.0 eq), DIPEA (0.3 mL, 1.74 mmol, 3 eq) and HATU (440 mg, 1.16 mmol, 2 eq) at RT under inert condition. The resulting mixture stirred for 16h at same temperature. The reaction was monitored by TLC and LCMS. Ice cold water (20 mL) was added and extracted with ethyl acetate (3×20 mL), the combined organic layer washed with brine solution (1×50 mL), dried over $Na_2SO_4$, filtered and distilled purified by reverse phase column chromatography to get the desired product (70 mg, 26%) the desired product obtained was further purified by chiral column to obtain the desired enantiomers (R)-3-amino-5-phenyl-N-(1-(pyrazin-2-yl)ethyl)-6-(quinolin-6-yl)pyrazine-2-carboxamide and (S)-3-amino-5-phenyl-N-(1-(pyrazin-2-yl)ethyl)-6-(quinolin-6-yl)pyrazine-2-carboxamide; LCMS:448 [M+1]$^+$; $^1$H NMR (DMSO-d6, 400 MHz): δ 9.07 (s, 1H), 8.80 (d, 1H), 8.61-8.63 (m, 1H), 8.57 (d, 1H), 8.05 (s, 1H), 7.92 (d, 1H), 7.73-7.78 (m, 1H), 7.41 (s, 1H), 7.26-7.40 (m, 4H), 4.94-5.62 (m, 1H), 1.60 (d, 3H).

Example S-33: Synthesis of 3-amino-5-(1-methyl-1H-pyrazol-3-yl)-N-(1-(pyrimidin-2-yl)ethyl)-6-(quinolin-6-yl)pyrazine-2-carboxamide (Compound No. 460)

Example S-34: Synthesis of 3-amino-5-(1-methyl-1H-pyrazol-3-yl)-N-(1-(pyridin-2-yl)ethyl)-6-(quinolin-6-yl)pyrazine-2-carboxamide (Compound No. 459)

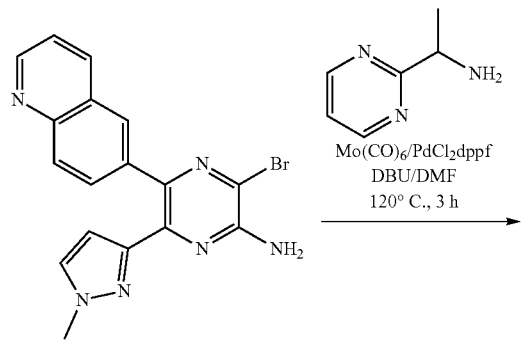

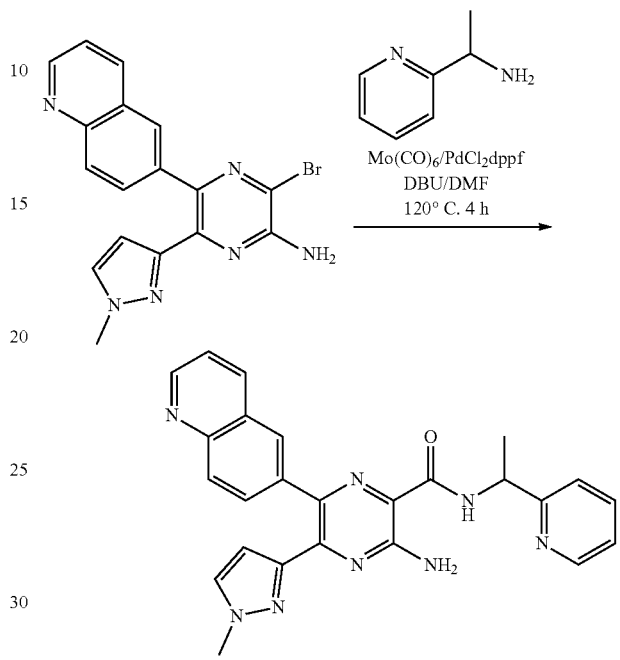

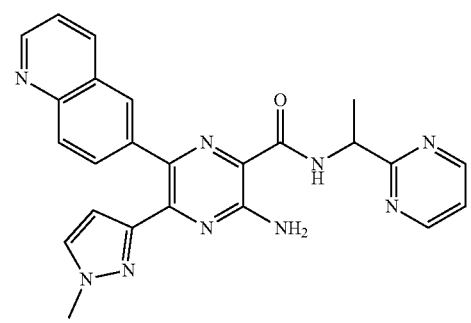

To a stirred solution of 3-bromo-6-(1-methyl-1H-pyrazol-3-yl)-5-(quinolin-6-yl)pyrazin-2-amine (200 mg, 0.52 mmol, 1.0 eq) in DMF (10 mL) was 1-(pyrimidin-2-yl)ethanamine (77 mg, 0.62 mmol, 1.2 eq). The reaction mixture was purged with nitrogen for 5 min then charged with $Mo(CO)_6$ (51 mg, 0.19 mmol, 0.37 eq) and $PdCl_2dppf$ (19 mg, 0.02 mmol, 0.05 eq). The reaction mixture was again purged with nitrogen for 5 min and then stirred at RT for 1 h followed by the addition of DBU (0.2 mL, 1.04 mmol, 2.2 eq). The reaction mixture was stirred at RT for 5 min and then heated at 120° C. for 3 h. The reaction was monitored by TLC and LCMS. The reaction mixture was filtered through celite and distilled. The reaction was diluted with water and extracted with ethyl acetate (3×200 mL). The combined organic layers were washed (brine), dried (anhydrous $Na_2SO_4$) and concentrated under vacuum to get the crude which was purified by reverse phase column chromatography to get the title compound (10 mg, 4.0%). LCMS: 45 2[M+1]$^+$; $^1$H NMR (DMSO-d6, 400 MHz) δ 8.99-9.09 (m, 2H), 8.81 (d, J=4.82 Hz, 2H), 8.62 (br s, 2H), 8.24 (br s, 1H), 8.03 (d, J=8.77 Hz, 1H), 7.85 (d, J=8.33 Hz, 1H), 7.61-7.76 (m, 3H), 7.43 (t, J=5.04 Hz, 1H), 6.27 (d, J=2.19 Hz, 1H), 5.17-5.26 (m, 1H), 3.70 (s, 3H), 1.58 (d, J=6.58 Hz, 3H).

To a stirred solution of 3-bromo-6-(1-methyl-1H-pyrazol-3-yl)-5-(quinolin-6-yl)pyrazin-2-amine (200 mg, 0.52 mmol, 1 eq) in DMF (8 mL) was added 1-(pyridin-2-yl)ethanamine (129.4 mg, 1.052 mmol, 2.0 eq). The reaction mixture was purged with nitrogen for 5 min then charged with $Mo(CO)_6$ (55 mg, 0.21 mmol, 0.4 eq) and $PdCl_2dppf$ (20 mg, 0.02 mmol, 0.05 eq). The reaction mixture was again purged with nitrogen for 5 min and then stirred at RT for 1 h followed by the addition of DBU (0.2 mL, 1.15 mmol, 2.2 eq). The reaction mixture was stirred at RT for 5 min and then heated at 120° C. for 4 h. The reaction was monitored by TLC and LCMS. The reaction mixture was filtered through celite and distilled. The reaction was diluted with water and extracted with ethyl acetate (3×100 mL). The combined organic layers were washed (brine), dried (anhydrous $Na_2SO_4$) and concentrated under vacuum to get the crude which was purified by reverse phase column chromatography to get the title compound (7 mg, 3%). LCMS: 451[M+1]$^+$; $^1$H NMR (DMSO-d6, 400 MHz) δ 9.08 (d, 1H), 8.90 (d, 1H), 8.53 (d, 1H), 8.35 (d, 1H), 8.07-8.13 (m, 1H), 7.95 (d, 1H), 7.70-7.83 (m, 3H), 7.64 (d, 2H), 7.54 (dd, 1H), 7.47 (d, 1H), 7.29 (dd, 1H), 6.19 (d, 1H), 5.22 (d, 1H), 3.71 (s, 3H), 1.52 (d, 3H).

It is understood that compounds from the Tables (2-72, 74, 77-88, 90-97, 130-458, 461, 462, 2-1, 2-3, 2-4, 2-5, 2-8, 2-9, 2-11, 2-12) are synthesized using the General Synthetic Schemes 1 to 3 or using the experimental procedures as described above and the steps involved in the synthetic routes are clearly familiar to those skilled in the art, wherein the substituents described in compounds of Formula (I), (II) and (III) herein can be varied with a choice of appropriate starting materials and reagents utilized in the steps presented.

BIOLOGICAL EXAMPLES

Example B1. Radioligand Binding Competition Assay

Example B1(a)

Binding of selected compounds to the adenosine $A_{2A}$, $A_1$, $A_{2B}$, and $A_3$ receptors is tested using a binding competition assay.

The general protocol for the radioligand binding competition assay is as follows. Competition binding is performed in duplicate in the wells of a 96 well plate (Master Block, Greiner, 786201) containing binding buffer (optimized for each receptor), membrane extracts (amount of protein/well optimized for each receptor), radiotracer (final concentration optimized for each receptor), and test compound. Nonspecific binding is determined by co-incubation with 200-fold excess of cold competitor. The samples are incubated in a final volume of 0.1 mL at 25° C. for 60 minutes and then filtered over filter plates. Filters are washed six times with 0.5 mL of ice-cold washing buffer (optimized for each receptor) and 50 µL of Microscint 20 (Packard) are added on each filter. The filter plates are sealed, incubated 15 min on an orbital shaker and scintillation counted with a TopCount for 30 sec/filter.

For the $A_{2A}$ adenosine receptor radioligand binding assay, the following modifications are made to the general protocol. GF/C filters (Perkin Elmer, 6005174), presoaked in 0.01% Brij for 2h at room temperature are used. Filters are washed six times with 0.5 mL of ice-cold washing buffer (50 mM Tris pH 7.4) and 50 µL of Microscint 20 (Packard) are added in each well. The plates are then incubated for 15 min on an orbital shaker and then counted with a TopCount™ for 1 min/well. Another radioligand binding assay used to evaluate the binding affinity for the adenosine $A_{2A}$ receptor assay is performed in duplicate in the wells of a 384 plate. Assay buffer contains DPBS 500 mM, $MgCl_2$ 0.1 mM, and 1% DMSO. Membrane-bead suspension is prepared by mixing 25.98 µL of human adenosine $A_{2A}$ membrane preparation (Perkin Elmer, RBHA2AM400UA) at 33.4 µg/mL, 28 µL of ADA at 20 µg/mL, and 932 µL of SPA beads at 3.33 mg/mL) and the mixture is incubated for 20 min at room temperature. 20 µL of radiotracer ($^3$H-SCH 58261) at 15 nM is mixed into each well containing test articles at various concentrations and the plate is centrifuged at 1000 rpm for 1 minute. 30 µL of the membrane-bead suspension is added to each well. The plates are sealed and incubated for 1 hr at room temperature with vigorous mixing on a plate mixer. Plates are read on Microbeta$^2$ (Perkin Elmer, 2450-0010).

For the adenosine $A_1$ radioligand binding competition assay, a similar procedure is used except that the following reagents are used: CHO-KI-A1 cell membranes; binding buffer comprising HEPES 25 mM pH 7.4, $MgCl_2$ 5 mM, $CaCl_2$ 1 mM, NaCl 100 mM, saponin 10 pg/mL; wash buffer comprising HEPES 25 mM pH 7.4, $MgCl_2$ 5 mM, $CaCl_2$ 1 mM, NaCl 100 mM; a Unifilter GF/B—treated for 2h with 0.5% PEI; and 1.6 nM of $^3$H-DPCPX as the tracer.

Similarly, the following reagents are used for the adenosine $A_{2B}$ radioligand binding competition assay: HEK-293-$A_{2B}$ cell membranes, 20 µg/well, preincubated 30 min at RT with 25 µg/mL Adenosine Deaminase; a binding buffer comprising HEPES 10 mM pH 7.4, EDTA 1 mM, 0.5% BSA; a wash buffer comprising HEPES 10 mM pH 7.4, EDTA 1 mM; a Unifilter GF/C—treated for 2h with 0.5% PEI; and 10 nM $^3$H-DPCPX as the tracer.

For the adenosine $A_3$ radioligand binding competition assay, the following reagents are used: CHO-K1-A3 cell membranes, 1.5 µg/well; a binding buffer comprising HEPES 25 mM pH 7.4, $MgCl_2$ 5 mM, $CaCl_2$ 1 mM, 0.5% BSA; a wash buffer comprising HEPES 25 mM pH 7.4, $MgCl_2$ 5 mM, $CaCl_2$ 1 mM; a Unifilter GF/C—treated for 2h with 0.5% BS; and 0.4 nM of $^{125}$I-AB-MECA as the tracer.

The results of the binding assay are given as percent residual binding at a given concentration. Percent of residual binding means binding of a compound in the presence of competitor normalized to the amount of binding in the absence of competitor.

Example B1(b)

A second $A_{2A}$ adenosine receptor radioligand binding assay protocol was used. The protocol used adenosine A2a (human) membrane (PerkinElmer RBHA2AM400UA) at a concentration of 5 µg/well/100 µl and the radioligand [3H] CGS-21680 (Cat No. PerkinElmer-NET1021250UC) at a final concentration of 6 nM. Testing compounds were diluted with DMSO to make 8-point 4-fold serial dilution, starting at 0.2 mM. CGS-15943 was the reference compound. 1 µl of compounds/high control/low control was transferred to the assay plate according to a plate map, followed by 100 µl of membrane stocks and 100 µl of radioligand, in assay buffer (50 mM Tris-HCl, 10 mM $MgCl_2$, 1 mM EDTA, pH 7.4). The plate was sealed and incubated at RT for 2 hours. Unifilter-96 GF/C filter plates (Perkin Elmer Cat #6005174) were soaked with 50 µl of 0.3% PEI per well for at least 0.5 hour at room temperature. When the binding assays were completed, the reaction mixtures were filtered through GF/C plates using Perkin Elmer Filtermate Harvester, and each plate washed 4 times with cold wash buffer (50 mM Tris-HCl, 154 mM NaCl, pH 7.4). The filter plates were dried for 1 hour at 50 degrees. After drying, the bottom of the filter plate wells was sealed, 50 µl of Perkin Elmer Microscint 20 cocktail was added, and the top of the filter plate was sealed. $^3$H trapped on the filter was counted using Perkin Elmer MicroBeta2 Reader. The data were analyzed with GraphPad Prism 5 to obtain binding $IC_{50}$ values. The "Inhibition [% Control]" was calculated using the equation: % Inh=(1-Background subtracted Assay value/Background subtracted HC value)*100, where HC is high control. A2a binding $IC_{50}$ values are shown in Table B1.

A second $A_1$ adenosine receptor radioligand binding assay protocol was used. The protocol used adenosine A1 (human) membrane (PerkinElmer ES-010-M400UA) at a concentration of 2.5 µg/well/100 µl and the radioligand [3H] DPCPX (Cat No. PerkinElmer-NET974250UC) at a final concentration of 1 nM. Testing compounds were tested at a final concentration of 200 nM. CGS-15943, the reference compound, was tested in an 8-point 4-fold serial dilution, starting at a top concentration of 1 µM. 1 µl of compounds/ high control/low control was transferred to the assay plate according to a plate map, followed by 100 µl of membrane stocks and 100 µl of radioligand, in assay buffer (25 mM HEPES, 5 mM $MgCl_2$, 1 mM $CaCl_2$, 100 mM NaCl, pH 7.4). The plate was sealed and incubated at RT for 1 hour. Unifilter-96 GF/C filter plates (Perkin Elmer Cat #6005174) were soaked with 50 µl of 0.3% PEI per well for at least 0.5 hour at room temperature. When the binding assays were completed, the reaction mixtures were filtered through GF/C plates using Perkin Elmer Filtermate Harvester, and each plate washed 4 times with cold wash buffer (25 mM HEPES, 5 mM $MgCl_2$, 1 mM $CaCl_2$, 100 mM NaCl, pH 7.4). The filter plates were dried for 1 hour at 50 degrees. After drying, the bottom of the filter plate wells was sealed, 50 µl of Perkin Elmer Microscint 20 cocktail was added, and the top of the filter plate was sealed. $^3$H trapped on the filter was counted using Perkin Elmer MicroBeta2 Reader. The data were analyzed with GraphPad Prism 5 to obtain binding $IC_{50}$ values for the reference compound. The "Inhibition [% Control]" was calculated using the equation: % Inh=(1-Background subtracted Assay value/Background subtracted HC value)*100, where HC is high control. A1 binding inhibition values are shown in Table B1.

TABLE B1

| Compound No. | A2a binding $IC_{50}$ (nM) | A1 binding inhibition at 200 nM (%) |
| --- | --- | --- |
| 73 | 3.1 | 61 |
| 75 | 2.5 | 63 |
| 76 | 3.4 | 45 |
| 89 | 16 | ND |
| 98 | 0.8 | 92 |
| 2-2 | ND | 30 |
| 2-6 | 3.7 | 90 |
| 2-7 | ND | 81 |
| 2-10 | 3.1 | 79 |
| 2-13 | ND | 54 |
| 100 | 1.6 | 70 |
| 101 | ND | 66 |
| 102 | 1.9 | 93 |
| 103 | ND | 19 |
| 104 | 0.9 | 68 |
| 105 | 1.2 | 94 |
| 106 | ND | 34 |
| 107 | ND | 49 |
| 108 | 1.3 | 47 |
| 109 | 3.8 | 49 |
| 110 | 2.9 | 38 |
| 111 | 3.9 | 92 |
| 112 | 1.6 | 77 |
| 113 | 4.7 | 58 |
| 114 | 3.5 | 95 |
| 115 | 64 | 74 |
| 116 | 5.4 | 98 |
| 117 | 269 | 56 |
| 118 | 16 | 92 |
| 119 | 12 | 92 |
| 120 | 6.8 | 45 |
| 121 | 1.1 | 80 |
| 122 | <0.6 | 96 |
| 123 | 1.1 | 89 |
| 124 | 3.7 | 95 |
| 125 | 1.2 | ND |
| 126 | 1.8 | 41 |
| 127 | 3.9 | 84 |
| 128 | 2 | 92 |
| 129 | 3.9 | 61 |
| 459 | 4.7 | ND |
| 460 | 7.3 | ND |

ND: Not Determined

Example B2. cAMP Assay

The functional activity of compounds was tested using Assay 2, below, to detect the presence of cAMP. Assay 1 is an alternative assay for this purpose. Activation of G-protein coupled receptors (such as $A_{2A}$) results in activation of adenylyl cyclase which converts ATP into cAMP which is used as a downstream signaling molecule. Therefore, molecules which act as GPCR (or specifically $A_{2A}$ receptor) antagonists cause a decrease in intracellular cAMP concentration.

Assay 1: This assay uses HEK-293 cells expressing human recombinant adenosine $A_{2A}$ receptor that are grown prior to the test in media without antibiotic. The cells are detached by gentle flushing with PBS-EDTA (5 mM EDTA), recovered by centrifugation and suspended in assay buffer (KRH: 5 mM KCl, 1.25 mM $MgSO_4$, 124 mM NaCl, 25 mM HEPES, 13.3 mM Glucose, 1.25 mM $KH_2PO_4$, 1.45 mM $CaCl_2$, 0.5 g/L BSA, supplemented with Rolipram).

12 µL of cells are mixed with 6 µL of the test compound at increasing concentrations and then incubated for 10 min. Thereafter 6 µL of the reference agonist is added at a final concentration corresponding to the historical $EC_{80}$. The plates are then incubated for 30 min at room temperature. After addition of the lysis buffer and 1 hour incubation, cAMP concentrations are estimated, according to the manufacturer specification, with the HTRF® kit.

Assay 2 (Table B2): This assay used HEK-293 cells expressing human recombinant adenosine $A_{2A}$ receptor (or, alternatively, $A_1$ receptor) that were grown prior to the test in media without antibiotic. 100 nL of test articles at 100x of final concentration were transferred to assay plate by Echo. Cells were washed twice with 5 mL of PBS and 10 µL of cells were mixed with 5 mL PBS. After aspirating the PBS and adding 1.5 mL versine, cells were incubated at 37° C. for 2-5 min. After centrifugation, 4 mL of medium was added and adjusted cell density to 5,000 cells/well with Stimulation Buffer. 10 µL of cells were aliquoted to the assay plate, centrifuged at 1000 rpm for 1 minute, and incubated for 60 minutes at room temperature. 5 µL 4× Eu-cAMP tracer solution and 5 µL 4× Ulight™-anti-cAMP solution were added to assay plate, followed by centrifugation and 60-minute incubation at room temperature. Plates were read on EnVision.

As shown in Table B2, certain of the compounds disclosed herein strongly reduced intracellular levels of cAMP. For example, compound 89 had an $IC_{50}$ for reducing cAMP levels of 58 nM in the $A_{2A}$ assay.

TABLE B2

| Compound No. | A1 cAMP $IC_{50}$ (nM) | A2a cAMP $IC_{50}$ (nM) |
| --- | --- | --- |
| 1 | ND | 262 |
| 73 | 403 | 53 |
| 75 | 219 | 25 |
| 76 | 804 | 24 |
| 89 | ND | 58 |
| 98 | 11 | 18 |
| 2-2 | ND | 327 |
| 2-6 | 5 | 44 |
| 2-7 | ND | 130 |
| 2-10 | 27 | 39 |
| 2-13 | ND | 527 |
| 99 | ND | 72 |
| 100 | 22 | 28 |
| 101 | ND | 238 |
| 102 | 24 | 143 |
| 103 | ND | 1421 |
| 104 | 117 | 76 |
| 105 | 10 | 48 |
| 106 | ND | 165 |
| 107 | ND | 191 |
| 108 | 326 | 55 |
| 110 | ND | 75 |
| 122 | ND | 33 |
| 125 | ND | 27 |
| 126 | ND | 110 |

ND: Not Determined

Example B3 GTPγ$^{35}$S Scintillation Proximity Assay for $A_{2A}$ Receptor

A scintillation proximity assay (SPA) is used to determine the kinetic profile of the binding of test compound to the $A_{2A}$ receptor.

For antagonist testing, membrane extracts are prepared from HEK-293 cells expressing recombinant human $A_{2A}$ receptor, are mixed with GDP (volume:volume) and are incubated in assay buffer comprising 20 mM HEPES pH 7.4; 100 mM NaCl, 10 μg/mL saponin, 5 mM $MgCl_2$ for at least 15 min on ice. In parallel, GTPγ[$^{35}$S] is mixed with the beads (volume:volume) just before starting the reaction. The following reagents are successively added in the wells of an Optiplate (Perkin Elmer): 25 μL of test compound or reference ligand, 25 μL of the membranes: GDP mix, 25 μL of reference agonist at historical $EC_{80}$ and 25 μL of GTPγ[$^{35}$S] (PerkinElmer NEG030X), diluted in assay buffer to give 0.1 nM. The plate is incubated at room temperature for 1 hour. Then, 20 μL of IGEPAL is added for 30 minutes at room temperature. Following this incubation, 20 μL of beads (PVT-anti rabbit (PerkinElmer, RPNQ0016)), diluted in assay buffer at 50 mg/mL (0.5 mg/10 μL) and 20 μL of an Anti-GαS/olf antibody are added for a final incubation of 3 hours at room temperature. Then, the plates are centrifuged for 10 min at 2000 rpm, incubated at room temperature for 1 hour and counted for 1 min/well with a PerkinElmer TopCount reader

Example B4 Functional T Cell Assay

Human T Cell Activation Assay: Fresh human blood is diluted with the same volume of PBS and the buffy coat containing peripheral blood mononuclear cells (PBMCs) is prepared and resuspended in culture medium at a density of $2\times10^6$/mL. $2\times10^5$ PBMCs (in 100 μL) are plated to each well of a 96-well flat bottom plate. 25 μL of 8× final concentration of 10-fold serial diluted or single concentration compounds are added to indicated wells and incubated for 30 mins in 37° C./5% $CO_2$. 25 μL of 8× final concentration of NECA (1 PM) is added to indicated wells and incubated for 30 min in 37° C./5% $CO_2$. Beads included in T cell activation/expansion kit (Miltenyi biotec Cat #130-091-441) at a bead-to-cell ratio of 1:6 in 50 μL is added to all wells with the final concentration of DMSO at 0.1% and final volume at 200 μL. 60 μL of supernatant post 24 hr and 48 hr incubation is collected for TNF-α and IFN-γ concentration evaluation using TNF-α ELISA ready-set-go kit (eBioscience, Cat #88-7346-77) and IFN-γ ELISA ready-set-go kit (eBioscience, Cat #88-7316-77), respectively.

Example B5 cAMP Assay

In a 96-well plate coated with anti-CD3 antibody, $CD8^+$ T-cells ($1\times10^5$) are cultured alone, with 3 μM of NECA, or in the presence of 1 μM of the compound of interest with or without 3 μM of NECA. The cells are incubated for 30 min at 37° C. and 5% $CO_2$, and the reaction is stopped by addition of 200 μL, 0.1 M hydrochloric acid. cAMP levels are determined by an ELISA kit.

Example B6 Anti-Tumor Activities in Immuno-Oncology Mouse Models

The anti-tumor activities of test articles are evaluated in selective mouse models (e.g., syngeneic model, xenograft model, or PDX) as a monotherapy or combination therapies. Using MC-38 syngeneic model as an example: female C57BL/6 mice are inoculated subcutaneously at right flank with MC-38 cells for tumor development. Five days after tumor inoculation, mice with tumor size ranging from 40-85 $mm^3$ are selected and assigned into sub-groups using stratified randomization with 10 mice per group based upon their tumor volumes. Mice receive pre-defined treatments include vehicle, test article at various doses alone, test article at various doses plus other anti-cancer therapy, and other anti-cancer therapy control. Body weight and tumor sizes are measured three times per week during the treatment. Tumor volume is expressed in $mm^3$ using the formula: $V=0.5$ $a\times b^2$ where a and b are the long and short diameters of the tumor, respectively. The tumor sizes are used for the calculations of both tumor growth inhibition (TGI) and T/C values. When an individual animal reaches to the termination endpoint (e.g., with TV>1000 $mm^3$), the mouse is euthanized. The time from inoculation to the termination are deemed as its survival time. Survival curves are plotted by the Kaplan-Meier method. At the end of study, plasma and tumor samples are collected to explore biomarkers.

Example B7 Mouse Splenocyte Assay $IC_{50}$ values of compounds for reversal of NECA suppression of mIFNγ release is determined in mouse splenocytes isolated from Balb/c mice. The mIFNγ release is CD3e/CD28-induced release. Mouse splenocytes ($2\times10^5$ cells/well) are activated with Anti-mouse CD3e (2.5 μg/ml, coated overnight at 4° C.; Cat #14-0032-82, eBioscience) and then incubated with serial dilutions of compounds (3 fold, 8 point dose response starting at 1 μM) in the presence of NECA (at a concentration such as 0.1, 3.0, or 6.0 μM; Cat #E2387, Sigma) for 30 min at 37° C., 5% $CO_2$ in an incubator (cell culture conditions) prior to treating them with Anti-mouse CD28 (0.1 μg/ml soluble; Cat #16-0289-81, eBiosciences). Splenocytes are further incubated under cell culture conditions for 72 hr; the supernatant is then harvested and diluted to 1:100, and ELISA is performed as per the manufacturer's protocol (mIFN-γ kit; Cat #555138 and 550534, BD Biosciences). Plates are read in a plate reader by measuring absorbance at 450 nm. Values for the reversal of NECA suppressed mIFN-γ release by compounds are calculated by the following formula:

$$\text{Normalized } mIFN\text{-}\gamma \text{ release} = \frac{([mIFN\text{-}\gamma]_{test} - [mIFN\text{-}\gamma]_{blank})}{([mIFN\text{-}\gamma]_{NECA} - [mIFN\text{-}\gamma]_{blank})}$$

where $[mIFN\text{-}\gamma]_{test}$ is the test reading, $[mIFN\text{-}\gamma]_{blank}$ is the average reading obtained from blank wells, and $[mIFN\text{-}\gamma]_{NECA}$ is the average reading obtained from NECA treated, activated cells. The $IC_{50}$ values are calculated by fitting the curve to the "four-parameter variable slope logistic model" using Graph Pad Prism.

Although the foregoing invention has been described in some detail by way of illustration and example for purposes of clarity of understanding, it is apparent to those skilled in the art that certain minor changes and modifications will be practiced in light of the above teaching. Therefore, the description and examples should not be construed as limiting the scope of the invention.

All references throughout, such as publications, patents, and published patent applications, are incorporated herein by reference in their entireties.

What is claimed is:
1. A compound of the formula (III):

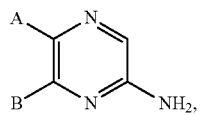

or a tautomer or stereoisomer thereof, or a pharmaceutically acceptable salt of any of the foregoing, wherein:

A is

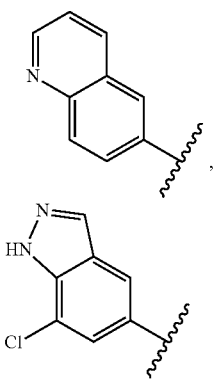 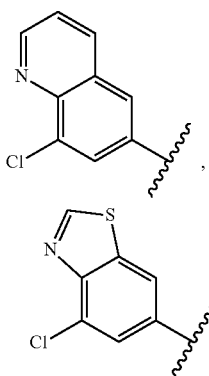

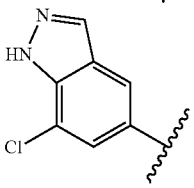 or 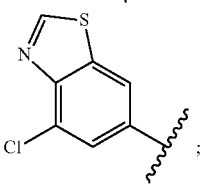;

and
B is a phenyl substituted with 1 to 3 groups which may be the same or different, wherein at least one group is —CN, and wherein each group is halogen, —CF$_3$, —OH, —OCH$_3$, —CN, —C(O)OCH$_3$, —C(O)OC$_2$H$_5$, —NH$_2$, —NHCH$_3$ or C$_1$-C$_6$ alkyl optionally substituted by halogen, —OH or oxo.

2. The compound of claim 1, or a tautomer or stereoisomer thereof, or a pharmaceutically acceptable salt of any of the foregoing, wherein B is selected from the group consisting of

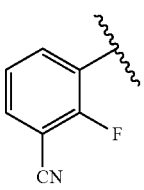, 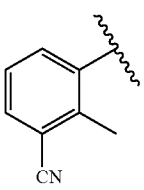, and 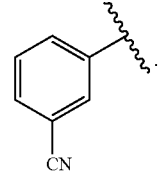.

3. The compound of claim 1, or a pharmaceutically acceptable salt thereof, wherein the compound is selected from the group consisting of

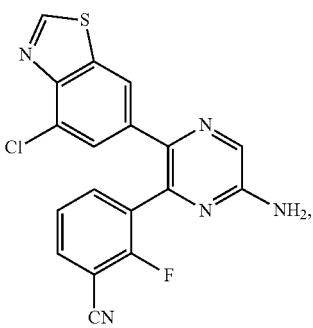

-continued

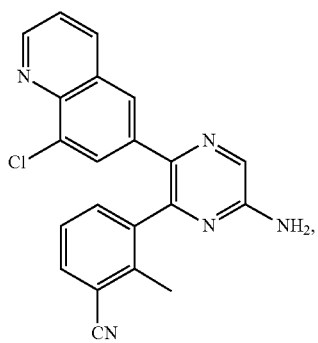

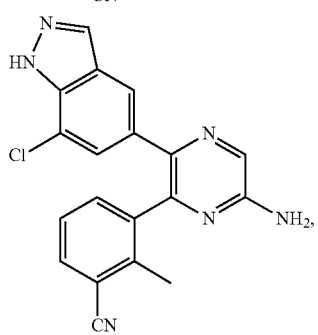

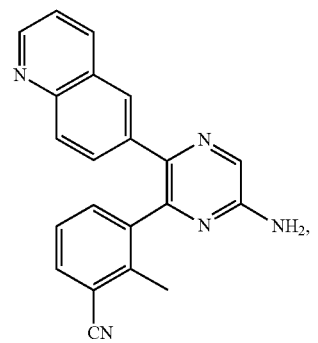

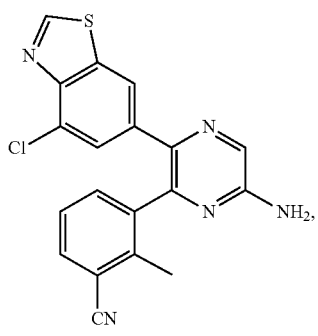

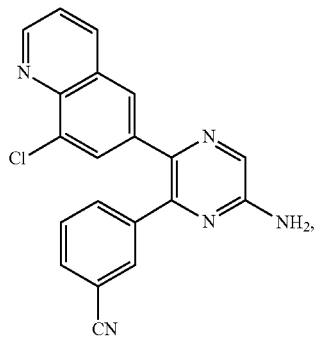 [SMILES: N#Cc1cccc(-c2nc(N)cnc2-c2cc(Cl)c3ncccc3c2)c1]

-continued

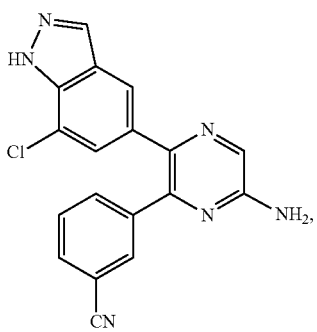

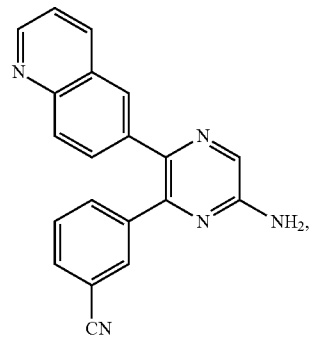

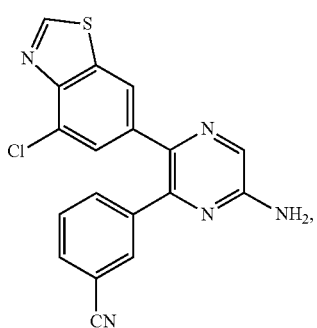

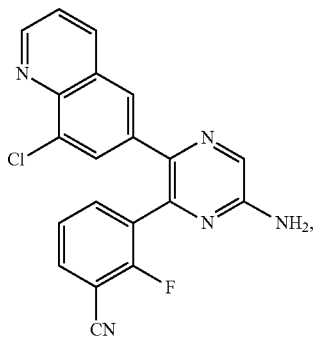

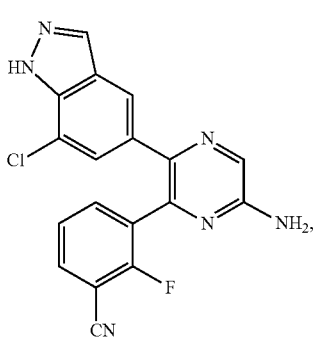

-continued

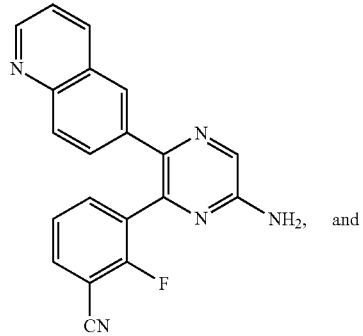
and

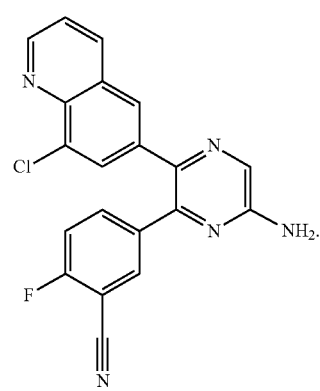

4. A pharmaceutical composition comprising a compound of claim 1, or a tautomer or stereoisomer thereof, or a pharmaceutically acceptable salt of any of the foregoing, and a pharmaceutically acceptable carrier.

5. A method of inhibiting an adenosine receptor of subtype $A_{2A}$, $A_{2B}$ or $A_3$ in a cell, comprising administering a compound of claim 1, or a tautomer or stereoisomer thereof, or a pharmaceutically acceptable salt of any of the foregoing, to the cell.

6. The method of claim 5, wherein the adenosine receptor is of subtype $A_{2A}$.

7. A kit comprising a compound of claim 1, or a tautomer or stereoisomer thereof, or a pharmaceutically acceptable salt of any of the foregoing.

8. The compound of claim 3, or a pharmaceutically acceptable salt thereof, wherein the compound is

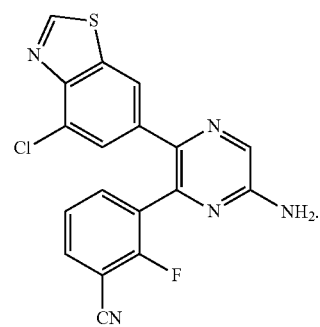 [SMILES: N#Cc1cccc(-c2nc(N)cnc2-c2cc(Cl)c3ncsc3c2)c1F]

9. The compound of claim 3, or a pharmaceutically acceptable salt thereof, wherein the compound is

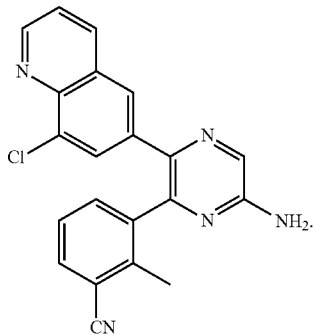 [SMILES: Cc1c(C#N)cccc1-c1nc(N)cnc1-c1cc(Cl)c2ncccc2c1]

10. The compound of claim 3, or a pharmaceutically acceptable salt thereof, wherein the compound is

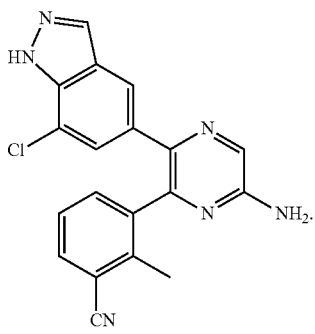

11. The compound of claim 3, or a pharmaceutically acceptable salt thereof, wherein the compound is

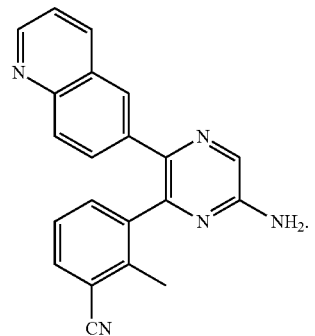 [SMILES: Cc1c(C#N)cccc1-c1nc(N)cnc1-c1ccc2ncccc2c1]

12. The compound of claim 3, or a pharmaceutically acceptable salt thereof, wherein the compound is

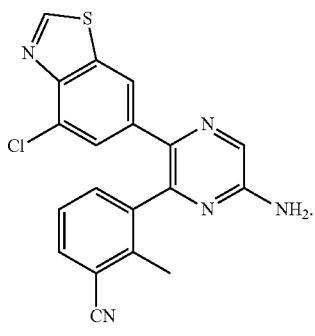 [SMILES: Cc1c(C#N)cccc1-c1nc(N)cnc1-c1cc(Cl)c2ncsc2c1]

13. The compound of claim 3, or a pharmaceutically acceptable salt thereof, wherein the compound is

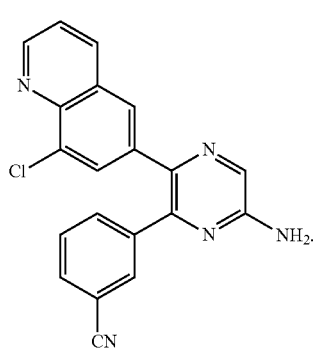 [SMILES: N#Cc1cccc(-c2nc(N)cnc2-c2cc(Cl)c3ncccc3c2)c1]

14. The compound of claim 3, or a pharmaceutically acceptable salt thereof, wherein the compound is

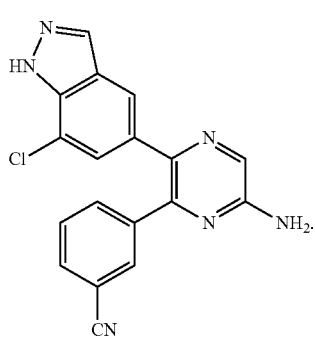 [SMILES: N#Cc1cccc(-c2nc(N)cnc2-c2cc(Cl)c3[nH]ncc3c2)c1]

15. The compound of claim 3, or a pharmaceutically acceptable salt thereof, wherein the compound is

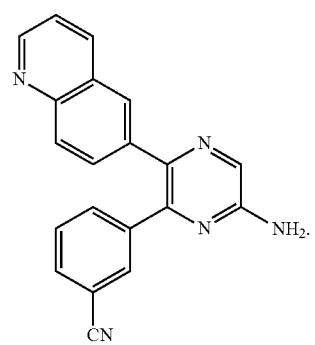 [SMILES: N#Cc1cccc(-c2nc(N)cnc2-c2ccc3ncccc3c2)c1]

16. The compound of claim 3, or a pharmaceutically acceptable salt thereof, wherein the compound is

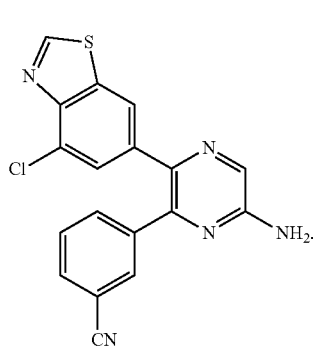 [SMILES: N#Cc1cccc(-c2nc(N)cnc2-c2cc(Cl)c3ncsc3c2)c1]

17. The compound of claim 3, or a pharmaceutically acceptable salt thereof, wherein the compound is

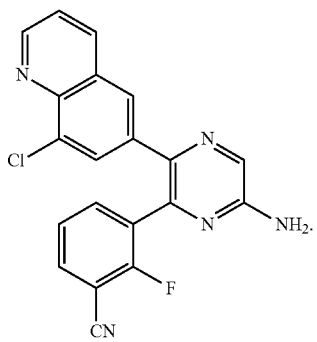 [SMILES: N#Cc1cccc(-c2nc(N)cnc2-c2cc(Cl)c3ncccc3c2)c1F]

18. The compound of claim 3, or a pharmaceutically acceptable salt thereof, wherein the compound is

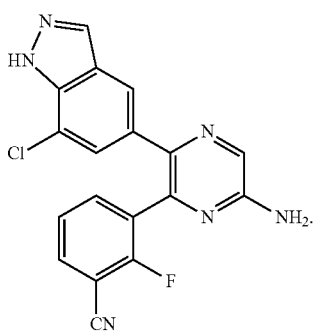 [SMILES: N#Cc1cccc(-c2nc(N)cnc2-c2cc(Cl)c3[nH]ncc3c2)c1F]

19. The compound of claim 3, or a pharmaceutically acceptable salt thereof, wherein the compound is

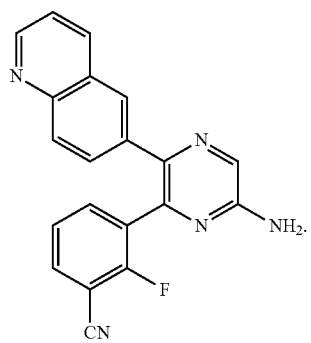 [SMILES: N#Cc1cccc(-c2nc(N)cnc2-c2ccc3ncccc3c2)c1F]

20. The compound of claim 3, or a pharmaceutically acceptable salt thereof, wherein the compound is

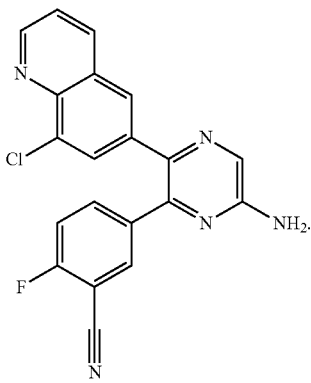 [SMILES: N#Cc1cc(-c2nc(N)cnc2-c2cc(Cl)c3ncccc3c2)ccc1F]

* * * * *